US012703760B2

(12) United States Patent
Dimitrov et al.

(10) Patent No.: US 12,703,760 B2
(45) Date of Patent: Aug. 11, 2026

(54) MOLECULES THAT BIND TO CD66e POLYPEPTIDES

(71) Applicant: UNIVERSITY OF PITTSBURGH—OF THE COMMONWEALTH SYSTEM OF HIGHER EDUCATION, Pittsburgh, PA (US)

(72) Inventors: Dimiter Stanchev Dimitrov, Pittsburgh, PA (US); John W. Mellors, Pittsburgh, PA (US); Dusan Baek, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 410 days.

(21) Appl. No.: 18/281,157

(22) PCT Filed: Mar. 8, 2022

(86) PCT No.: PCT/US2022/019375

§ 371 (c)(1),
(2) Date: Sep. 8, 2023

(87) PCT Pub. No.: WO2022/192281

PCT Pub. Date: Sep. 15, 2022

(65) Prior Publication Data

US 2024/0166760 A1 May 23, 2024

Related U.S. Application Data

(60) Provisional application No. 63/158,205, filed on Mar. 8, 2021.

(51) Int. Cl.

| | |
|---|---|
| ***C07K 16/30*** | (2006.01) |
| ***A61K 39/395*** | (2006.01) |
| ***A61K 40/11*** | (2025.01) |
| ***A61K 40/31*** | (2025.01) |
| ***A61K 40/42*** | (2025.01) |
| ***A61K 47/68*** | (2017.01) |
| ***A61P 35/00*** | (2006.01) |
| ***C07K 14/705*** | (2006.01) |
| ***C07K 16/28*** | (2006.01) |
| ***C12N 5/0783*** | (2010.01) |

(52) U.S. Cl.

CPC ...... *C07K 16/3007* (2013.01); *A61K 39/3955* (2013.01); *A61K 40/11* (2025.01); *A61K 40/31* (2025.01); *A61K 40/4202* (2025.01); *A61K 40/4266* (2025.01); *A61K 47/68031* (2023.08); *A61K 47/68033* (2023.08); *A61K 47/68035* (2023.08); *A61K 47/6853* (2017.08); *A61P 35/00* (2018.01); *C07K 14/7051* (2013.01); *C07K 16/2803* (2013.01); *C07K 16/2809* (2013.01); *C07K 16/283* (2013.01); *C07K 16/2851* (2013.01); *C12N 5/0636* (2013.01); *A61K 2239/31* (2023.05); *A61K 2239/58* (2023.05); *C07K 2317/622* (2013.01); *C07K 2319/02* (2013.01); *C07K 2319/03* (2013.01); *C07K 2319/30* (2013.01)

(58) Field of Classification Search

CPC ............ C07K 16/3007; C07K 14/7051; C07K 16/2803; C07K 16/2809; C07K 16/283; C07K 16/2851; C07K 2317/622; C07K 2319/02; C07K 2319/03; C07K 2319/30; C07K 2317/21; C07K 2317/31; C07K 2317/33; C07K 2317/34; C07K 2317/55; C07K 2317/56; C07K 2317/732; C07K 2317/92; C07K 2319/33; A61K 39/3955; A61K 40/11; A61K 40/31; A61K 40/4202; A61K 40/4266; A61K 47/68031; A61K 47/68033; A61K 47/68035; A61K 47/6853; A61K 2239/31; A61K 2239/58; A61K 2039/505; A61P 35/00; C12N 5/0636

See application file for complete search history.

(56) References Cited

U.S. PATENT DOCUMENTS

| | | | |
|---|---|---|---|
| 6,750,325 | B1 | 6/2004 | Jolliffe et al. |
| 9,617,345 | B2 | 4/2017 | Berne et al. |
| 2004/0086503 | A1 | 5/2004 | Cohen et al. |
| 2005/0058649 | A1 | 3/2005 | Landes et al. |
| 2011/0052606 | A1 | 3/2011 | Spee et al. |

(Continued)

FOREIGN PATENT DOCUMENTS

| | | | |
|---|---|---|---|
| JP | 2016-506370 | A | 3/2016 |
| WO | WO 1998/022143 | A1 | 5/1998 |

(Continued)

OTHER PUBLICATIONS

Bacac et al., "CEA TCB: A novel head-to-tail 2:1 T cell bispecific antibody for treatment of CEA-positive solid tumors," Oncoimmunology, Jun. 2016, 5(8):e1203498.

(Continued)

*Primary Examiner* — Misook Yu
*Assistant Examiner* — Grace H Lunde
(74) *Attorney, Agent, or Firm* — Fish & Richardson P.C.

(57) ABSTRACT

This document provides methods and materials involved in binding a binder (e.g., an antibody, antigen binding fragment, antibody domain, CAR, cell engager, and/or ADC) to a CD66e polypeptide. For example, binders (e.g., antibodies, antigen binding fragments, antibody domains, CARs, cell engagers, and/or ADCs) that bind to a CD66e polypeptide and methods and materials for using one or more such binding molecules to treat a mammal (e.g., a human) having cancer are provided.

17 Claims, 64 Drawing Sheets

Specification includes a Sequence Listing.

(56) References Cited

U.S. PATENT DOCUMENTS

| | | | |
|---|---|---|---|
| 2011/0150870 | A1 | 6/2011 | Rader et al. |
| 2014/0308278 | A1 | 10/2014 | Hansen et al. |
| 2015/0111279 | A1 | 4/2015 | Hansen et al. |
| 2017/0368169 | A1 | 12/2017 | Loew et al. |
| 2018/0369373 | A1 | 12/2018 | Anceriz et al. |
| 2019/0233498 | A1 | 8/2019 | Loomis et al. |
| 2019/0233522 | A1 | 8/2019 | Forssmann et al. |
| 2019/0241667 | A1 | 8/2019 | Papadopoulos et al. |

FOREIGN PATENT DOCUMENTS

| | | | |
|---|---|---|---|
| WO | WO 1998/046778 | A1 | 10/1998 |
| WO | WO 2000/017376 | A1 | 3/2000 |
| WO | WO 2018/039626 | A1 | 3/2018 |
| WO | WO 2019/204827 | A2 | 10/2019 |
| WO | WO 2020/244526 | A1 | 12/2020 |
| WO | WO 2020/247392 | A1 | 12/2020 |

OTHER PUBLICATIONS

Extended European Search Report in European Appln. No. 22767820.8, mailed on Dec. 4, 2024, 10 pages.

Hombach et al., "T Cell Activation by Antibody-Like Immunoreceptors: The Position of the Binding Epitope within the Target Molecule Determines the Efficiency of Activation of Redirected T Cells," J. Immunol., Apr. 2007, 178(7):4650-4657.

Blumenthal et al., "Inhibition of adhesion, invasion, and metastasis by antibodies targeting CEACAM6 (NCA-90) and CEACAM5 (Carcinoembryonic Antigen)," Cancer Res., Oct. 2005, 65(19):8809-8817.

Brinkmann et al., "The making of bispecific antibodies," MAbs, Feb. 2017, 9(2):182-212.

Chen et al., "Fusion protein linkers: property, design and functionality," Adv. Drug Deliv. Rev., Oct. 2013, 65(10):1357-1369.

Durbin et al., "An epitope on carcinoembryonic antigen defined by the clinically relevant antibody PR1A3," Proc. Natl. Acad. Sci. USA, May 1994, 91(10):4313-4317.

Fisher et al., "A novel adenovirus-adeno-associated virus hybrid vector that displays efficient rescue and delivery of the AAV genome," Hum. Gene Ther., Nov. 1996, 7(17):2079-2087.

Frenzel et al., "Expression of recombinant antibodies," Front. Immunol., Jul. 2013, 4:217.

Gervasi et al., "Parenteral protein formulations: An overview of approved products within the European Union," Eur. J. Pharm. Biopharm., Oct. 2018, 131:8-24.

Hornig et al., "Production of bispecific antibodies: diabodies and tandem scFv," Methods Mol. Biol., 2012, 907:713-727.

International Preliminary Report on Patentability in International Appln. No. PCT/US2022/019375, mailed on Sep. 12, 2023, 8 pages.

International Search Report and Written Opinion in International Appln. No. PCT/US2022/019375, mailed on Aug. 19, 2022, 12 pages.

Lee et al., "Systemic surfaceome profiling identifies target antigens for immune-based therapy in subtypes of advanced prostate cancer," Proc. Natl. Acad. Sci. USA, May 2018, 115(19):E4473-E4482.

McCall et al. "Isolation and characterization of an anti-CD16 single-chain Fv fragment and construction of an anti-HER2/neu/anti-CD16 bispecific scFv that triggers CD16-dependent tumor cytolysis," Mol. Immunol., May 1999, 36(7):433-445.

Metzinger et al., "Chimeric Antigen Receptor T-Cell Therapy: Reach to Solid Tumor Experience," Oncology, Jul. 2019, 97(2):59-74.

Neumann et al., "Gene transfer into mouse lyoma cells by electroporation in high electric fields," EMBO J., 1982, 1(7):841-845.

Peng et al., "The CEA/CD3-Bispecific Antibody MEDI-565 (MT111) Binds a Nonlinear Epitope in the Full-Length but Not a Short Splice Variant of Cea," PLoS One, May 2012, 7(5):e36412.

Pishvaian et al., "Phase 1 Dose Escalation Study of MEDI-565, a Bispecific T-Cell Engager that Targets Human Carcinoembryonic Antigen, in Patients With Advanced Gastrointestinal Adenocarcinomas," Clin. Colorectal Cancer, Dec. 2016, 15(4):345-351 [Accepted Manuscript].

Powell et al., "A functional genomic screen in vivo identifies CEACAM5 as a clinically relevant driver of breast cancer metastasis," NPJ Breast Cancer, Apr. 2018, 4:9.

Stewart et al., "Humanisation and characterisation of PR1A3, a monoclonal antibody specific for cell-bound carcinoembryonic antigen," Cancer Immunol. Immunother., Feb. 1999, 47(6):299-306.

Zheng et al., "A novel anti-CEACAM5 monoclonal antibody, CC4, suppresses colorectal tumor growth and enhances NK cells-mediated tumor immunity," PLoS One, Jun. 2011, 6(6):e21146.

Zheng et al., "Genomic integration and gene expression by a modified adenoviral vector," Nat. Biotechnol., Feb. 2000, 18(2):176-180.

Zoller, "New recombinant DNA methodology for protein engineering," Curr. Opin. Biotechnol., Aug. 1992, 3(4):348-354.

Osada et al., "Metastatic colorectal cancer cells from patients previously treated with chemotherapy are sensitive to T-cell killing mediated by CEA/CD3-bispecific T-cell-engaging BiTE antibody," British Journal of Cancer, Jan. 5, 2010, 102(1):124-133.

Figure 1

MESPSAPPHRWCIPWQRLLLTASLLTFWNPPTTAKLTIESTPFNVAEGKEVLLLVHNLPQH
LFGYSWYKGERVDGNRQIIGYVIGTQQATPGPAYSGREIIYPNASLLIQNIIQNDTGFYTLH
VIKSDLVNEEATGQFRVYPELPKPSISSNNSKPVEDKDAVAFTCEPETQDATYLWWVNNQ
SLPVSPRLQLSNGNRTLTLFNVTRNDTASYKCETQNPVSARRSDSVILNVLYGPDAPTISP
LNTSYRSGENLNLSCHAASNPPAQYSWFVNGTFQQSTQELFIPNITVNNSGSYTCQAHNS
DTGLNRTTVTTITVYAEPPKPFITSNNSNPVEDEDAVALTCEPEIQNTTYLWWVNNQSLPV
SPRLQLSNDNRTLTLLSVTRNDVGPYECGIQNKLSVDHSDPVILNVLYGPDDPTISPSYTY
YRPGVNLSLSCHAASNPPAQYSWLIDGNIQQHTQELFISNITEKNSGLYTCQANNSASGH
SRTTVKTITVSAELPKPSISSNNSKPVEDKDAVAFTCEPEAQNTTYLWWVNGQSLPVS
PRLQLSNGNRTLTLFNVTRNDARAYVCGIQNSVSANRSDPVTLDVLYGPDTPIISPPD
SSYLSGANLNLSCHSASNPSPQYSWRINGIPQQHTQVLFIAKITPNNNGTYACFVSNL
ATGRNNSIVKSITVSASGTSPGLSAGATVGIMIGVLVGVALI (SEQ ID NO:150)

Figure 2A
Anti-CD66e Clone #1 (also referred to as 1G9) (Fab)

Heavy chain variable domain (without first constant domain and partial hinge):
QVQLVESGGGLVKPGGSLRLSCAASGFTFSDYYMSWIRQAPGKGLEWVSYISSSGSTIY
YADSVKGRFTISRDNAKNSLYLQMNSLRAEDTAVYYCARIGRYSYGLRSYYYYGMDV
WGQGTTVTVSS (SEQ ID NO:8)

Framework Region 1 of heavy chain variable domain:
QVQLVESGGGLVKPGGSLRLSCAASGFTFS (SEQ ID NO:4)

CDR1 of heavy chain variable domain:
DYYMS (SEQ ID NO:1)

Framework Region 2 of heavy chain variable domain:
WIRQAPGKGLEWVS (SEQ ID NO:5)

CDR2 of heavy chain variable domain:
YISSSGSTIYYADSVKG (SEQ ID NO:2)

Framework Region 3 of heavy chain variable domain:
RFTISRDNAKNSLYLQMNSLRAEDTAVYYCAR (SEQ ID NO:6)

CDR3 of heavy chain variable domain:
IGRYSYGLRSYYYYGMDV (SEQ ID NO:3)

Framework Region 4 of heavy chain variable domain:
WGQGTTVTVSS (SEQ ID NO:7)

Human IgG1 heavy chain constant domain 1 (CH1):
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKV (SEQ ID NO:33)

Human immunoglobulin G1 hinge region (partial):
EPKSCDKT (SEQ ID NO:152)

Figure 2B
Anti-CD66e Clone #1 (also referred to as 1G9) (Fab)

Light chain variable domain (without kappa/lambda constant domain):
DIQMTQSPSSLSASVGDRVTITCRASQSISSYLNWYQQKPGKAPKLLIYAASSLQSGVPS
RFSGSGSGTDFTLTISSLQPEDFGVYYCMQALQTPVTFGQGTRLEIKR (SEQ ID NO:16)

Framework Region 1 of light chain variable domain:
DIQMTQSPSSLSASVGDRVTITC (SEQ ID NO:12)

CDR1 of light chain variable domain:
RASQSISSYLN (SEQ ID NO:9)

Framework Region 2 of light chain variable domain:
WYQQKPGKAPKLLIY (SEQ ID NO:13)

CDR2 of light chain variable domain:
AASSLQS (SEQ ID NO:10)

Framework Region 3 of light chain variable domain:
GVPSRFSGSGSGTDFTLTISSLQPEDFGVYYC (SEQ ID NO:14)

CDR3 of light chain variable domain:
MQALQTPVT (SEQ ID NO:11)

Framework Region 4 of light chain variable domain:
FGQGTRLEIKR (SEQ ID NO:15)

Human kappa light chain constant domain:
TVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC (SEQ ID NO:34)

Figure 3A
Anti-CD66e Clone #2 (also referred to as 1C1) (Fab)

Heavy chain variable domain (without first constant domain and partial hinge):
QVQLVESGGGLVKPGGSLRLSCAASGFTFSDYYMSWIRQAPGKGLEWVSYISSSGSTIY YADSVKGRFTISRDNAKNSLYLQMNSLRAEDTAMYYCARVARQYRKSYYYYGMDV WGQGTTVTVSS (SEQ ID NO:24)

Framework Region 1 of heavy chain variable domain:
QVQLVESGGGLVKPGGSLRLSCAASGFTFS (SEQ ID NO:20)

CDR1 of heavy chain variable domain:
DYYMS (SEQ ID NO:17)

Framework Region 2 of heavy chain variable domain:
WIRQAPGKGLEWVS (SEQ ID NO:21)

CDR2 of Heavy chain variable domain:
YISSSGSTIYYADSVKG (SEQ ID NO:18)

Framework Region 3 of heavy chain variable domain:
RFTISRDNAKNSLYLQMNSLRAEDTAMYYCAR (SEQ ID NO:22)

CDR3 of heavy chain variable domain:
VARQYRKSYYYYGMDV (SEQ ID NO:19)

Framework Region 4 of heavy chain variable domain:
WGQGTTVTVSS (SEQ ID NO:23)

Human IgG1 heavy chain constant domain 1 (CH1):
ASTKGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKV (SEQ ID NO:33)

Human immunoglobulin G1 hinge region (partial):
EPKSCDKT (SEQ ID NO:152)

Figure 3B
Anti-CD66e Clone #2 (also referred to as 1C1) (Fab)

Light chain variable domain (without kappa/lambda constant domain):
DIQMTQSPSSLSASVGDRVTITCRASQSISSYLNWYQQKPGKAPKLLIYAASSLQSGVPS
RFSGSGSGTDFTLTISSLQPEDVGVYYCMQALQTPLTFGGGTKLEIKR (SEQ ID NO:32)

Framework Region 1 of light chain variable domain:
DIQMTQSPSSLSASVGDRVTITC (SEQ ID NO:28)

CDR1 of light chain variable domain:
RASQSISSYLN (SEQ ID NO:25)

Framework Region 2 of light chain variable domain:
WYQQKPGKAPKLLIY (SEQ ID NO:29)

CDR2 of light chain variable domain:
AASSLQS (SEQ ID NO:26)

Framework Region 3 of light chain variable domain:
GVPSRFSGSGSGTDFTLTISSLQPEDVGVYYC (SEQ ID NO:30)

CDR3 of light chain variable domain:
MQALQTPLT (SEQ ID NO:27)

Framework Region 4 of light chain variable domain:
FGGGTKLEIKR (SEQ ID NO:31)

Human Kappa light chain constant domain:
TVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC (SEQ ID NO:34)

Figure 4

Clone #1

Nucleic acid encoding SEQ ID NO:8 (Clone #1; Heavy Chain):
CAAGTTCAATTAGTGGAGAGCGGCGGCGGATTGGTTAAACCGGGGGGCAGTCTGCG
TTTAAGCTGCGCAGCTTCCGGGTTTACTTTTTCGGATTACTATATGAGCTGGATTCGT
CAGGCTCCCGGTAAAGGGTTGGAATGGGTTAGCTACATCTCAAGTTCCGGCTCTACA
ATCTACTATGCAGATTCCGTGAAAGGGCGCTTCACCATCTCTCGTGACAATGCAAAG
AACAGTTTATACTTACAAATGAACTCGCTGCGTGCGGAAGATACGGCTGTGTATTAC
TGTGCACGGATTGGGCGGTACAGCTATGGTCTCCGGTCCTACTACTACTACGGTATG
GACGTCTGGGGCCAAGGGACCACGGTCACCGTCTCCTCA (SEQ ID NO:35)

Nucleic acid encoding SEQ ID NO:16 (Clone #1; Light Chain):
GATATTCAAATGACCCAGTCTCCTTCTTCCTTGAGCGCGTCTGTGGGAGACCGTGTA
ACTATCACGTGTCGTGCATCCCAAAGCATTTCGAGTTACTTGAACTGGTATCAACAA
AAGCCTGGTAAAGCGCCCAAACTGTTGATCTATGCTGCCAGTAGTCTTCAATCTGGT
GTGCCCTCGCGCTTCTCAGGTTCGGGGTCAGGAACGGACTTTACCCTGACCATTAGC
TCTCTGCAACCGGAGGATTTTGGGGTTTATTACTGCATGCAAGCTCTACAAACTCCG
GTCACCTTCGGCCAAGGGACACGACTGGAGATTAAACGT (SEQ ID NO:36)

Clone #2

Nucleic acid encoding SEQ ID NO:24 (Clone #2; Heavy Chain):
CAAGTTCAATTAGTGGAGAGCGGCGGCGGATTGGTTAAACCGGGGGGCAGTCTGCG
TTTAAGCTGCGCAGCTTCCGGGTTTACTTTTTCGGATTACTATATGAGCTGGATTCGT
CAGGCTCCCGGTAAAGGGTTGGAATGGGTTAGCTACATCTCAAGTTCCGGCTCTACA
ATCTACTATGCAGATTCCGTGAAAGGGCGCTTCACCATCTCTCGTGACAATGCAAAG
AACAGTTTATACTTACAAATGAACTCGCTGCGTGCGGAAGATACGGCCATGTATTAC
TGTGCGAGAGTGGCACGGCAATATCGGAAAAGCTACTACTACTACGGTATGGACGT
CTGGGGCCAAGGGACCACGGTCACCGTCTCCTCA (SEQ ID NO:37)

Nucleic acid encoding SEQ ID NO:32 (Clone #2; Light Chain):
GATATTCAAATGACCCAGTCTCCTTCTTCCTTGAGCGCGTCTGTGGGAGACCGTGTA
ACTATCACGTGTCGTGCATCCCAAAGCATTTCGAGTTACTTGAACTGGTATCAACAA
AAGCCTGGTAAAGCGCCCAAACTGTTGATCTATGCTGCCAGTAGTCTTCAATCTGGT
GTGCCCTCGCGCTTCTCAGGTTCGGGGTCAGGAACGGACTTTACCCTGACCATTAGC
TCTCTGCAACCGGAGGATGTTGGGGTTTATTACTGCATGCAAGCTCTACAAACTCCG
CTCACTTTCGGCGGAGGGACCAAGCTGGAGATCAAACGT (SEQ ID NO:38)

Figure 5

Exemplary Ig (e.g., IgG1) structure
Heavy chain: Heavy Chain Variable Domain + CH1 + Hinge + CH2 + CH3
Light chain: Light Chain Variable Domain + Constant Light (Kappa or Lambda)

Human immunoglobulin G1 hinge region:

EPKSCDKTHTCPPCP (SEQ ID NO:39)

GAGCCCAAATCTTGTGACAAAACTCACACATGCCCACCGTGCCCA (SEQ ID NO:40)

Human immunoglobulin G1 heavy chain constant domains 2 and 3 (CH2-CH3):

APELLGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGK (SEQ ID NO:41)

GCACCTGAACTCCTGGGGGGACCGTCAGTCTTCCTCTTCCCCCCAAAACCCAAGGAC
ACCCTCATGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCATAATGC
CAAGACAAAGCCGCGGGAGGAGCAGTACAACAGCACGTACCGTGTGGTCAGCGTCC
TCACCGTCCTGCACCAGGACTGGCTGAATGGCAAGGAGTACAAGTGCAAGGTCTCC
AACAAAGCCCTCCCAGCCCCCATCGAGAAAACCATCTCCAAAGCCAAAGGGCAGCC
CCGAGAACCACAGGTGTACACCCTGCCCCCATCCCGGGATGAGCTGACCAAGAACC
AGGTCAGCCTGACCTGCCTGGTCAAAGGCTTCTATCCCAGCGACATCGCCGTGGAGT
GGGAGAGCAATGGGCAGCCGGAGAACAACTACAAGACCACGCCTCCCGTGCTGGAC
TCCGACGGCTCCTTCTTCCTCTACAGCAAGCTCACCGTGGACAAGAGCAGGTGGCAG
CAGGGGAACGTCTTCTCATGCTCCGTGATGCATGAGGCTCTGCACAACCACTACACG
CAGAAGAGCCTCTCCCTGTCTCCGGGTAAA (SEQ ID NO:42)

Figure 6A

Exemplary scFv structure:
Heavy Chain Variable Domain/Region + Linker + Light Chain Variable Domain/Region Exemplary scFv structure:
Light Chain Variable Domain/Region + Linker + Heavy Chain Variable Domain/Region

Figure 6B

Exemplary scFv structures

Variable Heavy Region:
QVQLVESGGGLVKPGGSLRLSCAASGFTFS$\underline{(X1)_n}$WIRQAPGKGLEWVS$\underline{(X2)_n}$RFTISRDNAKNSLYLQMNSLRAEDTAVYYCAR$\underline{(X3)_n}$WGQGTTVTVSS (SEQ ID NO:43)

Framework Region 1 of Variable Heavy Region:
QVQLVESGGGLVKPGGSLRLSCAASGFTFS (SEQ ID NO:4)

CDR1 of Variable Heavy Region:
$(X1)_n$

Framework Region 2 of Variable Heavy Region:
WIRQAPGKGLEWVS (SEQ ID NO:5)

CDR2 of Variable Heavy Region:
$(X2)_n$

Framework Region 3 of Variable Heavy Region:
RFTISRDNAKNSLYLQMNSLRAEDTAVYYCAR (SEQ ID NO:6)

CDR3 of Variable Heavy Region:
$(X3)_n$

Framework Region 4 of Variable Heavy Region:
WGQGTTVTVSS (SEQ ID NO:7)

Figure 6C

Exemplary scFv structures

Variable Light Region:
DIQMTQSPSSLSASVGDRVTITC<u>(X4)</u>$_n$WYQQKPGKAPKLLIY<u>(X5)</u>$_n$GVPSRFSGSGSGTDF
TLTISSLQPEDFGVYYC<u>(X6)</u>$_n$FGQGTRLEIKR (SEQ ID NO:44)

Framework Region 1 of Variable Light Region:
DIQMTQSPSSLSASVGDRVTITC (SEQ ID NO:12)

CDR1 of Variable Light Region:
$(X4)_n$

Framework Region 2 of Variable Light Region:
WYQQKPGKAPKLLIY (SEQ ID NO:13)

CDR2 of Variable Light Region:
$(X5)_n$

Framework Region 3 of Variable Light Region:
GVPSRFSGSGSGTDFTLTISSLQPEDFGVYYC (SEQ ID NO:14)

CDR3 of Variable Light Region:
$(X6)_n$

Framework Region 4 of Variable Light Region:
FGQGTRLEIKR (SEQ ID NO:15)

Figure 6D

Exemplary scFv structure

Variable Light Region + Linker (e.g., $(G_4S)_5$ linker) + Variable Heavy Region using CDRs of Clone #1:
DIQMTQSPSSLSASVGDRVTITCRASQSISSYLNWYQQKPGKAPKLLIYAASSLQSGVPSRFSGSGSGTDFTLTISSLQPEDFGVYYCMQALQTPVTFGQGTRLEIKRGGGGSGGGGSGGGGSGGGGSGGGGSQVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARIGRYSYGLRSYYYYGMDVWGQGTTVTVSS (SEQ ID NO:45)

GATATTCAAATGACCCAGTCTCCTTCTTCCTTGAGCGCGTCTGTGGGAGACCGTGTA
ACTATCACGTGTCGTGCATCCCAAAGCATTTCGAGTTACTTGAACTGGTATCAACAA
AAGCCTGGTAAAGCGCCCAAACTGTTGATCTATGCTGCCAGTAGTCTTCAATCTGGT
GTGCCCTCGCGCTTCTCAGGTTCGGGGTCAGGAACGGACTTTACCCTGACCATTAGC
TCTCTGCAACCGGAGGATTTTGGGGTTTATTACTGCATGCAAGCTCTACAAACTCCG
GTCACCTTCGGCCAAGGGACACGACTGGAGATTAAACGTGGAGGCGGTGGGAGCGG
GGGCGGAGGTAGTGGCGGTGGAGGGAGCGGTGGCGGGGGAAGTGGAGGGGGTGGC
AGCCAAGTTCAATTAGTGGAGAGCGGCGGCGGATTGGTTAAACCGGGGGGCAGTCT
GCGTTTAAGCTGCGCAGCTTCCGGGTTTACTTTTTCGGATTACTATATGAGCTGGATT
CGTCAGGCTCCCGGTAAAGGGTTGGAATGGGTTAGCTACATCTCAAGTTCCGGCTCT
ACAATCTACTATGCAGATTCCGTGAAAGGGCGCTTCACCATCTCTCGTGACAATGCA
AAGAACAGTTTATACTTACAAATGAACTCGCTGCGTGCGGAAGATACGGCTGTGTAT
TACTGTGCACGGATTGGGCGGTACAGCTATGGTCTCCGGTCCTACTACTACTACGGT
ATGGACGTCTGGGGCCAAGGGACCACGGTCACCGTCTCCTCA (SEQ ID NO:46)

Figure 6E

Exemplary scFv structure

Variable Light Region + Linker (e.g., $(G_4S)_3$ linker) + Variable Heavy Region using CDRs of Clone #1:
DIQMTQSPSSLSASVGDRVTITCRASQSISSYLNWYQQKPGKAPKLLIYAASSLQSGVPS
RFSGSGSGTDFTLTISSLQPEDFGVYYCMQALQTPVTFGQGTRLEIKRGGGGSGGGGSG
GGGSQVQLVESGGGLVKPGGSLRLSCAASGFTFSDYYMSWIRQAPGKGLEWVSYISSS
GSTIYYADSVKGRFTISRDNAKNSLYLQMNSLRAEDTAVYYCARIGRYSYGLRSYYYY
GMDVWGQGTTVTVSS (SEQ ID NO:47)

GATATTCAAATGACCCAGTCTCCTTCTTCCTTGAGCGCGTCTGTGGGAGACCGTGTA
ACTATCACGTGTCGTGCATCCCAAAGCATTTCGAGTTACTTGAACTGGTATCAACAA
AAGCCTGGTAAAGCGCCCAAACTGTTGATCTATGCTGCCAGTAGTCTTCAATCTGGT
GTGCCCTCGCGCTTCTCAGGTTCGGGGTCAGGAACGGACTTTACCCTGACCATTAGC
TCTCTGCAACCGGAGGATTTTGGGGTTTATTACTGCATGCAAGCTCTACAAACTCCG
GTCACCTTCGGCCAAGGGACACGACTGGAGATTAAACGTGGCGGTGGAGGGAGCGG
TGGCGGGGGAAGTGGAGGGGGTGGCAGCCAAGTTCAATTAGTGGAGAGCGGCGGC
GGATTGGTTAAACCGGGGGGCAGTCTGCGTTTAAGCTGCGCAGCTTCCGGGTTTACT
TTTTCGGATTACTATATGAGCTGGATTCGTCAGGCTCCCGGTAAAGGGTTGGAATGG
GTTAGCTACATCTCAAGTTCCGGCTCTACAATCTACTATGCAGATTCCGTGAAAGGG
CGCTTCACCATCTCTCGTGACAATGCAAAGAACAGTTTATACTTACAAATGAACTCG
CTGCGTGCGGAAGATACGGCTGTGTATTACTGTGCACGGATTGGGCGGTACAGCTAT
GGTCTCCGGTCCTACTACTACTACGGTATGGACGTCTGGGGCCAAGGGACCACGGTC
ACCGTCTCCTCA (SEQ ID NO:48)

Figure 6F

Exemplary scFv structure

Variable Heavy Region + <u>Linker (e.g., $(G_4S)_5$ linker)</u> + Variable Light Region using CDRs of Clone #1:
QVQLVESGGGLVKPGGSLRLSCAASGFTFSDYYMSWIRQAPGKGLEWVSYISSSGSTIY YADSVKGRFTISRDNAKNSLYLQMNSLRAEDTAVYYCARIGRYSYGLRSYYYYGMDV WGQGTTVTVSS<u>GGGGSGGGGSGGGGSGGGGSGGGGS</u>DIQMTQSPSSLSASVGDRVTIT CRASQSISSYLNWYQQKPGKAPKLLIYAASSLQSGVPSRFSGSGSGTDFTLTISSLQPEDF GVYYCMQALQTPVTFGQGTRLEIKR (SEQ ID NO:49)

CAAGTTCAATTAGTGGAGAGCGGCGGCGGATTGGTTAAACCGGGGGGCAGTCTGCG
TTTAAGCTGCGCAGCTTCCGGGTTTACTTTTTCGGATTACTATATGAGCTGGATTCGT
CAGGCTCCCGGTAAAGGGTTGGAATGGGTTAGCTACATCTCAAGTTCCGGCTCTACA
ATCTACTATGCAGATTCCGTGAAAGGGCGCTTCACCATCTCTCGTGACAATGCAAAG
AACAGTTTATACTTACAAATGAACTCGCTGCGTGCGGAAGATACGGCTGTGTATTAC
TGTGCACGGATTGGGCGGTACAGCTATGGTCTCCGGTCCTACTACTACTACGGTATG
GACGTCTGGGGCCAAGGGACCACGGTCACCGTCTCCTCAGGAGGCGGTGGGAGCGG
GGGCGGAGGTAGTGGCGGTGGAGGGAGCGGTGGCGGGGGAAGTGGAGGGGGTGGC
AGCGATATTCAAATGACCCAGTCTCCTTCTTCCTTGAGCGCGTCTGTGGGAGACCGT
GTAACTATCACGTGTCGTGCATCCCAAAGCATTTCGAGTTACTTGAACTGGTATCAA
CAAAAGCCTGGTAAAGCGCCCAAACTGTTGATCTATGCTGCCAGTAGTCTTCAATCT
GGTGTGCCCTCGCGCTTCTCAGGTTCGGGGTCAGGAACGGACTTTACCCTGACCATT
AGCTCTCTGCAACCGGAGGATTTTGGGGTTTATTACTGCATGCAAGCTCTACAAACT
CCGGTCACCTTCGGCCAAGGGACACGACTGGAGATTAAACGT (SEQ ID NO:50)

Figure 6G

Exemplary scFv structure

Variable Heavy Region + Linker (e.g., $(G_4S)_3$ linker) + Variable Light Region using CDRs of Clone #1:
QVQLVESGGGLVKPGGSLRLSCAASGFTFSDYYMSWIRQAPGKGLEWVSYISSSGSTIY
YADSVKGRFTISRDNAKNSLYLQMNSLRAEDTAVYYCARIGRYSYGLRSYYYYGMDV
WGQGTTVTVSSGGGGSGGGGSGGGGSDIQMTQSPSSLSASVGDRVTITCRASQSISSYL
NWYQQKPGKAPKLLIYAASSLQSGVPSRFSGSGSGTDFTLTISSLQPEDFGVYYCMQAL
QTPVTFGQGTRLEIKR (SEQ ID NO:51)

CAAGTTCAATTAGTGGAGAGCGGCGGCGGATTGGTTAAACCGGGGGGCAGTCTGCG
TTTAAGCTGCGCAGCTTCCGGGTTTACTTTTTCGGATTACTATATGAGCTGGATTCGT
CAGGCTCCCGGTAAAGGGTTGGAATGGGTTAGCTACATCTCAAGTTCCGGCTCTACA
ATCTACTATGCAGATTCCGTGAAAGGGCGCTTCACCATCTCTCGTGACAATGCAAAG
AACAGTTTATACTTACAAATGAACTCGCTGCGTGCGGAAGATACGGCTGTGTATTAC
TGTGCACGGATTGGGCGGTACAGCTATGGTCTCCGGTCCTACTACTACTACGGTATG
GACGTCTGGGGCCAAGGGACCACGGTCACCGTCTCCTCAGGCGGTGGAGGGAGCGG
TGGCGGGGGAAGTGGAGGGGGTGGCAGCGATATTCAAATGACCCAGTCTCCTTCTT
CCTTGAGCGCGTCTGTGGGAGACCGTGTAACTATCACGTGTCGTGCATCCCAAAGCA
TTTCGAGTTACTTGAACTGGTATCAACAAAAGCCTGGTAAAGCGCCCAAACTGTTGA
TCTATGCTGCCAGTAGTCTTCAATCTGGTGTGCCCTCGCGCTTCTCAGGTTCGGGGTC
AGGAACGGACTTTACCCTGACCATTAGCTCTCTGCAACCGGAGGATTTTGGGGTTTA
TTACTGCATGCAAGCTCTACAAACTCCGGTCACCTTCGGCCAAGGGACACGACTGGA
GATTAAACGT (SEQ ID NO:52)

Figure 7A

Exemplary scFv structures

Variable Heavy Region:
QVQLVESGGGLVKPGGSLRLSCAASGFTFS$\underline{(X1)_n}$WIRQAPGKGLEWVS$\underline{(X2)_n}$RFTISRDNAKNSLYLQMNSLRAEDTAMYYCAR$\underline{(X3)_n}$WGQGTTVTVSS (SEQ ID NO:53)

Framework Region 1 of Variable Heavy Region:
QVQLVESGGGLVKPGGSLRLSCAASGFTFS (SEQ ID NO:4)

CDR1 of Variable Heavy Region:
$(X1)_n$

Framework Region 2 of Variable Heavy Region:
WIRQAPGKGLEWVS (SEQ ID NO:5)

CDR2 of Variable Heavy Region:
$(X2)_n$

Framework Region 3 of Variable Heavy Region:
RFTISRDNAKNSLYLQMNSLRAEDTAMYYCAR (SEQ ID NO:22)

CDR3 of Variable Heavy Region:
$(X3)_n$

Framework Region 4 of Variable Heavy Region:
WGQGTTVTVSS (SEQ ID NO:7)

Figure 7B

Exemplary scFv structures

Variable Light Region:
DIQMTQSPSSLSASVGDRVTITC<u>(X4)$_n$</u>WYQQKPGKAPKLLIY<u>(X5)$_n$</u>GVPSRFSGSGSGTDF TLTISSLQPEDVGVYYC<u>(X6)$_n$</u>FGGGTKLEIKR (SEQ ID NO:54)

Framework Region 1 of Variable Light Region:
DIQMTQSPSSLSASVGDRVTITC (SEQ ID NO:12)

CDR1 of Variable Light Region:
$(X4)_n$

Framework Region 2 of Variable Light Region:
WYQQKPGKAPKLLIY (SEQ ID NO:13)

CDR2 of Variable Light Region:
$(X5)_n$

Framework Region 3 of Variable Light Region:
GVPSRFSGSGSGTDFTLTISSLQPEDVGVYYC (SEQ ID NO:30)

CDR3 of Variable Light Region:
$(X6)_n$

Framework Region 4 of Variable Light Region:
FGGGTKLEIKR (SEQ ID NO:31)

Figure 7C

Exemplary scFv structures

Variable Light Region + Linker (e.g., $(G_4S)_3$ linker) + Variable Heavy Region using CDRs of Clone #2:
DIQMTQSPSSLSASVGDRVTITCRASQSISSYLNWYQQKPGKAPKLLIYAASSLQSGVPSRFSGSGSGTDFTLTISSLQPEDFGVYYCMQALQTPVTFGQGTRLEIKRGGGGSGGGGSGGGGSQVQLVESGGGLVKPGGSLRLSCAASGFTFSDYYMSWIRQAPGKGLEWVSYISSSGSTIYYADSVKGRFTISRDNAKNSLYLQMNSLRAEDTAMYYCARVARQYRKSYYYYGMDVWGQGTTVTVSS (SEQ ID NO:55)

Variable Heavy Region + Linker (e.g., $(G_4S)_3$ linker) + Variable Light Region using CDRs of Clone #2:
QVQLVESGGGLVKPGGSLRLSCAASGFTFSDYYMSWIRQAPGKGLEWVSYISSSGSTIYYADSVKGRFTISRDNAKNSLYLQMNSLRAEDTAMYYCARVARQYRKSYYYYGMDVWGQGTTVTVSSGGGGSGGGGSGGGGSDIQMTQSPSSLSASVGDRVTITCRASQSISSYLNWYQQKPGKAPKLLIYAASSLQSGVPSRFSGSGSGTDFTLTISSLQPEDFGVYYCMQALQTPVTFGQGTRLEIKR (SEQ ID NO:56)

Figure 8A

Exemplary scFv structures

Variable Heavy Region:
EVQLVQSGGGLVQPGGSLRLSCSAS(X1)$_n$MHWVRQAPGKGLEYVSA(X2)$_n$YYADSVKG
RFTISRDNSKNTLYLQMNSLRAEDTAVYYC(X3)$_n$WGQGTMVTVSS (SEQ ID NO:57)

Framework Region 1 of Variable Heavy Region:
EVQLVQSGGGLVQPGGSLRLSCSAS (SEQ ID NO:58)

CDR1 of Variable Heavy Region:
(X1)$_n$

Framework Region 2 of Variable Heavy Region:
MHWVRQAPGKGLEYVSA (SEQ ID NO:59)

CDR2 of Variable Heavy Region:
(X2)$_n$

Framework Region 3 of Variable Heavy Region:
YYADSVKGRFTISRDNSKNTLYLQMNSLRAEDTAVYYC (SEQ ID NO:60)

CDR3 of Variable Heavy Region:
(X3)$_n$

Framework Region 4 of Variable Heavy Region:
WGQGTMVTVSS (SEQ ID NO:61)

Figure 8B

Exemplary scFv structure

Variable Light Region:
EATLTQSPSSLSASVGDRVTITCRAS<u>(X4)$_n$</u>LNWYQQKPGRAPKLLIY<u>(X5)$_n$</u>SLQSGVPSRFSGSGSGTDFTLTISSLQPEDFATYYC<u>(X6)$_n$</u>FGQGTRLEIKR (SEQ ID NO:62)

Framework Region 1 of Variable Light Region:
EATLTQSPSSLSASVGDRVTITCRAS (SEQ ID NO:63)

CDR1 of Variable Light Region:
$(X4)_n$

Framework Region 2 of Variable Light Region:
LNWYQQKPGRAPKLLIY (SEQ ID NO:64)

CDR2 of Variable Light Region:
$(X5)_n$

Framework Region 3 of Variable Light Region:
SLQSGVPSRFSGSGSGTDFTLTISSLQPEDFATYYC (SEQ ID NO:65)

CDR3 of Variable Light Region:
$(X6)_n$

Framework Region 4 of Variable Light Region:
FGQGTRLEIKR (SEQ ID NO:15)

Figure 9A

Exemplary scFv structures

Variable Heavy Region:
EVQLVQSGGGLVQPGGSLRLSCAAS(X1)$_n$MTWVRQAPGKGLEWVST(X2)$_n$YYADSVKG RFTISRDNDKNTLYLQMNSLRADDTAVYYC(X3)$_n$WGQGTLVTVSS (SEQ ID NO:66)

Framework Region 1 of Variable Heavy Region:
EVQLVQSGGGLVQPGGSLRLSCAAS (SEQ ID NO:67)

CDR1 of Variable Heavy Region:
$(X1)_n$

Framework Region 2 of Variable Heavy Region:
MTWVRQAPGKGLEWVST (SEQ ID NO:68)

CDR2 of Variable Heavy Region:
$(X2)_n$

Framework Region 3 of Variable Heavy Region:
YYADSVKGRFTISRDNDKNTLYLQMNSLRADDTAVYYC (SEQ ID NO:69)

CDR3 of Variable Heavy Region:
$(X3)_n$

Framework Region 4 of Variable Heavy Region:
WGQGTLVTVSS (SEQ ID NO:70)

Figure 9B

Exemplary scFv structures

Variable Light Region:
QSVVTQPPSASGSPGQSVTISCTGT$(X4)_n$VSWYQQHPGKAPKLLIY$(X5)_n$ERPSGVPDRFSGSKSDNKASLTIIGLQTEDEADYYC$(X6)_n$FGTGTKLTVLR (SEQ ID NO:71)

Framework Region 1 of Variable Light Region:
QSVVTQPPSASGSPGQSVTISCTGT (SEQ ID NO:72)

CDR1 of Variable Light Region:
$(X4)_n$

Framework Region 2 of Variable Light Region:
VSWYQQHPGKAPKLLIY (SEQ ID NO:73)

CDR2 of Variable Light Region:
$(X5)_n$

Framework Region 3 of Variable Light Region:
ERPSGVPDRFSGSKSDNKASLTIIGLQTEDEADYYC (SEQ ID NO:74)

CDR3 of Variable Light Region:
$(X6)_n$

Framework Region 4 of Variable Light Region:
FGTGTKLTVLR (SEQ ID NO:75)

Figure 10

Exemplary Linker Sequences for scFv's, CARs, and/or cell engagers:

a) GGGGSGGSGSGGGGS (SEQ ID NO:76)
b) GGGGSGGSGSSGGGS (SEQ ID NO:77)
c) GGGGSGGGGSGGGGS (SEQ ID NO:78)
d) GGGGSGSGASSGGGS (SEQ ID NO:79)
e) GGGGSGSGASGGGGS (SEQ ID NO:80)
f) SGGGSGGGGSGGGGS (SEQ ID NO:81)
g) GSTSGSGKPGSGEGSTKG (SEQ ID NO:82)
h) PNGASQSSSASHTGSAPGS (SEQ ID NO:83)
i) PNGASNSGSAPDTSSAPGS (SEQ ID NO:84)
j) PNGASHSGSAPNTSSAPGS (SEQ ID NO:85)
k) PNGASESGSASKTSSASGS (SEQ ID NO:86)
l) PNGASNSGSAPKTGSASGS (SEQ ID NO:87)
m) PNGASKSGSASQTSSAPGS (SEQ ID NO:88)
n) PNGASHSSSASQTGSAPGS (SEQ ID NO:89)
o) PNGASKRSAPGS (SEQ ID NO:90)
p) PNGASHSGSAPHTSSASGS (SEQ ID NO:91)
q) RGRGRGRGRSRGGGS (SEQ ID NO:92)
r) SHGGSHGGGSGGGGS (SEQ ID NO:93)
s) GQAGR (SEQ ID NO:94)
t) GGGSGGGG (SEQ ID NO:95)
u) SGGGG (SEQ ID NO:96)
v) GGGGS (SEQ ID NO:97)
w) GGGGSGGGGSGGGGSGGGGSGGGGSGGGGS (SEQ ID NO:98)
x) GGGGGSGGGGSGGGGS (SEQ ID NO:99)
y) GGGGGSGGGGSGGGGSGGGGSGGGGS (SEQ ID NO:100)
z) GGGGSGGGGSGGGGSGGGGSGGGGS (SEQ ID NO:101)
a1) AAA (SEQ ID NO:102)

Figure 11A

Exemplary CAR structures:

Signal Peptide + scFv + $(\text{Linker/Hinge})_{n1}$ + Transmembrane Domain + $(\text{Intracellular Signaling Domain})_{n2}$ $n1 = 0, 1, 2, \text{ or } 3$ $n2 = 1, 2, 3, 4, \text{ or } 5$ with or without a linker located between consecutive intracellular signaling domains Signal Peptide + scFv + Linker + Hinge + Transmembrane Domain + Intracellular Signaling Domain + Intracellular Signaling Domain + Linker + Intracellular Signaling Domain Signal Peptide + scFv + Linker + Hinge + Transmembrane Domain + Intracellular Signaling Domain + Linker + Intracellular Signaling Domain Signal Peptide + scFv + Hinge + Transmembrane Domain + Intracellular Signaling Domain + Intracellular Signaling Domain + Linker + Intracellular Signaling Domain Signal Peptide + scFv + Hinge + Transmembrane Domain + Intracellular Signaling Domain + Intracellular Signaling Domain + Intracellular Signaling Domain Signal Peptide + scFv + Linker + Transmembrane Domain + Intracellular Signaling Domain + Intracellular Signaling Domain + Intracellular Signaling Domain

Figure 11B

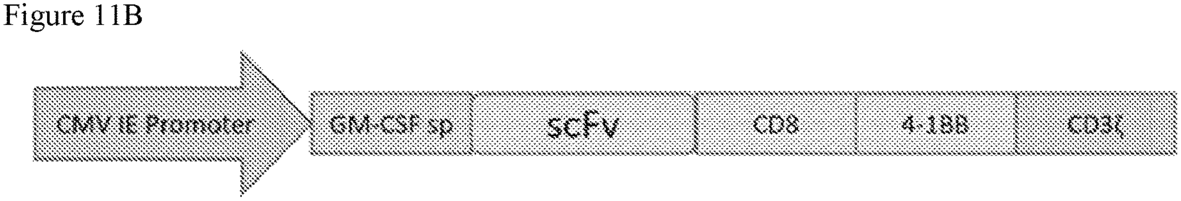

Figure 12

Exemplary signal peptides for CARs

Exemplary human IGKV1-39-derived signal peptide:
MDMRVPAQLLGLLLLWLRGARC (SEQ ID NO:103)

ATGGATATGAGGGTCCCCGCACAATTGCTCGGTCTCCTTCTGCTTTGGCTCCGGGGC
GCGCGGTGC (SEQ ID NO:104)

Exemplary human IGKV1-16-derived signal peptide:
MDMRVLAQLLGLLLLCFPGARC (SEQ ID NO:155)

Exemplary human IGKV3-11-derived signal peptide:
MEAPAQLLFLLLLWLPDTTG (SEQ ID NO:156)

Exemplary human IGKV4-1-derived signal peptide:
MVLQTQVFISLLLWISGAYG (SEQ ID NO:157)

Exemplary human IGKV6-21-derived signal peptide:
MLPSQLIGFLLLWVPASRG (SEQ ID NO:158)

Exemplary human IGKV1-33-derived signal peptide:
MDMRVPAQLLGLLLLWLSGARC (SEQ ID NO:159)

Figure 13

Exemplary hinges for CARs

Exemplary human IgG1-derived hinge:
EPKSCDKTHTCPPCP (SEQ ID NO:105)

Exemplary human IgG2-derived hinge:
DKTHTCPPCPAPPVA (SEQ ID NO:106)

Exemplary human IgG4-derived hinges:
ESKYGPPCPPCP (SEQ ID NO:107)
ESKYGPPCPSCP (SEQ ID NO:108)

Exemplary human CD8α-derived hinge:
KPTTTPAPRPPTPAPTIASQPLSLRPEACRPAAGGAVHTRGLDFACDIY (SEQ ID NO:109)

Exemplary human CD28-derived hinges:
IEVMYPPPYLDNERSNGTIIHVKGKHLCPSPLFPGPSKP (SEQ ID NO:110)
TTTPAPRPPTPAPTIASQPLSLRPEACRPAAGGAVHTRGLDFACDIY (SEQ ID NO:111)
TTTPAPRPPTPAPTIASQPLSLRPEACRPAAGGAVHTRGLDFACD (SEQ ID NO:112)

Figure 14

Exemplary transmembrane domains for CARs

Exemplary human CD3ζ transmembrane domain:
LCYLLDGILFIYGVILTALFL (SEQ ID NO:113)

Exemplary human CD4 transmembrane domain:
MALIVLGGVAGLLLFIGLGIFF (SEQ ID NO:114)

Exemplary human CD8α transmembrane domains:
IYIWAPLAGTCGVLLLSLVIT (SEQ ID NO:115)
IYIWAPLAGTCGVLLLSLVITLYC (SEQ ID NO:116)
IWAPLAGTCGVLLLSLVITLYC (SEQ ID NO:117)
IWAPLAGTCGVLLLSLVIT (SEQ ID NO:118)

Exemplary human CD28 transmembrane domain:
FWVLVVVGGVLACYSLLVTVAFIIFWV (SEQ ID NO:119)

Exemplary human CD278 transmembrane domain:
FWLPIGCAAFVVVCILGCILI (SEQ ID NO:120)

Figure 15

Exemplary intracellular signaling domains for CARs

Exemplary human CD3ζ intracellular signaling domain:
RVKFSRSADAPAYQQGQNQLYNELNLGRREEYDVLDKRRGRDPEMGGKPQRRKNPQE
GLYNELQKDKMAEAYSEIGMKGERRRGKGHDGLYQGLSTATKDTYDALHMQALPPR
(SEQ ID NO:121)

Exemplary human 4-1BB (CD137) intracellular signaling domains:
KRGRKKLLYIFKQPFMRPVQTTQEEDGCSCRFPEEEEGGCEL (SEQ ID NO:122)
KRGRKKLLYIFKQPFMRPVQTTQEEDGCSCRFPEEEE (SEQ ID NO:123)

Exemplary human CD28 intracellular signaling domain:
RSKRSRLLHSDYMNMTPRRPGPTRKHYQPYAPPRDFAAYRS (SEQ ID NO:124)

Exemplary human OX40 (CD134) intracellular signaling domain:
ALYLLRRDQRLPPDAHKPPGGGSFRTPIQEEQADAHSTLAKI (SEQ ID NO:125)

Exemplary human CD278 intracellular signaling domain:
CWLTKKKYSSSVHDPNGEYMFMRAVNTAKKSRLTDVTL (SEQ ID NO:126)

Exemplary human DAP10 intracellular signaling domain:
LCARPRRSPAQEDGKVYINMPGRG (SEQ ID NO:127)

Exemplary human DAP12 intracellular signaling domain:
YFLGRLVPRGRGAAEAATRKQRITETESPYQELQGQRSDVYSDLNTQRPYYK (SEQ ID NO:128)

Exemplary human CD27 intracellular signaling domain:
QRRKYRSNKGESPVEPAEPCHYSCPREEEGSTIPIQEDYRKPEPACSP (SEQ ID NO:129)

Figure 16

CAR designed using CDRs of Clone #1:

IGKV1-39 Signal Peptide + scFv of Figure 6D + Linker + IgG4-derived Hinge + CD28 Transmembrane Domain + CD28 Intracellular Signaling Domain + 4-1BB Intracellular Signaling Domain + Linker + CD3ζ Intracellular Signaling Domain

MDMRVPAQLLGLLLLWLRGARCDIQMTQSPSSLSASVGDRVTITCRASQSISSYLNW
YQQKPGKAPKLLIYAASSLQSGVPSRFSGSGSGTDFTLTISSLQPEDFGVYYCMQALQTP
VTFGQGTRLEIKGGGGGSGGGGSGGGGSGGGGSGGGGSQVQLVESGGGLVKPGGSLRL
SCAASGFTFSDYYMSWIRQAPGKGLEWVSYISSSGSTIYYADSVKGRFTISRDNAKNSLY
LQMNSLRAEDTAVYYCARIGRYSYGLRSYYYYGMDVWGQGTTVTVSSAAAESKYGPP
CPSCPFWVLVVVGGVLACYSLLVTVAFIIFWVRSKRSRLLHSDYMNMTPRRPGPTRK
HYQPYAPPRDFAAYRSKRGRKKLLYIFKQPFMRPVQTTQEEDGCSCRFPEEEEGGG
GS**RVKFSRSADAPAYQQGQNQLYNELNLGRREEYDVLDKRRGRDPEMGGKPQRR
KNPQEGLYNELQKDKMAEAYSEIGMKGERRRGKGHDGLYQGLSTATKDTYDALH
MQALPPR** (SEQ ID NO:130)

ATGGATATGAGGGTCCCCGCACAATTGCTCGGTCTCCTTCTGCTTTGGCTCCGGGGC
GCGCGGTGCGATATTCAGATGACCCAGAGCCCGTCCTCACTTTCAGCTAGCGTCGGT
GACCGGGTGACCATTACATGCAGGGCAAGTCAAAGTATCAGCTCATATTTGAATTGG
TACCAGCAGAAACCAGGTAAAGCCCCCAAGCTCCTTATTTACGCAGCTTCATCACTG
CAATCCGGAGTACCGTCtAGaTTCTCTGGCAGTGGCAGCGGGACCGACTTTACGTTGA
CTATTTCTTCCCTTCAACCTGAGGACTTTGGTGTTTACTACTGCATGCAAGCGCTCCA
GACTCCTGTTACATTTGGCCAGGGCACCCGGCTTGAAATTAAGGGCGGGGGCGGTG
GAAGTGGGGGAGGAGGATCAGGGGGTGGTGGGTCTGGAGGGGGAGGTAGTGGCGG
TGGAGGAAGTCAAGTGCAATTGGTAGAGAGCGGCGGCGGaCTaGTAAAACCTGGGG
GAAGCCTGCGGCTGTCCTGCGCAGCAAGCGGATTCACTTTCAGTGATTATTACATGA
GCTGGATTCGCCAGGCGCCTGGTAAAGGTTTGGAGTGGGTGTCCTACATCAGTTCAT
CCGGGTCCACAATCTACTATGCGGATAGTGTGAAAGGTCGGTTCACAATAAGTAGG
GATAATGCAAAGAACTCACTGTATCTCCAGATGAATAGTCTTAGAGCCGAAGATAC
CGCTGTCTATTATTGTGCGCGAATCGGTCGATATTCATACGGGTTGAGAAGCTATTA
CTATTATGGCATGGACGTTTGGGGCCAGGGTACTACAGTCACTGTATCTAGTGCGGC
cGCGGAGTCTAAATACGGTCCTCCATGTCCCAGCTGTCCCTTTTGGGTTCTCGTCGTA
GTCGGAGGAGTATTGGCCTGCTATTCTCTTCTCGTAACTGTCGCTTTTATAATTTTCT
GGGTACGAAGTAAGCGAAGTAGGTTGCTTCATAGTGATTACATGAATATGACACCA
CGACGGCCCGGCCCCACTCGGAAGCACTACCAACCGTATGCTCCCCCTCGAGACTTT
GCCGCGTATCGATCTAAACGGGGCCGAAAAAAGTTGCTGTACATCTTTAAACAACC
ATTTATGAGACCAGTTCAAACGACCCAGGAAGAAGATGGATGCTCATGCCGCTTCCC
AGAAGAGGAAGAAGGGGGGGGTGGTTCACGGGTTAAATTCTCAAGGTCTGCTGATG
CCCCCGCCTATCAACAGGGACAGAATCAGTTGTACAACGAGCTCAATCTTGGAAGG
CGCGAAGAGTATGATGTGTTGGATAAAAGAAGAGGTCGCGACCCTGAAATGGGGGG

Figure 16 (continued)

CAAGCCTCAGAGACGCAAAAACCCTCAGGAGGGACTCTATAATGAGTTGCAGAAGG
ATAAGATGGCCGAAGCATACTCAGAGATAGGTATGAAAGGGGAGCGACGAAGAGG
GAAGGGACATGATGGGCTGTACCAAGGGCTCAGTACTGCGACGAAGGACACATATG
ACGCACTCCATATGCAGGCTTTGCCACCTCGC (SEQ ID NO:131)

Figure 17A

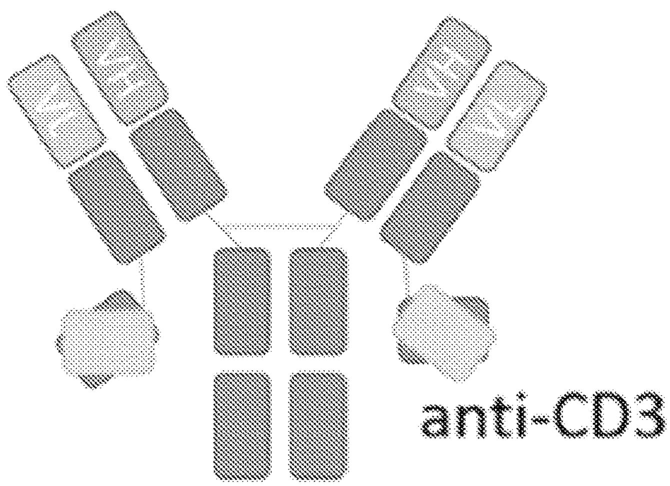

Figure 17B

Linker + gOKT3-7 (anti-CD3 scFv)

GGGGSGGGGSGGGGSQVQLVQSGGGVVQPGRSLRLSCKASGYTFTRYTMHWVRQAPG
KGLEWIGYINPSRGYTNYNQKVKDRFTISRDNSKNTAFLQMDSLRPEDTGVYFCARYY
DDHYCLDYWGQGTPVTVSSGGGGSGGGGSGGGGSGGGGSGGGGSGGGGSDIQMTQSP
SSLSASVGDRVTITCSASSSVSYMNWYQQTPGKAPKRWIYDTSKLASGVPSRFSGSGSG
TDYTFTISSLQPEDIATYYCQQWSSNPFTFGQGTKLQITR (SEQ ID NO:153)

GGAGGTGGCGGGTCTGGTGGAGGCGGAAGCGGTGGTGGCGGATCCCAGGTCCAACT
GGTGCAAAGTGGAGGCGGCGTAGTACAGCCCGGTCGGTCCCTGCGGCTCAGCTGTA
AAGCAAGTGGGTACACTTTCACCAGATATACAATGCACTGGGTTAGACAGGCCCCC
GGCAAGGGTCTTGAATGGATAGGATATATCAACCCATCCCGCGGATATACAAACTA
CAATCAGAAGGTGAAGGACCGGTTCACGATTAGTAGAGACAACTCCAAAAACACTG
CGTTCCTTCAAATGGACTCATTGCGACCCGAGGACACTGGAGTGTATTTCTGTGCCA
GGTATTATGACGACCATTATTGCCTGGACTACTGGGGCAAGGCACACCGGTTACGG
TATCTTCCGGAGGTGGCGGGTCTGGTGGAGGCGGAAGCGGTGGTGGCGGATCCGGG
GGAGGAGGCTCTGGCGGAGGCGGATCAGGGGGTGGAGGTTCCGACATTCAAATGAC
ACAATCCCCTAGTTCTTTGTCTGCGTCCGTGGGGGATCGGGTAACAATCACTTGCTCT
GCATCAAGCAGTGTTTCTTATATGAACTGGTATCAGCAGACACCCGGTAAGGCCCCA
AAACGATGGATTTATGACACGAGTAAACTCGCATCCGGGGTGCCTTCACGCTTCTCC
GGTTCTGGTTCCGGCACGGATTACACTTTCACCATCAGTAGCCTGCAACCTGAGGAC
ATTGCAACTTATTACTGTCAACAATGGAGCAGTAATCCATTCACGTTCGGCCAAGGG
ACAAAACTGCAGATTACTAGG (SEQ ID NO:154)

Figure 18

Exemplary antigen binding domains that bind to T cells

Exemplary anti-human CD3 scFv (clone OKT3):

Heavy chain:

QVQLVQSGGGVVQPGRSLRLSCKASGYTFTRYTMHWVRQAPGKGLEWIGYINPSRGYT
NYNQKVKDRFTISRDNSKNTAFLQMDSLRPEDTGVYFCARYYDDHYCLDYWGQGTPV
TVSS (SEQ ID NO:132)

Light chain:

DIQMTQSPSSLSASVGDRVTITCSASSSVSYMNWYQQTPGKAPKRWIYDTSKLASGVPS
RFSGSGSGTDYTFTISSLQPEDIATYYCQQWSSNPFTFGQGTKLQITR (SEQ ID NO:133)

Exemplary anti-human CD3 scFv (clone UCHT1):

Heavy chain:

EVQLQQSGPELVKPGASMKISCKASGYSFTGYTMNWVKQSHGKNLEWMGLINPYKGV
STYNQKFKDKATLTVDKSSSTAYMELLSLTSEDSAVYYCARSGYYGDSDWYFDVWGQ
GTTLTVFS (SEQ ID NO:134)

Light chain:

MDIQMTQTTSSLSASLGDRVTISCRASQDIRNYLNWYQQKPDGTVKLLIYYTSRLHSGV
PSKFSGSGSGTDYSLTISNLEQEDIATYFCQQGNTLPWTFAGGTKLEIK (SEQ ID NO:135)

Figure 19

Exemplary antigen binding domains that bind to NK cells

Exemplary anti-human CD16a scFv:

Heavy chain:
EVQLVESGGGVVRPGGSLRLSCAASGFTFDDYGMSWVRQAPGKGLEWVSGINWNGGS
TGYADSVKGRFTISRDNAKNSLYLQMNSLRAEDTAVYYCARGRSLLFDYWGQGTLVT
VSR (SEQ ID NO:136)

Light chain:
SSELTQDPAVSVALGQTVRITCQGDSLRSYYASWYQQKPGQAPVLVIYGKNNRPSGIPD
RFSGSSSGNTASLTITGAQAEDEADYYCNSRDSSGNHVVFGGGTKLTVG (SEQ ID
NO:137)

Exemplary anti-human NKG2A scFv:

Heavy chain:
QVQLVQSGAEVKKPGASVKVSCKASGYTFTSYWMNWVRQAPGQGLEWMGRIDPYDS
ETHYAQKLQGRVTMTTDTSTSTAYMELRSLRSDDTAVYYCARGGYDFDVGTLYWFFD
VWGQGTTVTVSS (SEQ ID NO:160)

Light chain:
DIQMTQSPSSLSASVGDRVTITCRASENIYSYLAWYQQKPGKAPKLLIYNAKTLAEGVPS
RFSGSGSGTDFTLTISSLQPEDFATYYCQHHYGTPRTFGGGTKVEIK (SEQ ID NO:161)

Exemplary anti-human NKG2A scFv:

Heavy chain:
EVQLVESGGGLVKPGGSLRLSCAASGFTFSSYAMSWVRQAPGKGLEWVSEISS
GGSYTYYADSVKGRFTISRDNAKNSLYLQMNSLRAEDTAVYYCARHGDYPRFF
DVWGQGTTVTVSS (SEQ ID NO:138)

Light chain:
EIVLTQSPATLSLSPGERATLSCSASSSVSSYIYWYQQKPGQAPRLLIYLTSNLASGIPARF
SGSGSGTDFTLTISSLEPEDFAVYYCQQWSGNPYTFGQGTKLEIK (SEQ ID NO:139)

Exemplary anti-human NKG2D scFv:

Heavy chain:
QVQLVESGGGLVKPGGSLRLSCAASGFTFSSYGMHWVRQAPGKGLEWVAFIRYDGSN
KYYADSVKGRFTISRDNSKNTLYLQMNSLRAEDTAVYYCAKDRGLGDGTYFDYWGQG
TTVTVSS (SEQ ID NO:140)

Light chain:
QSALTQPASVSGSPGQSITISCSGSSSNIGNNAVNWYQQLPGKAPKLLIYYDDLLPS
GVSDRFSGSKSGTSAFLAISGLQSEDEADYYCAAWDDSLNGPVFGGGTKLTVL (SEQ ID
NO:141)

Figure 19 (continued)

Exemplary anti-human NKp30 scFv:

Alternative heavy chains with underline indicating the differences:

QVQLVQSGAEVKKPGASVKVSCKASGHTFTSYFMHWVRQAPGQGLEWMGIINPSDDY ANYAQKFQGRVTMTRDTSTSTVYMELSSLRSEDTAVYYCATAIFDYWGQGTLVTVSS (SEQ ID NO:142)

or

QVQLVQSGAEVKKPGASVKVSCKASGHTFTSYFMHWVRQAPGQGLEWMGIINPSDDY ANYAQKFQGRVTMTRDTSTSTVYMELSSLRSEDTAVYYCATAIFDYWGQGTPVTVSS (SEQ ID NO:143)

Light chain:

DIQMTQSPSSLSASVGDRVTITCRASQSISSYLNWYQQKPGKAPKLLIYAASSLQSGVPSR FSGSGSGTDFTLTISSLQPEDFATYYCQQSYSTPLTFGGGTKVEIK (SEQ ID NO:144)

Exemplary anti-human NKp46 scFv

Heavy chain:

EIQLQQSGAELVKPGASVKLSCTASGFNIKDTYFHWVKQRPEQGLEWIGRIDPANGNTK YDPKFHDKATIIADISSNTAYLQFSSLTSEDTAVYYCAANRYGYWGQGTTLTVSS (SEQ ID NO:145)

Light chain:

DIVMTQAAPSIPVTPGESVSISCRSSKSLLYINGNTHLFWFLQRPGQSPQLLIYRMSNLAS GVPDRFSGSGSGTAFTLRISRVEAEDVGVYYCMQHLEYPFTFGSGTKLEIK (SEQ ID NO:146)

Exemplary anti-human NKp46 scFv

Heavy chain:

QVQLQQSGPELVKPGASVKMSCKASGYTFTDYVINWGKQRSGQGLEWIGEIYPGSGTN YYNEKFKAKATLTADKSSNIAYMQLSSLTSEDSAVYFCARRGRYGLYAMDYWGQGTS VTVSS (SEQ ID NO:147)

Light chain:

DIQMTQTTSSLSASLGDRVTISCRASQDISNYLNWYQQKPDGTVKLLIYYTSRLHSGVPS RFSGSGSGTDYSLTINNLEQEDIATYFCQQGNTRPWTFGGGTKLEIK (SEQ ID NO:148)

Exemplary anti-human CD16a VH domain:

EVQLVESGGGLVQPGGSLRLSCAASGFTFSNYGMSWVRQAPGKGLEWIGSIYYSGSTN YNPSLKSLVTISRDNSKNTLYLQMNSLRAEDTATYYCARESIDYWGQGTLVTVSS (SEQ ID NO:149)

Figure 19 (continued)

Examplary BiKE that binds to CD66e and NK cells:

1G9 (Clone #1) VL + (G$_4$S)$_3$ linker + 1G9 (Clone #1) VH + (G$_4$S) linker + Anti-NKG2A VH + linker + Anti-NKG2A VL + 6xHis-tag

DIQMTQSPSSLSASVGDRVTITCRASQSISSYLNWYQQKPGKAPKLLIYAASSLQSGVPSR
FSGSGSGTDFTLTISSLQPEDFGVYYCMQALQTPVTFGQGTRLEIKGGGGSGGGGSGG
GGSQVQLVESGGGLVKPGGSLRLSCAASGFTFSDYYMSWIRQAPGKGLEWVSYISSSGS
TIYYADSVKGRFTISRDNAKNSLYLQMNSLRAEDTAVYYCARIGRYSYGLRSYYYYGM
DVWGQGTTVTVSSGGGGSQVQLVQSGAEVKKPGASVKVSCKASGYTFTSYWMNWVR
QAPGQGLEWMGRIDPYDSETHYAQKLQGRVTMTTDTSTSTAYMELRSLRSDDTAVYY
CARGGYDFDVGTLYWFFDVWGQGTTVTVSSVEGGSGGSGGSGGSGGVDDIQMTQSP
SSLSASVGDRVTITCRASENIYSYLAWYQQKPGKAPKLLIYNAKTLAEGVPSRFSGSGSG
TDFTLTISSLQPEDFATYYCQHHYGTPRTFGGGTKVEIKHHHHHH (SEQ ID NO:164)

GACATCCAAATGACGCAGAGCCCGAGCTCACTTTCAGCCTCTGTGGGAGACCGCGT
CACGATCACTTGCCGCGCAAGTCAGTCCATTAGCTCATATCTTAATTGGTACCAACA
GAAACCCGGTAAAGCACCGAAACTGTTAATCTATGCTGCCAGCTCCCTTCAGAGCG
GAGTCCCTTCCCGTTTTAGTGGGTCCGGAAGTGGTACAGACTTCACACTGACTATCA
GTTCCTTACAACCTGAAGACTTCGGTGTCTATTATTGTATGCAAGCGCTGCAAACCC
CGGTGACTTTCGGCCAAGGAACACGTTTGGAAATCAAGGGCGGCGGAGGCTCGGG
AGGCGGGGGCAGTGGTGGTGGAGGCTCTCAAGTGCAGCTTGTAGAAAGTGGGGG
GGGTCTGGTGAAGCCGGGGGGGTCACTTCGCCTGTCCTGTGCAGCTTCAGGATTTAC
ATTTTCGGATTATTATATGAGCTGGATTCGCCAAGCTCCAGGCAAGGGACTGGAGTG
GGTCTCGTACATCTCATCAAGCGGGAGCACTATCTATTATGCAGACTCGGTCAAAGG
ACGTTTCACCATTTCTCGCGATAATGCCAAGAACAGCCTTTACTTACAAATGAATTC
ACTTCGCGCCGAAGACACAGCAGTATATTATTGTGCTCGCATCGGTCGTTATAGTTA
CGGGTTGCGCTCTTACTATTATTACGGGATGGACGTATGGGGTCAGGGCACTACGGT
CACCGTCAGCTCGGGGGGTGGTGGAGCCAGGTTCAGCTGGTGCAATCCGGAGCT
GAAGTCAAAAAGCCTGGGGCAAGTGTTAAGGTTTCTTGTAAGGCCAGTGGTTATAC
ATTTACGTCATATTGGATGAACTGGGTGCGTCAAGCGCCAGGACAGGGTCTTGAGTG
GATGGGCCGTATTGATCCTTATGATTCTGAGACACATTACGCACAGAAATTACAAGG
TCGTGTAACGATGACGACAGACACATCCACCTCGACCGCCTATATGGAATTGCGTAG
CTTACGTTCCGACGATACTGCGGTGTATTATTGCGCGCGTGGAGGTTACGATTTCGA
CGTTGGCACTTTGTATTGGTTCTTCGACGTTTGGGGACAAGGAACGACGGTAACAGT
GTCCTCCGTGGAGGGAGGATCAGGGGGTAGTGGCGGCTCTGGCGGGAGCGGG
GGGGTGGATGACATCCAGATGACTCAGTCTCCCAGTAGTTTAAGTGCTTCGGTGGG
AGATCGCGTGACCATTACCTGCCGCGCCTCGGAGAATATCTACTCATATTTGGCCTG
GTATCAACAAAAACCGGGGAAAGCCCCCAAATTACTGATTTATAACGCTAAAACAC
TGGCCGAAGGAGTGCCGTCACGCTTTTCAGGGAGCGGCTCCGGAACTGACTTCACA
T
TAACAATTAGTTCTCTGCAACCGGAAGACTTCGCCACTTACTATTGTCAGCATCATT
ACGGTACTCCACGTACCTTCGGGGGGGGTACTAAGGTGGAGATTAAGCATCACCAC
CACCACCAT (SEQ ID NO:165)

MOLECULES THAT BIND TO CD66e POLYPEPTIDES

CROSS-REFERENCE TO RELATED APPLICATIONS

This application is a National Stage application under 35 U.S.C. § 371 of International Application No. PCT/US2022/019375, having an International Filing Date of Mar. 8, 2022, which claims the benefit of U.S. Provisional Application Ser. No. 63/158,205, filed Mar. 8, 2021. The disclosure of the prior applications are considered part of (and are incorporated by reference in) the disclosure of this application.

SEQUENCE LISTING

This application contains a Sequence Listing that has been submitted electronically as an ASCII text file named "45049-0045WO1.txt." The ASCII text file, created on Apr. 29, 2022, is 142000 bytes in size. The material in the ASCII text file is hereby incorporated by reference in its entirety.

BACKGROUND

1. Technical Field

This document relates to methods and materials involved in binding a molecule (e.g., an antibody, a fragment of an antibody, an antibody domain, a chimeric antigen receptor (CAR), a cell engager, or an antibody-drug conjugate (ADC)) to a CD66e polypeptide. For example, this document provides binders (e.g., antibodies, antigen binding fragments, antibody domains, CARs, cell engagers, or ADCs) that bind to a CD66e polypeptide and methods and materials for using such binders to treat cancer. This document also provides cells (e.g., host cells) designed to express one or more binders (e.g., antibodies, antigen binding fragments, antibody domains, CARs, or cell engagers) having the ability to bind to a CD66e polypeptide and methods and materials for using such cells to treat cancer.

2. Background Information

CD66e, also known as carcinoembryonic antigen-related cell adhesion molecule 5 (CEACAM5), is a member of the carcinoembryonic antigen (CEA) gene family. CD66e is highly expressed in neuroendocrine prostate cancer, and it contains an N-terminal Ig variable-region-like (IgV) domain and six Ig constant region-type 2-like (IgC2-like) domains, called A1-B1-A2-B2-A3-B3. The A3-B3 domains are regarded as membrane-proximal regions, and these two domains are present in splice variants of CD66e in numerous cancers.

SUMMARY

This document provides methods and materials involved in binding a molecule (e.g., an antibody, an antigen binding fragment, an antibody domain, a CAR, a cell engager, or an ADC) to a CD66e polypeptide. For example, this document provides binders (e.g., antibodies, antigen binding fragments, antibody domains, CARs, cell engagers, or ADCs) that bind to a CD66e polypeptide and methods and materials for using one or more such binders to treat a mammal (e.g., a human) having cancer.

This document also provides cells (e.g., host cells) designed to express one or more binders (e.g., antibodies, antigen binding fragments, antibody domains, CARs, or cell engagers) having the ability to bind to a CD66e polypeptide and methods and materials for using such cells to treat cancer.

As described herein, binders (e.g., one or more antibodies, one or more antigen binding fragments, one or more antibody domains, one or more CARs, one or more cell engagers, and/or one or more ADCs) can be designed to have the ability to bind to a CD66e polypeptide. For example, a binder (e.g., an antibody, an antigen binding fragment, an antibody domain, a CAR, a cell engager, or an ADC) provided herein can have the ability to bind to a polypeptide comprising, consisting essentially of, or consisting of the amino acid sequence of a human CD66e polypeptide as set forth in SEQ ID NO:150 or SEQ ID NO:151 (see, e.g., FIG. 1).

In some cases, two sets of three CDRs of an antigen binding fragment provided herein (e.g., SEQ ID NOs:1-3 and 9-11 or SEQ ID NOs:17-19 and 25-27) can be engineered into a CAR to create $CAR^+$ cells (e.g., $CAR^+$ T cells, $CAR^+$ stem cells such as $CAR^+$ induced pluripotent stem cells, or $CAR^+$ natural killer (NK) cells) having the ability to target $CD66e^+$ cells (e.g., $CD66e^+$ tumor cells and/or $CD66e^+$ tumor vasculature), can be engineered into an antibody structure that includes an Fc region to create antibodies having the ability to target $CD66e^+$ cells (e.g., $CD66e^+$ tumor cells and/or $CD66e^+$ tumor vasculature) and induce antibody-dependent cell-mediated cytotoxicity (ADCC) against the target $CD66e^+$ cells, and/or can be engineered into a cell engager such as a bi-specific T cell engager (e.g., a BiTE), a bi-specific killer engager (e.g., a BiKE), and/or a tri-specific killer engager (e.g., a TriKE) to create cell engagers having the ability to target $CD66e^+$ cells (e.g., $CD66e^+$ tumor cells and/or $CD66e^+$ tumor vasculature) and induce one or more immune responses (e.g., T cell immune responses and/or ADCC using a cell engager in the absence of an Fc-containing antibody) against the target $CD66e^+$ cells. It is noted that BiKE- and TriKE-mediated killing can be referred to ADCC even though it is not initiated by an Fc domain.

In addition, as described herein, binders (e.g., one or more antibodies, one or more antigen binding fragments, and/or one or more antibody domains) provided herein can be used to create conjugates that include the binder and a drug. For example, ADCs such as full antibody-drug conjugates, Fab-drug conjugates, and/or antibody domain-drug conjugates can be designed to include an appropriate binder provided herein to create the conjugate. Such conjugates can be used to deliver the drug payload to target cells such as cancer cells (e.g., $CD66e^+$ cancer cells) or cancer vasculature (e.g., $CD66e^+$ cancer vasculature).

As also described herein, binders (e.g., one or more antibodies, one or more antigen binding fragments, one or more antibody domains, one or more cell engagers, and/or one or more ADCs) provided herein can be used to treat a mammal (e.g., a human) having cancer. For example, a mammal (e.g., a human) having cancer (e.g., a $CD66e^+$ cancer) can be administered a composition comprising one or more binders (e.g., one or more antibodies, one or more antigen binding fragments, one or more antibody domains, one or more cell engagers, and/or one or more ADCs) described herein to reduce the number of cancer cells within the mammal, to induce ADCC against cancer cells within the mammal, and/or to increase the survival duration of the mammal from cancer.

As also described herein, cells (e.g., host cells) can be designed to express one or more binders (e.g., antibodies, antigen binding fragments, antibody domains, CARs, or cell engagers) having the ability to bind to a CD66e polypeptide. For example, cells such as T cells (e.g., CTLs), stem cells (e.g., induced pluripotent stem cells), or NK cells can be engineered to express one or more CARs having the ability to bind to a CD66e polypeptide. Such cells (e.g., CD66e-specific $CAR^+$ T cells or NK cells) can be used to treat cancer.

In some cases, a binder (e.g., an antibody, antigen binding fragment, and/or antibody domain) provided herein can be used to detect the presence or absence of a CD66e polypeptide. For example, a binder (e.g., an antibody, antigen binding fragment, and/or antibody domain) provided herein can be used to determine whether or not a sample (e.g., a biological sample such tumor biopsy) obtained from a mammal (e.g., a human) contains $CD66e^+$ cells (e.g., $CD66e^+$ cancer cells). Having the ability to detect the presence or absence of a CD66e polypeptide (e.g., $CD66e^+$ cancer cells) can allow clinicians, health professionals, and patients to make better decisions about possible treatment options. For example, detection of $CD66e^+$ cancer cells within a mammal can allow clinicians, health professionals, and patients to select an appropriate anti-cancer treatment that targets the $CD66e^+$ cancer cells. Such treatments that targets the $CD66e^+$ cancer cells can include administration of an anti-CD66e antibody such as SAR408701 and/or one or more of the binders described herein having the ability to bind to a CD66e polypeptide and/or administration of one or more cells (e.g., CD66e-specific $CAR^+$ T cells or NK cells) designed to express a binder described herein.

In general, one aspect of this document features an antibody comprising (or consisting essentially of or consisting of): (i) a heavy chain variable domain or region comprising the amino acid sequences set forth in SEQ ID NO:1 (or SEQ ID NO:1 with one, two, or three amino acid additions, deletions, or substitutions), SEQ ID NO:2 (or SEQ ID NO:2 with one, two, or three amino acid additions, deletions, or substitutions), and SEQ ID NO:3 (or SEQ ID NO:3 with one, two, or three amino acid additions, deletions, or substitutions), and a light chain variable domain or region comprising the amino acid sequences set forth in SEQ ID NO:9 (or SEQ ID NO:9 with one, two, or three amino acid additions, deletions, or substitutions), SEQ ID NO:10 (or SEQ ID NO:10 with one, two, or three amino acid additions, deletions, or substitutions), and SEQ ID NO:11 (or SEQ ID NO:11 with one, two, or three amino acid additions, deletions, or substitutions); or (ii) a heavy chain variable domain or region comprising the amino acid sequences set forth in SEQ ID NO:17 (or SEQ ID NO:17 with one, two, or three amino acid additions, deletions, or substitutions), SEQ ID NO:18 (or SEQ ID NO:18 with one, two, or three amino acid additions, deletions, or substitutions), and SEQ ID NO:19 (or SEQ ID NO:19 with one, two, or three amino acid additions, deletions, or substitutions), and a light chain variable domain or region comprising the amino acid sequences set forth in SEQ ID NO:25 (or SEQ ID NO:25 with one, two, or three amino acid additions, deletions, or substitutions), SEQ ID NO:26 (or SEQ ID NO:26 with one, two, or three amino acid additions, deletions, or substitutions), and SEQ ID NO:27 (or SEQ ID NO:27 with one, two, or three amino acid additions, deletions, or substitutions). The antibody can comprise the ability to bind to SEQ ID NO:150 or SEQ ID NO:151. The antibody can comprise the heavy chain variable domain or region of the (i). The heavy chain variable domain or region can comprise an amino acid sequence having at least 90 percent identity to the amino acid sequence set forth in SEQ ID NO:8. The antibody can comprise the light chain variable domain or region of the (i). The light chain variable domain or region can comprise an amino acid sequence having at least 90 percent identity to the amino acid sequence set forth in SEQ ID NO:16. The antibody can comprise the heavy chain variable domain or region of the (ii). The heavy chain variable domain or region can comprise an amino acid sequence having at least 90 percent identity to the amino acid sequence set forth in SEQ ID NO:24. The antibody can comprise the light chain variable domain or region of the (ii). The light chain variable domain or region can comprise an amino acid sequence having at least 90 percent identity to the amino acid sequence set forth in SEQ ID NO:32. The antibody can be a monoclonal antibody. The antibody can be an scFv antibody.

In another aspect, this document features an antigen binding fragment comprising (or consisting essentially of or consisting of): (i) a heavy chain variable domain or region comprising the amino acid sequences set forth in SEQ ID NO:1 (or SEQ ID NO:1 with one, two, or three amino acid additions, deletions, or substitutions), SEQ ID NO:2 (or SEQ ID NO:2 with one, two, or three amino acid additions, deletions, or substitutions), and SEQ ID NO:3 (or SEQ ID NO:3 with one, two, or three amino acid additions, deletions, or substitutions), and a light chain variable domain or region comprising the amino acid sequences set forth in SEQ ID NO:9 (or SEQ ID NO:9 with one, two, or three amino acid additions, deletions, or substitutions), SEQ ID NO:10 (or SEQ ID NO:10 with one, two, or three amino acid additions, deletions, or substitutions), and SEQ ID NO:11 (or SEQ ID NO:11 with one, two, or three amino acid additions, deletions, or substitutions); or (ii) a heavy chain variable domain or region comprising the amino acid sequences set forth in SEQ ID NO:17 (or SEQ ID NO:17 with one, two, or three amino acid additions, deletions, or substitutions), SEQ ID NO:18 (or SEQ ID NO:18 with one, two, or three amino acid additions, deletions, or substitutions), and SEQ ID NO:19 (or SEQ ID NO:19 with one, two, or three amino acid additions, deletions, or substitutions), and a light chain variable domain or region comprising the amino acid sequences set forth in SEQ ID NO:25 (or SEQ ID NO:25 with one, two, or three amino acid additions, deletions, or substitutions), SEQ ID NO:26 (or SEQ ID NO:26 with one, two, or three amino acid additions, deletions, or substitutions), and SEQ ID NO:27 (or SEQ ID NO:27 with one, two, or three amino acid additions, deletions, or substitutions). The antigen binding fragment can comprise the ability to bind to SEQ ID NO:150 or SEQ ID NO:151. The antigen binding fragment can comprise the heavy chain variable domain or region of the (i). The heavy chain variable domain or region can comprise an amino acid sequence having at least 90 percent identity to the amino acid sequence set forth in SEQ ID NO:8. The antigen binding fragment can comprise the light chain variable domain or region of the (i). The light chain variable domain or region can comprise an amino acid sequence having at least 90 percent identity to the amino acid sequence set forth in SEQ ID NO:16. The antigen binding fragment can comprise the heavy chain variable domain or region of the (ii). The heavy chain variable domain or region can comprise an amino acid sequence having at least 90 percent identity to the amino acid sequence set forth in SEQ ID NO:24. The antigen binding fragment can comprise the light chain variable domain or region of the (ii). The light chain variable domain or region can comprise an amino acid sequence having at least 90 percent identity to the amino acid sequence set forth in SEQ ID NO:32. The antigen binding fragment can be monoclonal. The antigen binding fragment can be an Fab.

In another aspect, this document features a chimeric antigen receptor comprising (or consisting essentially of or consisting of) an antigen binding domain, a hinge, a transmembrane domain, and one or more signaling domains, wherein the antigen binding domain comprises an antibody or an antigen-binding fragment. The antibody can comprise (or consist essentially of or consist of): (i) a heavy chain variable domain or region comprising the amino acid sequences set forth in SEQ ID NO:1 (or SEQ ID NO:1 with one, two, or three amino acid additions, deletions, or substitutions), SEQ ID NO:2 (or SEQ ID NO:2 with one, two, or three amino acid additions, deletions, or substitutions), and SEQ ID NO:3 (or SEQ ID NO:3 with one, two, or three amino acid additions, deletions, or substitutions), and a light chain variable domain or region comprising the amino acid sequences set forth in SEQ ID NO:9 (or SEQ ID NO:9 with one, two, or three amino acid additions, deletions, or substitutions), SEQ ID NO:10 (or SEQ ID NO:10 with one, two, or three amino acid additions, deletions, or substitutions), and SEQ ID NO:11 (or SEQ ID NO:11 with one, two, or three amino acid additions, deletions, or substitutions); or (ii) a heavy chain variable domain or region comprising the amino acid sequences set forth in SEQ ID NO:17 (or SEQ ID NO:17 with one, two, or three amino acid additions, deletions, or substitutions), SEQ ID NO:18 (or SEQ ID NO:18 with one, two, or three amino acid additions, deletions, or substitutions), and SEQ ID NO:19 (or SEQ ID NO:19 with one, two, or three amino acid additions, deletions, or substitutions), and a light chain variable domain or region comprising the amino acid sequences set forth in SEQ ID NO:25 (or SEQ ID NO:25 with one, two, or three amino acid additions, deletions, or substitutions), SEQ ID NO:26 (or SEQ ID NO:26 with one, two, or three amino acid additions, deletions, or substitutions), and SEQ ID NO:27 (or SEQ ID NO:27 with one, two, or three amino acid additions, deletions, or substitutions). The antibody can comprise the ability to bind to SEQ ID NO:150 or SEQ ID NO:151. The antibody can comprise the heavy chain variable domain or region of the (i). The heavy chain variable domain or region can comprise an amino acid sequence having at least 90 percent identity to the amino acid sequence set forth in SEQ ID NO:8. The antibody can comprise the light chain variable domain or region of the (i). The light chain variable domain or region can comprise an amino acid sequence having at least 90 percent identity to the amino acid sequence set forth in SEQ ID NO:16. The antibody can comprise the heavy chain variable domain or region of the (ii). The heavy chain variable domain or region can comprise an amino acid sequence having at least 90 percent identity to the amino acid sequence set forth in SEQ ID NO:24. The antibody can comprise the light chain variable domain or region of the (ii). The light chain variable domain or region can comprise an amino acid sequence having at least 90 percent identity to the amino acid sequence set forth in SEQ ID NO:32. The antibody can be a monoclonal antibody. The antibody can be an scFv antibody. The antigen binding fragment can comprise (or consist essentially of or consist of): (i) a heavy chain variable domain or region comprising the amino acid sequences set forth in SEQ ID NO:1 (or SEQ ID NO:1 with one, two, or three amino acid additions, deletions, or substitutions), SEQ ID NO:2 (or SEQ ID NO:2 with one, two, or three amino acid additions, deletions, or substitutions), and SEQ ID NO:3 (or SEQ ID NO:3 with one, two, or three amino acid additions, deletions, or substitutions), and a light chain variable domain or region comprising the amino acid sequences set forth in SEQ ID NO:9 (or SEQ ID NO:9 with one, two, or three amino acid additions, deletions, or substitutions), SEQ ID NO:10 (or SEQ ID NO:10 with one, two, or three amino acid additions, deletions, or substitutions), and SEQ ID NO:11 (or SEQ ID NO:11 with one, two, or three amino acid additions, deletions, or substitutions); or (ii) a heavy chain variable domain or region comprising the amino acid sequences set forth in SEQ ID NO:17 (or SEQ ID NO:17 with one, two, or three amino acid additions, deletions, or substitutions), SEQ ID NO:18 (or SEQ ID NO:18 with one, two, or three amino acid additions, deletions, or substitutions), and SEQ ID NO:19 (or SEQ ID NO:19 with one, two, or three amino acid additions, deletions, or substitutions), and a light chain variable domain or region comprising the amino acid sequences set forth in SEQ ID NO:25 (or SEQ ID NO:25 with one, two, or three amino acid additions, deletions, or substitutions), SEQ ID NO:26 (or SEQ ID NO:26 with one, two, or three amino acid additions, deletions, or substitutions), and SEQ ID NO:27 (or SEQ ID NO:27 with one, two, or three amino acid additions, deletions, or substitutions). The antigen binding fragment can comprise the ability to bind to SEQ ID NO:150 or SEQ ID NO:151. The antigen binding fragment can comprise the heavy chain variable domain or region of the (i). The heavy chain variable domain or region can comprise an amino acid sequence having at least 90 percent identity to the amino acid sequence set forth in SEQ ID NO:8. The antigen binding fragment can comprise the light chain variable domain or region of the (i). The light chain variable domain or region can comprise an amino acid sequence having at least 90 percent identity to the amino acid sequence set forth in SEQ ID NO:16. The antigen binding fragment can comprise the heavy chain variable domain or region of the (ii). The heavy chain variable domain or region can comprise an amino acid sequence having at least 90 percent identity to the amino acid sequence set forth in SEQ ID NO:24. The antigen binding fragment can comprise the light chain variable domain or region of the (ii). The light chain variable domain or region can comprise an amino acid sequence having at least 90 percent identity to the amino acid sequence set forth in SEQ ID NO:32. The antigen binding fragment can be monoclonal. The antigen binding fragment can be an Fab. The antigen binding domain can comprise a scFv having the ability to bind to a CD66e polypeptide. The hinge can comprise a hinge set forth in FIG. 13. The transmembrane domain can comprise a transmembrane domain set forth in FIG. 14. The chimeric antigen receptor can comprise one or more signaling domains set forth in FIG. 15.

In another aspect, this document features a cell comprising a chimeric antigen receptor of the preceding paragraph. The cell can be a T cell, a stem cell, or an NK cell. For example, one aspect of this document features an isolated population of cells, wherein at least one cell of the population comprises a chimeric antigen receptor of the preceding paragraph. The cell can be a T cell, a stem cell, or an NK cell. In some embodiments, at least 50 percent, at least 75 percent, at least 95 percent, at least 99 percent, or 100 percent of the cells of the population can comprise the chimeric antigen receptor.

In another aspect, this document features a cell engager comprising (or consisting essentially of or consisting of) a first antigen binding domain, a linker, and a second antigen binding domain, wherein the first antigen binding domain comprises an antibody or an antigen-binding fragment. The antibody can comprise (or consist essentially of or consist of): (i) a heavy chain variable domain or region comprising the amino acid sequences set forth in SEQ ID NO:1 (or SEQ ID NO:1 with one, two, or three amino acid additions, deletions, or substitutions), SEQ ID NO:2 (or SEQ ID NO:2 with one, two, or three amino acid additions, deletions, or substitutions), and SEQ ID NO:3 (or SEQ ID NO:3 with one, two, or three amino acid additions, deletions, or substitutions), and a light chain variable domain or region comprising the amino acid sequences set forth in SEQ ID NO:9 (or SEQ ID NO:9 with one, two, or three amino acid additions, deletions, or substitutions), SEQ ID NO:10 (or SEQ ID NO:10 with one, two, or three amino acid additions, deletions, or substitutions), and SEQ ID NO:11 (or SEQ ID NO:11 with one, two, or three amino acid additions, deletions, or substitutions); or (ii) a heavy chain variable domain or region comprising the amino acid sequences set forth in SEQ ID NO:17 (or SEQ ID NO:17 with one, two, or three amino acid additions, deletions, or substitutions), SEQ ID NO:18 (or SEQ ID NO:18 with one, two, or three amino acid additions, deletions, or substitutions), and SEQ ID NO:19 (or SEQ ID NO:19 with one, two, or three amino acid additions, deletions, or substitutions), and a light chain variable domain or region comprising the amino acid sequences set forth in SEQ ID NO:25 (or SEQ ID NO:25 with one, two, or three amino acid additions, deletions, or substitutions), SEQ ID NO:26 (or SEQ ID NO:26 with one, two, or three amino acid additions, deletions, or substitutions), and SEQ ID NO:27 (or SEQ ID NO:27 with one, two, or three amino acid additions, deletions, or substitutions). The antibody can comprise the ability to bind to SEQ ID NO:150 or SEQ ID NO:151. The antibody can comprise the heavy chain variable domain or region of the (i). The heavy chain variable domain or region can comprise an amino acid sequence having at least 90 percent identity to the amino acid sequence set forth in SEQ ID NO:8. The antibody can comprise the light chain variable domain or region of the (i). The light chain variable domain or region can comprise an amino acid sequence having at least 90 percent identity to the amino acid sequence set forth in SEQ ID NO:16. The antibody can comprise the heavy chain variable domain or region of the (ii). The heavy chain variable domain or region can comprise an amino acid sequence having at least 90 percent identity to the amino acid sequence set forth in SEQ ID NO:24. The antibody can comprise the light chain variable domain or region of the (ii). The light chain variable domain or region can comprise an amino acid sequence having at least 90 percent identity to the amino acid sequence set forth in SEQ ID NO:32. The antibody can be a monoclonal antibody. The antibody can be an scFv antibody. The antigen binding fragment can comprise (or consist essentially of or consist of): (i) a heavy chain variable domain or region comprising the amino acid sequences set forth in SEQ ID NO:1 (or SEQ ID NO:1 with one, two, or three amino acid additions, deletions, or substitutions), SEQ ID NO:2 (or SEQ ID NO:2 with one, two, or three amino acid additions, deletions, or substitutions), and SEQ ID NO:3 (or SEQ ID NO:3 with one, two, or three amino acid additions, deletions, or substitutions), and a light chain variable domain or region comprising the amino acid sequences set forth in SEQ ID NO:9 (or SEQ ID NO:9 with one, two, or three amino acid additions, deletions, or substitutions), SEQ ID NO:10 (or SEQ ID NO:10 with one, two, or three amino acid additions, deletions, or substitutions), and SEQ ID NO:11 (or SEQ ID NO:11 with one, two, or three amino acid additions, deletions, or substitutions); or (ii) a heavy chain variable domain or region comprising the amino acid sequences set forth in SEQ ID NO:17 (or SEQ ID NO:17 with one, two, or three amino acid additions, deletions, or substitutions), SEQ ID NO:18 (or SEQ ID NO:18 with one, two, or three amino acid additions, deletions, or substitutions), and SEQ ID NO:19 (or SEQ ID NO:19 with one, two, or three amino acid additions, deletions, or substitutions), and a light chain variable domain or region comprising the amino acid sequences set forth in SEQ ID NO:25 (or SEQ ID NO:25 with one, two, or three amino acid additions, deletions, or substitutions), SEQ ID NO:26 (or SEQ ID NO:26 with one, two, or three amino acid additions, deletions, or substitutions), and SEQ ID NO:27 (or SEQ ID NO:27 with one, two, or three amino acid additions, deletions, or substitutions). The antigen binding fragment can comprise the ability to bind to SEQ ID NO:150 or SEQ ID NO:151. The antigen binding fragment can comprise the heavy chain variable domain or region of the (i). The heavy chain variable domain or region can comprise an amino acid sequence having at least 90 percent identity to the amino acid sequence set forth in SEQ ID NO:8. The antigen binding fragment can comprise the light chain variable domain or region of the (i). The light chain variable domain or region can comprise an amino acid sequence having at least 90 percent identity to the amino acid sequence set forth in SEQ ID NO:16. The antigen binding fragment can comprise the heavy chain variable domain or region of the (ii). The heavy chain variable domain or region can comprise an amino acid sequence having at least 90 percent identity to the amino acid sequence set forth in SEQ ID NO:24. The antigen binding fragment can comprise the light chain variable domain or region of the (ii). The light chain variable domain or region can comprise an amino acid sequence having at least 90 percent identity to the amino acid sequence set forth in SEQ ID NO:32. The antigen binding fragment can be monoclonal. The antigen binding fragment can be an Fab. The first antigen binding domain can comprise a scFv having the ability to bind to a CD66e polypeptide. The first antigen binding domain can be an IgG having the ability to bind to a CD66e polypeptide. The linker can comprise a linker set forth in FIG. 10 or FIG. 13. The second antigen binding domain can bind to a polypeptide expressed on the surface of T cells. The polypeptide expressed on the surface of T cells can be a CD3 polypeptide. The second antigen binding domain can be an antigen binding domain set forth in FIG. 18. The second antigen binding domain can bind to a polypeptide expressed on the surface of NK cells. The polypeptide expressed on the surface of NK cells can be a CD16a, NKG2A, NKG2D, NKp30, NKp44, or NKp46 polypeptide. The second antigen binding domain can be an antigen binding domain set forth in FIG. 19. The cell engager can comprise a third antigen binding domain. The third antigen binding domain can bind to a polypeptide expressed on the surface of NK cells. The polypeptide expressed on the surface of NK cells can be a CD16a, NKG2A, NKG2D, NKp30, NKp44, or NKp46 polypeptide. The third antigen binding domain can be an antigen binding domain set forth in FIG. 19.

In another aspect, this document features a nucleic acid (e.g., an isolated nucleic acid) comprising (or consisting essentially of or consisting of) a nucleic acid sequence encoding at least part of an antibody or an antigen-binding fragment. The antibody can comprise (or consist essentially of or consist of): (i) a heavy chain variable domain or region comprising the amino acid sequences set forth in SEQ ID NO:1 (or SEQ ID NO:1 with one, two, or three amino acid additions, deletions, or substitutions), SEQ ID NO:2 (or SEQ ID NO:2 with one, two, or three amino acid additions, deletions, or substitutions), and SEQ ID NO:3 (or SEQ ID NO:3 with one, two, or three amino acid additions, deletions, or substitutions), and a light chain variable domain or region comprising the amino acid sequences set forth in SEQ ID NO:9 (or SEQ ID NO:9 with one, two, or three amino acid additions, deletions, or substitutions), SEQ ID NO:10 (or SEQ ID NO:10 with one, two, or three amino acid additions, deletions, or substitutions), and SEQ ID NO:11 (or SEQ ID NO:11 with one, two, or three amino acid additions, deletions, or substitutions); or (ii) a heavy chain variable domain or region comprising the amino acid sequences set forth in SEQ ID NO:17 (or SEQ ID NO:17 with one, two, or three amino acid additions, deletions, or substitutions), SEQ ID NO:18 (or SEQ ID NO:18 with one, two, or three amino acid additions, deletions, or substitutions), and SEQ ID NO:19 (or SEQ ID NO:19 with one, two, or three amino acid additions, deletions, or substitutions), and a light chain variable domain or region comprising the amino acid sequences set forth in SEQ ID NO:25 (or SEQ ID NO:25 with one, two, or three amino acid additions, deletions, or substitutions), SEQ ID NO:26 (or SEQ ID NO:26 with one, two, or three amino acid additions, deletions, or substitutions), and SEQ ID NO:27 (or SEQ ID NO:27 with one, two, or three amino acid additions, deletions, or substitutions). The antibody can comprise the ability to bind to SEQ ID NO:150 or SEQ ID NO:151. The antibody can comprise the heavy chain variable domain or region of the (i). The heavy chain variable domain or region can comprise an amino acid sequence having at least 90 percent identity to the amino acid sequence set forth in SEQ ID NO:8. The antibody can comprise the light chain variable domain or region of the (i). The light chain variable domain or region can comprise an amino acid sequence having at least 90 percent identity to the amino acid sequence set forth in SEQ ID NO:16. The antibody can comprise the heavy chain variable domain or region of the (ii). The heavy chain variable domain or region can comprise an amino acid sequence having at least 90 percent identity to the amino acid sequence set forth in SEQ ID NO:24. The antibody can comprise the light chain variable domain or region of the (ii). The light chain variable domain or region can comprise an amino acid sequence having at least 90 percent identity to the amino acid sequence set forth in SEQ ID NO:32. The antibody can be a monoclonal antibody. The antibody can be an scFv antibody. The antigen binding fragment can comprise (or consist essentially of or consist of): (i) a heavy chain variable domain or region comprising the amino acid sequences set forth in SEQ ID NO:1 (or SEQ ID NO:1 with one, two, or three amino acid additions, deletions, or substitutions), SEQ ID NO:2 (or SEQ ID NO:2 with one, two, or three amino acid additions, deletions, or substitutions), and SEQ ID NO:3 (or SEQ ID NO:3 with one, two, or three amino acid additions, deletions, or substitutions), and a light chain variable domain or region comprising the amino acid sequences set forth in SEQ ID NO:9 (or SEQ ID NO:9 with one, two, or three amino acid additions, deletions, or substitutions), SEQ ID NO:10 (or SEQ ID NO:10 with one, two, or three amino acid additions, deletions, or substitutions), and SEQ ID NO:11 (or SEQ ID NO:11 with one, two, or three amino acid additions, deletions, or substitutions); or (ii) a heavy chain variable domain or region comprising the amino acid sequences set forth in SEQ ID NO:17 (or SEQ ID NO:17 with one, two, or three amino acid additions, deletions, or substitutions), SEQ ID NO:18 (or SEQ ID NO:18 with one, two, or three amino acid additions, deletions, or substitutions), and SEQ ID NO:19 (or SEQ ID NO:19 with one, two, or three amino acid additions, deletions, or substitutions), and a light chain variable domain or region comprising the amino acid sequences set forth in SEQ ID NO:25 (or SEQ ID NO:25 with one, two, or three amino acid additions, deletions, or substitutions), SEQ ID NO:26 (or SEQ ID NO:26 with one, two, or three amino acid additions, deletions, or substitutions), and SEQ ID NO:27 (or SEQ ID NO:27 with one, two, or three amino acid additions, deletions, or substitutions). The antigen binding fragment can comprise the ability to bind to SEQ ID NO:150 or SEQ ID NO:151. The antigen binding fragment can comprise the heavy chain variable domain or region of the (i). The heavy chain variable domain or region can comprise an amino acid sequence having at least 90 percent identity to the amino acid sequence set forth in SEQ ID NO:8. The antigen binding fragment can comprise the light chain variable domain or region of the (i). The light chain variable domain or region can comprise an amino acid sequence having at least 90 percent identity to the amino acid sequence set forth in SEQ ID NO:16. The antigen binding fragment can comprise the heavy chain variable domain or region of the (ii). The heavy chain variable domain or region can comprise an amino acid sequence having at least 90 percent identity to the amino acid sequence set forth in SEQ ID NO:24. The antigen binding fragment can comprise the light chain variable domain or region of the (ii). The light chain variable domain or region can comprise an amino acid sequence having at least 90 percent identity to the amino acid sequence set forth in SEQ ID NO:32. The antigen binding fragment can be monoclonal. The antigen binding fragment can be an Fab. The nucleic acid sequence can encode the heavy chain variable domain or region of any one of the (i)-(ii). The nucleic acid sequence can encode the light chain variable domain or region of any one of the (i)-(ii). The nucleic acid can be a viral vector. The nucleic acid can be a phagemid.

In another aspect, this document features a nucleic acid (e.g., an isolated nucleic acid) comprising (or consisting essentially of or consisting of) a nucleic acid sequence encoding a chimeric antigen receptor described above or a cell engager described above. The nucleic acid can be a viral vector. The nucleic acid can be a phagemid.

In another aspect, this document features a host cell comprising a nucleic acid of either of the two preceding paragraphs. For example, one aspect of this document features an isolated population of host cells, wherein at least one host cell of the population comprises a nucleic acid of either of the two preceding paragraphs. In some embodiments, at least 50 percent, at least 75 percent, at least 95 percent, at least 99 percent, or 100 percent of the cells of the population can comprise a nucleic acid of either of the two preceding paragraphs.

In another aspect, this document features a host cell that expresses a chimeric antigen receptor described above or a cell engager described above. The host cell can be a T cell, stem cell, or NK cell. For example, one aspect of this document features an isolated population of host cells, wherein at least one host cell of the population expresses a chimeric antigen receptor described above or a cell engager described above. In some embodiments, at least 50 percent, at least 75 percent, at least 95 percent, at least 99 percent, or 100 percent of the cells of the population can express a chimeric antigen receptor described above or a cell engager described above.

In another aspect, this document features an antibody-drug conjugate (ADC) comprising (or consisting essentially of or consisting of) an antigen binding domain covalently linked to a drug, wherein the antigen binding domain comprises an antibody or an antigen binding fragment. The antibody can comprise (or consist essentially of or consist of): (i) a heavy chain variable domain or region comprising the amino acid sequences set forth in SEQ ID NO:1 (or SEQ ID NO:1 with one, two, or three amino acid additions, deletions, or substitutions), SEQ ID NO:2 (or SEQ ID NO:2 with one, two, or three amino acid additions, deletions, or substitutions), and SEQ ID NO:3 (or SEQ ID NO:3 with one, two, or three amino acid additions, deletions, or substitutions), and a light chain variable domain or region comprising the amino acid sequences set forth in SEQ ID NO:9 (or SEQ ID NO:9 with one, two, or three amino acid additions, deletions, or substitutions), SEQ ID NO:10 (or SEQ ID NO:10 with one, two, or three amino acid additions, deletions, or substitutions), and SEQ ID NO:11 (or SEQ ID NO:11 with one, two, or three amino acid additions, deletions, or substitutions); or (ii) a heavy chain variable domain or region comprising the amino acid sequences set forth in SEQ ID NO:17 (or SEQ ID NO:17 with one, two, or three amino acid additions, deletions, or substitutions), SEQ ID NO:18 (or SEQ ID NO:18 with one, two, or three amino acid additions, deletions, or substitutions), and SEQ ID NO:19 (or SEQ ID NO:19 with one, two, or three amino acid additions, deletions, or substitutions), and a light chain variable domain or region comprising the amino acid sequences set forth in SEQ ID NO:25 (or SEQ ID NO:25 with one, two, or three amino acid additions, deletions, or substitutions), SEQ ID NO:26 (or SEQ ID NO:26 with one, two, or three amino acid additions, deletions, or substitutions), and SEQ ID NO:27 (or SEQ ID NO:27 with one, two, or three amino acid additions, deletions, or substitutions). The antibody can comprise the ability to bind to SEQ ID NO:150 or SEQ ID NO:151. The antibody can comprise the heavy chain variable domain or region of the (i). The heavy chain variable domain or region can comprise an amino acid sequence having at least 90 percent identity to the amino acid sequence set forth in SEQ ID NO:8. The antibody can comprise the light chain variable domain or region of the (i). The light chain variable domain or region can comprise an amino acid sequence having at least 90 percent identity to the amino acid sequence set forth in SEQ ID NO:16. The antibody can comprise the heavy chain variable domain or region of the (ii). The heavy chain variable domain or region can comprise an amino acid sequence having at least 90 percent identity to the amino acid sequence set forth in SEQ ID NO:24. The antibody can comprise the light chain variable domain or region of the (ii). The light chain variable domain or region can comprise an amino acid sequence having at least 90 percent identity to the amino acid sequence set forth in SEQ ID NO:32. The antibody can be a monoclonal antibody. The antibody can be an scFv antibody. The antigen binding fragment can comprise (or consist essentially of or consist of): (i) a heavy chain variable domain or region comprising the amino acid sequences set forth in SEQ ID NO:1 (or SEQ ID NO:1 with one, two, or three amino acid additions, deletions, or substitutions), SEQ ID NO:2 (or SEQ ID NO:2 with one, two, or three amino acid additions, deletions, or substitutions), and SEQ ID NO:3 (or SEQ ID NO:3 with one, two, or three amino acid additions, deletions, or substitutions), and a light chain variable domain or region comprising the amino acid sequences set forth in SEQ ID NO:9 (or SEQ ID NO:9 with one, two, or three amino acid additions, deletions, or substitutions), SEQ ID NO:10 (or SEQ ID NO:10 with one, two, or three amino acid additions, deletions, or substitutions), and SEQ ID NO:11 (or SEQ ID NO:11 with one, two, or three amino acid additions, deletions, or substitutions); or (ii) a heavy chain variable domain or region comprising the amino acid sequences set forth in SEQ ID NO:17 (or SEQ ID NO:17 with one, two, or three amino acid additions, deletions, or substitutions), SEQ ID NO:18 (or SEQ ID NO:18 with one, two, or three amino acid additions, deletions, or substitutions), and SEQ ID NO:19 (or SEQ ID NO:19 with one, two, or three amino acid additions, deletions, or substitutions), and a light chain variable domain or region comprising the amino acid sequences set forth in SEQ ID NO:25 (or SEQ ID NO:25 with one, two, or three amino acid additions, deletions, or substitutions), SEQ ID NO:26 (or SEQ ID NO:26 with one, two, or three amino acid additions, deletions, or substitutions), and SEQ ID NO:27 (or SEQ ID NO:27 with one, two, or three amino acid additions, deletions, or substitutions). The antigen binding fragment can comprise the ability to bind to SEQ ID NO:150 or SEQ ID NO:151. The antigen binding fragment can comprise the heavy chain variable domain or region of the (i). The heavy chain variable domain or region can comprise an amino acid sequence having at least 90 percent identity to the amino acid sequence set forth in SEQ ID NO:8. The antigen binding fragment can comprise the light chain variable domain or region of the (i). The light chain variable domain or region can comprise an amino acid sequence having at least 90 percent identity to the amino acid sequence set forth in SEQ ID NO:16. The antigen binding fragment can comprise the heavy chain variable domain or region of the (ii). The heavy chain variable domain or region can comprise an amino acid sequence having at least 90 percent identity to the amino acid sequence set forth in SEQ ID NO:24. The antigen binding fragment can comprise the light chain variable domain or region of the (ii). The light chain variable domain or region can comprise an amino acid sequence having at least 90 percent identity to the amino acid sequence set forth in SEQ ID NO:32. The antigen binding fragment can be monoclonal. The antigen binding fragment can be an Fab. The antigen binding domain can comprise a scFv having the ability to bind to a CD66e polypeptide. The antigen binding domain can be an IgG having the ability to bind to a CD66e polypeptide. The drug can be selected from the group consisting of auristatins, mertansine, or pyrrolobenzodiazepine (PBD) dimers.

In another aspect, this document features a composition comprising (or consisting essentially of or consisting of) an antibody or an antigen binding fragment. The antibody can comprise (or consist essentially of or consist of): (i) a heavy chain variable domain or region comprising the amino acid sequences set forth in SEQ ID NO:1 (or SEQ ID NO:1 with one, two, or three amino acid additions, deletions, or substitutions), SEQ ID NO:2 (or SEQ ID NO:2 with one, two, or three amino acid additions, deletions, or substitutions), and SEQ ID NO:3 (or SEQ ID NO:3 with one, two, or three amino acid additions, deletions, or substitutions), and a light chain variable domain or region comprising the amino acid sequences set forth in SEQ ID NO:9 (or SEQ ID NO:9 with one, two, or three amino acid additions, deletions, or substitutions), SEQ ID NO:10 (or SEQ ID NO:10 with one, two, or three amino acid additions, deletions, or substitutions), and SEQ ID NO:11 (or SEQ ID NO:11 with one, two, or three amino acid additions, deletions, or substitutions); or (ii) a heavy chain variable domain or region comprising the amino acid sequences set forth in SEQ ID NO:17 (or SEQ ID NO:17 with one, two, or three amino acid additions, deletions, or substitutions), SEQ ID NO:18 (or SEQ ID NO:18 with one, two, or three amino acid additions, deletions, or substitutions), and SEQ ID NO:19 (or SEQ ID NO:19 with one, two, or three amino acid additions, deletions, or substitutions), and a light chain variable domain or region comprising the amino acid sequences set forth in SEQ ID NO:25 (or SEQ ID NO:25 with one, two, or three amino acid additions, deletions, or substitutions), SEQ ID NO:26 (or SEQ ID NO:26 with one, two, or three amino acid additions, deletions, or substitutions), and SEQ ID NO:27 (or SEQ ID NO:27 with one, two, or three amino acid additions, deletions, or substitutions). The antibody can comprise the ability to bind to SEQ ID NO:150 or SEQ ID NO:151. The antibody can comprise the heavy chain variable domain or region of the (i). The heavy chain variable domain or region can comprise an amino acid sequence having at least 90 percent identity to the amino acid sequence set forth in SEQ ID NO:8. The antibody can comprise the light chain variable domain or region of the (i). The light chain variable domain or region can comprise an amino acid sequence having at least 90 percent identity to the amino acid sequence set forth in SEQ ID NO:16. The antibody can comprise the heavy chain variable domain or region of the (ii). The heavy chain variable domain or region can comprise an amino acid sequence having at least 90 percent identity to the amino acid sequence set forth in SEQ ID NO:24. The antibody can comprise the light chain variable domain or region of the (ii). The light chain variable domain or region can comprise an amino acid sequence having at least 90 percent identity to the amino acid sequence set forth in SEQ ID NO:32. The antibody can be a monoclonal antibody. The antibody can be an scFv antibody. The antigen binding fragment can comprise (or consist essentially of or consist of): (i) a heavy chain variable domain or region comprising the amino acid sequences set forth in SEQ ID NO:1 (or SEQ ID NO:1 with one, two, or three amino acid additions, deletions, or substitutions), SEQ ID NO:2 (or SEQ ID NO:2 with one, two, or three amino acid additions, deletions, or substitutions), and SEQ ID NO:3 (or SEQ ID NO:3 with one, two, or three amino acid additions, deletions, or substitutions), and a light chain variable domain or region comprising the amino acid sequences set forth in SEQ ID NO:9 (or SEQ ID NO:9 with one, two, or three amino acid additions, deletions, or substitutions), SEQ ID NO:10 (or SEQ ID NO:10 with one, two, or three amino acid additions, deletions, or substitutions), and SEQ ID NO:11 (or SEQ ID NO:11 with one, two, or three amino acid additions, deletions, or substitutions); or (ii) a heavy chain variable domain or region comprising the amino acid sequences set forth in SEQ ID NO:17 (or SEQ ID NO:17 with one, two, or three amino acid additions, deletions, or substitutions), SEQ ID NO:18 (or SEQ ID NO:18 with one, two, or three amino acid additions, deletions, or substitutions), and SEQ ID NO:19 (or SEQ ID NO:19 with one, two, or three amino acid additions, deletions, or substitutions), and a light chain variable domain or region comprising the amino acid sequences set forth in SEQ ID NO:25 (or SEQ ID NO:25 with one, two, or three amino acid additions, deletions, or substitutions), SEQ ID NO:26 (or SEQ ID NO:26 with one, two, or three amino acid additions, deletions, or substitutions), and SEQ ID NO:27 (or SEQ ID NO:27 with one, two, or three amino acid additions, deletions, or substitutions). The antigen binding fragment can comprise the ability to bind to SEQ ID NO:150 or SEQ ID NO:151. The antigen binding fragment can comprise the heavy chain variable domain or region of the (i). The heavy chain variable domain or region can comprise an amino acid sequence having at least 90 percent identity to the amino acid sequence set forth in SEQ ID NO:8. The antigen binding fragment can comprise the light chain variable domain or region of the (i). The light chain variable domain or region can comprise an amino acid sequence having at least 90 percent identity to the amino acid sequence set forth in SEQ ID NO:16. The antigen binding fragment can comprise the heavy chain variable domain or region of the (ii). The heavy chain variable domain or region can comprise an amino acid sequence having at least 90 percent identity to the amino acid sequence set forth in SEQ ID NO:24. The antigen binding fragment can comprise the light chain variable domain or region of the (ii). The light chain variable domain or region can comprise an amino acid sequence having at least 90 percent identity to the amino acid sequence set forth in SEQ ID NO:32. The antigen binding fragment can be monoclonal. The antigen binding fragment can be an Fab. The composition can comprise the antibody. The composition can comprise the antigen binding fragment. The composition can comprise a checkpoint inhibitor. The checkpoint inhibitor can be selected from the group consisting of cemiplimab, nivolumab, pembrolizumab, JTX-4014, spartalizumab, camrelizumab, sintilimab, tislelizumab, toripalimab, dostarlimab, INCMGA00012, AMP-224, AMP-514, avelumab, durvalumab, atezolizumab, KN035, CK-301, AUNP12, CA-170, BMS-986189, and ipilimumab.

In another aspect, this document features a composition comprising (or consisting essentially of or consisting of) a cell engager described above. The composition can comprise a checkpoint inhibitor. The checkpoint inhibitor can be selected from the group consisting of cemiplimab, nivolumab, pembrolizumab, JTX-4014, spartalizumab, camrelizumab, sintilimab, tislelizumab, toripalimab, dostarlimab, INCMGA00012, AMP-224, AMP-514, avelumab, durvalumab, atezolizumab, KN035, CK-301, AUNP12, CA-170, BMS-986189, and ipilimumab.

In another aspect, this document features a composition comprising (or consisting essentially of or consisting of) a cell described above. The composition can comprise a checkpoint inhibitor. The checkpoint inhibitor can be selected from the group consisting of cemiplimab, nivolumab, pembrolizumab, JTX-4014, spartalizumab, camrelizumab, sintilimab, tislelizumab, toripalimab, dostarlimab, INCMGA00012, AMP-224, AMP-514, avelumab, durvalumab, atezolizumab, KN035, CK-301, AUNP12, CA-170, BMS-986189, and ipilimumab.

In another aspect, this document features a composition comprising (or consisting essentially of or consisting of) an ADC described above. The composition can comprise a checkpoint inhibitor. The checkpoint inhibitor can be selected from the group consisting of cemiplimab, nivolumab, pembrolizumab, JTX-4014, spartalizumab, camrelizumab, sintilimab, tislelizumab, toripalimab, dostarlimab, INCMGA00012, AMP-224, AMP-514, avelumab, durvalumab, atezolizumab, KN035, CK-301, AUNP12, CA-170, BMS-986189, and ipilimumab.

In another aspect, this document features a method of treating a mammal having cancer. The method comprises (or consists essentially of or consists of) administering, to the mammal, a composition of any of the four preceding paragraphs. The mammal can be a human. The cancer can be a $CD66e^+$ cancer. The $CD66e^+$ cancer can be selected from the group consisting of $CD66e^+$ lung cancer, $CD66e^+$ prostate cancer, $CD66e^+$ esophageal cancer, $CD66e^+$ stomach cancer, $CD66e^+$ colorectal cancer, $CD66e^+$ liver cancer, $CD66e^+$ vaginal cancer, or $CD66e^+$ cervical cancer. The number of cancer cells within the mammal can be reduced following the administering step.

In another aspect, this document features a method of treating a mammal having cancer. The method comprises (or consists essentially of or consists of) (a) administering, to the mammal, the composition of any of those same four preceding paragraphs referenced in the preceding paragraph, and (b) administering, to the mammal, a composition comprising a checkpoint inhibitor. The mammal can be a human. The cancer can be a $CD66e^+$ cancer. The $CD66e^+$ cancer can be selected from the group consisting of $CD66e^+$ lung cancer, $CD66e^+$ prostate cancer, $CD66e^+$ esophageal cancer, $CD66e^+$ stomach cancer, $CD66e^+$ colorectal cancer, $CD66e^+$ liver cancer, $CD66e^+$ vaginal cancer, or $CD66e^+$ cervical cancer. The checkpoint inhibitor can be selected from the group consisting of cemiplimab, nivolumab, pembrolizumab, JTX-4014, spartalizumab, camrelizumab, sintilimab, tislelizumab, toripalimab, dostarlimab, INCMGA00012, AMP-224, AMP-514, avelumab, durvalumab, atezolizumab, KN035, CK-301, AUNP12, CA-170, BMS-986189, and ipilimumab. The number of cancer cells within the mammal can be reduced following the administering steps (a) and (b).

In another aspect, this document features a method for binding a binding molecule to a CD66e polypeptide. The method comprises (or consists essentially of or consists of) contacting the CD66e polypeptide with an antibody or an antigen binding fragment. The antibody can comprise (or consist essentially of or consist of): (i) a heavy chain variable domain or region comprising the amino acid sequences set forth in SEQ ID NO:1 (or SEQ ID NO:1 with one, two, or three amino acid additions, deletions, or substitutions), SEQ ID NO:2 (or SEQ ID NO:2 with one, two, or three amino acid additions, deletions, or substitutions), and SEQ ID NO:3 (or SEQ ID NO:3 with one, two, or three amino acid additions, deletions, or substitutions), and a light chain variable domain or region comprising the amino acid sequences set forth in SEQ ID NO:9 (or SEQ ID NO:9 with one, two, or three amino acid additions, deletions, or substitutions), SEQ ID NO:10 (or SEQ ID NO:10 with one, two, or three amino acid additions, deletions, or substitutions), and SEQ ID NO:11 (or SEQ ID NO:11 with one, two, or three amino acid additions, deletions, or substitutions); or (ii) a heavy chain variable domain or region comprising the amino acid sequences set forth in SEQ ID NO:17 (or SEQ ID NO:17 with one, two, or three amino acid additions, deletions, or substitutions), SEQ ID NO:18 (or SEQ ID NO:18 with one, two, or three amino acid additions, deletions, or substitutions), and SEQ ID NO:19 (or SEQ ID NO:19 with one, two, or three amino acid additions, deletions, or substitutions), and a light chain variable domain or region comprising the amino acid sequences set forth in SEQ ID NO:25 (or SEQ ID NO:25 with one, two, or three amino acid additions, deletions, or substitutions), SEQ ID NO:26 (or SEQ ID NO:26 with one, two, or three amino acid additions, deletions, or substitutions), and SEQ ID NO:27 (or SEQ ID NO:27 with one, two, or three amino acid additions, deletions, or substitutions). The antibody can comprise the ability to bind to SEQ ID NO:150 or SEQ ID NO:151. The antibody can comprise the heavy chain variable domain or region of the (i). The heavy chain variable domain or region can comprise an amino acid sequence having at least 90 percent identity to the amino acid sequence set forth in SEQ ID NO:8. The antibody can comprise the light chain variable domain or region of the (i). The light chain variable domain or region can comprise an amino acid sequence having at least 90 percent identity to the amino acid sequence set forth in SEQ ID NO:16. The antibody can comprise the heavy chain variable domain or region of the (ii). The heavy chain variable domain or region can comprise an amino acid sequence having at least 90 percent identity to the amino acid sequence set forth in SEQ ID NO:24. The antibody can comprise the light chain variable domain or region of the (ii). The light chain variable domain or region can comprise an amino acid sequence having at least 90 percent identity to the amino acid sequence set forth in SEQ ID NO:32. The antibody can be a monoclonal antibody. The antibody can be an scFv antibody. The antigen binding fragment can comprise (or consist essentially of or consist of): (i) a heavy chain variable domain or region comprising the amino acid sequences set forth in SEQ ID NO:1 (or SEQ ID NO:1 with one, two, or three amino acid additions, deletions, or substitutions), SEQ ID NO:2 (or SEQ ID NO:2 with one, two, or three amino acid additions, deletions, or substitutions), and SEQ ID NO:3 (or SEQ ID NO:3 with one, two, or three amino acid additions, deletions, or substitutions), and a light chain variable domain or region comprising the amino acid sequences set forth in SEQ ID NO:9 (or SEQ ID NO:9 with one, two, or three amino acid additions, deletions, or substitutions), SEQ ID NO:10 (or SEQ ID NO:10 with one, two, or three amino acid additions, deletions, or substitutions), and SEQ ID NO:11 (or SEQ ID NO:11 with one, two, or three amino acid additions, deletions, or substitutions); or (ii) a heavy chain variable domain or region comprising the amino acid sequences set forth in SEQ ID NO:17 (or SEQ ID NO:17 with one, two, or three amino acid additions, deletions, or substitutions), SEQ ID NO:18 (or SEQ ID NO:18 with one, two, or three amino acid additions, deletions, or substitutions), and SEQ ID NO:19 (or SEQ ID NO:19 with one, two, or three amino acid additions, deletions, or substitutions), and a light chain variable domain or region comprising the amino acid sequences set forth in SEQ ID NO:25 (or SEQ ID NO:25 with one, two, or three amino acid additions, deletions, or substitutions), SEQ ID NO:26 (or SEQ ID NO:26 with one, two, or three amino acid additions, deletions, or substitutions), and SEQ ID NO:27 (or SEQ ID NO:27 with one, two, or three amino acid additions, deletions, or substitutions). The antigen binding fragment can comprise the ability to bind to SEQ ID NO:150 or SEQ ID NO:151. The antigen binding fragment can comprise the heavy chain variable domain or region of the (i). The heavy chain variable domain or region can comprise an amino acid sequence having at least 90 percent identity to the amino acid sequence set forth in SEQ ID NO:8. The antigen binding fragment can comprise the light chain variable domain or region of the (i). The light chain variable domain or region can comprise an amino acid sequence having at least 90 percent identity to the amino acid sequence set forth in SEQ ID NO:16. The antigen binding fragment can comprise the heavy chain variable domain or region of the (ii). The heavy chain variable domain or region can comprise an amino acid sequence having at least 90 percent identity to the amino acid sequence set forth in SEQ ID NO:24. The antigen binding fragment can comprise the light chain variable domain or region of the (ii). The light chain variable domain or region can comprise an amino acid sequence having at least 90 percent identity to the amino acid sequence set forth in SEQ ID NO:32. The antigen binding fragment can be monoclonal. The antigen binding fragment can be an Fab. The contacting can be performed in vitro. The contacting can be performed in vivo. The contacting can be performed within a mammal by administering the antibody or the antigen binding fragment to the mammal. The mammal can be a human.

In another aspect, this document features a method for binding a binding molecule to a CD66e polypeptide. The method comprises (or consists essentially of or consists of)

contacting the CD66e polypeptide with a chimeric antigen receptor described above, a cell engager described above, or an ADC described above. The contacting can be performed in vitro. The contacting can be performed in vivo. The contacting can be performed within a mammal by administering the chimeric antigen receptor, the cell engager, or the ADC to the mammal. The mammal can be a human.

Unless otherwise defined, all technical and scientific terms used herein have the same meaning as commonly understood by one of ordinary skill in the art to which this disclosure pertains. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 depicts amino acid residues 1 to 702 of a human CD66e polypeptide (SEQ ID NO:150). The underlined and bolded amino acid sequence (residues 501 to 682) of this human CD66e polypeptide depicts the A3-B3 domains (SEQ ID NO:151) and was used to identify CD66e binders.

FIGS. 2A and 2B depict the amino acid sequences of the heavy chain variable domain (FIG. 2A) and the light chain variable domain (FIG. 2B) of an Fab designated Clone #1 (ab1). The CDRs, framework sequences, and constant domains of each also are provided and delineated.

FIGS. 3A and 3B depict the amino acid sequences of the heavy chain variable domain (FIG. 3A) and the light chain variable domain (FIG. 3B) of an Fab designated Clone #2 (ab2). The CDRs, framework sequences, and constant domains of each also are provided and delineated.

FIG. 4 depicts the nucleic acid sequences encoding the indicated chains/domains of Clones #1-#2.

FIG. 5 depicts the structure of an exemplary Ig and provides the amino acid and nucleic acid sequences of an exemplary hinge, CH2, and CH3 regions/domains.

FIG. 6A depicts the structure of exemplary scFv's. FIGS. 6B and 6C depict the amino acid sequences of an exemplary heavy chain variable domain (FIG. 6B) and an exemplary light chain variable domain (FIG. 6C) of an exemplary scFv. The CDRs and framework sequences of each also are delineated. An exemplary linker amino acid sequence such as a linker amino acid sequence set forth in FIG. 10 can be used to link the heavy chain variable domain and the light chain variable domain together to form a scFv. FIGS. 6D-6G depict the structures of exemplary scFv's and provide the amino acid and nucleic acid sequences with the linker, CDRs, and framework sequences delineated. Linker sequences shown include a $(G_4S)_3$ linker (SEQ ID NO:78; FIGS. 6D and 6F) and a $(G_4S)_5$ linker (SEQ ID NO:101; FIGS. 6E and 6G).

FIGS. 7A and 7B depict the amino acid sequences of an exemplary heavy chain variable domain (FIG. 7A) and an exemplary light chain variable domain (FIG. 7B) of an exemplary scFv. The CDRs and framework sequences of each also are delineated. An exemplary linker amino acid sequence such as a linker amino acid sequence set forth in FIG. 10 can be used to link the heavy chain variable domain and the light chain variable domain together to form a scFv. FIG. 7C depicts the structures of exemplary scFv's and provides the amino acid and nucleic acid sequences with the linkers, CDRs, and framework sequences delineated. Linker sequences shown include a $(G_4S)_3$ linker (SEQ ID NO:78).

FIGS. 8A and 8B depict the amino acid sequences of an exemplary heavy chain variable domain (FIG. 8A) and an exemplary light chain variable domain (FIG. 8B) of an exemplary scFv. The CDRs and framework sequences of each also are delineated. An exemplary linker amino acid sequence such as a linker amino acid sequence set forth in FIG. 10 can be used to link the heavy chain variable domain and the light chain variable domain together to form a scFv.

FIGS. 9A and 9B depict the amino acid sequences of an exemplary heavy chain variable domain (FIG. 9A) and an exemplary light chain variable domain (FIG. 9B) of an exemplary scFv. The CDRs and framework sequences of each also are delineated. An exemplary linker amino acid sequence such as a linker amino acid sequence set forth in FIG. 10 can be used to link the heavy chain variable domain and the light chain variable domain together to form a scFv.

FIG. 10 depicts exemplary linker amino acid sequences that can be used to link a heavy chain variable domain and a light chain variable domain together to form a scFv. These linker sequences also can be used to create CARs and cell engagers.

FIG. 11A depicts the structure of an exemplary CARs. FIG. 11B is a schematic of an exemplary CAR construct designed to express a CAR. A promotor sequence (e.g., a CMV immediate early promotor sequence) can be followed by a signal peptide sequence (e.g., a GM-CSF signal peptide sequence), followed by a scFv provided herein (e.g., a scFv designed to include two sets of three CDRs such as CDR1, CDR2, and CDR3 of a heavy chain and CDR1, CDR2, and CDR3 of a light chain (in either order) of an antigen binding fragment provided herein, for example, SEQ ID NOs:1-3 and 9-11 or SEQ ID NOs:17-19 and 25-27), followed by an optional linker (not shown), followed by an optional hinge (e.g., a CD8 hinge sequence; not shown), followed by a transmembrane sequence (e.g., a CD8 transmembrane sequence), followed by one or more intracellular signaling domain sequences (e.g., a 4-1BB (CD137) intracellular signaling domain sequence and a CD3ζ intracellular signaling domain sequence).

FIG. 12 depicts the amino acid sequences of exemplary signal peptides that can be used to design a CAR.

FIG. 13 depicts the amino acid sequences of exemplary hinges that can be used to design a CAR.

FIG. 14 depicts the amino acid sequences of exemplary transmembrane domains that can be used to design a CAR.

FIG. 15 depicts the amino acid sequences of exemplary intracellular signaling domains that can be used to design a CAR.

FIG. 16 depicts an amino acid sequence of a CAR (CAR #1) designed to include a scFv created using the CDRs of the Clone #1 Fab and a nucleic acid sequence encoding that CAR. The various components of this CAR (e.g., domains and linkers) are provided and delineated.

FIG. 17A is a schematic of an exemplary BiTE designed using CDR1, CDR2, and CDR3 of a heavy chain provided herein and CDR1, CDR2, and CDR3 of a light chain provided herein in an Ig format (e.g., an IgG1 format). A humanized anti-CD3 scFv (e.g., an gOKT3-7 scFv set forth in U.S. Pat. No. 6,750,325) can be linked to the C-terminus of the light chain via a linker (e.g., a $(G_4S)_3$ linker (SEQ ID NO:78)). FIG. 17B depicts an amino acid sequence of a linker sequence (SEQ ID NO:162; nucleic acid sequence of the linker is SEQ ID NO:163) followed by an gOKT3-7 scFv sequence, which can be attached to a light chain as shown in FIG. 17A. FIG. 17B also depicts a nucleic acid sequence encoding that linker and gOKT3-7 scFv.

FIG. 18 depicts the amino acid sequences of exemplary antigen binding domains that can be used to design cell engagers that bind to T cells.

FIG. 19 depicts the amino acid sequences of exemplary antigen binding domains that can be used to design cell engagers that bind to NK cells and the amino acid and nucleic acid sequence for an exemplary BiKE. Sequences shown in the exemplary BiKE that binds to CD66e and NK cells include a $(G_4S)_3$ linker (SEQ ID NO:78), a $(G_4S)$ linker (SEQ ID NO:97), and a 6×His-tag (SEQ ID NO:246)

DETAILED DESCRIPTION

Figure 20A:
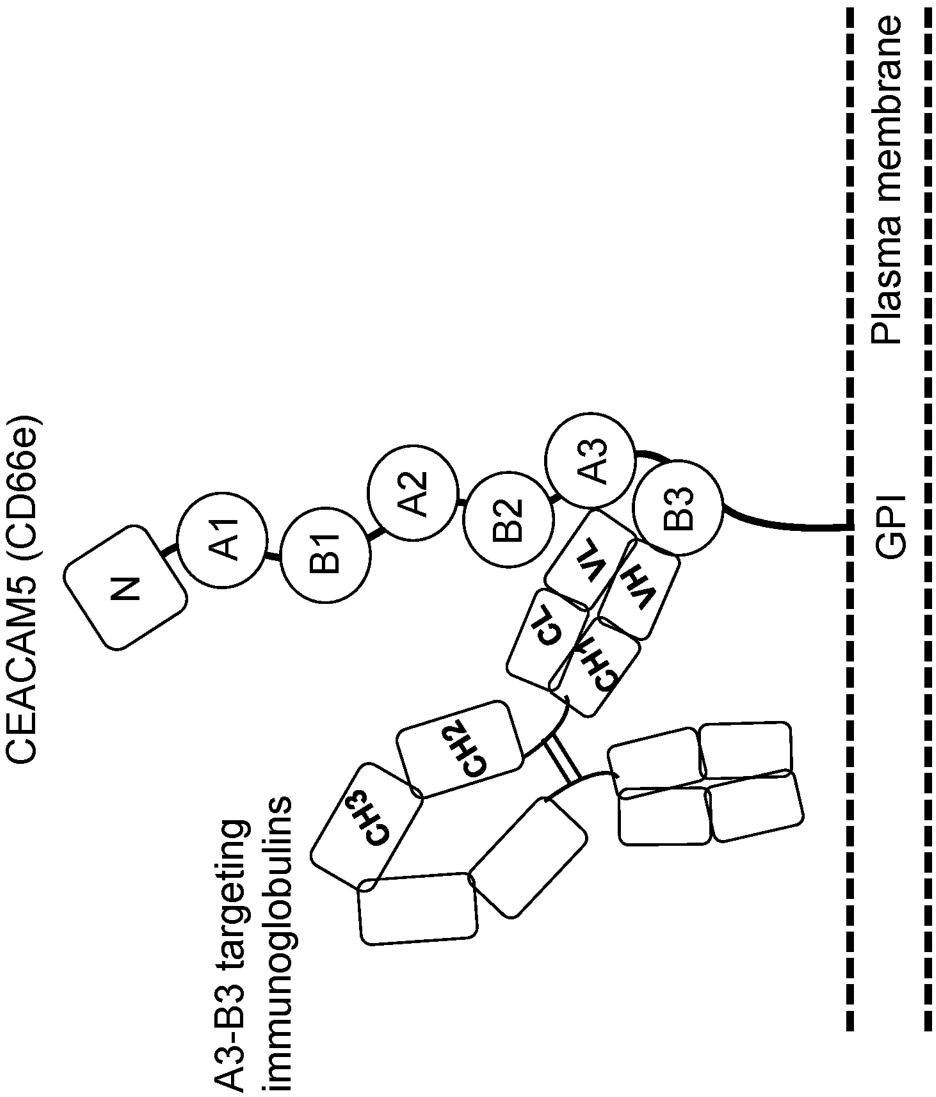
FIG. 20A is a schematic depicting the binding of exemplary antibodies provided herein to a CEACAM5 A3B3 domain.

This document provides binders (e.g., antibodies, antigen binding fragments, antibody domains, CARs, cell engagers, and ADCs) that bind (e.g., specifically bind) to a CD66e polypeptide (e.g., a human CD66e polypeptide). For example, the document provides binders (e.g., antibodies, antigen binding fragments, antibody domains, CARs, cell engagers, and ADCs) that bind (e.g., specifically bind) to a polypeptide comprising, consisting essentially of, or consisting of the amino acid set forth in SEQ ID NO:150 or SEQ ID NO:151 (see, e.g., FIG. 1). In some cases, a binder (e.g., an antibody, an antigen binding fragment, an antibody domain, a CAR, a cell engager, or an ADC) provided herein can have the ability to bind to a CD66e polypeptide and can lack the ability to bind to a CD66c polypeptide. For example, a binder (e.g., an antibody, an antigen binding fragment, an antibody domain, a CAR, a cell engager, or an ADC) provided herein can have the ability to bind to a human CD66e polypeptide and can lack the ability to bind to a human CD66c polypeptide.

The term “antibody” as used herein includes polyclonal antibodies, monoclonal antibodies, recombinant antibodies, humanized antibodies, human antibodies, chimeric antibodies, multi-specific antibodies (e.g., bispecific antibodies) formed from at least two antibodies, diabodies, single-chain variable fragment antibodies (e.g., scFv antibodies), and tandem single-chain variable fragments antibody (e.g., taFv). A diabody can include two chains, each having a heavy chain variable domain and a light chain variable domain, either from the same or from different antibodies (see, e.g., Hornig and Farber-Schwarz, *Methods Mol. Biol.,* 907:713-27 (2012); and Brinkmann and Kontermann, *MAbs.,* 9(2):182-212 (2017)). The two variable regions can be connected by a polypeptide linker (e.g., a polypeptide linker having five to ten residues in length or a polypeptide linker as set forth in FIG. 10). In some cases, an interdomain disulfide bond can be present in one or both of the heavy chain variable domain and light chain variable domain pairs of the diabody. A scFv is a single-chain polypeptide antibody in which the heavy chain variable domain and the light chain variable domain are directly connected or connected via a polypeptide linker (e.g., a polypeptide linker having eight to 18 residues in length or a polypeptide linker as set forth in FIG. 10). See, also, Chen et al., *Adv. Drug Deliv. Rev.,* 65(10):1357-1369 (2013). A scFv can be designed to have an orientation with the heavy chain variable domain being followed by the light chain variable domain or can be designed to have an orientation with the light chain variable domain being followed by the heavy chain variable domain. In both cases, the optional linker can be located between the two domains. Examples of scFv structures of scFv's provided herein include, without limitation, those structures set forth in FIGS. 6A-6Q 7A-7C, 8A-8B, and 9A-9B.

An antibody provided herein can include the CDRs as described herein (e.g., as described in Table 13) and can be configured to be a human antibody, a humanized antibody, or a chimeric antibody. In some cases, an antibody provided herein can include the CDRs as described herein (e.g., as described in Table 13) and can be a monoclonal antibody. In some cases, an antibody provided herein can include the CDRs as described herein (e.g., as described in Table 13) and can be configured as a scFv antibody.

The term "antigen binding fragment" as used herein refers to a fragment of an antibody (e.g., a fragment of a humanized antibody, a fragment of a human antibody, or a fragment of a chimeric antibody) having the ability to bind to an antigen. Examples of antigen binding fragments include, without limitation, Fab, Fab', or $F(ab')_2$ antigen binding fragments. An antigen binding fragment provided herein can include the CDRs as described herein (e.g., as described in Table 13) and can be configured to be a human antigen binding fragment, a humanized antigen binding fragment, or a chimeric antigen binding fragment. In some cases, an antigen binding fragment provided herein can include the CDRs as described herein (e.g., as described in Table 13) and can be a monoclonal antigen binding fragment. In some cases, an antigen binding fragment provided herein can include the CDRs as described herein (e.g., as described in Table 13) and can be configured as an Fab antibody. In some cases, a Fab antibody can include a partial hinge sequence (e.g., SEQ ID NO:152) for disulfide bonding between heavy and light chains of the Fab.

The term "antibody domain" as used herein refers to a domain of an antibody such as a heavy chain variable domain (VH domain) or a light chain variable domain (VL domain) in the absence of one or more other domains of an antibody. In some cases, an antibody domain can be a single antibody domain (e.g., a VH domain or a VL domain) having the ability to bind to an antigen. An antibody domain provided herein can include the CDRs as described herein (e.g., as described in Table 13) and can be a human antibody domain (e.g., a human VH domain), a humanized antibody domain (e.g., a humanized VH domain), or a chimeric antibody domain (e.g., a chimeric VH domain). In some cases, an antibody domain provided herein can include the CDRs as described herein (e.g., as described in Table 13) and can be a monoclonal antibody domain. In some cases, an antibody domain provided herein can include the CDRs as described herein (e.g., as described in Table 13) and can be engineered as a single VH domain or a single VL domain.

An anti-CD66e antibody, anti-CD66e antigen binding fragment, or anti-CD66e antibody domain provided herein can be of the IgA-, IgD-, IgE-, IgG-, or IgM-type, including IgG- or IgM-types such as, without limitation, $IgG_1$-, $IgG_2$-, $IgG_3$-, $IgG_4$-, $IgM_1$-, and $IgM_2$-types. In some cases, an antibody provided herein (e.g., an anti-CD66e antibody) can be a scFv antibody. In some cases, an antigen binding fragment provided herein (e.g., an anti-CD66e antibody fragment) can be an Fab. In some cases, an antibody provided herein (e.g., an anti-CD66e antibody) can be a fully intact antibody having the structure set forth in FIG. 5. In some cases, an antibody domain provided herein (e.g., an anti-CD66e antibody domain) can be a VH domain.

The term "chimeric antigen receptor" as used herein refers to a chimeric polypeptide that is designed to include an optional signal peptide, an antigen binding domain, an optional hinge, a transmembrane domain, and one or more intracellular signaling domains. As described herein, the antigen binding domain of a CAR provided herein can be designed to bind to a CD66e polypeptide (e.g., a human CD66e polypeptide). For example, a CAR provided herein can be designed to include the components of an antibody, antigen binding fragment, and/or antibody domain described herein (e.g., a combination of CDRs) as an antigen binding domain provided that that antigen binding domain has the ability to bind to a CD66e polypeptide (e.g., a human CD66e polypeptide). In some examples, a CAR provided herein can be designed to include an antigen binding domain that includes two sets of three CDRs (e.g., CDR1, CDR2, and CDR3 of a heavy chain and CDR1, CDR2, and CDR3 of a light chain) of an antigen binding fragment provided herein (e.g., SEQ ID NOs:1-3 and 9-11 or SEQ ID NOs:17-19 and 25-27). In some cases, an antigen binding domain of a CAR targeting a CD66e polypeptide can be designed to include a VH domain described herein or a scFv antibody described herein.

Examples of CAR structures that can be used to make a CAR provided herein include, without limitation, those set forth in FIGS. 11A and 11B.

In some cases, a CAR provided herein can be designed to include a signal peptide. Any appropriate signal peptide can be used to design a CAR described herein. Examples of signal peptide that can be used to make a CAR described herein include without limitation, a human IGKV1-39-derived signal peptide, IGKV1-16, IGKV1-33, IGKV3-11, IGKV4-1, or IGKV6-21. In some cases, a CAR provided herein can be designed to include a signal peptide that comprises, consists essentially of, or consists of one of the amino acid sequences set forth in FIG. 12. In some cases, a CAR provided herein can be designed to include a signal peptide that comprises, consists essentially of, or consists of one of the amino acid sequences set forth in FIG. 12 with one, two, three, four, five, six, seven, eight, nine, or ten amino acid deletions, additions, substitutions, or combinations thereof. In some cases, a CAR provided herein can be designed to include a signal peptide that comprises, consists essentially of, or consists of one of the amino acid sequences set forth in FIG. 12 with two or less, three or less, four or less, five or less, six or less, seven or less, eight or less, nine or less, or ten or less amino acid deletions, additions, substitutions, or combinations thereof.

In some cases, a CAR provided herein can be designed to include a hinge. Any appropriate hinge can be used to design a CAR described herein. Examples of hinges that can be used to make a CAR described herein include, without limitation, Ig-derived hinges (e.g., an IgG1-derived hinge, an $IgG_2$-derived hinge, or an $IgG_4$-derived hinge), Ig-derived hinges containing a CD2 domain and a CD3 domain, Ig-derived hinges containing a CD2 domain and lacking a CD3 domain, Ig-derived hinges containing a CD3 domain and lacking a CD2 domain, Ig-derived hinges lacking a CD2 domain and lacking a CD3 domain, CD8α-derived hinges, CD28-derived hinges, and CD3ζ-derived hinges. A CAR provided herein can be designed to include a hinge of any appropriate length. For example, a CAR provided herein can be designed to include a hinge that is from about 3 to about 75 (e.g., from about 3 to about 65, from about 3 to about 50, from about 5 to about 75, from about 10 to about 75, from about 5 to about 50, from about 10 to about 50, from about 10 to about 40, or from about 10 to about 30) amino acid residues in length. In some cases, a linker sequence can be used as a hinge to make a CAR described herein. For example, any one of the linker sequences set forth in FIG. 10 can be used as a hinge of a CAR described herein.

In some cases, a CAR provided herein can be designed to include a hinge that comprises, consists essentially of, or consists of one of the amino acid sequences set forth in FIG. 10 or FIG. 13. In some cases, a CAR provided herein can be designed to include a hinge that comprises, consists essentially of, or consists of one of the amino acid sequences set forth in FIG. 10 or FIG. 13 with one, two, three, four, five, six, seven, eight, nine, or ten amino acid deletions, additions, substitutions, or combinations thereof. In some cases, a CAR provided herein can be designed to include a hinge that comprises, consists essentially of, or consists of one of the amino acid sequences set forth in FIG. 10 or FIG. 13 with two or less, three or less, four or less, five or less, six or less, seven or less, eight or less, nine or less, or ten or less amino acid deletions, additions, substitutions, or combinations thereof.

A CAR provided herein can be designed to include any appropriate transmembrane domain. For example, the transmembrane domain of a CAR provided herein can be, without limitation, a CD3ζ transmembrane domain, a CD4 transmembrane domain, a CD8α transmembrane domain, a CD28 transmembrane domain, and a 4-1BB transmembrane domain. In some cases, a CAR provided herein can be designed to include a transmembrane domain that comprises, consists essentially of, or consists of one of the amino acid sequences set forth in FIG. 14. In some cases, a CAR provided herein can be designed to include a transmembrane domain that comprises, consists essentially of, or consists of one of the amino acid sequences set forth in FIG. 14 with one, two, three, four, five, six, seven, eight, nine, or ten amino acid deletions, additions, substitutions, or combinations thereof. In some cases, a CAR provided herein can be designed to include a transmembrane domain that comprises, consists essentially of, or consists of one of the amino acid sequences set forth in FIG. 14 with two or less, three or less, four or less, five or less, six or less, seven or less, eight or less, nine or less, or ten or less amino acid deletions, additions, substitutions, or combinations thereof.

A CAR provided herein can be designed to include one or more intracellular signaling domains. For example, a CAR provided herein can be designed to include one, two, three, or four intracellular signaling domains. Any appropriate intracellular signaling domain or combination of intracellular signaling domains can be used to make a CAR described herein. Examples of intracellular signaling domains that can be used to make a CAR described herein include, without limitation, CD3ζ intracellular signaling domains, CD27 intracellular signaling domains, CD28 intracellular signaling domains, OX40 (CD134) intracellular signaling domains, 4-1BB (CD137) intracellular signaling domains, CD278 intracellular signaling domains, DAP10 intracellular signaling domains, and DAP12 intracellular signaling domains. In some cases, a CAR described herein can be designed to be a first generation CAR having a CD3ζ intracellular signaling domain. In some cases, a CAR described herein can be designed to be a second generation CAR having a CD28 intracellular signaling domain followed by a CD3ζ intracellular signaling domain. In some cases, a CAR described herein can be designed to be a third generation CAR having (a) a CD28 intracellular signaling domain followed by (b) a CD27 intracellular signaling domain, an OX40 intracellular signaling domains, or a 4-1BB intracellular signaling domain followed by (c) a CD3ζ intracellular signaling domain. In some cases, a CAR provided herein can be designed to include at least one intracellular signaling domain that comprises, consists essentially of, or consists of one of the amino acid sequences set forth in FIG. 15. In some cases, a CAR provided herein can be designed to include at least one intracellular signaling domain that comprises, consists essentially of, or consists of one of the amino acid sequences set forth in FIG. 15 with one, two, three, four, five, six, seven, eight, nine, or ten amino acid deletions, additions, substitutions, or combinations thereof, provided that that intracellular signaling domain has at least some activity to activate intracellular signaling. In some cases, a CAR provided herein can be designed to include at least one intracellular signaling domain that comprises, consists essentially of, or consists of one of the amino acid sequences set forth in FIG. 15 with two or less, three or less, four or less, five or less, six or less, seven or less, eight or less, nine or less, or ten or less amino acid deletions, additions, substitutions, or combinations thereof, provided that that intracellular signaling domain has at least some activity to activate intracellular signaling.

In some cases, a CAR targeting a CD66e polypeptide can be designed to include an scFv having a heavy chain variable domain comprising SEQ ID NO:1, SEQ ID NO:2, and SEQ ID NO:3, followed by a linker such as a linker set forth in FIG. 10, followed by a light chain variable domain comprising SEQ ID NO:9, SEQ ID NO:10, and SEQ ID NO:11, followed by a hinge such as a hinge/linker set forth in FIG. 10 or FIG. 13 (e.g., an $IgG_4$-derived hinge, a CD8α hinge, or a linker plus $IgG_4$-derived hinge), followed by a transmembrane domain such as a transmembrane domain set forth in FIG. 14 (e.g., a human CD28 transmembrane domain or a CD8α transmembrane domain), followed by one or more intracellular signaling domains such as one or more intracellular signaling domain set forth in FIG. 15 (e.g., a human 4-1BB intracellular signaling domain followed by a human CD3ζ intracellular signaling domain). For example, a CAR targeting a CD66e polypeptide can be designed to include an scFv having a heavy chain variable domain comprising SEQ ID NO:1, SEQ ID NO:2, and SEQ ID NO:3, followed by SEQ ID NO:100, followed by a light chain variable domain comprising SEQ ID NO:9, SEQ ID NO:10, and SEQ ID NO:11, followed by SEQ ID NO:102, followed by SEQ ID NO:108, followed by SEQ ID NO:119, followed by SEQ ID NO:124, followed by SEQ ID NO:123, followed by SEQ ID NO:97, followed by SEQ ID NO:121.

In some cases, a CAR targeting a CD66e polypeptide can be designed to include an scFv having a heavy chain variable domain comprising SEQ ID NO:8, followed by a linker such as a linker set forth in FIG. 10, followed by a light chain variable domain comprising SEQ ID NO:16, followed by a hinge such as a hinge/linker set forth in FIG. 10 or FIG. 13 (e.g., an $IgG_4$-derived hinge, a CD8α hinge, or a linker plus $IgG_4$-derived hinge), followed by a transmembrane domain such as a transmembrane domain set forth in FIG. 14 (e.g., a human CD28 transmembrane domain or a CD8α transmembrane domain), followed by one or more intracellular signaling domains such as one or more intracellular signaling domain set forth in FIG. 15 (e.g., a human 4-1BB intracellular signaling domain followed by a human CD3ζ intracellular signaling domain). For example, a CAR targeting a CD66e polypeptide can be designed to include an scFv having a heavy chain variable domain comprising SEQ ID NO:8, followed by SEQ ID NO:100, followed by a light chain variable domain comprising SEQ ID NO:16, followed by SEQ ID NO:102, followed by SEQ ID NO:108, followed by SEQ ID NO:119, followed by SEQ ID NO:124, followed by SEQ ID NO:123, followed by SEQ ID NO:97, followed by SEQ ID NO:121.

In some cases, a CAR targeting a CD66e polypeptide can be designed to include an scFv having a light chain variable domain comprising SEQ ID NO:9, SEQ ID NO:10, and SEQ ID NO:11, followed by a linker such as a linker set forth in FIG. 10, followed by a heavy chain variable domain comprising SEQ ID NO:1, SEQ ID NO:2, and SEQ ID NO:3, followed by a hinge such as a hinge/linker set forth in FIG. 10 or FIG. 13 (e.g., an $IgG_4$-derived hinge, a CD8α hinge, or a linker plus $IgG_4$-derived hinge), followed by a transmembrane domain such as a transmembrane domain set forth in FIG. 14 (e.g., a human CD28 transmembrane domain or a CD8α transmembrane domain), followed by one or more intracellular signaling domains such as one or more intracellular signaling domain set forth in FIG. 15 (e.g., a human 4-1BB intracellular signaling domain followed by a human CD3ζ intracellular signaling domain). For example, a CAR targeting a CD66e polypeptide can be designed to include an scFv having a light chain variable domain comprising SEQ ID NO:9, SEQ ID NO:10, and SEQ ID NO:11, followed by SEQ ID NO:100, followed by a heavy chain variable domain comprising SEQ ID NO:1, SEQ ID NO:2, and SEQ ID NO:3, followed by SEQ ID NO:102, followed by SEQ ID NO:108, followed by SEQ ID NO:119, followed by SEQ ID NO:124, followed by SEQ ID NO:123, followed by SEQ ID NO:97, followed by SEQ ID NO:121 (see, e.g., FIG. 16).

In some cases, a CAR targeting a CD66e polypeptide can be designed to include an scFv having a light chain variable domain comprising SEQ ID NO:16, followed by a linker such as a linker set forth in FIG. 10, followed by a heavy chain variable domain comprising SEQ ID NO:8, followed by a hinge such as a hinge/linker set forth in FIG. 10 or FIG. 13 (e.g., an $IgG_4$-derived hinge, a CD8α hinge, or a linker plus $IgG_4$-derived hinge), followed by a transmembrane domain such as a transmembrane domain set forth in FIG. 14 (e.g., a human CD28 transmembrane domain or a CD8α transmembrane domain), followed by one or more intracellular signaling domains such as one or more intracellular signaling domain set forth in FIG. 15 (e.g., a human 4-1BB intracellular signaling domain followed by a human CD3ζ intracellular signaling domain). For example, a CAR targeting a CD66e polypeptide can be designed to include an scFv having a light chain variable domain comprising SEQ ID NO:16, followed by SEQ ID NO:100, followed by a heavy chain variable domain comprising SEQ ID NO:8, followed by SEQ ID NO:102, followed by SEQ ID NO:108, followed by SEQ ID NO:119, followed by SEQ ID NO:124, followed by SEQ ID NO:123, followed by SEQ ID NO:97, followed by SEQ ID NO:121 (see, e.g., FIG. 16).

In some cases, a CAR targeting a CD66e polypeptide can be designed to include an scFv having a heavy chain variable domain comprising SEQ ID NO:17, SEQ ID NO:18, and SEQ ID NO:19, followed by a linker such as a linker set forth in FIG. 10, followed by a light chain variable domain comprising SEQ ID NO:25, SEQ ID NO:26, and SEQ ID NO:27, followed by a hinge such as a hinge/linker set forth in FIG. 10 or FIG. 13 (e.g., an $IgG_4$-derived hinge, a CD8α hinge, or a linker plus $IgG_4$-derived hinge), followed by a transmembrane domain such as a transmembrane domain set forth in FIG. 14 (e.g., a human CD28 transmembrane domain or a CD8α transmembrane domain), followed by one or more intracellular signaling domains such as one or more intracellular signaling domain set forth in FIG. 15 (e.g., a human 4-1BB intracellular signaling domain followed by a human CD3ζ intracellular signaling domain). For example, a CAR targeting a CD66e polypeptide can be designed to include an scFv having a heavy chain variable domain comprising SEQ ID NO:17, SEQ ID NO:18, and SEQ ID NO:19, followed by SEQ ID NO:100, followed by a light chain variable domain comprising SEQ ID NO:25, SEQ ID NO:26, and SEQ ID NO:27, followed by SEQ ID NO:102, followed by SEQ ID NO:108, followed by SEQ ID NO:119, followed by SEQ ID NO:124, followed by SEQ ID NO:123, followed by SEQ ID NO:97, followed by SEQ ID NO:121.

In some cases, a CAR targeting a CD66e polypeptide can be designed to include an scFv having a heavy chain variable domain comprising SEQ ID NO:24, followed by a linker such as a linker set forth in FIG. 10, followed by a light chain variable domain comprising SEQ ID NO:32, followed by a hinge such as a hinge/linker set forth in FIG. 10 or FIG. 13 (e.g., an $IgG_4$-derived hinge, a CD8α hinge, or a linker plus $IgG_4$-derived hinge), followed by a transmembrane domain such as a transmembrane domain set forth in FIG. 14 (e.g., a human CD28 transmembrane domain or a CD8α transmembrane domain), followed by one or more intracellular signaling domains such as one or more intracellular signaling domain set forth in FIG. 15 (e.g., a human 4-1BB intracellular signaling domain followed by a human CD3ζ intracellular signaling domain). For example, a CAR targeting a CD66e polypeptide can be designed to include an scFv having a heavy chain variable domain comprising SEQ ID NO:24, followed by SEQ ID NO:100, followed by a light chain variable domain comprising SEQ ID NO:32, followed by SEQ ID NO:102, followed by SEQ ID NO:108, followed by SEQ ID NO:119, followed by SEQ ID NO:124, followed by SEQ ID NO:123, followed by SEQ ID NO:97, followed by SEQ ID NO:121.

In some cases, a CAR targeting a CD66e polypeptide can be designed to include an scFv having a light chain variable domain comprising SEQ ID NO:25, SEQ ID NO:26, and SEQ ID NO:27, followed by a linker such as a linker set forth in FIG. 10, followed by a heavy chain variable domain comprising SEQ ID NO:17, SEQ ID NO:18, and SEQ ID NO:19, followed by a hinge such as a hinge/linker set forth in FIG. 10 or FIG. 13 (e.g., an $IgG_4$-derived hinge, a CD8α hinge, or a linker plus $IgG_4$-derived hinge), followed by a transmembrane domain such as a transmembrane domain set forth in FIG. 14 (e.g., a human CD28 transmembrane domain or a CD8α transmembrane domain), followed by one or more intracellular signaling domains such as one or more intracellular signaling domain set forth in FIG. 15 (e.g., a human 4-1BB intracellular signaling domain followed by a human CD3ζ intracellular signaling domain). For example, a CAR targeting a CD66e polypeptide can be designed to include an scFv having a light chain variable domain comprising SEQ ID NO:25, SEQ ID NO:26, and SEQ ID NO:27, followed by SEQ ID NO:100, followed by a heavy chain variable domain comprising SEQ ID NO:17, SEQ ID NO:18, and SEQ ID NO:19, followed by SEQ ID NO:102, followed by SEQ ID NO:108, followed by SEQ ID NO:119, followed by SEQ ID NO:124, followed by SEQ ID NO:123, followed by SEQ ID NO:97, followed by SEQ ID NO:121.

In some cases, a CAR targeting a CD66e polypeptide can be designed to include an scFv having a light chain variable domain comprising SEQ ID NO:32, followed by a linker such as a linker set forth in FIG. 10, followed by a heavy chain variable domain comprising SEQ ID NO:24, followed by a hinge such as a hinge/linker set forth in FIG. 10 or FIG. 13 (e.g., an $IgG_4$-derived hinge, a CD8α hinge, or a linker plus $IgG_4$-derived hinge), followed by a transmembrane domain such as a transmembrane domain set forth in FIG. 14 (e.g., a human CD28 transmembrane domain or a CD8α transmembrane domain), followed by one or more intracellular signaling domains such as one or more intracellular signaling domain set forth in FIG. 15 (e.g., a human 4-1BB intracellular signaling domain followed by a human CD3ζ intracellular signaling domain). For example, a CAR targeting a CD66e polypeptide can be designed to include an scFv having a light chain variable domain comprising SEQ ID NO:32, followed by SEQ ID NO:100, followed by a heavy chain variable domain comprising SEQ ID NO:24, followed by SEQ ID NO:102, followed by SEQ ID NO:108, followed by SEQ ID NO:119, followed by SEQ ID NO:124, followed by SEQ ID NO:123, followed by SEQ ID NO:97, followed by SEQ ID NO:121.

The term "cell engager" as used herein refers to a polypeptide that includes two or more antigen binding domains (e.g., two, three, or four antigen binding domains) and has the ability to link two cells together. Examples of cell engagers include, without limitation, BiTEs, BiKEs, and TriKEs. In general, a cell engager provided herein can be designed to include at least one antigen binding domain having the ability to bind to a CD66e polypeptide (e.g., a human CD66e polypeptide) and at least one antigen binding domain having the ability to bind to an antigen expressed on the surface of a cell (e.g., a T cell or an NK cell). In some cases, a cell engager described herein can link a $CD66e^{+}$ cell (e.g., a $CD66e^{+}$ cancer cell) to another cell (e.g., a T cell or an NK cell) via the two or more antigen binding domains of the cell engager. An example of a cell engager structure of cell engagers provided herein includes, without limitation, the structure set forth in FIG. 17A. In some cases, the anti-CD3 scFv depicted in FIG. 17A can be replace with a different antigen binding domain having the ability to bind to an antigen expressed on the surface of a cell (e.g., a T cell or an NK cell).

When a cell engager includes an antigen binding domain having the ability to bind to a CD66e polypeptide (e.g., a human CD66e polypeptide) and two or more other antigen binding domains (e.g., two, three, or four other antigen binding domains), each of those other antigen binding domains can bind to different antigens expressed on the surface of different cell types or can bind to different antigens expressed on the surface of the same cell type. For example, a TriKE can be designed to have a first antigen binding domain having the ability to bind to a CD66e polypeptide (e.g., a human CD66e polypeptide), a second antigen binding domain having the ability to bind to a first antigen expressed on the surface of an NK cell (e.g., a CD16 polypeptide such as a CD16a polypeptide), and a third antigen binding domain having the ability to bind to a second antigen expressed on the surface of an NK cell (e.g., an NKG2A polypeptide).

As described herein, at least one antigen binding domain of a cell engager provided herein can be designed to bind to a CD66e polypeptide (e.g., a human CD66e polypeptide). For example, a cell engager provided herein can be designed to include the components of an antibody, antigen binding fragment, and/or antibody domain described herein (e.g., a combination of CDRs) as an antigen binding domain provided that that antigen binding domain has the ability to bind to a CD66e polypeptide (e.g., a human CD66e polypeptide). In some examples, a cell engager provided herein can be designed to include an antigen binding domain that includes two sets of three CDRs (e.g., CDR1, CDR2, and CDR3 of a heavy chain and CDR1, CDR2, and CDR3 of a light chain) of an antigen binding fragment provided herein (e.g., SEQ ID NOs:1-3 and 9-11 or SEQ ID NOs:17-19 and 25-27). In some cases, an antigen binding domain of a cell engager targeting a CD66e polypeptide can be designed to include a VH domain described herein or a scFv/Fab antibody described herein. In some cases, an antigen binding domain of a CAR described herein that has the ability to bind to a CD66e polypeptide (e.g., a human CD66e polypeptide) can be used as an antigen binding domain of a cell engager that targets $CD66e^{+}$ cells.

As described herein, a cell engager can be designed to include at least one antigen binding domain having the ability to bind to a CD66e polypeptide (e.g., a human CD66e polypeptide) and at least one other antigen binding domain. That at least one other antigen binding domain can have the ability to bind to any appropriate antigen expressed on the surface of a cell. For example, when designing a cell engager such as a BiTE to link a $CD66e^{+}$ cell and a T cell, the cell engager can include an antigen binding domain having the ability to bind to a CD66e polypeptide (e.g., a human CD66e polypeptide) and an antigen binding domain having the ability to bind to a polypeptide expressed on the surface of a T cell. Examples example of polypeptides expressed on the surface of a T cell that can be targeted by an antigen binding domain of a cell engager provided herein include, without limitation, CD3 polypeptides. Examples of antigen binding domains having the ability to bind to a polypeptide expressed on the surface of a T cell that can be used to make a cell engager provided herein (e.g., a BiTE) include, without limitation, anti-CD3 scFvs and anti-CD3 VH domains. Additional examples of amino acid sequences that can be used as antigen binding domains having the ability to bind to a polypeptide expressed on the surface of a T cell (e.g., CD3) are described in U.S. Pat. No. 6,750,325 (see, e.g., the sequence listing of U.S. Pat. No. 6,750,325).

In some cases, a cell engager provided herein can be designed to include an antigen binding domain that comprises, consists essentially of, or consists of one of the amino acid sequences set forth in FIG. 18. In some cases, a cell engager provided herein can be designed to include an antigen binding domain that comprises, consists essentially of, or consists of one of the amino acid sequences set forth in FIG. 18 with one, two, three, four, five, six, seven, eight, nine, or ten amino acid deletions, additions, substitutions, or combinations thereof, provided that the antigen binding domain has the ability to bind to a polypeptide expressed on the surface of a T cell. In some cases, a cell engager provided herein can be designed to include an antigen binding domain that comprises, consists essentially of, or consists of one of the amino acid sequences set forth in FIG. 18 with two or less, three or less, four or less, five or less, six or less, seven or less, eight or less, nine or less, or ten or less amino acid deletions, additions, substitutions, or combinations thereof, provided that the antigen binding domain has the ability to bind to a polypeptide expressed on the surface of a T cell.

When designing a cell engager such as a BiKE or a TriKE to link a CD66e$^{+}$ cell and an NK cell, the cell engager can include an antigen binding domain having the ability to bind to a CD66e polypeptide (e.g., a human CD66e polypeptide) and one or more (e.g., one, two, or three) antigen binding domains having the ability to bind to a polypeptide expressed on the surface of an NK cell. Examples of polypeptides expressed on the surface of an NK cell that can be targeted by an antigen binding domain of a cell engager provided herein include, without limitation, CD16 polypeptides (e.g., CD16a polypeptides), NKG2A polypeptides, NKG2D polypeptides, NKp30 polypeptides, NKp44 polypeptides, and NKp46 polypeptides. Examples of antigen binding domains having the ability to bind to a polypeptide expressed on the surface of an NK cell that can be used to make a cell engager provided herein (e.g., a BiKE or TriKE) include, without limitation, anti-CD16a scFvs, anti-NKG2A scFvs, anti-NKG2D scFvs, anti-NKp30 scFvs (see, e.g., BioLegend Catalog #325207), anti-NKp44 scFvs, anti-NKp46 scFvs, anti-CD16a VH domains, anti-NKG2A VH domains, anti-NKG2D VH domains, anti-NKp30 VH domains, anti-NKp44 VH domains, and anti-NKp46 VH domains. Additional examples of amino acid sequences that can be used as antigen binding domains having the ability to bind to a polypeptide expressed on the surface of an NK cell (e.g., CD16, NKG2A, NKG2D, or NKp46) are described in McCall et al. (*Mol. Immunol.,* 36(7):433-445 (1999); see, e.g., anti-CD16 scFv sequences); International Patent Application Publication No. PCT/US2017/048721 (see, e.g., the CDRs and sequence listing for anti-CD16a binding domains); U.S. Patent Application Publication No. 2011/0052606 (see, e.g., the CDRs and the sequence listing for anti-NKG2Antibodies such as Z199); U.S. Patent Application Publication No. 2011/0150870 (see, e.g., the CDRs and sequence listing for anti-NKG2D antibodies); U.S. Patent Application Publication No. 2018/0369373 (see, e.g., the CDRs and sequence listing for anti-NKp46 antibodies); and U.S. Patent Application Publication No. 2017/0368169 (see, e.g., the CDRs and sequence listing for anti-NKp46 antibodies).

In some cases, a cell engager provided herein can be designed to include an antigen binding domain (e.g., a scFv or VH) that comprises, consists essentially of, or consists of one or more of the amino acid sequences set forth in FIG. 19. In some cases, a cell engager provided herein can be designed to include an antigen binding domain (e.g., a scFv or VH) that comprises, consists essentially of, or consists of one of the amino acid sequences set forth in FIG. 19 with one, two, three, four, five, six, seven, eight, nine, or ten amino acid deletions, additions, substitutions, or combinations thereof, provided that the antigen binding domain has the ability to bind to a polypeptide expressed on the surface of an NK cell. In some cases, a cell engager provided herein can be designed to include an antigen binding domain (e.g., a scFv or VH) that comprises, consists essentially of, or consists of one of the amino acid sequences set forth in FIG. 19 with two or less, three or less, four or less, five or less, six or less, seven or less, eight or less, nine or less, or ten or less amino acid deletions, additions, substitutions, or combinations thereof, provided that the antigen binding domain has the ability to bind to a polypeptide expressed on the surface of an NK cell.

In some cases, a cell engager provided herein can be designed to include a linker located between each antigen binding domain. Any appropriate linker can be used to design a cell engager provided herein. Examples of linkers that can be used to make a cell engager described herein include, without limitation, the linker sequences set forth in FIG. 10. A cell engager provided herein can be designed to include a linker of any appropriate length. For example, a cell engager provided herein can be designed to include a linker that is from about 3 to about 100 (e.g., from about 3 to about 90, from about 3 to about 80, from about 3 to about 70, from about 3 to about 60, from about 3 to about 50, from about 3 to about 40, from about 3 to about 30, from about 3 to about 20, from about 3 to about 15, from about 5 to about 100, from about 10 to about 100, from about 20 to about 100, from about 30 to about 100, from about 40 to about 100, from about 50 to about 100, from about 60 to about 100, from about 70 to about 100, from about 10 to about 50, from about 10 to about 40, from about 10 to about 30, from about 10 to about 20, or from about 12 to about 17) amino acid residues in length. In some cases, a cell engager provided herein (e.g., a BiTE) can be designed to include a GGGGSGGGGSGGGGS (SEQ ID NO:78) linker. In some cases, a hinge of a CAR described herein can be used as a linker to make a cell engager described herein. For example, any one of the sequences set forth in FIG. 13 can be used as a linker of a cell engager described herein.

In some cases, a cell engager provided herein can be designed to include a linker that comprises, consists essentially of, or consists of one of the amino acid sequences set forth in FIG. 10 or FIG. 13. In some cases, a cell engager provided herein can be designed to include a linker that comprises, consists essentially of, or consists of one of the amino acid sequences set forth in FIG. 10 or FIG. 13 with one, two, three, four, five, six, seven, eight, nine, or ten amino acid deletions, additions, substitutions, or combinations thereof. In some cases, a cell engager provided herein can be designed to include a linker that comprises, consists essentially of, or consists of one of the amino acid sequences set forth in FIG. 10 or FIG. 13 with two or less, three or less, four or less, five or less, six or less, seven or less, eight or less, nine or less, or ten or less amino acid deletions, additions, substitutions, or combinations thereof.

In some cases, a cell engager (e.g., a BiTE) targeting a CD66e polypeptide can be designed to include an scFv having a heavy chain variable domain comprising SEQ ID NO:1, SEQ ID NO:2, and SEQ ID NO:3, followed by a linker such as a linker set forth in FIG. 10, followed by a light chain variable domain comprising SEQ ID NO:9, SEQ ID NO:10, and SEQ ID NO:11, followed by a linker such as a hinge/linker set forth in FIG. 10 or FIG. 13 (e.g., SEQ ID NO:78), followed by an antigen binding domain having the ability to bind to a polypeptide expressed on the surface of a T cell (e.g., an anti-human CD3 scFv).

In some cases, a cell engager (e.g., a BiTE) targeting a CD66e polypeptide can be designed to include an scFv having a light chain variable domain comprising SEQ ID NO:9, SEQ ID NO:10, and SEQ ID NO:11, followed by a linker such as a linker set forth in FIG. 10, followed by a heavy chain variable domain comprising SEQ ID NO:1, SEQ ID NO:2, and SEQ ID NO:3, followed by a linker such as a hinge/linker set forth in FIG. 10 or FIG. 13 (e.g., SEQ ID NO:78), followed by an antigen binding domain having the ability to bind to a polypeptide expressed on the surface of a T cell (e.g., an anti-human CD3 scFv).

In some cases, a cell engager (e.g., a BiTE) targeting a CD66e polypeptide can be designed to include an scFv having a heavy chain variable domain comprising SEQ ID NO:8, followed by a linker such as a linker set forth in FIG. 10, followed by a light chain variable domain comprising SEQ ID NO:16, followed by a linker such as a hinge/linker set forth in FIG. 10 or FIG. 13 (e.g., SEQ ID NO:78), followed by an antigen binding domain having the ability to bind to a polypeptide expressed on the surface of a T cell (e.g., an anti-human CD3 scFv).

In some cases, a cell engager (e.g., a BiTE) targeting a CD66e polypeptide can be designed to include an scFv having a light chain variable domain comprising SEQ ID NO:16, followed by a linker such as a linker set forth in FIG. 10, followed by a heavy chain variable domain comprising SEQ ID NO:8, followed by a linker such as a hinge/linker set forth in FIG. 10 or FIG. 13 (e.g., SEQ ID NO:78), followed by an antigen binding domain having the ability to bind to a polypeptide expressed on the surface of a T cell (e.g., an anti-human CD3 scFv).

In some cases, a cell engager (e.g., a BiKE or a TriKE) targeting a CD66e polypeptide can be designed to include an scFv having a heavy chain variable domain comprising SEQ ID NO:1, SEQ ID NO:2, and SEQ ID NO:3, followed by a linker such as a linker set forth in FIG. 10, followed by a light chain variable domain comprising SEQ ID NO:9, SEQ ID NO:10, and SEQ ID NO:11, followed by a linker such as a hinge/linker set forth in FIG. 10 or FIG. 13 (e.g., SEQ ID NO:78), followed by one or more antigen binding domains having the ability to bind to a polypeptide expressed on the surface of an NK cell (e.g., an anti-human CD16a scFv for a BiKE or an anti-human CD16a scFv and an anti-human NKG2A scFv for a TriKE).

In some cases, a cell engager (e.g., a BiKE or a TriKE) targeting a CD66e polypeptide can be designed to include an scFv having a light chain variable domain comprising SEQ ID NO:9, SEQ ID NO:10, and SEQ ID NO:11, followed by a linker such as a linker set forth in FIG. 10, followed by a heavy chain variable domain comprising SEQ ID NO:1, SEQ ID NO:2, and SEQ ID NO:3, followed by a linker such as a hinge/linker set forth in FIG. 10 or FIG. 13 (e.g., SEQ ID NO:78), followed by one or more antigen binding domains having the ability to bind to a polypeptide expressed on the surface of an NK cell (e.g., an anti-human CD16a scFv for a BiKE or an anti-human CD16a scFv and an anti-human NKG2A scFv for a TriKE).

In some cases, a cell engager (e.g., a BiKE or a TriKE) targeting a CD66e polypeptide can be designed to include an scFv having a heavy chain variable domain comprising SEQ ID NO:8, followed by a linker such as a linker set forth in FIG. 10, followed by a light chain variable domain comprising SEQ ID NO:16, followed by a linker such as a hinge/linker set forth in FIG. 10 or FIG. 13 (e.g., SEQ ID NO:78), followed by one or more antigen binding domains having the ability to bind to a polypeptide expressed on the surface of an NK cell (e.g., an anti-human CD16a scFv for a BiKE or an anti-human CD16a scFv and an anti-human NKG2A scFv for a TriKE).

In some cases, a cell engager (e.g., a BiKE or a TriKE) targeting a CD66e polypeptide can be designed to include an scFv having a light chain variable domain comprising SEQ ID NO:16, followed by a linker such as a linker set forth in FIG. 10, followed by a heavy chain variable domain comprising SEQ ID NO:8, followed by a linker such as a hinge/linker set forth in FIG. 10 or FIG. 13 (e.g., SEQ ID NO:78), followed by one or more antigen binding domains having the ability to bind to a polypeptide expressed on the surface of an NK cell (e.g., an anti-human CD16a scFv for a BiKE or an anti-human CD16a scFv and an anti-human NKG2A scFv for a TriKE).

In some cases, a cell engager (e.g., a BiTE) targeting a CD66e polypeptide can be designed to include an scFv having a heavy chain variable domain comprising SEQ ID NO:17, SEQ ID NO:18, and SEQ ID NO:19, followed by a linker such as a linker set forth in FIG. 10, followed by a light chain variable domain comprising SEQ ID NO:25, SEQ ID NO:26, and SEQ ID NO:27, followed by a linker such as a hinge/linker set forth in FIG. 10 or FIG. 13 (e.g., SEQ ID NO:78), followed by an antigen binding domain having the ability to bind to a polypeptide expressed on the surface of a T cell (e.g., an anti-human CD3 scFv).

In some cases, a cell engager (e.g., a BiTE) targeting a CD66e polypeptide can be designed to include an scFv having a light chain variable domain comprising SEQ ID NO:25, SEQ ID NO:26, and SEQ ID NO:27, followed by a linker such as a linker set forth in FIG. 10, followed by a heavy chain variable domain comprising SEQ ID NO:17, SEQ ID NO:18, and SEQ ID NO:19, followed by a linker such as a hinge/linker set forth in FIG. 10 or FIG. 13 (e.g., SEQ ID NO:78), followed by an antigen binding domain having the ability to bind to a polypeptide expressed on the surface of a T cell (e.g., an anti-human CD3 scFv).

In some cases, a cell engager (e.g., a BiTE) targeting a CD66e polypeptide can be designed to include an scFv having a heavy chain variable domain comprising SEQ ID NO:24, followed by a linker such as a linker set forth in FIG. 10, followed by a light chain variable domain comprising SEQ ID NO:32, followed by a linker such as a hinge/linker set forth in FIG. 10 or FIG. 13 (e.g., SEQ ID NO:78), followed by an antigen binding domain having the ability to bind to a polypeptide expressed on the surface of a T cell (e.g., an anti-human CD3 scFv).

In some cases, a cell engager (e.g., a BiTE) targeting a CD66e polypeptide can be designed to include an scFv having a light chain variable domain comprising SEQ ID NO:32, followed by a linker such as a linker set forth in FIG. 10, followed by a heavy chain variable domain comprising SEQ ID NO:24, followed by a linker such as a hinge/linker set forth in FIG. 10 or FIG. 13 (e.g., SEQ ID NO:78), followed by an antigen binding domain having the ability to bind to a polypeptide expressed on the surface of a T cell (e.g., an anti-human CD3 scFv).

In some cases, a cell engager (e.g., a BiKE or a TriKE) targeting a CD66e polypeptide can be designed to include an scFv having a heavy chain variable domain comprising SEQ ID NO:17, SEQ ID NO:18, and SEQ ID NO:19, followed by a linker such as a linker set forth in FIG. 10, followed by a light chain variable domain comprising SEQ ID NO:25, SEQ ID NO:26, and SEQ ID NO:27, followed by a linker such as a hinge/linker set forth in FIG. 10 or FIG. 13 (e.g., SEQ ID NO:78), followed by one or more antigen binding domains having the ability to bind to a polypeptide expressed on the surface of an NK cell (e.g., an anti-human CD16a scFv for a BiKE or an anti-human CD16a scFv and an anti-human NKG2A scFv for a TriKE).

In some cases, a cell engager (e.g., a BiKE or a TriKE) targeting a CD66e polypeptide can be designed to include an scFv having a light chain variable domain comprising SEQ ID NO:25, SEQ ID NO:26, and SEQ ID NO:27, followed by a linker such as a linker set forth in FIG. 10, followed by a heavy chain variable domain comprising SEQ ID NO:17, SEQ ID NO:18, and SEQ ID NO:19, followed by a linker such as a hinge/linker set forth in FIG. 10 or FIG. 13 (e.g., SEQ ID NO:78), followed by one or more antigen binding domains having the ability to bind to a polypeptide expressed on the surface of an NK cell (e.g., an anti-human CD16a scFv for a BiKE or an anti-human CD16a scFv and an anti-human NKG2A scFv for a TriKE).

In some cases, a cell engager (e.g., a BiKE or a TriKE) targeting a CD66e polypeptide can be designed to include an scFv having a heavy chain variable domain comprising SEQ ID NO:24, followed by a linker such as a linker set forth in FIG. 10, followed by a light chain variable domain comprising SEQ ID NO:32, followed by a linker such as a hinge/linker set forth in FIG. 10 or FIG. 13 (e.g., SEQ ID NO:78), followed by one or more antigen binding domains having the ability to bind to a polypeptide expressed on the surface of an NK cell (e.g., an anti-human CD16a scFv for a BiKE or an anti-human CD16a scFv and an anti-human NKG2A scFv for a TriKE).

In some cases, a cell engager (e.g., a BiKE or a TriKE) targeting a CD66e polypeptide can be designed to include an scFv having a light chain variable domain comprising SEQ ID NO:32, followed by a linker such as a linker set forth in FIG. 10, followed by a heavy chain variable domain comprising SEQ ID NO:24, followed by a linker such as a hinge/linker set forth in FIG. 10 or FIG. 13 (e.g., SEQ ID NO:78), followed by one or more antigen binding domains having the ability to bind to a polypeptide expressed on the surface of an NK cell (e.g., an anti-human CD16a scFv for a BiKE or an anti-human CD16a scFv and an anti-human NKG2A scFv for a TriKE).

In some cases, a cell engager (e.g., a BiTE) targeting a CD66e polypeptide can be designed to include an IgG (e.g., IgG1) configuration having (a) a heavy chain comprising, consisting essentially of, or consisting of a heavy chain variable domain comprising SEQ ID NO:1, SEQ ID NO:2, and SEQ ID NO:3, an Ig hinge, and constant domains (e.g., CH1, CH2, and CH3 domains) and (b) a light chain comprising, consisting essentially of, or consisting of a light chain variable domain comprising SEQ ID NO:9, SEQ ID NO:10, and SEQ ID NO:11, a constant domain (e.g., a kappa or lambda constant domain), and an antigen binding domain having the ability to bind to a polypeptide expressed on the surface of a T cell (e.g., an anti-human CD3 scFv).

In some cases, a cell engager (e.g., a BiTE) targeting a CD66e polypeptide can be designed to include an IgG (e.g., IgG1) configuration having (a) a heavy chain comprising, consisting essentially of, or consisting of a heavy chain variable domain comprising SEQ ID NO:8, an Ig hinge, and constant domains (e.g., CH1, CH2, and CH3 domains) and (b) a light chain comprising, consisting essentially of, or consisting of a light chain variable domain comprising SEQ ID NO:16, a constant domain (e.g., a kappa or lambda constant domain), and an antigen binding domain having the ability to bind to a polypeptide expressed on the surface of a T cell (e.g., an anti-human CD3 scFv).

In some cases, a cell engager (e.g., a BiKE) targeting a CD66e polypeptide can be designed to include an IgG (e.g., IgG1) configuration having (a) a heavy chain comprising, consisting essentially of, or consisting of a heavy chain variable domain comprising SEQ ID NO:1, SEQ ID NO:2, and SEQ ID NO:3, an Ig hinge, and constant domains (e.g., CH1, CH2, and CH3 domains) and (b) a light chain comprising, consisting essentially of, or consisting of a light chain variable domain comprising SEQ ID NO:9, SEQ ID NO:10, and SEQ ID NO:11, a constant domain (e.g., a kappa or lambda constant domain), and an antigen binding domain having the ability to bind to a polypeptide expressed on the surface of an NK cell (e.g., an anti-human CD16a scFv or an anti-human NKG2A scFv).

In some cases, a cell engager (e.g., a BiKE) targeting a CD66e polypeptide can be designed to include an IgG (e.g., IgG1) configuration having (a) a heavy chain comprising, consisting essentially of, or consisting of a heavy chain variable domain comprising SEQ ID NO:8, an Ig hinge, and constant domains (e.g., CH1, CH2, and CH3 domains) and (b) a light chain comprising, consisting essentially of, or consisting of a light chain variable domain comprising SEQ ID NO:16, a constant domain (e.g., a kappa or lambda constant domain), and an antigen binding domain having the ability to bind to a polypeptide expressed on the surface of an NK cell (e.g., an anti-human CD16a scFv or an anti-human NKG2A scFv).

In some cases, a cell engager (e.g., a BiTE) targeting a CD66e polypeptide can be designed to include an IgG (e.g., IgG1) configuration having (a) a heavy chain comprising, consisting essentially of, or consisting of a heavy chain variable domain comprising SEQ ID NO:17, SEQ ID NO:18, and SEQ ID NO:19, an Ig hinge, and constant domains (e.g., CH1, CH2, and CH3 domains) and (b) a light chain comprising, consisting essentially of, or consisting of a light chain variable domain comprising SEQ ID NO:25, SEQ ID NO:26, and SEQ ID NO:27, a constant domain (e.g., a kappa or lambda constant domain), and an antigen binding domain having the ability to bind to a polypeptide expressed on the surface of a T cell (e.g., an anti-human CD3 scFv).

In some cases, a cell engager (e.g., a BiTE) targeting a CD66e polypeptide can be designed to include an IgG (e.g., IgG1) configuration having (a) a heavy chain comprising, consisting essentially of, or consisting of a heavy chain variable domain comprising SEQ ID NO:24, an Ig hinge, and constant domains (e.g., CH1, CH2, and CH3 domains) and (b) a light chain comprising, consisting essentially of, or consisting of a light chain variable domain comprising SEQ ID NO:32, a constant domain (e.g., a kappa or lambda constant domain), and an antigen binding domain having the ability to bind to a polypeptide expressed on the surface of a T cell (e.g., an anti-human CD3 scFv).

In some cases, a cell engager (e.g., a BiKE) targeting a CD66e polypeptide can be designed to include an IgG (e.g., IgG1) configuration having (a) a heavy chain comprising, consisting essentially of, or consisting of a heavy chain variable domain comprising SEQ ID NO:17, SEQ ID NO:18, and SEQ ID NO:19, an Ig hinge, and constant domains (e.g., CH1, CH2, and CH3 domains) and (b) a light chain comprising, consisting essentially of, or consisting of a light chain variable domain comprising SEQ ID NO:25, SEQ ID NO:26, and SEQ ID NO:27, a constant domain (e.g., a kappa or lambda constant domain), and an antigen binding domain having the ability to bind to a polypeptide expressed on the surface of an NK cell (e.g., an anti-human CD16a scFv or an anti-human NKG2A scFv).

In some cases, a cell engager (e.g., a BiKE) targeting a CD66e polypeptide can be designed to include an IgG (e.g., IgG1) configuration having (a) a heavy chain comprising, consisting essentially of, or consisting of a heavy chain variable domain comprising SEQ ID NO:24, an Ig hinge, and constant domains (e.g., CH1, CH2, and CH3 domains) and (b) a light chain comprising, consisting essentially of, or consisting of a light chain variable domain comprising SEQ ID NO:32, a constant domain (e.g., a kappa or lambda constant domain), and an antigen binding domain having the ability to bind to a polypeptide expressed on the surface of an NK cell (e.g., an anti-human CD16a scFv or an anti-human NKG2A scFv).

In one embodiment, a binder (e.g., an antibody, antigen binding fragment, antibody domain, a CAR, a cell engager, and/or an ADC) provided herein having the ability to bind to a CD66e polypeptide (e.g., a human CD66e polypeptide) can include (i) a heavy chain variable domain having a CDR1 having the amino acid sequence set forth in SEQ ID NO:1 (or a variant of SEQ ID NO:1 with one or two amino acid modifications), a CDR2 having the amino acid sequence set forth in SEQ ID NO:2 (or a variant of SEQ ID NO:2 with one or two amino acid modifications), and a CDR3 having the amino acid sequence set forth in SEQ ID NO:3 (or a variant of SEQ ID NO:3 with one or two amino acid modifications); and/or (ii) a light chain variable domain having a CDR1 having the amino acid sequence set forth in SEQ ID NO:9 (or a variant of SEQ ID NO:9 with one or two amino acid modifications), a CDR2 having the amino acid sequence set forth in SEQ ID NO:10 (or a variant of SEQ ID NO:10 with one or two amino acid modifications), and a CDR3 having the amino acid sequence set forth SEQ ID NO:11 (or a variant of SEQ ID NO:11 with one or two amino acid modifications). An example of such an antigen binding fragment having these CDRs and the ability to bind to a CD66e polypeptide (e.g., a human CD66e polypeptide) includes, without limitation, the Fab set forth in FIGS. 2A and 2B.

In some cases, a binder (e.g., an antibody, antigen binding fragment, antibody domain, a CAR, a cell engager, and/or an ADC) provided herein having the ability to bind to a CD66e polypeptide (e.g., a human CD66e polypeptide) and (a) a heavy chain variable domain having a CDR1 having the amino acid sequence set forth in SEQ ID NO:1 (or a variant of SEQ ID NO:1 with one or two amino acid modifications), a CDR2 having the amino acid sequence set forth in SEQ ID NO:2 (or a variant of SEQ ID NO:2 with one or two amino acid modifications), and a CDR3 having the amino acid sequence set forth in SEQ ID NO:3 (or a variant of SEQ ID NO:3 with one or two amino acid modifications) and/or (b) a light chain variable domain having a CDR1 having the amino acid sequence set forth in SEQ ID NO:9 (or a variant of SEQ ID NO:9 with one or two amino acid modifications), a CDR2 having the amino acid sequence set forth in SEQ ID NO:10 (or a variant of SEQ ID NO:10 with one or two amino acid modifications), and a CDR3 having the amino acid sequence set forth SEQ ID NO:11 (or a variant of SEQ ID NO:11 with one or two amino acid modifications) can include any appropriate framework regions. For example, such a binder (e.g., an antibody, antigen binding fragment, antibody domain, a CAR, a cell engager, and/or an ADC) can include (a) a heavy chain variable domain that includes a framework region 1 having the amino acid sequence set forth in SEQ ID NO:4 (or a variant of SEQ ID NO:4 with one, two, three, four, five, six, seven, eight, nine, ten, or more amino acid modifications), a framework region 2 having the amino acid sequence set forth in SEQ ID NO:5 (or a variant of SEQ ID NO:5 with one, two, three, four, five, six, seven, eight, nine, ten, or more amino acid modifications), a framework region 3 having the amino acid sequence set forth in SEQ ID NO:6 (or a variant of SEQ ID NO:6 with one, two, three, four, five, six, seven, eight, nine, ten, or more amino acid modifications), and a framework region 4 having the amino acid sequence set forth in SEQ ID NO:7 (or a variant of SEQ ID NO:7 with one, two, three, four, five, six, seven, eight, nine, ten, or more amino acid modifications) and/or (b) a light chain variable domain that includes a framework region 1 having the amino acid sequence set forth in SEQ ID NO:12 (or a variant of SEQ ID NO:12 with one, two, three, four, five, six, seven, eight, nine, ten, or more amino acid modifications), a framework region 2 having the amino acid sequence set forth in SEQ ID NO:13 (or a variant of SEQ ID NO:13 with one, two, three, four, five, six, seven, eight, nine, ten, or more amino acid modifications), a framework region 3 having the amino acid sequence set forth in SEQ ID NO:14 (or a variant of SEQ ID NO:14 with one, two, three, four, five, six, seven, eight, nine, ten, or more amino acid modifications), and a framework region 4 having the amino acid sequence set forth in SEQ ID NO:15 (or a variant of SEQ ID NO:15 with one, two, three, four, five, six, seven, eight, nine, ten, or more amino acid modifications).

In some cases, a binder (e.g., an antibody, antigen binding fragment, antibody domain, a CAR, a cell engager, and/or an ADC) having any of the CDRs set forth in FIG. 2A or 2B can be designed to include framework regions as set forth in FIGS. 2A and 2B or can be designed to include one or more framework regions from another antibody, antibody fragment, or antibody domain. For example, an Fab can be designed to include the six CDRs set forth in FIGS. 2A and 2B and the framework regions set forth in FIGS. 2A and 2B except that framework region 1 having the amino acid set forth in SEQ ID NO:4 is replaced with a framework region 1 having the amino acid set forth in SEQ ID NO:58 or a framework region 1 having the amino acid set forth in SEQ ID NO:67 or a framework region 1 having the amino acid set forth in SEQ ID NO:72. In some cases, a scFv can be designed to include the six CDRs set forth in FIGS. 2A and 2B and the framework regions set forth in FIGS. 2A and 2B. In some cases, a scFv can be designed to include the six CDRs set forth in FIGS. 2A and 2B and the framework regions set forth in FIGS. 2A and 2B except that framework region 1 having the amino acid set forth in SEQ ID NO:4 is replaced with a framework region 1 having the amino acid set forth in SEQ ID NO:58, a framework region 1 having the amino acid set forth in SEQ ID NO:67, or a framework region 1 having the amino acid set forth in SEQ ID NO:72. In another example, a scFv can be designed to include the six CDRs set forth in FIGS. 2A and 2B and the framework regions set forth in FIGS. 6B and 6C, FIGS. 7A and 7B, FIGS. 8A and 8B, or FIGS. 9A and 9B.

In some cases, a binder (e.g., an antibody, antigen binding fragment, antibody domain, a CAR, a cell engager, and/or an ADC) provided herein having the ability to bind to a CD66e polypeptide (e.g., a human CD66e polypeptide) can include (a) a heavy chain variable domain that includes an amino acid sequence having at least 90 percent identity to the amino acid sequence set forth in SEQ ID NO:8 and/or (b) a light chain variable domain that includes an amino acid sequence having at least 90 percent identity to the amino acid sequence set forth in SEQ ID NO:16. For example, a binder (e.g., an antibody, antigen binding fragment, antibody domain, a CAR, a cell engager, and/or an ADC) provided herein can include (a) a heavy chain variable domain that includes an amino acid sequence having at least 90, 91, 92, 93, 94, 95, 96, 97, 98, or 99 percent identity to the amino acid sequence set forth in SEQ ID NO:8 and/or (b) a light chain variable domain that includes an amino acid sequence having at least 90, 91, 92, 93, 94, 95, 96, 97, 98, or 99 percent identity to the amino acid sequence set forth in SEQ ID NO:16. In some cases, a binder (e.g., an antibody, antigen binding fragment, antibody domain, a CAR, a cell engager, and/or an ADC) provided herein can include (a) a heavy chain variable domain that includes an amino acid sequence having 100 percent identity to the amino acid sequence set forth in SEQ ID NO:8 and/or (b) a light chain variable domain that includes an amino acid sequence having 100 percent identity to the amino acid sequence set forth in SEQ ID NO:16.

In some cases, a binder (e.g., an antibody, antigen binding fragment, antibody domain, a CAR, a cell engager, and/or an ADC) provided herein having the ability to bind to a CD66e polypeptide (e.g., a human CD66e polypeptide) can include (a) a heavy chain variable domain that includes an amino acid sequence having at least 90 percent identity to the amino acid sequence set forth in SEQ ID NO:8, provided that the heavy chain variable domain includes the amino acid sequences set forth in SEQ ID NOs:1, 2, and 3, and/or (b) a light chain variable domain that includes an amino acid sequence having at least 90 percent identity to the amino acid sequence set forth in SEQ ID NO:16, provided that the light chain variable domain includes the amino acid sequences set forth in SEQ ID NOs:9, 10, and 11. For example, a binder (e.g., an antibody, antigen binding fragment, antibody domain, a CAR, a cell engager, and/or an ADC) provided herein can include (a) a heavy chain variable domain that includes an amino acid sequence having at least 90, 91, 92, 93, 94, 95, 96, 97, 98, or 99 percent identity to the amino acid sequence set forth in SEQ ID NO:8, provided that the heavy chain variable domain includes the amino acid sequences set forth in SEQ ID NOs:1, 2, and 3, and/or (b) a light chain variable domain that includes an amino acid sequence having at least 90, 91, 92, 93, 94, 95, 96, 97, 98, or 99 percent identity to the amino acid sequence set forth in SEQ ID NO:16, provided that the light chain variable domain includes the amino acid sequences set forth in SEQ ID NOs:9, 10, and 11.

In some cases, a binder (e.g., an antibody, antigen binding fragment, antibody domain, a CAR, a cell engager, and/or an ADC) provided herein having the ability to bind to a CD66e polypeptide (e.g., a human CD66e polypeptide) can include (a) a heavy chain variable domain having the amino acid sequence set forth in SEQ ID NO:8 or the amino acid set forth in SEQ ID NO:8 with one, two, three, four, five, six, seven, eight, nine, or 10 amino acid modifications (e.g., amino acid substitutions, amino acid deletions, and/or amino acid additions) and/or (b) a light chain variable domain that includes the amino acid sequence set forth in SEQ ID NO:16 or the amino acid set forth in SEQ ID NO:16 with one, two, three, four, five, six, seven, eight, nine, or 10 amino acid modifications (e.g., amino acid substitutions, amino acid deletions, and/or amino acid additions). For example, an antibody or antigen binding fragment provided herein can have the ability to bind to a CD66e polypeptide (e.g., a human CD66e polypeptide), can include a heavy chain variable domain having the amino acid sequence set forth in SEQ ID NO:8 with one, two, three, four, five, six, seven, eight, nine, or 10 amino acid modifications (e.g., amino acid substitutions, amino acid deletions, and/or amino acid additions), provided that the heavy chain variable domain includes the amino acid sequences set forth in SEQ ID NOs:1, 2, and 3, and can include a light chain variable domain having the amino acid sequence set forth in SEQ ID NO:16 with one, two, three, four, five, six, seven, eight, nine, or 10 amino acid modifications (e.g., amino acid substitutions, amino acid deletions, and/or amino acid additions), provided that the light chain variable domain includes the amino acid sequences set forth in SEQ ID NOs:9, 10, and 11.

In some cases, a binder (e.g., an antibody, antigen binding fragment, antibody domain, a CAR, a cell engager, and/or an ADC) provided herein having the ability to bind to a CD66e polypeptide (e.g., a human CD66e polypeptide) can include (a) a heavy chain variable domain comprising (i) a CDR1 that comprises, consists essentially of, or consists of the amino acid sequence set forth in SEQ ID NO:1, (ii) a CDR2 that comprises, consists essentially of, or consists of the amino acid sequence set forth in SEQ ID NO:2, and (iii) a CDR3 that comprises, consists essentially of, or consists of the amino acid sequence set forth in SEQ ID NO:3, and/or (b) a light chain variable domain comprising (i) a CDR1 that comprises, consists essentially of, or consists of the amino acid sequence set forth in SEQ ID NO:9, (ii) a CDR2 that comprises, consists essentially of, or consists of the amino acid sequence set forth in SEQ ID NO:10, and (iii) a CDR3 that comprises, consists essentially of, or consists of the amino acid sequence set forth in SEQ ID NO:11. As used herein, a "CDR1 that consists essentially of the amino acid sequence set forth in SEQ ID NO:1" is a CDR1 that has zero, one, or two amino acid substitutions within SEQ ID NO:1, that has zero, one, two, three, four, or five amino acid residues directly preceding SEQ ID NO:1, and/or that has zero, one, two, three, four, or five amino acid residues directly following SEQ ID NO:1, provided that the binder (e.g., an antibody, antigen binding fragment, antibody domain, a CAR, a cell engager, and/or an ADC) maintains its basic ability to bind to a CD66e polypeptide (e.g., a human CD66e polypeptide). Examples of a CDR1 that consists essentially of the amino acid sequence set forth in SEQ ID NO:1 include, without limitation, those set forth in Table 1.

TABLE 1

Exemplary CDR1s that consist essentially of the amino acid sequence set forth in SEQ ID NO: 1.

| Sequence | SEQ ID NO: |
|---|---|
| SYYMS | 166 |
| DYAMS | 167 |
| DYYTS | 168 |
| DYYMH | 169 |
| NYYMS | 170 |
| DNYMS | 171 |
| DYGMS | 172 |
| DYYMN | 173 |
| GYYMS | 174 |
| DAYMS | 175 |

As used herein, a "CDR2 that consists essentially of the amino acid sequence set forth in SEQ ID NO:2" is a CDR2 that has zero, one, or two amino acid substitutions within SEQ ID NO:2, that has zero, one, two, three, four, or five amino acid residues directly preceding SEQ ID NO:2, and/or that has zero, one, two, three, four, or five amino acid residues directly following SEQ ID NO:2, provided that the binder (e.g., an antibody, antigen binding fragment, antibody domain, a CAR, a cell engager, and/or an ADC) maintains its basic ability to bind to a CD66e polypeptide (e.g., a human CD66e polypeptide). Examples of a CDR2 that consists essentially of the amino acid sequence set forth in SEQ ID NO:2 include, without limitation, those set forth in Table 2.

TABLE 2

Exemplary CDR2s that consist essentially of the amino acid sequence set forth in SEQ ID NO: 2.

| Sequence | SEQ ID NO: |
|---|---|
| VISSSGSTIYYADSVKG | 176 |
| YVSSGSTIYYADSVKG | 177 |
| YIGSSGSTIYYADSVKG | 178 |
| YISYSGSTIYYADSVKG | 179 |
| YISSDGSTIYYADSVKG | 180 |
| YISSSSSTIYYADSVKG | 181 |
| YISSSGGTIYYADSVKG | 182 |
| YISSSGSSIYYADSVKG | 183 |
| YISSSGSTTYYADSVKG | 184 |
| YISSSGSTIHYADSVKG | 185 |

As used herein, a "CDR3 that consists essentially of the amino acid sequence set forth in SEQ ID NO:3" is a CDR3 that has zero, one, or two amino acid substitutions within SEQ ID NO:3, that has zero, one, two, three, four, or five amino acid residues directly preceding SEQ ID NO:3, and/or that has zero, one, two, three, four, or five amino acid residues directly following SEQ ID NO:3, provided that the binder (e.g., an antibody, antigen binding fragment, antibody domain, a CAR, a cell engager, and/or an ADC) maintains its basic ability to bind to a CD66e polypeptide (e.g., a human CD66e polypeptide). Examples of a CDR3 that consists essentially of the amino acid sequence set forth in SEQ ID NO:3 include, without limitation, those set forth in Table 3.

TABLE 3

Exemplary CDR3s that consist essentially of the amino acid sequence set forth in SEQ ID NO: 3.

| Sequence | SEQ ID NO: |
|---|---|
| LGRYSYGLRSYYYYGMDV | 186 |
| ISRYSYGLRSYYYYGMDV | 187 |
| IGKYSYGLRSYYYYGMDV | 188 |
| IGRFSYGLRSYYYYGMDV | 189 |
| IGRYTYGLRSYYYYGMDV | 190 |
| IGRYSFGLRSYYYYGMDV | 191 |
| IGRYSYSLRSYYYYGMDV | 192 |
| IGRYSYGIRSYYYYGMDV | 193 |
| IGRYSYGLKSYYYYGMDV | 194 |
| IGRYSYGLRTYYYYGMDV | 195 |

As used herein a "CDR1 that consists essentially of the amino acid sequence set forth in SEQ ID NO:9" is a CDR1 that has zero, one, or two amino acid substitutions within SEQ TD NO:9, that has zero, one, two, three, four, or five amino acid residues directly preceding SEQ ID NO:9, and/or that has zero, one, two, three, four, or five amino acid residues directly following SEQ ID NO:9, provided that the binder (e.g., an antibody, antigen binding fragment, antibody domain, a CAR, a cell engager, and/or an ADC) maintains its basic ability to bind to a CD66e polypeptide (e.g., a human CD66e polypeptide). Examples of a CDR1 that consists essentially of the amino acid sequence set forth in SEQ ID NO:9 include, without limitation, those set forth in Table 4.

TABLE 4

Exemplary CDR1s that consist essentially of the amino acid sequence set forth in SEQ ID NO: 9.

| Sequence | SEQ ID NO: |
|---|---|
| QASQSISSYLN | 196 |
| RMSQSISSYLN | 197 |
| RARQSISSYLN | 198 |
| RASESISSYLN | 199 |
| RASQGISSYLN | 200 |
| RASQSIRSYLN | 201 |
| RASQSISNYLN | 202 |
| RASQSISSWLN | 203 |
| RASQSISSYLA | 204 |
| WASQSISSYLN | 205 |

As used herein, a "CDR2 that consists essentially of the amino acid sequence set forth in SEQ ID NO:10" is a CDR2 that has zero, one, or two amino acid substitutions within SEQ ID NO:10, that has zero, one, two, three, four, or five amino acid residues directly preceding SEQ ID NO:10, and/or that has zero, one, two, three, four, or five amino acid residues directly following SEQ ID NO:10, provided that the binder (e.g., an antibody, antigen binding fragment, antibody domain, a CAR, a cell engager, and/or an ADC) maintains its basic ability to bind to a CD66e polypeptide (e.g., a human CD66e polypeptide). Examples of a CDR2 that consists essentially of the amino acid sequence set forth in SEQ ID NO:10 include, without limitation, those set forth in Table 5.

TABLE 5

Exemplary CDR2s that consist essentially of the amino acid sequence set forth in SEQ ID NO: 10.

| Sequence | SEQ ID NO: |
|---|---|
| DASSLQS | 206 |
| AAKSLQS | 207 |
| AASTLQS | 208 |
| AASSLES | 209 |
| AASSLQT | 210 |
| SASSLQS | 211 |
| AAPSLQS | 212 |
| AASNLQS | 213 |

TABLE 5-continued

| Exemplary CDR2s that consist essentially of the amino acid sequence set forth in SEQ ID NO: 10. | |
|---|---|
| Sequence | SEQ ID NO: |
| AASSLHS | 214 |
| AASSLQP | 215 |

As used herein, a "CDR3 that consists essentially of the amino acid sequence set forth in SEQ ID NO:11" is a CDR3 that has zero, one, or two amino acid substitutions within SEQ ID NO:11, that has zero, one, two, three, four, or five amino acid residues directly preceding SEQ ID NO:11, and/or that has zero, one, two, three, four, or five amino acid residues directly following SEQ ID NO:11, provided that the binder (e.g., an antibody, antigen binding fragment, antibody domain, a CAR, a cell engager, and/or an ADC) maintains its basic ability to bind to a CD66e polypeptide (e.g., a human CD66e polypeptide). Examples of a CDR3 that consists essentially of the amino acid sequence set forth in SEQ ID NO:11 include, without limitation, those set forth in Table 6.

TABLE 6

| Exemplary CDR3s that consist essentially of the amino acid sequence set forth in SEQ ID NO: 11. | |
|---|---|
| Sequence | SEQ ID NO: |
| QQALQTPVT | 216 |
| MRALQTPVT | 217 |
| MQYLQTPVT | 218 |
| MQANQTPVT | 219 |
| MQALSTPVT | 220 |
| MQALQYPVT | 221 |
| MQALQTPAT | 222 |
| MQALQTPIT | 223 |
| MQALQTPLT | 224 |
| KQALQTPVT | 225 |

In another embodiment, a binder (e.g., an antibody, antigen binding fragment, antibody domain, a CAR, a cell engager, and/or an ADC) provided herein having the ability to bind to a CD66e polypeptide (e.g., a human CD66e polypeptide) can include (i) a heavy chain variable domain having a CDR1 having the amino acid sequence set forth in SEQ ID NO:17 (or a variant of SEQ ID NO:17 with one or two amino acid modifications), a CDR2 having the amino acid sequence set forth in SEQ ID NO:18 (or a variant of SEQ ID NO:18 with one or two amino acid modifications), and a CDR3 having the amino acid sequence set forth in SEQ ID NO:19 (or a variant of SEQ ID NO:19 with one or two amino acid modifications); and/or (ii) a light chain variable domain having a CDR1 having the amino acid sequence set forth in SEQ ID NO:25 (or a variant of SEQ ID NO:25 with one or two amino acid modifications), a CDR2 having the amino acid sequence set forth in SEQ ID NO:26 (or a variant of SEQ ID NO:26 with one or two amino acid modifications), and a CDR3 having the amino acid sequence set forth SEQ ID NO:27 (or a variant of SEQ ID NO:27 with one or two amino acid modifications). An example of such an antigen binding fragment having these CDRs and the ability to bind to a CD66e polypeptide (e.g., a human CD66e polypeptide) includes, without limitation, the Fab set forth in FIGS. 3A and 3B.

In some cases, a binder (e.g., an antibody, antigen binding fragment, antibody domain, a CAR, a cell engager, and/or an ADC) provided herein having the ability to bind to a CD66e polypeptide (e.g., a human CD66e polypeptide) and having (a) a heavy chain variable domain having a CDR1 having the amino acid sequence set forth in SEQ ID NO:17 (or a variant of SEQ ID NO:17 with one or two amino acid modifications), a CDR2 having the amino acid sequence set forth in SEQ ID NO:18 (or a variant of SEQ ID NO:18 with one or two amino acid modifications), and a CDR3 having the amino acid sequence set forth in SEQ ID NO:19 (or a variant of SEQ ID NO:19 with one or two amino acid modifications) and/or (b) a light chain variable domain having a CDR1 having the amino acid sequence set forth in SEQ ID NO:25 (or a variant of SEQ ID NO:25 with one or two amino acid modifications), a CDR2 having the amino acid sequence set forth in SEQ ID NO:26 (or a variant of SEQ ID NO:26 with one or two amino acid modifications), and a CDR3 having the amino acid sequence set forth SEQ ID NO:27 (or a variant of SEQ ID NO:27 with one or two amino acid modifications) can include any appropriate framework regions. For example, such a binder (e.g., an antibody, antigen binding fragment, antibody domain, a CAR, a cell engager, and/or an ADC) can include (a) a heavy chain variable domain that includes a framework region 1 having the amino acid sequence set forth in SEQ ID NO:20 (or a variant of SEQ ID NO:20 with one, two, three, four, five, six, seven, eight, nine, ten, or more amino acid modifications), a framework region 2 having the amino acid sequence set forth in SEQ ID NO:21 (or a variant of SEQ ID NO:21 with one, two, three, four, five, six, seven, eight, nine, ten, or more amino acid modifications), a framework region 3 having the amino acid sequence set forth in SEQ ID NO:22 (or a variant of SEQ ID NO:22 with one, two, three, four, five, six, seven, eight, nine, ten, or more amino acid modifications), and a framework region 4 having the amino acid sequence set forth in SEQ ID NO:23 (or a variant of SEQ ID NO:23 with one, two, three, four, five, six, seven, eight, nine, ten, or more amino acid modifications) and/or (b) a light chain variable domain that includes a framework region 1 having the amino acid sequence set forth in SEQ ID NO:28 (or a variant of SEQ ID NO:28 with one, two, three, four, five, six, seven, eight, nine, ten, or more amino acid modifications), a framework region 2 having the amino acid sequence set forth in SEQ ID NO:29 (or a variant of SEQ ID NO:29 with one, two, three, four, five, six, seven, eight, nine, ten, or more amino acid modifications), a framework region 3 having the amino acid sequence set forth in SEQ ID NO:30 (or a variant of SEQ ID NO:30 with one, two, three, four, five, six, seven, eight, nine, ten, or more amino acid modifications), and a framework region 4 having the amino acid sequence set forth in SEQ ID NO:31 (or a variant of SEQ ID NO:31 with one, two, three, four, five, six, seven, eight, nine, ten, or more amino acid modifications).

In some cases, a binder (e.g., an antibody, antigen binding fragment, antibody domain, a CAR, a cell engager, and/or an ADC) having any of the CDRs set forth in FIG. 3A or 3B can be designed to include framework regions as set forth in FIGS. 3A and 3B or can be designed to include one or more framework regions from another antibody or antibody fragment. For example, an Fab can be designed to include the six CDRs set forth in FIGS. 3A and 3B and the framework regions set forth in FIGS. 3A and 3B except that framework region 1 having the amino acid set forth in SEQ ID NO:20 is replaced with a framework region 1 having the amino acid set forth in SEQ ID NO:58 or a framework region 1 having the amino acid set forth in SEQ ID NO:67 or a framework region 1 having the amino acid set forth in SEQ ID NO:72. In some cases, a scFv can be designed to include the six CDRs set forth in FIGS. 3A and 3B and the framework regions set forth in FIGS. 3A and 3B. In some cases, a scFv can be designed to include the six CDRs set forth in FIGS. 3A and 3B and the framework regions set forth in FIGS. 3A and 3B except that framework region 1 having the amino acid set forth in SEQ ID NO:20 is replaced with a framework region 1 having the amino acid set forth in SEQ ID NO:58, a framework region 1 having the amino acid set forth in SEQ ID NO:67, or a framework region 1 having the amino acid set forth in SEQ ID NO:72. In another example, a scFv can be designed to include the six CDRs set forth in FIGS. 3A and 3B and the framework regions set forth in FIGS. 6B and 6C, FIGS. 7A and 7B, FIGS. 8A and 8B, or FIGS. 9A and 9B.

In some cases, a binder (e.g., an antibody, antigen binding fragment, antibody domain, a CAR, a cell engager, and/or an ADC) provided herein having the ability to bind to a CD66e polypeptide (e.g., a human CD66e polypeptide) can include (a) a heavy chain variable domain that includes an amino acid sequence having at least 90 percent identity to the amino acid sequence set forth in SEQ ID NO:24 and/or (b) a light chain variable domain that includes an amino acid sequence having at least 90 percent identity to the amino acid sequence set forth in SEQ ID NO:32. For example, a binder (e.g., an antibody, antigen binding fragment, antibody domain, a CAR, a cell engager, and/or an ADC) provided herein can include (a) a heavy chain variable domain that includes an amino acid sequence having at least 90, 91, 92, 93, 94, 95, 96, 97, 98, or 99 percent identity to the amino acid sequence set forth in SEQ ID NO:24 and/or (b) a light chain variable domain that includes an amino acid sequence having at least 90, 91, 92, 93, 94, 95, 96, 97, 98, or 99 percent identity to the amino acid sequence set forth in SEQ ID NO:32. In some cases, a binder (e.g., an antibody, antigen binding fragment, antibody domain, a CAR, a cell engager, and/or an ADC) provided herein can include (a) a heavy chain variable domain that includes an amino acid sequence having 100 percent identity to the amino acid sequence set forth in SEQ ID NO:24 and/or (b) a light chain variable domain that includes an amino acid sequence having 100 percent identity to the amino acid sequence set forth in SEQ ID NO:32.

In some cases, a binder (e.g., an antibody, antigen binding fragment, antibody domain, a CAR, a cell engager, and/or an ADC) provided herein having the ability to bind to a CD66e polypeptide (e.g., a human CD66e polypeptide) can include (a) a heavy chain variable domain that includes an amino acid sequence having at least 90 percent identity to the amino acid sequence set forth in SEQ ID NO:24, provided that the heavy chain variable domain includes the amino acid sequences set forth in SEQ ID NOs:17, 18, and 19, and/or (b) a light chain variable domain that includes an amino acid sequence having at least 90 percent identity to the amino acid sequence set forth in SEQ ID NO:32, provided that the light chain variable domain includes the amino acid sequences set forth in SEQ ID NOs:25, 26, and 27. For example, a binder (e.g., an antibody, antigen binding fragment, antibody domain, a CAR, a cell engager, and/or an ADC) provided herein can include (a) a heavy chain variable domain that includes an amino acid sequence having at least 90, 91, 92, 93, 94, 95, 96, 97, 98, or 99 percent identity to the amino acid sequence set forth in SEQ ID NO:24, provided that the heavy chain variable domain includes the amino acid sequences set forth in SEQ ID NOs:17, 18, and 19, and/or (b) a light chain variable domain that includes an amino acid sequence having at least 90, 91, 92, 93, 94, 95, 96, 97, 98, or 99 percent identity to the amino acid sequence set forth in SEQ ID NO:32, provided that the light chain variable domain includes the amino acid sequences set forth in SEQ ID NOs:25, 26, and 27.

In some cases, a binder (e.g., an antibody, antigen binding fragment, antibody domain, a CAR, a cell engager, and/or an ADC) provided herein having the ability to bind to a CD66e polypeptide (e.g., a human CD66e polypeptide) can include (a) a heavy chain variable domain having the amino acid sequence set forth in SEQ ID NO:24 or the amino acid set forth in SEQ ID NO:24 with one, two, three, four, five, six, seven, eight, nine, or 10 amino acid modifications (e.g., amino acid substitutions, amino acid deletions, and/or amino acid additions) and/or (b) a light chain variable domain that includes the amino acid sequence set forth in SEQ ID NO:32 or the amino acid set forth in SEQ ID NO:32 with one, two, three, four, five, six, seven, eight, nine, or 10 amino acid modifications (e.g., amino acid substitutions, amino acid deletions, and/or amino acid additions). For example, an antibody or antigen binding fragment provided herein can have the ability to bind to a CD66e polypeptide (e.g., a human CD66e polypeptide), can include a heavy chain variable domain having the amino acid sequence set forth in SEQ ID NO:24 with one, two, three, four, five, six, seven, eight, nine, or 10 amino acid modifications (e.g., amino acid substitutions, amino acid deletions, and/or amino acid additions), provided that the heavy chain variable domain includes the amino acid sequences set forth in SEQ ID NOs:17, 18, and 19, and can include a light chain variable domain having the amino acid sequence set forth in SEQ ID NO:32 with one, two, three, four, five, six, seven, eight, nine, or 10 amino acid modifications (e.g., amino acid substitutions, amino acid deletions, and/or amino acid additions), provided that the light chain variable domain includes the amino acid sequences set forth in SEQ ID NOs:25, 26, and 27.

In some cases, a binder (e.g., an antibody, antigen binding fragment, antibody domain, a CAR, a cell engager, and/or an ADC) provided herein having the ability to bind to a CD66e polypeptide (e.g., a human CD66e polypeptide) can include (a) a heavy chain variable domain comprising (i) a CDR1 that comprises, consists essentially of, or consists of the amino acid sequence set forth in SEQ ID NO:17, (ii) a CDR2 that comprises, consists essentially of, or consists of the amino acid sequence set forth in SEQ ID NO:18, and (iii) a CDR3 that comprises, consists essentially of, or consists of the amino acid sequence set forth in SEQ ID NO:19, and/or (b) a light chain variable domain comprising (i) a CDR1 that comprises, consists essentially of, or consists of the amino acid sequence set forth in SEQ ID NO:25, (ii) a CDR2 that comprises, consists essentially of, or consists of the amino acid sequence set forth in SEQ ID NO:26, and (iii) a CDR3 that comprises, consists essentially of, or consists of the amino acid sequence set forth in SEQ ID NO:27. As used herein, a "CDR1 that consists essentially of the amino acid sequence set forth in SEQ ID NO:17" is a CDR1 that has zero, one, or two amino acid substitutions within SEQ ID NO:17, that has zero, one, two, three, four, or five amino acid residues directly preceding SEQ ID NO:17, and/or that has zero, one, two, three, four, or five amino acid residues directly following SEQ ID NO:17, provided that the binder (e.g., an antibody, antigen binding fragment, antibody domain, a CAR, a cell engager, and/or an ADC) maintains its basic ability to bind to a CD66e polypeptide (e.g., a human CD66e polypeptide). Examples of a CDR1 that consists essentially of the amino acid sequence set forth in SEQ ID NO:17 include, without limitation, those set forth in Table 7.

TABLE 7

Exemplary CDR1s that consist essentially of the amino acid sequence set forth in SEQ ID NO: 17.

| Sequence | SEQ ID NO: |
|---|---|
| SYYMS | 166 |
| DYAMS | 167 |
| DYYTS | 168 |
| DYYMH | 169 |
| NYYMS | 170 |
| DNYMS | 171 |
| DYGMS | 172 |
| DYYMN | 173 |
| GYYMS | 174 |
| DAYMS | 175 |

As used herein, a "CDR2 that consists essentially of the amino acid sequence set forth in SEQ ID NO:18" is a CDR2 that has zero, one, or two amino acid substitutions within SEQ TD NO:18, that has zero, one, two, three, four, or five amino acid residues directly preceding SEQ ID NO:18, and/or that has zero, one, two, three, four, or five amino acid residues directly following SEQ ID NO:18, provided that the binder (e.g., an antibody, antigen binding fragment, antibody domain, a CAR, a cell engager, and/or an ADC) maintains its basic ability to bind to a CD66e polypeptide (e.g., a human CD66e polypeptide). Examples of a CDR2 that consists essentially of the amino acid sequence set forth in SEQ ID NO:18 include, without limitation, those set forth in Table 8.

TABLE 8

Exemplary CDR2s that consist essentially of the amino acid sequence set forth in SEQ ID NO: 18.

| Sequence | SEQ ID NO: |
|---|---|
| LGRYSYGLRSYYYYGMDV | 247 |
| ISRYSYGLRSYYYYGMDV | 248 |
| IGKYSYGLRSYYYYGMDV | 249 |
| IGRFSYGLRSYYYYGMDV | 250 |
| IGRYTYGLRSYYYYGMDV | 251 |
| IGRYSFGLRSYYYYGMDV | 252 |
| IGRYSYSLRSYYYYGMDV | 253 |
| IGRYSYGIRSYYYYGMDV | 254 |

TABLE 8-continued

Exemplary CDR2s that consist essentially of the amino acid sequence set forth in SEQ ID NO: 18.

| Sequence | SEQ ID NO: |
|---|---|
| IGRYSYGLKSYYYYGMDV | 255 |
| IGRYSYGLRTYYYYGMDV | 256 |

As used herein, a "CDR3 that consists essentially of the amino acid sequence set forth in SEQ ID NO:19" is a CDR3 that has zero, one, or two amino acid substitutions within SEQ TD NO:19, that has zero, one, two, three, four, or five amino acid residues directly preceding SEQ ID NO:19, and/or that has zero, one, two, three, four, or five amino acid residues directly following SEQ ID NO:19, provided that the binder (e.g., an antibody, antigen binding fragment, antibody domain, a CAR, a cell engager, and/or an ADC) maintains its basic ability to bind to a CD66e polypeptide (e.g., a human CD66e polypeptide). Examples of a CDR3 that consists essentially of the amino acid sequence set forth in SEQ ID NO:19 include, without limitation, those set forth in Table 9.

TABLE 9

Exemplary CDR3s that consist essentially of the amino acid sequence set forth in SEQ ID NO: 19.

| Sequence | SEQ ID NO: |
|---|---|
| IARQYRKSYYYYGMDV | 226 |
| VVRQYRKSYYYYGMDV | 227 |
| VAKQYRKSYYYYGMDV | 228 |
| VARNYRKSYYYYGMDV | 229 |
| VARQFRKSYYYYGMDV | 230 |
| VARQYKKSYYYYGMDV | 231 |
| VARQYRRSYYYYGMDV | 232 |
| VARQYRKTYYYYGMDV | 233 |
| VARQYRKSFYYYGMDV | 234 |
| VARQYRKSYFYYGMDV | 235 |

As used herein, a "CDR1 that consists essentially of the amino acid sequence set forth in SEQ ID NO:25" is a CDR1 that has zero, one, or two amino acid substitutions within SEQ ID NO:25, that has zero, one, two, three, four, or five amino acid residues directly preceding SEQ ID NO:25, and/or that has zero, one, two, three, four, or five amino acid residues directly following SEQ ID NO:25, provided that the binder (e.g., an antibody, antigen binding fragment, antibody domain, a CAR, a cell engager, and/or an ADC) maintains its basic ability to bind to a CD66e polypeptide (e.g., a human CD66e polypeptide). Examples of a CDR1 that consists essentially of the amino acid sequence set forth in SEQ ID NO:25 include, without limitation, those set forth in Table 10.

TABLE 10

| Exemplary CDR1s that consist essentially of the amino acid sequence set forth in SEQ ID NO: 25. | |
|---|---|
| Sequence | SEQ ID NO: |
| QASQSISSYLN | 196 |
| RMSQSISSYLN | 197 |
| RARQSISSYLN | 198 |
| RASESISSYLN | 199 |
| RASQGISSYLN | 200 |
| RASQSIRSYLN | 201 |
| RASQSISNYLN | 202 |
| RASQSISSWLN | 203 |
| RASQSISSYLA | 204 |
| WASQSISSYLN | 205 |

As used herein, a "CDR2 that consists essentially of the amino acid sequence set forth in SEQ ID NO:26" is a CDR2 that has zero, one, or two amino acid substitutions within SEQ ID NO:26, that has zero, one, two, three, four, or five amino acid residues directly preceding SEQ ID NO:26, and/or that has zero, one, two, three, four, or five amino acid residues directly following SEQ ID NO:26, provided that the binder (e.g., an antibody, antigen binding fragment, antibody domain, a CAR, a cell engager, and/or an ADC) maintains its basic ability to bind to a CD66e polypeptide (e.g., a human CD66e polypeptide). Examples of a CDR2 that consists essentially of the amino acid sequence set forth in SEQ ID NO:26 include, without limitation, those set forth in Table 11.

TABLE 11

| Exemplary CDR2s that consist essentially of the amino acid sequence set forth in SEQ ID NO: 26. | |
|---|---|
| Sequence | SEQ ID NO: |
| DASSLQS | 206 |
| AAKSLQS | 207 |
| AASTLQS | 208 |
| AASSLES | 209 |
| AASSLQT | 210 |
| SASSLQS | 211 |
| AAPSLQS | 212 |
| AASNLQS | 213 |
| AASSLHS | 214 |
| AASSLQP | 215 |

As used herein, a "CDR3 that consists essentially of the amino acid sequence set forth in SEQ ID NO:27" is a CDR3 that has zero, one, or two amino acid substitutions within SEQ ID NO:27, that has zero, one, two, three, four, or five amino acid residues directly preceding SEQ ID NO:27, and/or that has zero, one, two, three, four, or five amino acid residues directly following SEQ ID NO:27, provided that the binder (e.g., an antibody, antigen binding fragment, antibody domain, a CAR, a cell engager, and/or an ADC) maintains its basic ability to bind to a CD66e polypeptide (e.g., a human CD66e polypeptide). Examples of a CDR3 that consists essentially of the amino acid sequence set forth in SEQ ID NO:27 include, without limitation, those set forth in Table 12.

TABLE 12

| Exemplary CDR3s that consist essentially of the amino acid sequence set forth in SEQ ID NO: 27. | |
|---|---|
| Sequence | SEQ ID NO: |
| QQALQTPLT | 236 |
| MRALQTPLT | 237 |
| MQYLQTPLT | 238 |
| MQANQTPLT | 239 |
| MQALSTPLT | 240 |
| MQALQYPLT | 241 |
| MQALQTSLT | 242 |
| MQALQTPIT | 243 |
| KQALQTPLT | 244 |
| MKALQTPLT | 245 |

When designing a single chain antibody (e.g., a scFv) having a heavy chain variable domain and a light chain variable domain, the two regions can be directly connected or can be connected using any appropriate linker sequence. For example, a heavy chain variable domain having the CDRs of SEQ ID NOs:1-3 or SEQ ID NOs:17-19 can be directly connected to a light chain variable domain having the CDRs of SEQ ID NOs:9-11 or SEQ ID NOs:25-27, respectively, via a linker sequence. Examples of linker sequences that can be used to connect a heavy chain variable domain and a light chain variable domain to create a scFv include, without limitation, those linkers set forth in FIG. 10.

As indicated herein, the amino acid sequences described herein can include amino acid modifications (e.g., the articulated number of amino acid modifications). Such amino acid modifications can include, without limitation, amino acid substitutions, amino acid deletions, amino acid additions, and combinations. In some cases, an amino acid modification can be made to improve the binding and/or contact with an antigen and/or to improve a functional activity of a binder (e.g., an antibody, antigen binding fragment, antibody domain, a CAR, a cell engager, and/or an ADC) provided herein. In some cases, an amino acid substitution within an articulated sequence identifier can be a conservative amino acid substitution. For example, conservative amino acid substitutions can be made by substituting one amino acid residue for another amino acid residue having a similar side chain. Families of amino acid residues having similar side chains can include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

In some cases, an amino acid substitution within an articulated sequence identifier can be a non-conservative amino acid substitution. Non-conservative amino acid substitutions can be made by substituting one amino acid residue for another amino acid residue having a dissimilar side chain. Examples of non-conservative substitutions include, without limitation, substituting (a) a hydrophilic residue (e.g., serine or threonine) for a hydrophobic residue (e.g., leucine, isoleucine, phenylalanine, valine, or alanine); (b) a cysteine or proline for any other residue; (c) a residue having a basic side chain (e.g., lysine, arginine, or histidine) for a residue having an acidic side chain (e.g., aspartic acid or glutamic acid); and (d) a residue having a bulky side chain (e.g., phenylalanine) for glycine or other residue having a small side chain.

Methods for generating an amino acid sequence variant (e.g., an amino acid sequence that includes one or more modifications with respect to an articulated sequence identifier) can include site-specific mutagenesis or random mutagenesis (e.g., by PCR) of a nucleic acid encoding the antibody or fragment thereof. See, for example, Zoller, *Curr Opin. Biotechnol.* 3: 348-354 (1992). Both naturally occurring and non-naturally occurring amino acids (e.g., artificially-derivatized amino acids) can be used to generate an amino acid sequence variant provided herein.

A representative number of binders (e.g., antibodies, antigen binding fragments, and/or antibody domains) having the ability to bind to a CD66e polypeptide (e.g., a human CD66e polypeptide) are further described in Table 13.

expressed in suitable host cells. FIG. 4 is a sequence listing of nucleic acid sequences encoding exemplary binders (e.g., antibodies, antigen binding fragments, and/or antibody domains) described herein. In some cases, a binder (e.g., an antibody, antigen binding fragment, antibody domain, CAR, and/or cell engager) provided herein can be recombinantly produced in prokaryotic hosts such as *E. coli, Bacillus brevis, Bacillus subtilis, Bacillus megaterium, Lactobacillus zeae casei*, or *Lactobacillus paracasei*. A binder (e.g., an antibody, antigen binding fragment, antibody domain, CAR, and/or cell engager) provided herein also can be recombinantly produced in eukaryotic hosts such as yeast (e.g., *Pichia pastoris, Saccharomyces cerevisiae, Hansenula polymorpha, Schizosaccharomyces pombe, Schwanniomyces occidentalis, Kluyveromyces lactis*, or *Yarrowia lipolytica*), filamentous fungi of the genera *Trichoderma* (e.g., *T. reesei*) and *Aspergillus* (e.g., *A. niger* and *A. oryzae*), protozoa such as *Leishmania tarentolae*, insect cells, or mammalian cells (e.g., mammalian cell lines such as Chinese hamster ovary (CHO) cells, Per.C6 cells, mouse myeloma NS0 cells, baby hamster kidney (BHK) cells, or human embryonic kidney cell line HEK293). See, for example, the Frenzel et al. reference (*Front Immunol.,* 4:217 (2013)).

In some cases, an antigen binding fragment or antibody domain provided herein can be produced by proteolytic digestion of an intact antibody. For example, an antigen binding fragment can be obtained by treating an antibody with an enzyme such as papain or pepsin. Papain digestion of whole antibodies can be used to produce $F(ab)_2$ or Fab fragments, while pepsin digestion of whole antibodies can be used to produce $F(ab')_2$ or Fab' fragments.

TABLE 13

Representative number of binders.

| Clone # (Antibody type) | SEQ ID NOs of Heavy Chain Variable Domain/ Region CDRs | SEQ ID NOs of Heavy Chain Variable Domain/ Region Framework Regions | SEQ ID NO of Heavy Chain Variable Domain/ Region | SEQ ID NOs of Light Chain Variable Domain/ Region CDRs | SEQ ID NOs of Light Chain Variable Domain/ Region Framework Regions | SEQ ID NO of Light Chain Variable Domain/ Region |
|---|---|---|---|---|---|---|
| #1 (Fab) | 1, 2, 3 | 4, 5, 6, 7 | 8 | 9, 10, 11 | 12, 13, 14, 15 | 16 |
| #2 (Fab) | 17, 18, 19 | 20, 21, 22, 23 | 24 | 25, 26, 27 | 28, 29, 30, 31 | 32 |

Table 14 includes an alternative designation that can be used to refer to each of Clones #1-#2.

TABLE 14

Alternative nomenclature for Clones #1-#2.

| Clone # | Alternative names |
|---|---|
| 1 | ab1 |
| 2 | ab2 |

The binders (e.g., antibodies, antigen binding fragments, antibody domains, CARs, cell engagers, and/or ADCs) provided herein can be produced using any appropriate method. For example, the binders (e.g., antibodies, antigen binding fragments, antibody domains, CARs, and/or cell engagers) provided herein can be produced in recombinant host cells. For example, a nucleic acid encoding a binder (e.g., an antibody, antigen binding fragment, antibody domain, CAR, and/or cell engager) provided herein can be constructed, introduced into an expression vector, and In some cases, a binder (e.g., an antibody, antigen binding fragment, antibody domain, CAR, cell engager, and/or ADC) provided herein can be substantially pure. The term "substantially pure" as used herein with reference to a binder (e.g., an antibody, antigen binding fragment, antibody domain, CAR, cell engager, and/or ADC) refers to the binder (e.g., an antibody, antigen binding fragment, antibody domain, CAR, cell engager, and/or ADC) as being substantially free of other polypeptides, lipids, carbohydrates, and nucleic acid with which it is naturally associated. Thus, a substantially pure binder (e.g., an antibody, antigen binding fragment, antibody domain, CAR, cell engager, and/or ADC) provided herein is any binder (e.g., an antibody, antigen binding fragment, antibody domain, CAR, cell engager, and/or ADC) that is removed from its natural environment and is at least 60 percent pure. A substantially pure binder (e.g., an antibody, antigen binding fragment, antibody domain, CAR, cell engager, and/or ADC) provided herein can be at least about 65, 70, 75, 80, 85, 90, 95, or 99 percent pure.

This document also provides bispecific binders (e.g., bispecific antibodies, bispecific antigen binding fragments, and/or bispecific antibody domains) that bind to two different epitopes with at least one being an epitope of a CD66e polypeptide (e.g., a human CD66e polypeptide). In some cases, a bispecific binder provided herein can be designed to bind to two different epitopes of the same CD66e polypeptide (e.g., a human CD66e polypeptide). In some cases, a bispecific binder provided herein can bind to a CD66e polypeptide (e.g., a human CD66e polypeptide) and to an epitope on a different polypeptide (e.g., a CD3 polypeptide). Bispecific binders can be produced by chemically conjugating two different binders (e.g., antibodies, antigen binding fragments, and/or antibody domains) together. Bispecific binders also can be produced by fusing two antibody-producing cells, e.g., hybridomas, to make a hybrid cell line that produces two different heavy and two different light chains within the same cell, which can result in, for example, bispecific IgG molecules. See, Brinkmann and Kontermann, MAbs., 9(2):182-212 (2017).

In some cases, a binder (e.g., an antibody, antigen binding fragment, antibody domain, CAR, and/or cell engager) provided herein can be fused or conjugated (e.g., covalently or non-covalently attached) to another polypeptide or other moiety to provide a fusion protein or conjugate. For example, a binder (e.g., an antibody, antigen binding fragment, antibody domain, CAR, and/or cell engager) provided herein can be conjugated (e.g., covalently or non-covalently attached) to a polymer (e.g., polyethylene glycol (PEG), polyethylenimine (PEI) modified with PEG (PEI-PEG), and/or polyglutamic acid (PGA) (N-(2-Hydroxypropyl) methacrylamide (HPMA) copolymers), hyaluronic acid, a fluorescent substance, a luminescent substance, a hapten, an enzyme, a metal chelate, a drug, a radioisotope, and/or a cytotoxic agent. Any appropriate method can be used to conjugate (e.g., covalently or non-covalently attach) another polypeptide or other moiety to a binder (e.g., an antibody, antigen binding fragment, antibody domain, CAR, and/or cell engager) provided herein. For example, another polypeptide or other moiety can be conjugated to a binder (e.g., an antibody, antigen binding fragment, antibody domain, CAR, and/or cell engager) provided herein using the methods described in U.S. Pat. No. 8,021,661.

In some cases, a binder (e.g., an antibody, antigen binding fragment, antibody domain, CAR, cell engager, and/or ADC) provided herein can be modified with a moiety that improves its stabilization and/or retention in circulation, for example, in blood, serum, or other tissues by, for example, at least 1.5-, 2-, 5-, 10-, or 50-fold. For example, a binder (e.g., an antibody, antigen binding fragment, antibody domain, CAR, cell engager, and/or ADC) provided herein can be attached (e.g., covalently or non-covalently attached) to a polymer such as a substantially non-antigenic polymer. Examples of substantially non-antigenic polymers that can be used as described herein include, without limitation, polyalkylene oxides and polyethylene oxides. In some cases, a polymer used herein can have any appropriate molecule weight. For example, a polymer having an average molecular weight from about 200 Daltons to about 35,000 Daltons (e.g., from about 1,000 to about 15,000 Daltons or from about 2,000 to about 12,500 Daltons) can be used. In some cases, a binder (e.g., an antibody, antigen binding fragment, antibody domain, CAR, cell engager, and/or ADC) provided herein can be attached (e.g., covalently or non-covalently) to a water soluble polymer. Examples of water soluble polymers that can be used as described herein include, without limitation, hydrophilic polyvinyl polymers, polyvinylalcohol, polyvinylpyrrolidone, polyalkylene oxide homopolymers, polyethylene glycol (PEG), polypropylene glycols, polyoxyethylenated polyols, and copolymers thereof and/or block copolymers thereof provided that the water solubility of the copolymer or block copolymers is maintained.

In some cases, a binder (e.g., an antibody, antigen binding fragment, antibody domain, CAR, cell engager, and/or ADC) provided herein can be attached (e.g., covalently or non-covalently attached) to one or more polyoxyalkylenes (e.g., polyoxyethylene, polyoxypropylene, or block copolymers of polyoxyethylene and polyoxypropylene), polymethacrylates, carbomers, branched or unbranched polysaccharides, or combinations thereof. For example, a binder (e.g., an antibody, antigen binding fragment, antibody domain, CAR, cell engager, and/or ADC) provided herein can be covalently attached to polyoxyethylene.

This document also provides ADCs. The term "ADC" as used herein refers to a conjugate that includes (a) an antigen binding domain and (b) at least one drug covalently linked directly or indirectly to that antigen binding domain. In some cases, an ADC described herein can include (a) an antigen binding domain having the ability to bind to a CD66e polypeptide (e.g., a human CD66e polypeptide) and (b) at least one drug covalently linked directly or indirectly to that antigen binding domain. Any appropriate binder (e.g., an antibody, antigen binding fragment, and/or antibody domain) provided herein and having the ability to bind to a CD66e polypeptide (e.g., a human CD66e polypeptide) can be used as an antigen binding domain to make an ADC described herein. For example, any of the binders set forth in Table 13 can be used to make an ADC having the ability to bind to a CD66e polypeptide (e.g., a human CD66e polypeptide). Examples of drugs that can be used to make an ADC described herein include, without limitation, auristatins (e.g., monomethyl auristatin E (MMAE)), mertansine (DM-1), and pyrrolobenzodiazepine (PBD) dimers. Any appropriate ADC linker can be used to covalently attach one or more drugs to an antigen binding domain having the ability to bind to a CD66e polypeptide (e.g., a human CD66e polypeptide) to form an ADC provided herein. For example, cleavable or non-cleavable ADC linkers can be used to covalently attach one or more drugs to an antigen binding domain having the ability to bind to a CD66e polypeptide (e.g., a human CD66e polypeptide) to form an ADC provided herein. Examples of ADC linkers can be used to covalently attach one or more drugs to an antigen binding domain having the ability to bind to a CD66e polypeptide (e.g., a human CD66e polypeptide) to form an ADC provided herein include, without limitation, ADC disulfide linkers, ADC hydrazone linkers, ADC peptide linkers, ADC thioether linkers, and ADC PEG-containing linkers.

This document also provides nucleic acid molecules (e.g., isolated nucleic acid molecules) having a nucleic acid sequence encoding at least part of a binder (e.g., an antibody, antigen binding fragment, antibody domain, CAR, and/or cell engager) provided herein. For example, an isolated nucleic acid molecule provided herein can include a nucleic acid sequence encoding a heavy chain variable domain such as a heavy chain variable domain as set forth in FIG. 2A or 3A. In another example, an isolated nucleic acid molecule provided herein can include a nucleic acid sequence encoding a light chain variable domain such as a light chain variable domain as set forth in FIG. 2B or 3B. In some cases, an isolated nucleic acid molecule provided herein can include a nucleic acid sequence encoding both (a) a heavy chain variable domain and (b) a light chain variable domain, with or without, encoding a linker polypeptide set forth in FIG. 10. A nucleic acid provided herein (e.g., an isolated nucleic acid molecule) can be single stranded or double stranded nucleic acid of any appropriate type (e.g., DNA, RNA, or DNA/RNA hybrids).

This document also provides vectors (e.g., plasmid vectors or viral vectors) containing one or more nucleic acids provided herein. An example of a plasmid vector that can be designed to include one or more nucleic acids having a nucleic acid sequence encoding at least part of a binder (e.g., an antibody, antigen binding fragment, antibody domain, CAR, and/or cell engager) provided herein includes, without limitation, phagemids. Examples of viral vectors that can be designed to include one or more nucleic acids having a nucleic acid sequence encoding at least part of a binder (e.g., an antibody, antigen binding fragment, antibody domain, CAR, and/or cell engager) provided herein include, without limitation, retroviral vectors, parvovirus-based vectors (e.g., adenoviral-based vectors and adeno-associated virus (AAV)-based vectors), lentiviral vectors (e.g., herpes simplex (HSV)-based vectors), poxviral vectors (e.g., vaccinia virus-based vectors and fowlpox virus-based vectors), and hybrid or chimeric viral vectors. For example, a viral vector having an adenoviral backbone with lentiviral components such as those described elsewhere (Zheng et al., *Nat. Biotech.,* 18(2): 176-80 (2000); WO 98/22143; WO 98/46778; and WO 00/17376) or viral vectors having an adenoviral backbone with AAV components such as those described elsewhere (Fisher et al., *Hum. Gene Ther.,* 7:2079-2087 (1996)) can be designed to include one or more nucleic acids having a nucleic acid sequence encoding at least part of a binder (e.g., an antibody, antigen binding fragment, antibody domain, CAR, and/or cell engager) provided herein.

In some cases, a vector (e.g., a plasmid vector or a viral vector) provided herein can include a nucleic acid sequence encoding scFv or antibody domain (e.g., a VH domain) provided herein. In some cases, a vector (e.g., a plasmid vector or a viral vector) provided herein can include a nucleic acid sequence encoding CAR provided herein. In some cases, a vector (e.g., a plasmid vector or a viral vector) provided herein can include a nucleic acid sequence encoding cell engager provided herein.

A vector provided herein (e.g., a plasmid vector or viral vector provided herein) can include any appropriate promoter and other regulatory sequence (e.g., transcription and translation initiation and termination codons) operably linked the nucleic acid sequence encoding at least part of a binder (e.g., an antibody, antigen binding fragment, antibody domain, CAR, and/or cell engager) provided herein. In some cases, a promoter used to drive expression can be a constitutive promotor or a regulatable promotor. Examples of regulatable promoters that can be used as described herein include, without limitation, inducible promotors, repressible promotors, and tissue-specific promoters. Examples of viral promotors that can be used as described herein include, without limitation, adenoviral promotors, vaccinia virus promotors, CMV promotors (e.g., immediate early CMV promotors), and AAV promoters.

Any appropriate method can be used to make a nucleic acid molecule (or vector such as a plasmid vector or viral vector) having a nucleic acid sequence encoding at least part of a binder (e.g., an antibody, antigen binding fragment, antibody domain, CAR, and/or cell engager) provided herein. For example, molecule cloning techniques can be used to make a nucleic acid molecule (or vector such as a plasmid vector or viral vector) having a nucleic acid sequence encoding at least part of a binder (e.g., an antibody, antigen binding fragment, antibody domain, CAR, and/or cell engager) provided herein as described elsewhere (see, e.g., Sambrook et al., Molecular Cloning: A Laboratory Manual, 2nd edition, Cold Spring Harbor Laboratory, N Y (1989); and Ausubel et al., Current Protocols in Molecular Biology, Green Publishing Associates and John Wiley & Sons, New York, N.Y. (1994)).

This document also provides host cells that include a nucleic acid provided herein (e.g., a nucleic acid having a nucleic acid sequence encoding at least part of a binder (e.g., an antibody, antigen binding fragment, antibody domain, CAR, and/or cell engager) provided herein). Host cells that can be designed to include one or more nucleic acids provided herein can be prokaryotic cells or eukaryotic cells. Examples of prokayotic cells that can be designed to include a nucleic acid provided herein include, without limitation, *E. coli* (e.g., Tb-1, TG-1, DH5a, XL-Blue MRF (Stratagene), SA2821, or Y1090 cells), *Bacillus subtilis, Salmonella typhimurium, Serratia marcescens*, or *Pseudomonas* (e.g., *P. aerugenosa*) cells. Examples of eukayotic cells that can be designed to include a nucleic acid provided herein include, without limitation, insect cells (e.g., Sf9 or Ea4 cells), yeast cells (e.g., *S. cerevisiae* cells), and mammalian cells (e.g., mouse, rat, hamster, monkey, or human cells). For example, VERO cells, HeLa cells, 3T3 cells, chinese hamster ovary (CHO) cells, W138 BHK cells, COS-7 cells, and MDCK cells can be designed to include a nucleic acid provided herein. Any appropriate method can be used to introduce one or more nucleic acids provided herein (e.g., a vector such as a plasmid vector or viral vector having a nucleic acid sequence encoding at least part of a binder provided herein) into a host cell. For example, calcium chloride-mediated transformation, transduction, conjugation, triparental mating, DEAE, dextran-mediated transfection, infection, membrane fusion with liposomes, high velocity bombardment with DNA-coated microprojectiles, direct microinjection into single cells, electroporation, or combinations thereof can be used to introduce a nucleic acid provided herein into a host cell (see, e.g., Sambrook et al., Molecular Biology: A Laboratory Manual, Cold Spring Harbor Laboratory, N Y (1989); Davis et al., Basic Methods in Molecular Biology (1986); and Neumann et al., EMBO J, 1:841 (1982)).

In some cases, cells such as T cells, stem cells (e.g., induced pluripotent stem cells or mesenchymal stem cells), or NK cells can be designed to express one or more nucleic acids encoding a CAR described herein. For example, a population of T cells can be infected with viral vectors designed to express nucleic acid encoding a CAR described herein (e.g., a CAR having the ability to bind to a CD66e polypeptide).

In some cases, cells such as T cells, stem cells (e.g., induced pluripotent stem cells or mesenchymal stem cells), or NK cells can be designed to express one or more nucleic acids encoding a cell engager described herein. For example, a population of T cells can be infected with viral vectors designed to express nucleic acid encoding a cell engager described herein (e.g., a cell engager having the ability to bind to a CD66e polypeptide).

In some cases, a binder (e.g., an antibody, antigen binding fragment, antibody domain, CAR, and/or cell engager) provided herein can be produced using a method that includes (a) introducing nucleic acid encoding the polypeptide into a host cell; (b) culturing the host cell in culture medium under conditions sufficient to express the polypeptide; (c) harvesting the polypeptide from the cell or culture medium; and (d) purifying the polypeptide (e.g., to reach at least 50, 60, 70, 80, 90, 95, 97, 98, or 99 percent purity).

In some cases, a binder (e.g., an antibody, antigen binding fragment, antibody domain, cell engager, and/or ADC) provided herein, a nucleic acid provided herein (e.g., nucleic acid encoding an antibody, antigen binding fragment, antibody domain, CAR, and/or cell engager provided herein), a vector provided herein (e.g., a viral vector designed to express an antibody, antigen binding fragment, antibody domain, CAR, and/or cell engager provided herein), and/or a host cell provided herein (e.g., a host cell designed to express an antibody, antigen binding fragment, antibody domain, CAR, and/or cell engager provided herein) can be formulated as a pharmaceutical composition for administration to a mammal (e.g. a human) having cancer to treat that mammal. In some cases, a binder (e.g., an antibody, antigen binding fragment, antibody domain, cell engager, and/or ADC) provided herein, a nucleic acid provided herein (e.g., nucleic acid encoding an antibody, antigen binding fragment, antibody domain, CAR, and/or cell engager provided herein), a vector provided herein (e.g., a viral vector designed to express an antibody, antigen binding fragment, antibody domain, CAR, and/or cell engager provided herein), and/or a host cell provided herein (e.g., a host cell designed to express an antibody, antigen binding fragment, antibody domain, CAR, and/or cell engager provided herein) can be formulated as a pharmaceutical composition for administration to a mammal (e.g. a human) to reduce the number of cancer cells within the mammal and/or to increase the survival of the mammal suffering from cancer. For example, a binder (e.g., an antibody, antigen binding fragment, antibody domain, cell engager, and/or ADC) provided herein having the ability to bind to a CD66e polypeptide (e.g., a human CD66e polypeptide) can be formulated as a pharmaceutical composition for administration to a mammal (e.g. a human). In some cases, a pharmaceutical composition provided herein can include a pharmaceutically acceptable carrier such as a buffer, a salt, a surfactant, a sugar, a tonicity modifier, or combinations thereof as, for example, described elsewhere (Gervasi, et al., *Eur. J Pharmaceutics and Biopharmaceutics,* 131:8-24 (2018)). Examples of pharmaceutically acceptable carriers that can be used to make a pharmaceutical composition provided herein include, without limitation, water, lactic acid, citric acid, sodium chloride, sodium citrate, sodium succinate, sodium phosphate, a surfactant (e.g., polysorbate 20, polysorbate 80, or poloxamer 188), dextran 40, or a sugar (e.g., sorbitol, mannitol, sucrose, dextrose, or trehalose), or combinations thereof. For example, a pharmaceutical composition designed to include a binder (e.g., an antibody, antigen binding fragment, antibody domain, CAR, cell engager, and/or ADC) provided herein (or a nucleic acid, a vector, or a host cell provided herein) can be formulated to include a buffer (e.g., an acetate, citrate, histidine, succinate, phosphate, or hydroxymethylaminomethane (Tris) buffer), a surfactant (e.g., polysorbate 20, polysorbate 80, or poloxamer 188), and a sugar such as sucrose. Other ingredients that can be included within a pharmaceutical composition provided herein include, without limitation, amino acids such as glycine or arginine, antioxidants such as ascorbic acid, methionine, or ethylenediaminetetraacetic acid (EDTA), anticancer agents such as enzalutamide, imanitib, gefitinib, erlotini, sunitinib, lapatinib, nilotinib, sorafenib, temsirolimus, everolimus, pazopanib, crizotinib, ruxolitinib, axitinib, bosutinib, cabozantinib, ponatinib, regorafenib, ibrutinib, trametinib, perifosine, bortezomib, carfilzomib, batimastat, ganetespib, obatoclax, navitoclax, taxol, paclitaxel, or bevacizumab, or combinations thereof. For example, a pharmaceutical composition provided herein can be formulated to include one or more binders (e.g., one or more antibodies, one or more antigen binding fragments, one or more antibody domains, one or more cells designed to express a CAR having the ability to bind to a CD66e polypeptide, one or more cell engagers, and/or one or more ADCs) provided herein in combination with one or more checkpoint inhibitors such as anti-PD-1 antibodies or PD-1 inhibitors (e.g., cemiplimab, nivolumab, pembrolizumab, JTX-4014, spartalizumab, camrelizumab, sintilimab, tislelizumab, toripalimab, dostarlimab, INCMGA00012, AMP-224, or AMP-514), anti-PD-L1 antibodies or PD-L1 inhibitors (e.g., avelumab, durvalumab, atezolizumab, KN035, CK-301, AUNP12, CA-170, or BMS-986189), and/or anti-CTLA-4 antibodies (e.g., ipilimumab).

In some cases, when a pharmaceutical composition is formulated to include one or more binders (e.g., one or more antibodies, one or more antigen binding fragments, one or more antibody domains, one or more cells designed to express a CAR having the ability to bind to a CD66e polypeptide, one or more cell engagers, and/or one or more ADCs) provided herein, any appropriate concentration of the binder can be used. For example, a pharmaceutical composition provided herein can be formulated to be a liquid that includes from about 1 mg to about 500 mg (e.g., from about 1 mg to about 500 mg, from about 10 mg to about 500 mg, from about 50 mg to about 500 mg, from about 100 mg to about 500 mg, from about 0.5 mg to about 250 mg, from about 0.5 mg to about 150 mg, from about 0.5 mg to about 100 mg, from about 0.5 mg to about 50 mg, from about 1 mg to about 300 mg, from about 2 mg to about 200 mg, from about 10 mg to about 300 mg, from about 25 mg to about 300 mg, from about 50 mg to about 150 mg, or from about 150 mg to about 300 mg) of a binder (e.g., an antibody, antigen binding fragment, antibody domain, $CAR^+$ cell population, cell engager, and/or ADC) provided herein per mL. In another example, a pharmaceutical composition provided herein can be formulated to be a solid or semi-solid that includes from about 0.5 mg to about 500 mg (e.g., from about 1 mg to about 500 mg, from about 10 mg to about 500 mg, from about 50 mg to about 500 mg, from about 100 mg to about 500 mg, from about 0.5 mg to about 250 mg, from about 0.5 mg to about 150 mg, from about 0.5 mg to about 100 mg, from about 0.5 mg to about 50 mg, from about 1 mg to about 300 mg, from about 10 mg to about 300 mg, from about 25 mg to about 300 mg, from about 50 mg to about 150 mg, or from about 150 mg to about 300 mg) of a binder (e.g., an antibody, antigen binding fragment, antibody domain, cell engager, and/or ADC) provided herein. In some cases, a pharmaceutical composition containing a binder (e.g., an antibody, antigen binding fragment, and/or antibody domain) provided herein can be formulated as a dosage form with a titer of the binder being from about $1\times10^5$ to about $1\times10^{12}$ (e.g., from about $1\times10^5$ to about $1\times10^{10}$, from about $1\times10^5$ to about $1\times10^8$, from about $1\times10^6$ to about $1\times10^{12}$, from about $1\times10^6$ to about $1\times10^{12}$, from about $1\times10^8$ to about $1\times10^{12}$, from about $1\times10^9$ to about $1\times10^{12}$, from about $1\times10^6$ to about $1\times10^{11}$, or from about $1\times10^7$ to about $1\times10^{10}$).

In some cases, when a pharmaceutical composition is formulated to include one or more nucleic acids (e.g., vectors such as viral vectors) encoding at least part of a binder (e.g., an antibody, antigen binding fragment, antibody domain, CAR, and/or cell engager) provided herein, any appropriate concentration of the nucleic acid can be used. For example, a pharmaceutical composition provided herein can be formulated to be a liquid that includes from about 0.5 mg to about 500 mg (e.g., from about 1 mg to about 500 mg, from about 10 mg to about 500 mg, from about 50 mg to about 500 mg, from about 100 mg to about 500 mg, from about 0.5 mg to about 250 mg, from about 0.5 mg to about 150 mg, from about 0.5 mg to about 100 mg, from about 0.5 mg to about 50 mg, from about 1 mg to about 300 mg, from about 2 mg to about 200 mg, from about 10 mg to about 300 mg, from about 25 mg to about 300 mg, from about 50 mg to about 150 mg, or from about 150 mg to about 300 mg) of a nucleic acid provided herein per mL. In another example, a pharmaceutical composition provided herein can be formulated to be a solid or semi-solid that includes from about 0.5 mg to about 500 mg (e.g., from about 1 mg to about 500 mg, from about 10 mg to about 500 mg, from about 50 mg to about 500 mg, from about 100 mg to about 500 mg, from about 0.5 mg to about 250 mg, from about 0.5 mg to about 150 mg, from about 0.5 mg to about 100 mg, from about 0.5 mg to about 50 mg, from about 1 mg to about 300 mg, from about 10 mg to about 300 mg, from about 25 mg to about 300 mg, from about 50 mg to about 150 mg, or from about 150 mg to about 300 mg) of a nucleic acid provided herein.

In some cases, a pharmaceutical composition designed to include a binder (e.g., an antibody, antigen binding fragment, antibody domain, cell engager, and/or ADC) provided herein can be formulated to include one or more agents capable of reducing aggregation of the binder when formulated. Examples of such agents that can be used as described herein include, without limitation, methionine, arginine, lysine, aspartic acid, glycine, glutamic acid, and combinations thereof. In some cases, one or more of these amino acids can be included within the formulation at a concentration from about 0.5 mM to about 145 mM (e.g., from about 1 mM to about 145 mM, from about 10 mM to about 145 mM, from about 100 mM to about 145 mM, from about 0.5 mM to about 125 mM, from about 0.5 mM to about 100 mM, from about 0.5 mM to about 75 mM, or from about 10 mM to about 100 mM).

A pharmaceutical composition provided herein can be in any appropriate form. For example, a pharmaceutical composition provided herein can designed to be a liquid, a semi-solid, or a solid. In some cases, a pharmaceutical composition provided herein can be a liquid solution (e.g., an injectable and/or infusible solution), a dispersion, a suspension, a tablet, a pill, a powder, a microemulsion, a liposome, or a suppository. In some cases, a pharmaceutical composition provided herein can be lyophilized. In some cases, a pharmaceutical composition provided herein (e.g., a pharmaceutical composition that includes one or more binders (e.g., one or more antibodies, one or more antigen binding fragments, one or more antibody domains, one or more cell engagers, and/or one or more ADCs) provided herein can be formulated with a carrier or coating designed to protect against rapid release. For example, a pharmaceutical composition provided herein can be formulated as a controlled release formulation or as a regulated release formulation as described elsewhere (U.S. Patent Application Publication Nos. 2019/0241667; 2019/0233522; and 2019/0233498).

This document also provides methods for administering a composition (e.g., a pharmaceutical composition provided herein) containing one or more binders (e.g., one or more antibodies, one or more antigen binding fragments, one or more antibody domains, one or more cell engagers, and/or one or more ADCs) provided herein (or a nucleic acid, vector, or host cell (e.g., $CAR^+$ cells) provided herein) to a mammal (e.g., a human). For example, a composition (e.g., a pharmaceutical composition provided herein) containing one or more binders (e.g., one or more antibodies, one or more antigen binding fragments, one or more antibody domains, one or more cell engagers, and/or one or more ADCs) provided herein (or a nucleic acid, vector, and/or host cell (e.g., $CAR^+$ cells) provided herein) can be administered to a mammal (e.g., a human) having cancer to treat that mammal. In some cases, a composition (e.g., a pharmaceutical composition provided herein) containing one or more binders (e.g., one or more antibodies, one or more antigen binding fragments, one or more antibody domains, one or more cell engagers, and/or one or more ADCs) provided herein (or a nucleic acid, vector, and/or host cell (e.g., $CAR^+$ cells) provided herein) can be administered to a mammal (e.g. a human) to reduce the number of cancer cells within the mammal and/or to increase the survival of the mammal suffering from cancer.

Any appropriate cancer can be treated using a composition (e.g., a pharmaceutical composition provided herein) containing one or more binders (e.g., one or more antibodies, one or more antigen binding fragments, one or more antibody domains, one or more cell engagers, and/or one or more ADCs) provided herein (or a nucleic acid, vector, or host cell (e.g., $CAR^+$ cells) provided herein). For example, a mammal (e.g., a human) having cancer can be treated by administering a composition (e.g., a pharmaceutical composition) containing one or more binders (e.g., one or more antibodies, one or more antigen binding fragments, one or more antibody domains, one or more cell engagers, and/or one or more ADCs) provided herein to that mammal. Examples of cancers that can be treated as described herein include, without limitation, lung cancer, prostate cancer, esophageal cancer, stomach cancer, colorectal cancer, liver cancer, vaginal cancer, cervical cancer, pancreatic cancer, and breast cancer. In some cases, a mammal (e.g., a human) having a $CD66e^+$ cancer (e.g., a $CD66e^+$ lung cancer, a $CD66e^+$ prostate cancer, a $CD66e^+$ esophageal cancer, a $CD66e^+$ stomach cancer, a $CD66e^+$ colorectal cancer, a $CD66e^+$ liver cancer, a $CD66e^+$ vaginal cancer, or a $CD66e^+$ cervical cancer) can be administered a composition (e.g., a pharmaceutical composition) containing one or more binders (e.g., one or more antibodies, one or more antigen binding fragments, one or more antibody domains, one or more cell engagers, and/or one or more ADCs) provided herein to treat that mammal (e.g., to reduce the number of cancer cells within the mammal).

Any appropriate method can be used to administer a composition (e.g., a pharmaceutical composition) provided herein to a mammal (e.g., a human). For example, a composition provided herein (e.g., a pharmaceutical composition containing one or more binders provided herein such as one or more antibodies, one or more antigen binding fragments, one or more antibody domains, one or more cell engagers, and/or one or more ADCs provided herein) can be administered to a mammal (e.g., a human) intravenously (e.g., via an intravenous injection or infusion), subcutaneously (e.g., via a subcutaneous injection), intraperitoneally (e.g., via an intraperitoneal injection), orally, via inhalation, or intramuscularly (e.g., via intramuscular injection). In some cases, the route and/or mode of administration of a composition (e.g., a pharmaceutical composition provided herein) can be adjusted for the mammal being treated.

In some cases, an effective amount of a composition containing one or more binders (e.g., one or more antibodies, one or more antigen binding fragments, one or more antibody domains, one or more cell engagers, and/or one or more ADCs) provided herein (or a nucleic acid, vector, or host cell (e.g., $CAR^+$ cells) provided herein) (e.g., a pharmaceutical composition provided herein) can be an amount that reduces the number of cancer cells within a mammal having cancer without producing significant toxicity to the mammal. In some cases, an effective amount of a composition containing one or more binders (e.g., one or more antibodies, one or more antigen binding fragments, one or more antibody domains, one or more cell engagers, and/or one or more ADCs) provided herein (or a nucleic acid, vector, or host cell (e.g., $CAR^+$ cells) provided herein) (e.g., a pharmaceutical composition provided herein) can be an amount that increases the survival time of a mammal having cancer as compared to a control mammal having comparable cancer and not treated with the composition. For example, an effective amount of a binder (e.g., an antibody, antigen binding fragment, antibody domain, cell engager, and/or ADC) provided herein can be from about 0.001 mg/kg to about 100 mg/kg (e.g., from about 0.001 mg/kg to about 90 mg/kg, from about 0.001 mg/kg to about 80 mg/kg, from about 0.001 mg/kg to about 70 mg/kg, from about 0.001 mg/kg to about 60 mg/kg, from about 0.001 mg/kg to about 50 mg/kg, from about 0.001 mg/kg to about 40 mg/kg, from about 0.001 mg/kg to about 30 mg/kg, from about 0.005 mg/kg to about 100 mg/kg, from about 0.01 mg/kg to about 100 mg/kg, from about 0.05 mg/kg to about 100 mg/kg, from about 0.1 mg/kg to about 100 mg/kg, from about 0.5 mg/kg to about 100 mg/kg, from about 1 mg/kg to about 100 mg/kg, from about 5 mg/kg to about 100 mg/kg, from about 0.01 mg/kg to about 25 mg/kg, from about 0.1 mg/kg to about 30 mg/kg, from about 0.15 mg/kg to about 25 mg/kg, from about 0.2 mg/kg to about 20 mg/kg, from about 0.5 mg/kg to about 20 mg/kg, from about 1 mg/kg to about 30 mg/kg, from about 1 mg/kg to about 25 mg/kg, from about 1 mg/kg to about 20 mg/kg, from about 2 mg/kg to about 20 mg/kg, from about 5 mg/kg to about 30 mg/kg, from about 10 mg/kg to about 30 mg/kg, from about 15 mg/kg to about 30 mg/kg, from about 20 mg/kg to about 30 mg/kg, from about 3 mg/kg to about 30 mg/kg, from about 0.5 mg/kg to about 10 mg/kg, from about 1 mg/kg to about 10 mg/kg, from about 1 mg/kg to about 5 mg/kg, or from about 1 mg/kg to about 3 mg/kg). The effective amount can remain constant or can be adjusted as a sliding scale or variable dose depending on the mammal's response to treatment. Various factors can influence the actual effective amount used for a particular application. For example, the severity of cancer when treating a mammal having cancer, the route of administration, the age and general health condition of the mammal, excipient usage, the possibility of co-usage with other therapeutic or prophylactic treatments such as use of other agents (e.g., checkpoint inhibitors), and the judgment of the treating physician may require an increase or decrease in the actual effective amount of a composition provided herein (e.g., a pharmaceutical composition containing one or more binders provided herein) that is administered.

In some cases, an effective frequency of administration of a composition containing one or more binders (e.g., one or more antibodies, one or more antigen binding fragments, one or more antibody domains, one or more cell engagers, and/or one or more ADCs) provided herein (or a nucleic acid, vector, or host cell (e.g., $CAR^+$ cells) provided herein) (e.g., a pharmaceutical composition provided herein) can be a frequency that reduces the number of cancer cells within a mammal having cancer without producing significant toxicity to the mammal. In some cases, an effective frequency of administration of a composition containing one or more binders (e.g., one or more antibodies, one or more antigen binding fragments, one or more antibody domains, one or more cell engagers, and/or one or more ADCs) provided herein (or a nucleic acid, vector, or host cell (e.g., $CAR^+$ cells) provided herein) (e.g., a pharmaceutical composition provided herein) can be a frequency that increases the survival time of a mammal having cancer as compared to a control mammal having comparable cancer and not treated with the composition. For example, an effective frequency of administration of a pharmaceutical composition provided herein such as a pharmaceutical composition containing one or more binders provided herein can be from about twice daily to about once a year (e.g., from about twice daily to about once a month, from about twice daily to about once a week, from about once daily to about once a month, or from one once daily to about once a week). In some cases, the frequency of administration of a pharmaceutical composition provided herein such as a pharmaceutical composition containing one or more binders provided herein can be daily. The frequency of administration of a pharmaceutical composition provided herein such as a pharmaceutical composition containing one or more binders provided herein can remain constant or can be variable during the duration of treatment. Various factors can influence the actual effective frequency used for a particular application. For example, the severity of the cancer, the route of administration, the age and general health condition of the mammal, excipient usage, the possibility of co-usage with other therapeutic or prophylactic treatments such as use of other agents (e.g., checkpoint inhibitors), and the judgment of the treating physician may require an increase or decrease in the actual effective frequency of administration of a composition provided herein (e.g., a pharmaceutical composition containing one or more binders provided herein).

In some cases, an effective duration of administration of a composition containing one or more binders (e.g., one or more antibodies, one or more antigen binding fragments, one or more antibody domains, one or more cell engagers, and/or one or more ADCs) provided herein (or a nucleic acid, vector, or host cell (e.g., $CAR^+$ cells) provided herein) (e.g., a pharmaceutical composition provided herein) can be a duration that reduces the number of cancer cells within a mammal without producing significant toxicity to the mammal. In some cases, an effective duration of administration of a composition containing one or more binders (e.g., one or more antibodies, one or more antigen binding fragments, one or more antibody domains, one or more cell engagers, and/or one or more ADCs) provided herein (or a nucleic acid, vector, or host cell (e.g., $CAR^+$ cells) provided herein) (e.g., a pharmaceutical composition provided herein) can be a duration that increases the survival time of a mammal having cancer as compared to a control mammal having comparable cancer and not treated with the composition. For example, an effective duration of administration of a pharmaceutical composition provided herein such as a pharmaceutical composition containing one or more binders provided herein can vary from a single time point of administration to several weeks to several months (e.g., 4 to 12 weeks). Multiple factors can influence the actual effective duration used for a particular application. For example, the severity of the cancer, the route of administration, the age and general health condition of the mammal, excipient usage, the possibility of co-usage with other therapeutic or prophylactic treatments such as use of other agents (e.g., checkpoint inhibitors), and the judgment of the treating physician may require an increase or decrease in the actual effective duration of administration of a composition provided herein (e.g., a pharmaceutical composition containing one or more binders provided herein).

In some cases, a binder (e.g., an antibody, antigen binding fragment, and/or antibody domain) provided herein can be used to detect the presence or absence of a CD66e polypeptide (e.g., a human CD66e polypeptide) in vitro, in situ, or in vivo (e.g., in vivo imaging within a mammal such as a human). For example, a binder (e.g., an antibody, antigen binding fragment, and/or antibody domain) provided herein can be designed to include a label (e.g., a covalently attached radioactive, enzymatic, colorimetric, or fluorescent label). The labelled binder can be used to detect the presence or absence of a CD66e polypeptide (e.g., a human CD66e polypeptide) within a biological sample in vitro. Examples of biological samples that can be assessed using a binder (e.g., an antibody, antigen binding fragment, and/or antibody domain) provided herein include, without limitation, serum samples, plasma samples, tissue samples, biopsy samples, cell line samples, and tissue culture samples. In some cases, a biological sample that can be assessed as described herein can include mammalian body tissues and/or cells such as leukocytes, ovary tissue or cells, prostate tissue or cells, heart tissue or cells, placenta tissue or cells, pancreas tissue or cells, liver tissue or cells, spleen tissue or cells, lung tissue or cells, breast tissue or cells, head and neck tissue or cells, endometrium tissue or cells, colon tissue or cells, colorectal tissue or cells, cervix tissue or cells, stomach tissue or cells, or umbilical tissue or cells that may express a CD66e polypeptide (e.g., a human CD66e polypeptide). In some cases, a binder (e.g., an antibody, antigen binding fragment, and/or antibody domain) provided herein can be immobilized, e.g., on a support, and retention of a CD66e polypeptide (e.g., a human CD66e polypeptide) from a biological sample on the support can be detected, and/or vice versa. In some cases, a binder (e.g., an antibody, antigen binding fragment, and/or antibody domain) provided herein can be used in applications such as fluorescence polarization, microscopy, ELISA, centrifugation, chromatography, and/or cell sorting (e.g., fluorescence activated cell sorting).

In some cases, a binder (e.g., an antibody, antigen binding fragment, and/or antibody domain) provided herein containing a label (e.g., a covalently attached radioactive label) can be used to detect the presence or absence of a CD66e polypeptide (e.g., a human CD66e polypeptide) within a mammal (e.g., a human). For example, a binder (e.g., an antibody, antigen binding fragment, and/or antibody domain) provided herein that is labelled (e.g., covalently labelled) with a radiolabel or an MRI detectable label can be administered to a mammal (e.g., a human), and that mammal can be assessed using a means for detecting the detectable label. In some cases, a mammal can be scanned to evaluate the location(s) of a labelled binder provided herein within the mammal. For example, the mammal can be imaged using NMR or other tomographic techniques.

Examples of labels that can be attached (e.g., covalently or non-covalently attached) to a binder (e.g., an antibody, antigen binding fragment, and/or antibody domain) provided herein include, without limitation, radiolabels such as $^{131}I$, $^{111}In$, $^{123}I$, $^{99m}Tc$, $^{32}P$, $^{33}P$, $^{125}I$, $^{3}H$, $^{14}C$, and $^{188}Rh$, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as a peroxidase or a phosphatase. In some cases, short-range radiation emitters such as isotopes detectable by short-range detector probes can be used.

The invention will be further described in the following examples, which do not limit the scope of the invention described in the claims.

EXAMPLES

Example 1—Obtaining Binders Having the Ability to Bind to a Human CD66e Polypeptide CD66e contains an N-terminal Ig variable-region-liken (IgV) domain and six Ig constant region-type 2-like (IgC2-like) domains, N-A1-B1-A2-B2-A3-B3 joined to a GPI-anchor to the plasma membrane. Notably, the membrane-proximal A3B3 domains are found in splice variants of CD66e in numerous cancers so they were considered potent therapeutic epitopes. Here, two Fab antibody fragments (Clones: #1 and #2; FIGS. 2 and 3) were identified. To identify these Fabs, Fc-fused soluble CEACAM5 and CEACAM6 domains were designed and applied to a panning process. Isolated Fabs bound A3B3 domains and dominantly bound B3 domain and N-linked glycans at N612 and N650 of CEACAM5 in high affinity and specificity. Moreover, they did not cross-reactive to either other domains of CEACAM5 or CEACAM family members.

The sequences of Clone #1 were used to make an hIgG1 that exhibited CEACAM5-dependent cytotoxic activity in ADCC assays with the NEPC cell line, NCI-H660, and the PrAd cell line, Du145 in the presence of either primary NK cells or PBMCs. Moreover, constructed third generation CARs containing an scFv having the CDRs of Clone #1 were delivered to T cells that were shown to efficiently kill CEACAM5 positive prostate cancer cells while no detectable cytotoxicity was founded in CEACAM5 negative cells. These results demonstrate an immunotherapeutic potential of Clone #1 hIgG1 for NEPC treatment with considerably low off-target toxicity.

Preparation of Soluble Fc-Fused Recombinant CEACAM5 and CEACAM6 Domains

Human immunoglobulin 1 Fc region (hIgG1 Fc) fused CEACAM5 A3B3 (residues 501-682), CEACAM5 A1B1 (residues 145-322), CEACAM5 A2B2 (residues 323-500), and CEACAM6 AB (residues 145-296) were synthesized and then cloned into pSectag2A plasmid (Invitrogen, V90020). Each plasmid DNA was complexed with PEI-Max (Polysciences, 24765-1) and supplied to culture of the Freestyle human embryonic kidney cell-line (Gibco, R79007) for the transient transfection. Seven days post-transfection, Fc-fused recombinant proteins were purified by affinity chromatography with protein A resin (Captiva, NC0997253). Elution of bound proteins to protein A was eluted by adding 50 mM Glycine buffer pH 3.0, and then storage buffer was changed to phospho-buffered saline pH 7.4 (PBS) by using PD-10 desalting column (GE, 45-000-148). Protein purity was estimated in either SDS-PAGE or size exclusion chromatography packed with Superdex 200 increase 10/300 GL (GE healthcare, 28990944). The concentration of each proteins was determined by Nano Drop spectrophotometer 2000C (Thermo, ND2000C). N-glycosylation mutants of A3B3 domain of CEACAM5 (N508Q, N529Q, N553Q, N560Q, N580Q, N612Q, N650Q, and N665Q) were constructed by site-directed mutagenesis with Q5-site directed mutagenesis kit (NEB, E0554S), and those proteins were expressed and purified in same manner for wild type of CEACAM5.

Construction of a Fab Library and Panning

A combinatorial phage-displayed human Fab library ($1\times10^{11}$ clones) was constructed by grafting naturally occurring V(D)J recombination regions of heavy chain (HC) and VJ recombination regions of light chain (LC) into the IGHV3-11 and IGKV1-39 germline framework, respectively. In order to amplify complementary determining region 3 (CDR3) and J genes for HC or LC, RNA extracted from PBMCs of 50 healthy blood donors was used for cDNA synthesis with Superscript™ IV first-strand Synthesis System (Invitrogen, 18091050) and random hexamer and oligo dT primers were applied to annealing step. Incorporation of amplified CDR3 and J-genes into the selected human frameworks was performed by subsequent overlapping PCR with Q5 polymerase (NEB, M0491), and prepared insert DNA and pCAT2 plasmid (in-house plasmid, modified pCom3X) were digested with NotI and ApaI restriction enzymes. Digested insert and vector were ligated in 1:1 ratio by using T4 DNA ligase (NEB, M0202). Circularized plasmid DNA was transformed into TG1 *E. coli* competent cells (Lucigen, 605502), and 100 times electroporation were carried out. M13KO7 helper phage (NEB, N0315S) was amplified in TOP10F' *E. coli* and then used for subsequent phage-displayed library production. For panning, phages were pre-blocked with 3% bovine serum albumin (BSA) in PBS (w/v) for 1 hour at room temperature. Blocked phages incubated with 10 nM biotinylated CEACAM5 A3B3-Fc for 1 hour at room temperature in the presence of 300 nM competitors comprising CEACAM5 A1B1-Fc, CEACAM5 A2B2-Fc, and CEACAM6 AB-Fc. Bound phages were separated by streptavidin coated magnetic beads (Invitrogen, 11-205-D) and washed 10 times with 1 mL of PBS pH 7.4 containing 0.1% Tween-20 (w/v). Elution of bound phages was conducted by adding 10 mM tris-HCl pH 8.0 containing 25 mM dithiothreitol (DTT) for 10 minutes. After three rounds of panning, binding of 192 individual clones was analyzed in ELISA and then selected clones were sequenced after plasmid rescue.

Purification of scFv, Fab, and IgG

The pCAT2 plasmid containing scFv or Fab was transformed into HB2151 *E. coli* competent cells, and then transformed colonies were selected in ampicillin containing LB plate (100 μg/mL final concentration) for overnight in incubator at 37° C. Next day, a colony was inoculated in liquid LB+ampicillin media and cultured in 37° C. shaking incubator. 0.1 mM of isopropyl β-D-1-thiogalactopyranoside (IPTG) as final concentration was added to culture at $OD_{600}$ of between 0.4-0.6 corresponding to around $4\times10^8$ cells/mL. The culture was relocated to shaking incubator set as 30° C., 200 rpm. Next day, induced *E. coli* cells were harvested and resuspended in 1/10 volume of periplasm extraction buffer containing polymyxin B (0.5 mg/mL in PBS pH 7.4) and then incubated on ice for an hour. Supernatant was collected then loaded into pre-packed Ni-NTA resin. Bound scFv or Fab was eluted by adding 300 mM imidazole in PBS pH 7.4 and then imidazole was removed. For IgG preparation, IgG cloned plasmid DNA was transfected to HEK239F cells, and expressed for 5-7 days post-transfection. IgGs were purified as previously described in Fc-fused antigen preparation.

Binding Assessment in ELISA

Binding and specificity of scFv, Fab, or IgG to CEACAM related proteins were analyzed through indirect ELISA. Briefly, Fc-fused CEACAM5 polypeptides, CEACAM6 polypeptides, extra-cellular domain of CEACAM5 (R&D systems, 4128-CM), CEACAM6 (R&D systems, 3934-CM), or cynomolgus CEACAM5 (Sino biological, 90891-C08H) was coated on a 96 well plate (Corning, 3690) at 200 ng/well (50 μL volume) in PBS for 2 hours at room temperature. Blocking was carried out with 3% BSA in PBS for overnight at 4° C. Next day, various concentration of scFv, Fab, or IgG was treated to antigen coated plates and incubated for 1 hour at room temperature. After washing three times, anti-FLAG mouse antibody (M2 clone)-HRP conjugated (Sigma, A8592, 1:3000 dilution) or anti-human kappa goat antibody-HRP conjugated (Invitrogen, A18853, 1:3000 dilution) was treated for binding detection. Same volume of TMB (Thermo, PI34028) was added as a substrate, and then enzymatic reaction was stopped by adding of 2N sulfonic acid. The monomeric Fc fused-CD16a (Fc γRIIIa), CD64 (Fc γRIa) and CD32 (Fc γRIIa) were obtained from Prof. Wei Li (University of Pittsburgh, PA) and used for Fc gamma receptor (FcγR) binding test.

Results

Figure 20B:
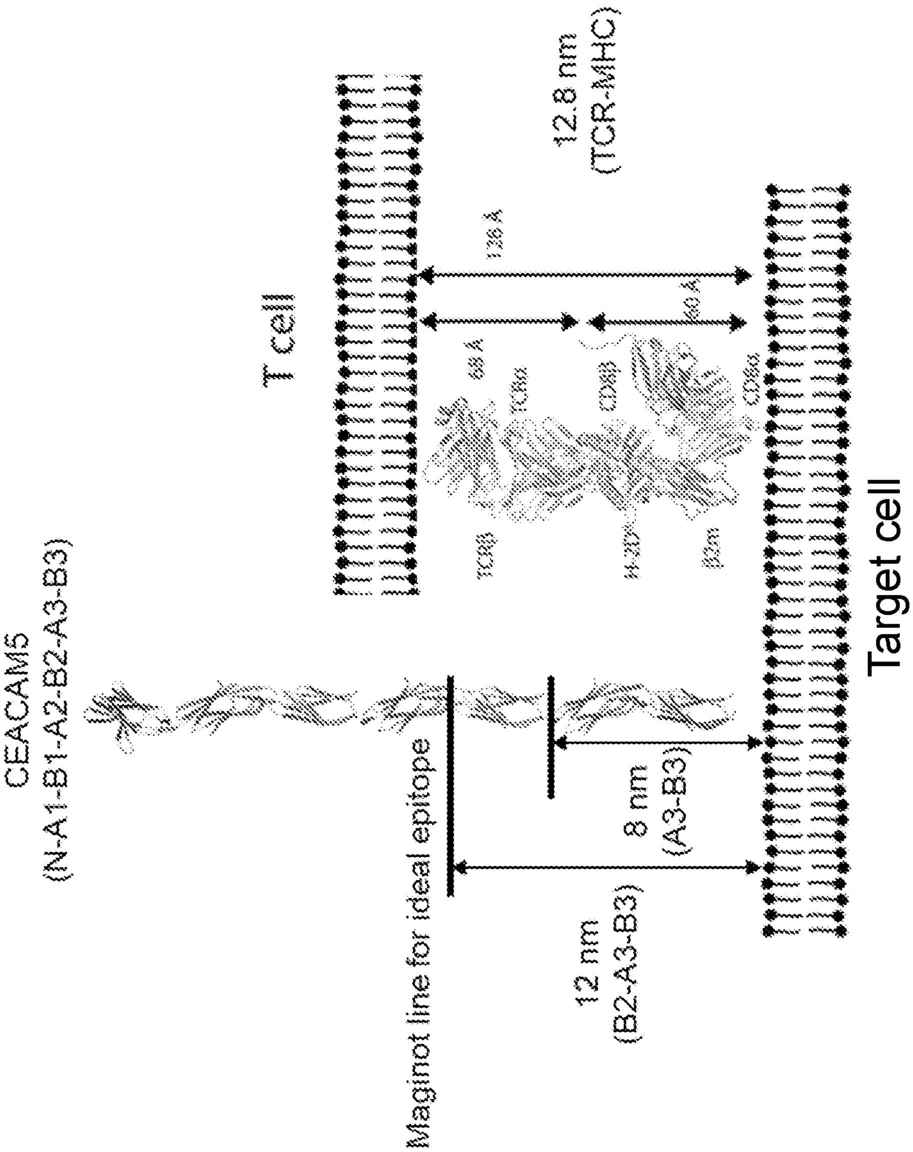
FIG. 20B is a schematic depicting one of the rationales of the use of the A3B3 domain as a major antigen for antibody discovery.
Figure 21:
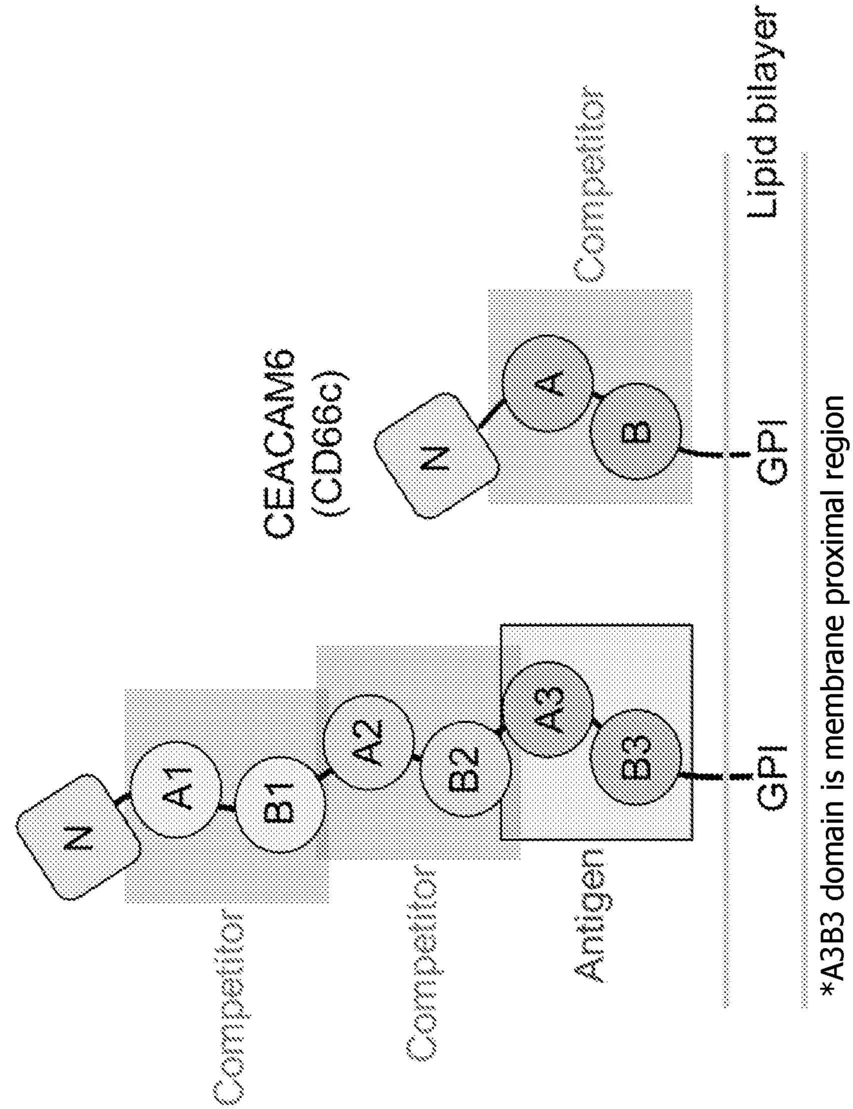
FIG. 21. Design of antigen and competitors for panning.
Figure 22:
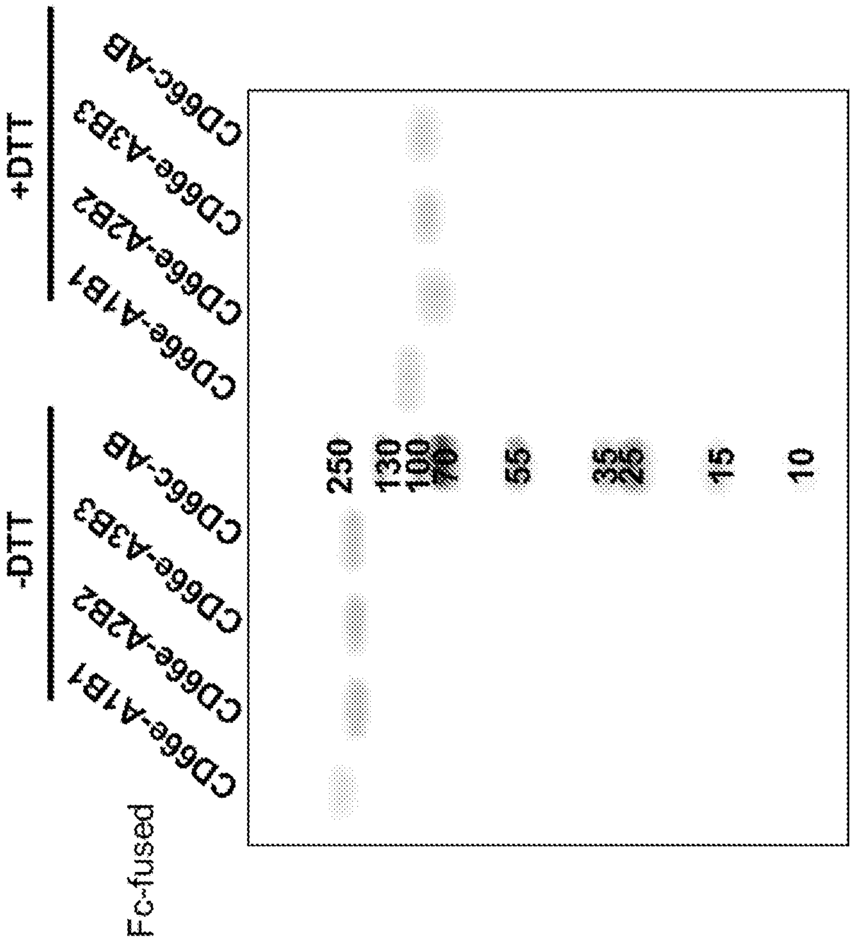
FIG. 22. SDS-PAGE analysis for purified Fc-fused CEACAM5 and CEACAM6 domains.
Figure 23:
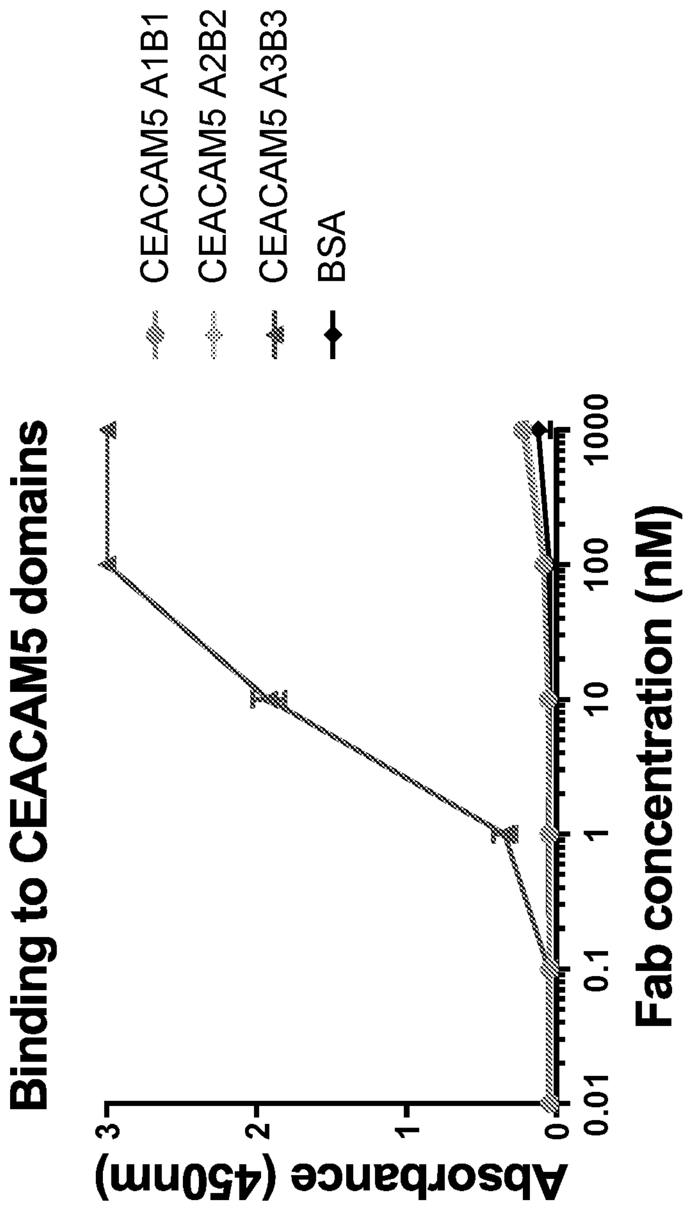
FIG. 23. Binding of 1G9 Fab to different domains of CEACAM5 in an indirect ELISA.
Figure 24:
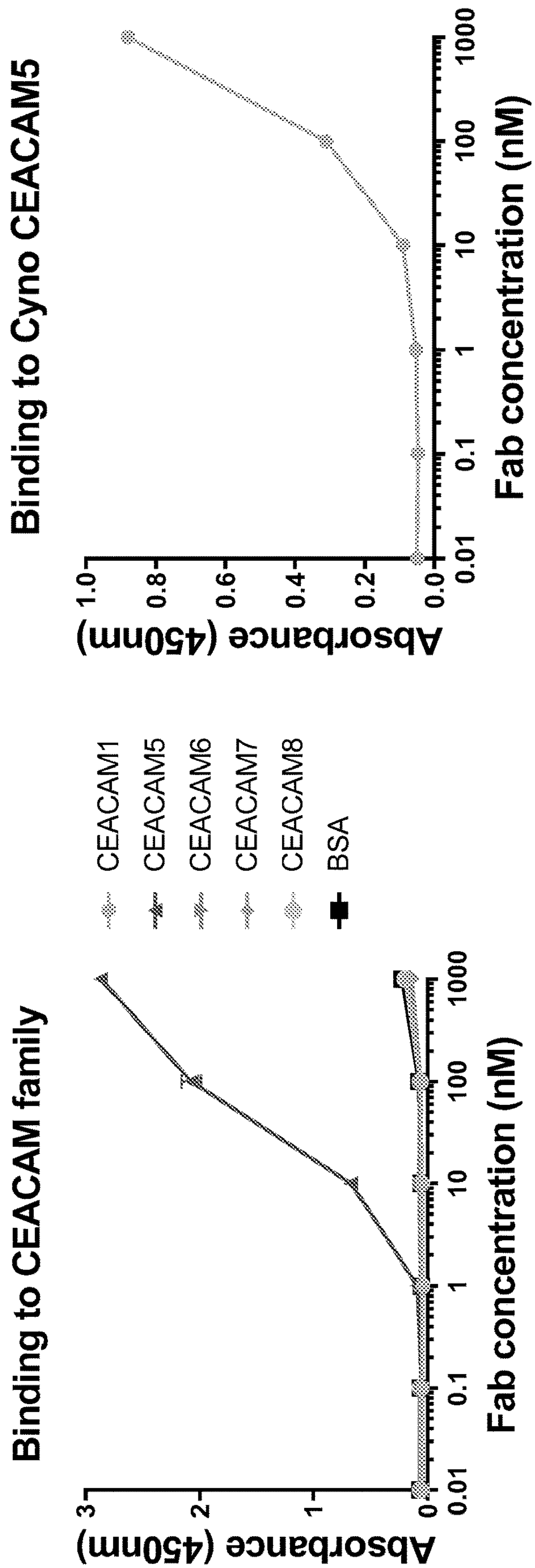
FIG. 24. Binding of 1G9 Fab and IgG1 to different CEACAM family members and cynomolgus CEACAM5 in indirect ELISA.
Figure 25:
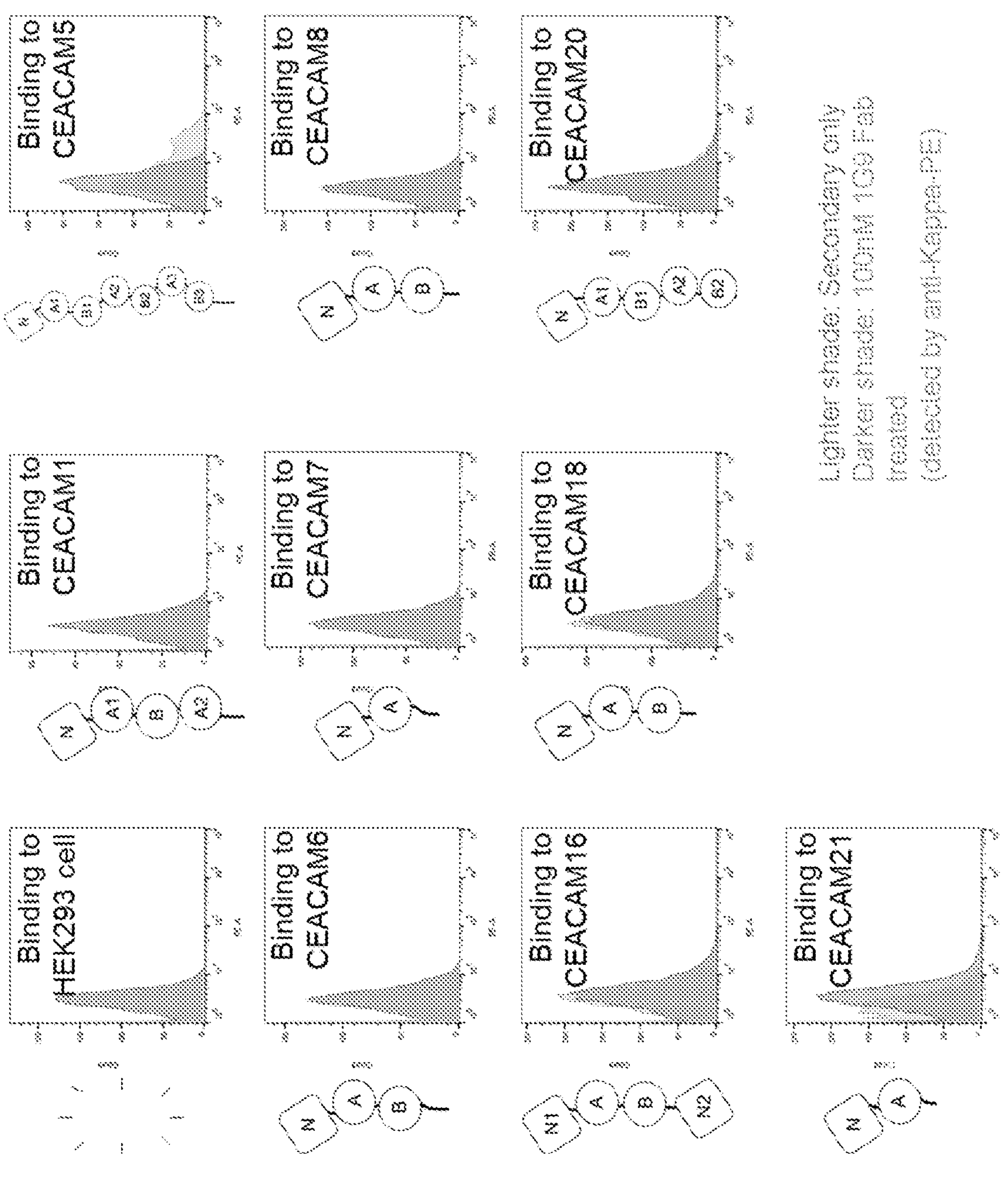
FIG. 25. Binding of 1G9 Fab to different domains of CEACAM family members in flow-cytometry analysis.
Figure 26:
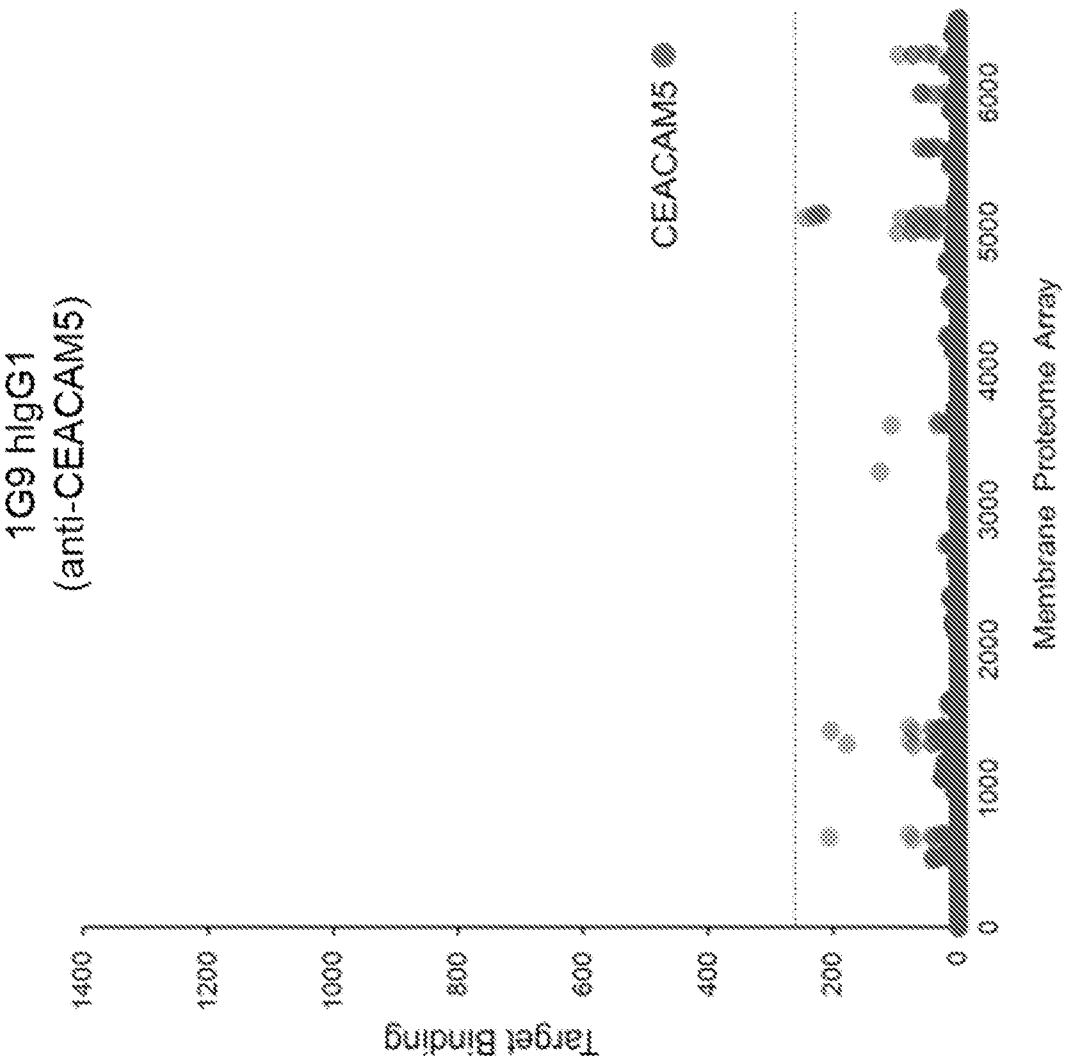
FIG. 26. Specificity of 1G9 IgG1 in the membrane proteome array (MPA) against >5,800 human membrane associated proteins.
Figure 27:
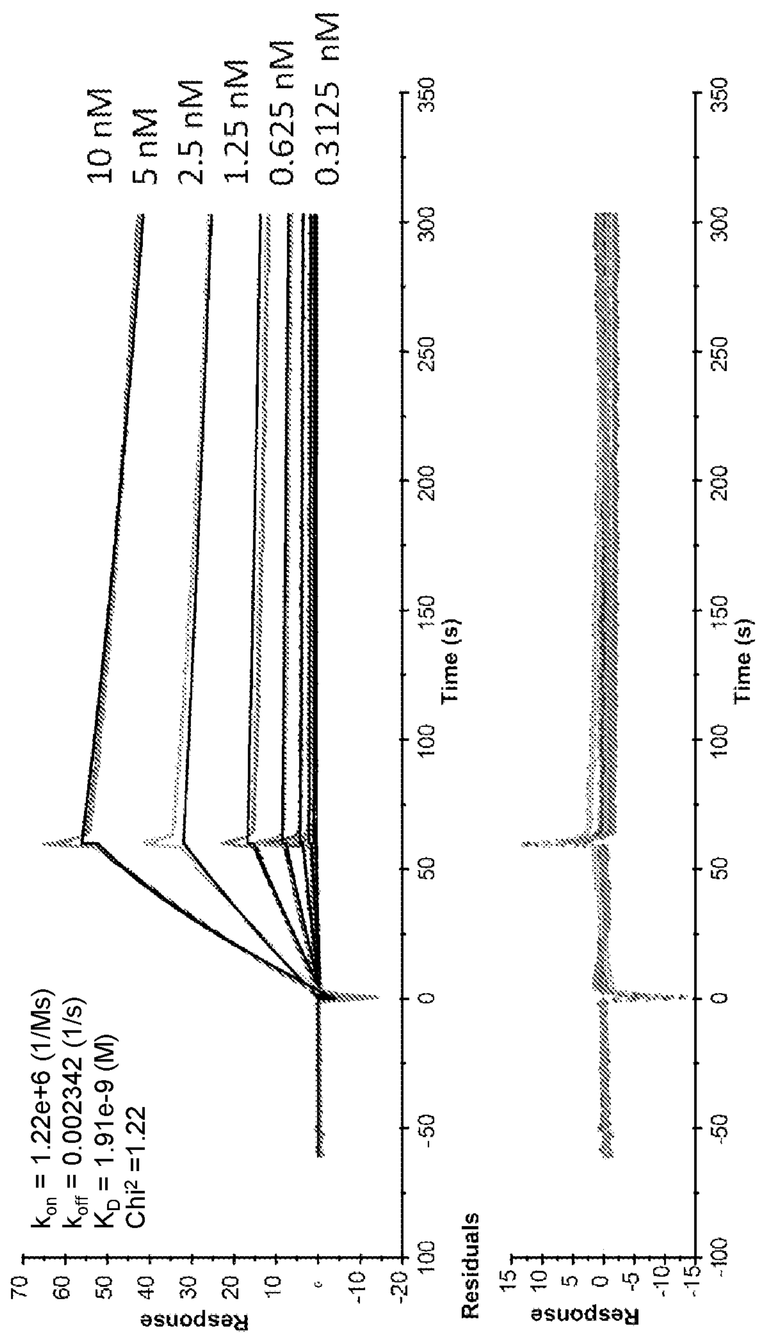
FIG. 27. An equilibrium dissociation constant measurement in surface plasmon resonance (SPR) analysis with Biacore.

Isolation of Clone #1 Fab Specifically targeting A3B3 Domains of CEACAM5 with High Specificity The following was performed to develop anti-CEACAM5 antibodies (e.g., fully human antibodies). Briefly, domains of CEACAM5 and CEACAM6 with fusion of human IgG1 Fc were designed and purified. A3B3 domain was regarded as an ideal epitope for targeting membrane proximal region of CEACAM5 (FIGS. 20A and 20B). In order to exclude potential nonspecific cross-reactive binders that can lead to toxicity in normal cells and to prevent binding to the membrane-distal region of the extracellular portion of CEACAM5, Fc fused-A1B2 and A2B2 domains of CEACAM5 and AB domains of CEACAM6 were used as competitors during phage library panning because those domains showed more than 70% primary sequence homology to A3B3 domains of CEACAM5 (FIG. 21). All recombinant proteins were purified in high-quality in SDS-PAGE analysis (FIG. 22). For a phage-displayed Fab library construction, a strategy was established to graft partial regions, occurring V(D)J and VJ recombination events, of VH and VL to human single germline VH3-11 and Vk1-39 framework, respectively. After 100 times electroporation, a large size of Fab library was generated showing 1011 specificities, and Clone #1 Fab (also referred to as 1G9 Fab) was successfully panned out through a competitive panning strategy using 10-fold molar excess of competitors with biotinylated Fc-fused A3B3 domains in every panning steps. Purified 1G9 Fab showed around 6 nM as half maximal effective concentration ($EC_{50}$) in an indirect ELISA (FIG. 23) and 3 nM as the equilibrium dissociation constant (KD) in BIAcore experiment against the A3B3 domains of CEACAM5 (FIG. 27) while no-significant signals were observed against A1B1, A2B2 domains of CEACAM5, or other CEACAM family members. Moreover, 1G9 $IgG_1$ bound to cynomolgus CEACAM5, suggesting that 1G9 based immunotherapeutics can be addressed for raised toxicity issues in monkey further since the cross-reactivity to both human and monkey CEACAM5 with comparable affinity is required for toxicity study in monkey (FIG. 24). In addition, 1G9 Fab exhibited superior specificity toward CEACAM5 in a flow-cytometry based analysis with HEK293F cells expressing different CEACAM family members (FIG. 25), and 1G9 hIgG1 showed a similar result in the Membrane Proteome Array (MPA), which is for testing antibody specificity using over 5,800 human cell lines that express different human membrane proteins (FIG. 26). Altogether, these results demonstrate that isolated 1G9 antibody binds to membrane-proximal domains of CEACAM5, A3B3 domains, in high affinity and high specificity without any off-target binding in three different experiments.

Epitope Mapping of IG9 Fab with N-Linked Glycan Removal Mutants of A3B3 Domains

Figure 28:
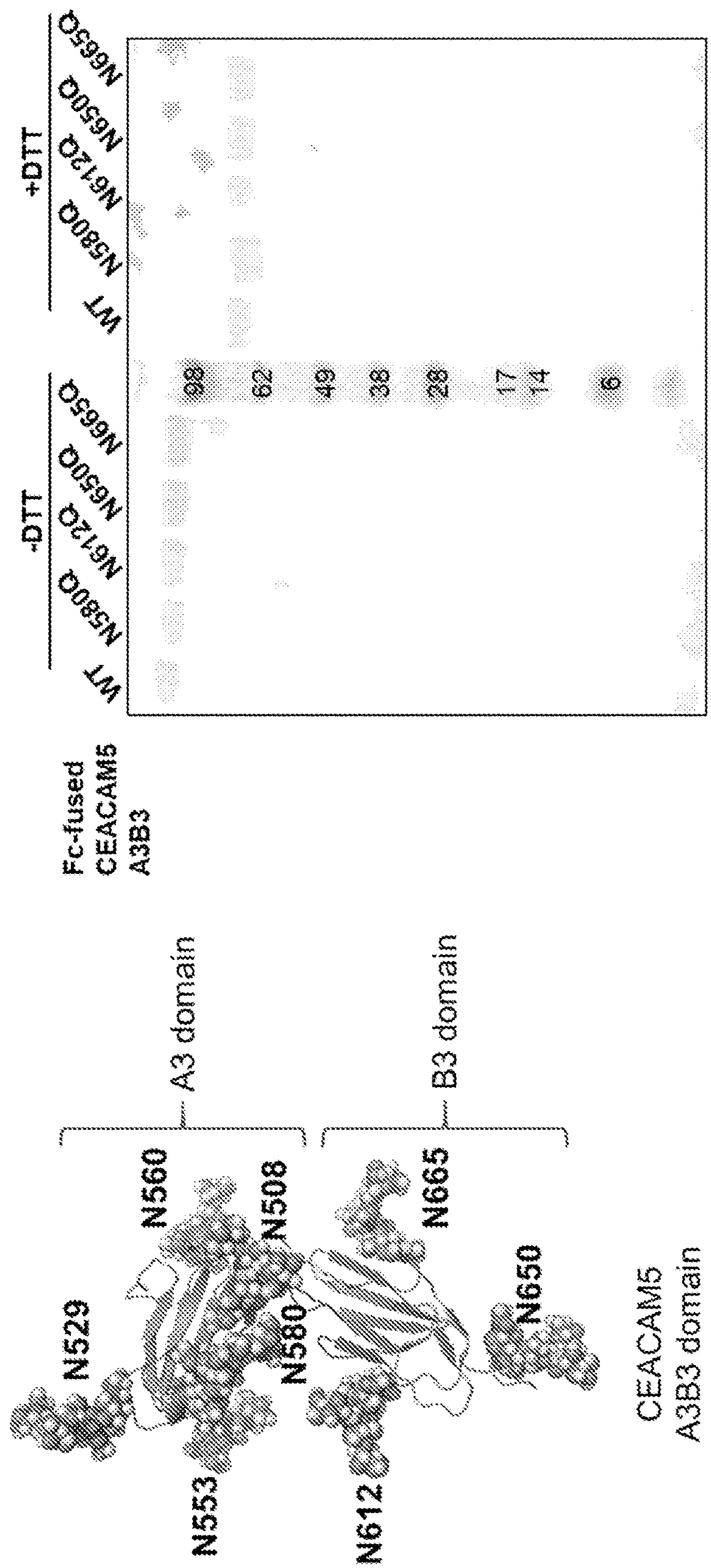
FIG. 28. N-linked glycosylation sites on A3B3 domain of CEACAM5 and SDS-PAGE analysis for purified Fc-fused A3B3 domain with Asn to Qln mutations.
Figure 29:
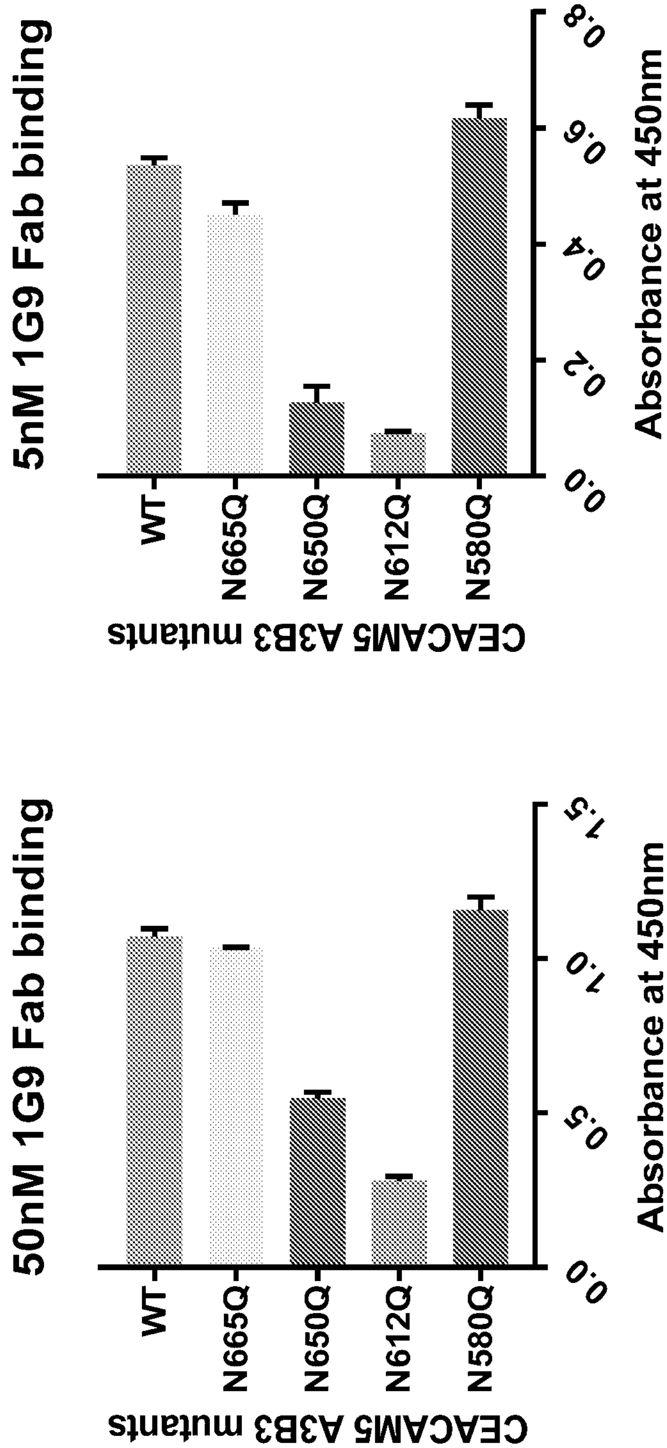
FIG. 29. Binding of 1G9 Fab to mutants of A3B3 domain.
Figure 33:
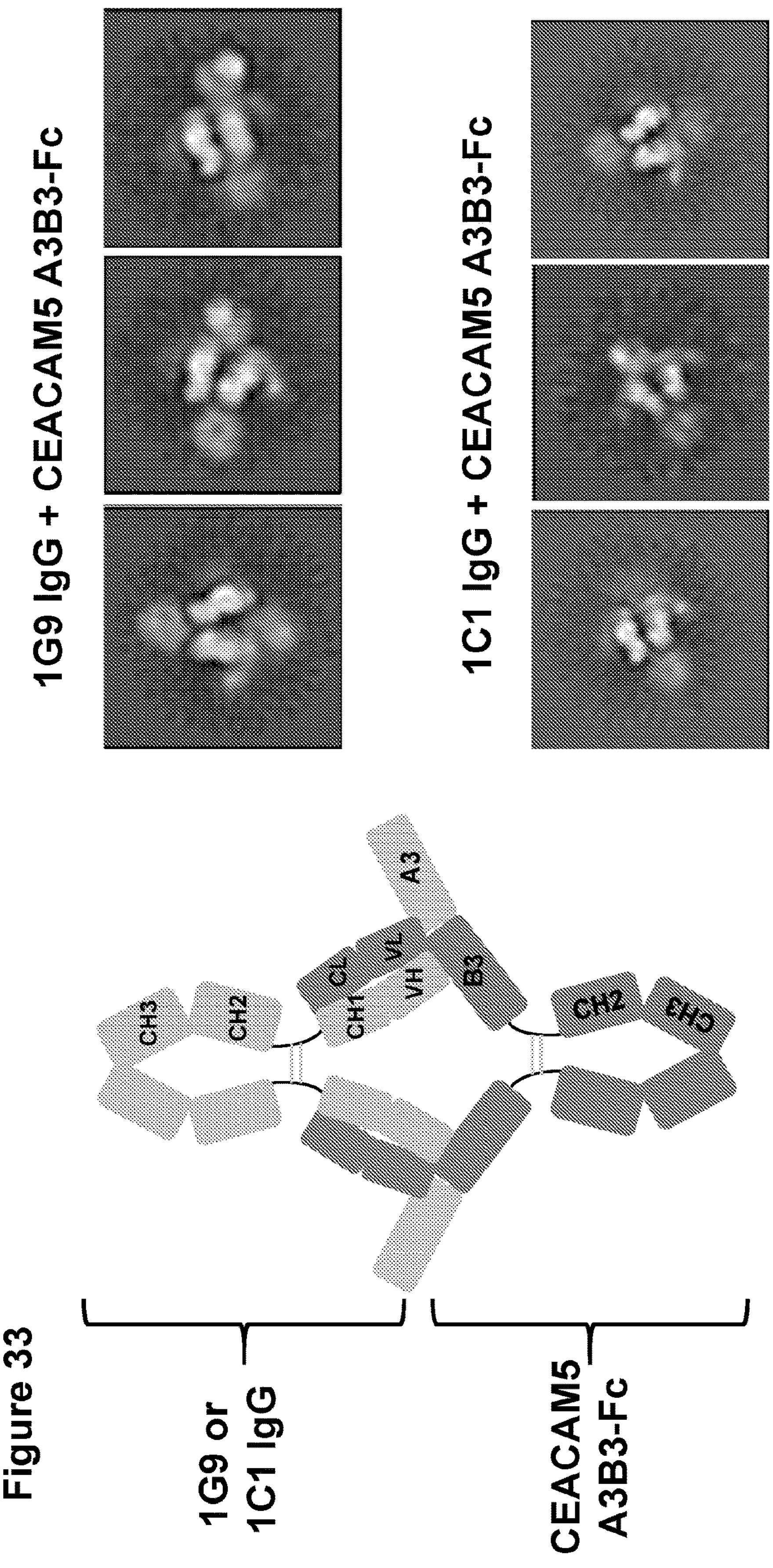
FIG. 33. Electron-Microscopic (EM) images for the complex of 1G9 or 1C1 hIgG1 with CEACAM5 A3B3 domain.
Figure 45:
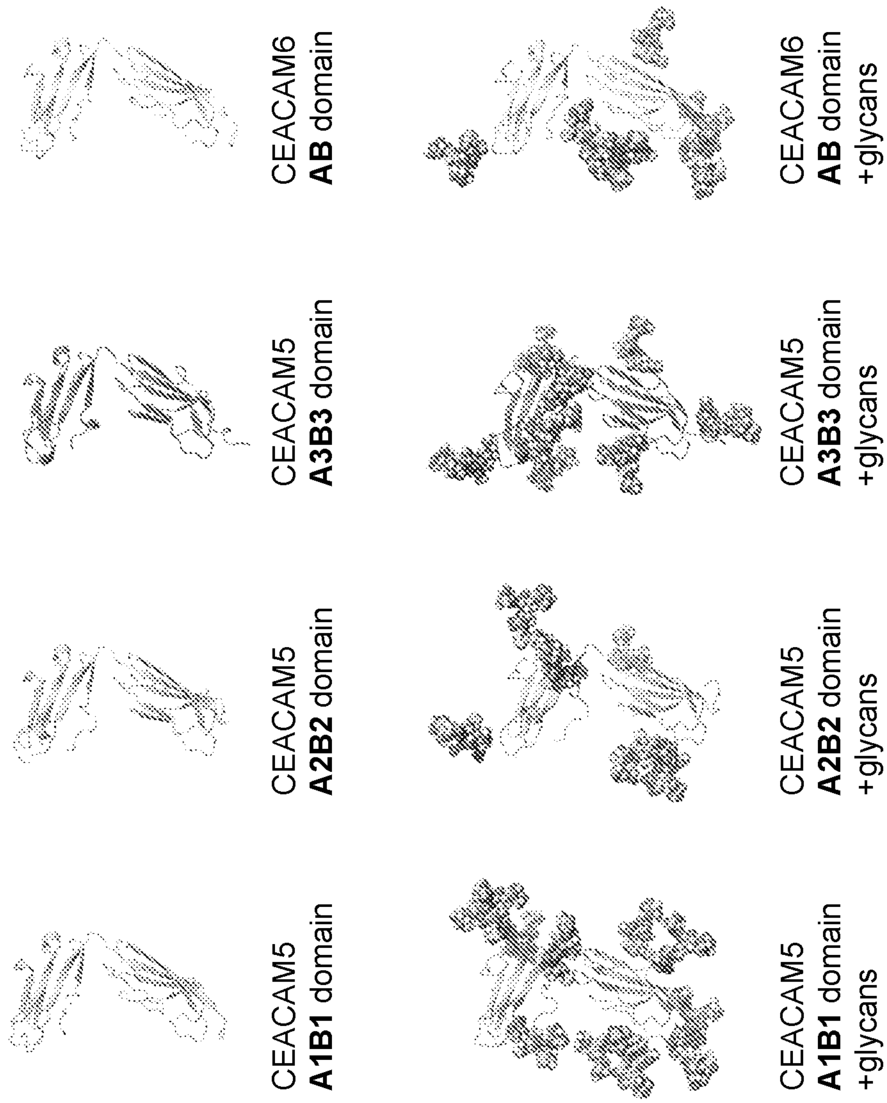
FIG. 45. Structure models for domains of CEACAM5 and CEACAM6 with addition of N-linked glycans.

It was hypothesized that N-linked glycans in A3B3 domains of CEACAM5 may be involved in the binding of 1G9 Fab either directly or indirectly because the A3B3 domains have eight N-linked glycosylation motifs (N-X-S/T; X is natural 19 amino acids except for proline) at N508, N529, N553, N560, N580 in A3 domain and N612, N650, N665 in B3 domain. Those N-linked glycans may cover exposed surface of A3B3 domains. To explore the contribution of N-linked glycans to generating epitopes for 1G9 Fab, eight mutant proteins of A3B3 domains were constructed with substituted asparagine (N) to glutamine (Q) at each N-glycosylation motif. The N580Q, N612Q, N650Q, and N665Q mutant proteins were successfully purified with lowering yield, but other four mutants, N508Q, N529Q, N553Q, and N560Q, were not expressed in HEK293F (FIG. 28). With those mutant proteins, 1G9 Fab showed attenuated binding to N612Q and N650Q mutants of B3 domain of CEACAM5 in an indirect ELISA. On the other hand, N580Q mutation slightly improved the binding of 1G9 Fab (FIG. 29). These results were corresponded to an image obtained in the electron microscopy (EM) with the complex of 1G9 hIgG and A3B3-Fc (FIG. 33). To visualize location and orientation of N-linked glycans of CEACAM5 and CEACAM6, molecular structures were modeled with added N-linked glycans to the modeling structure. Those four domains showed very similar tertiary structure as expected because they shared over 70% primary sequences and were already known as having Ig constant region-type 2-like (IgC2-like) domains. However, addition of N-linked glycans into structure models generated largely different antigenic surfaces resulting in creation of unique conformational epitopes within each domain (FIG. 45). Taken together, these results demonstrate that 1G9 Fab binds to A3B3 domain of CEACAM5 and three N-linked glycans at M580, N612 and N650 are involved in major epitopes.

Example 2—In Vitro Pre-Clinical Efficacy Assessment for hIgG1 and CAR-T Cell Lines NCI-H660, Du145, and 293T cells were purchased from ATCC. Du145 was maintained EMEM supplemented with 10% v/v FBS (Gibco) and 1% penicillin-streptomycin (P/S, Gibco). 293T was maintained DMEM supplemented with 10% FBS and 1% P/S. NCI-H660 was cultured RPMI1640 (ATCC) supplemented with 5% FBS, 1× insulin-transferrin-selenium (ITS-G Giboc), 10 nM hydrocortisone, extra 2 mM L-glutamine, and 1% P/S. Du145-CEACAM5 cells, stably expressed CEACAM5, was generated by stable infection with lentiviruses derived from the pLenti lentiviral plasmid (Origene, RC206434L3) using established methods, and were cultured in EMEM supplemented with 10% FBS, 1% P/S, and 1 μg/mL puromycin (Gibco).

Generation of CEACAM Family Expressing Cells

Freestyle 293F cells (Thermofisher) was used for generating of CEACAM family expressing cells. Plasmids cloned each gene for human CEACAM members were transfected to the cells with PEI Max (Polysciences). Each gene for human CEACAM members with FLAG-tag at C-terminal were purchased from Origene (RC224086 for CEACAM21; RC214882 for CEACAM20; RC215478 for CEACAM18; RC224965 for CEACAM16; RC230069 for CEACAM1; RC212214 for CEACAM7; RC204740 for CEACAM8; RC202454 for CEACAM6; and RC206434 for CEACAM5).

Generation of Third Generation of CAR-T Cells Using scFv Having the CDRs of Clone #1

The DNA for a third generation of CAR encoding an scFv having the CDRs of Clone #1, a human $IgG_4$ hinge, a CD28 transmembrane region, and costimulatory cytosolic domains of CD28, 4-1BB, and CD3 zeta was cloned into pLVX-EF1a-IRES-ZsGreen1 by EcoRI and BamHI restriction enzymes and T4 DNA ligase. For the production of lentiviral supernatant, the day before transduction, 293T cells were seeded at $4\times10^6$ cells per T75 flask. After 24 hours, the lentiviruses were generated by co-transfecting 293T cells with plasmids encoding anti-CEACAM5 CAR (8 μg), pMD.2G (2 μg), and a packaging vector psPAX2 (4 μg) using PEI-based transfection system. Supernatants were collected after 48 hours and 72 hours and filtered through a 0.45 μm membrane. Then, pan T cells (Precision for medicine) were activated by Dynabeads human T-activator CD3/CD28 (Gibco), were transduced with lentiviral supernatants with 8 μg/mL polybrene (Sigma), followed by centrifugation for 45 minutes at 800×g (no acceleration and no deceleration), and then incubated at 37° C. 24 hours later, media with viruses was changed, and T cells were expanded in the T cell media (RPMI1640 supplemented with an extra 2 mM glutamax, 10% human serum, and 1% P/S) in the presence of hIL-2 (fed every 2 days, 50 IU/mL, Miltenyi Biotec).

Flow Cytometry

To determine the cell surface expression levels of CEACAM5 or CEACAM family proteins, the cells were stained with PE-conjugated anti-CEACAM5 IgG1 (Miltenyi Biotec, 130-114-217) or PE-conjugated anti-FLAG mouse antibody (Miltenyi Biotec, 130-101-576). To confirm cell surface binding of selected antibodies, cells were treated with a hIgG1 having the CDRs of Clone #1, a hIgG1 having the CDRs of Clone #2, or the Clone #1 Fab for 1 hour at 4° C. and then stained with Alexa647-conjugated goat anti-human IgG (Invitrogen, A21445) or FITC conjugated-goat anti-human kappa light chain (Invitrogen, A18854) for 0.5 hours at 4° C. For the internalization assays, cells ($1\times10^5$ cells/well in 96-well plate) were treated with Alexa488-labeled antibodies for durations between 0 and 30 hours. After incubation of antibodies, cells were washed with cold PBS, and then the remained cell surface binding antibodies were analyzed using Alexa488 fluorescence. For CAR expression on anti-CEACAM5 CAR-T cells, $CD4^+$ T or $CD8^+$ T cells were gated using APC-conjugated anti-human CD4 antibody (ebioscience, 17-0049-42) and eFluor450-conjugated anti-human CD8 antibody (ebioscience, 48-0088-42), and CAR expression was examined using FITC-labeled recombinant Protein L (Acrobiosystems, RPL-PF141).

In Vitro Cytotoxicity Assay

The LDH-Glo cytotoxicity assay kit (Promega, J2381) was used to measure ADCC or cell killing activity of anti-CEACAM5 CAR-T through release of cytosolic LDH from target cells. For ADCC, PBMCs or enriched NK cells from PBMCs as effector cells were incubated with the NCI-H660 or Du145 ($1\times10^4$ cells/well in 96-well plate) as target cells at effector-to-target (E:T) ratio of 20:1 (for PBMCs) or 5:1 (for NK cells) in the presence of a hIgG1 having the CDRs of Clone #1 or a hIgG1 having the CDRs of Clone #2 for 4 hours. For cell killing activity of anti-CEACAM5 CAR-T, control T or CAR-T cells as effector cells were incubated with NCI-H660, Du145-CEACAM5, or Du145 cells as target cells at the indicated E:T ratio for 24 hours in 96-well plate. Controls conducted for the calculation of percent cytotoxicity (% cytotoxicity) were performed according to the manufacturer's instructions. % cytotoxicity with the following formula: (experimental-effector minimum-target minimum)/(target maximum-target minimum)×100.

The CellTiter-Glo Luminescent cell viability assay kit (Promega, G7571) was used to measure cell viability in the presence of the hIgG1 having the CDRs of Clone #1. Cells ($5\times10^3$ cells/well in white 96-well plate) were plated and cultured for 12 hours prior to treatment with the indicated antibodies for 72 hours. Normalized % ATP values were calculated by normalizing luminescence values for vehicle-treated wells.

Transwell Assay

Cell migration was measured using transwell (8-μm pore size, Corning 3422). Cells ($1\times10^5$ cells/well) were resuspended in serum-free medium and then added to the upper chamber in the presence of the hIgG1 having the CDRs of Clone #1. Lower chambers contained 10% FBS. No FBS condition was conducted as negative control. After incubation for 3 days at 37° C., cells remained at the upper surface of the membrane were removed using a swab, while the cells that migrated to the lower membrane surface were fixed and stained with 0.5% crystal violet in 20% methanol solution. Cells migrating through the filter were quantified by dissolving the stained cells using 10% acetic acid solution and then absorbance was measured at 590 nm. Normalized % of migration values were calculated by normalizing absorbance values for 10% FBS-treated wells in absence of antibody.

Cytokine ELISA

Control T cells and CAR-T cells were plated in 24-well plate ($2\times10^4$ cells/well) and co-cultured with target cells at the indicated E:T ratio for 48 hours at 37° C. Subsequently, cytokine levels of supernatants were analyzed using human IFNγ, TNFα, IL-2, IL-4, IL-13, and GM-CSF ELISA kit (Thermofisher) respectively, following the manufacturer's instructions.

Results

IG9 hIgG1 Induces CEACAM5-Dependent ADCC

Figure 30:
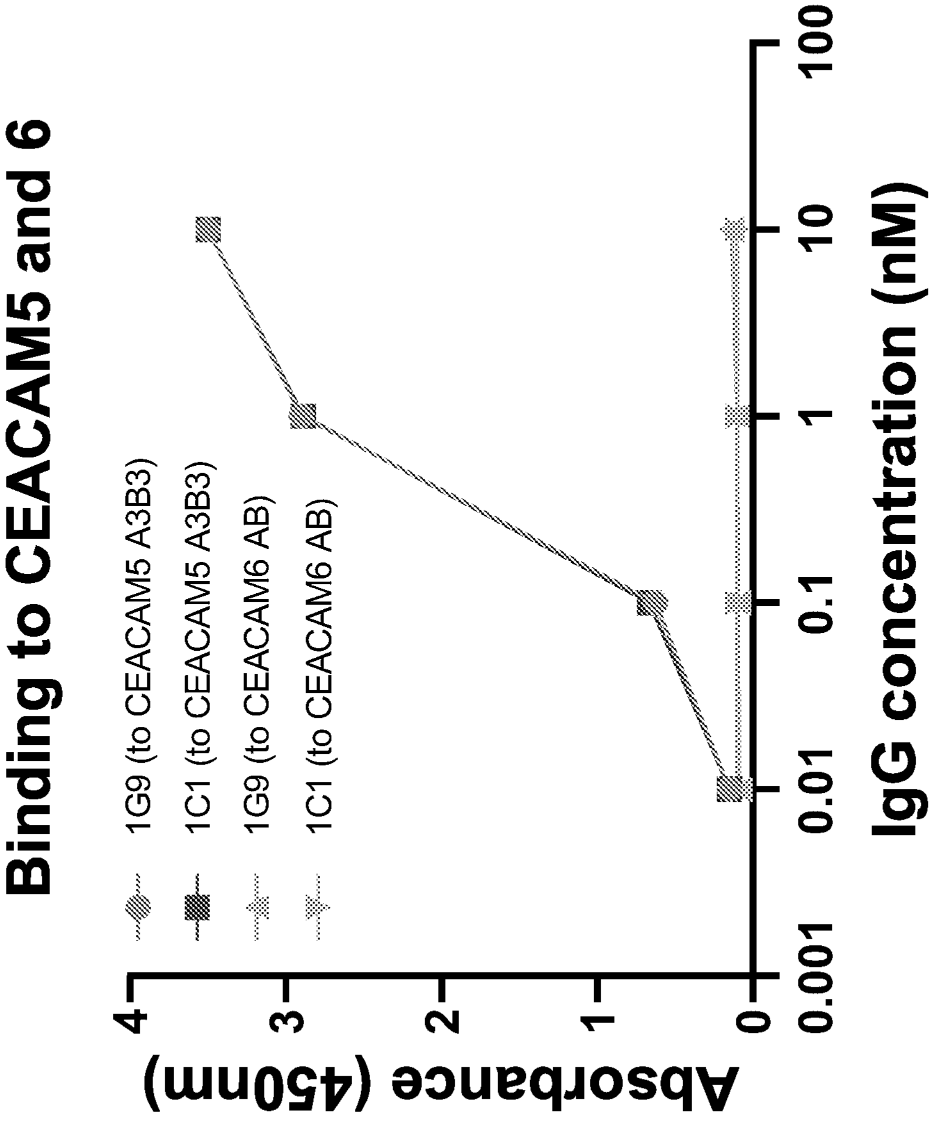
FIG. 30. Binding of 1G9 and 1C1 hIgG1 to A3B3 domain of CEACAM5 and AB domain of CEACAM6.
Figure 31:
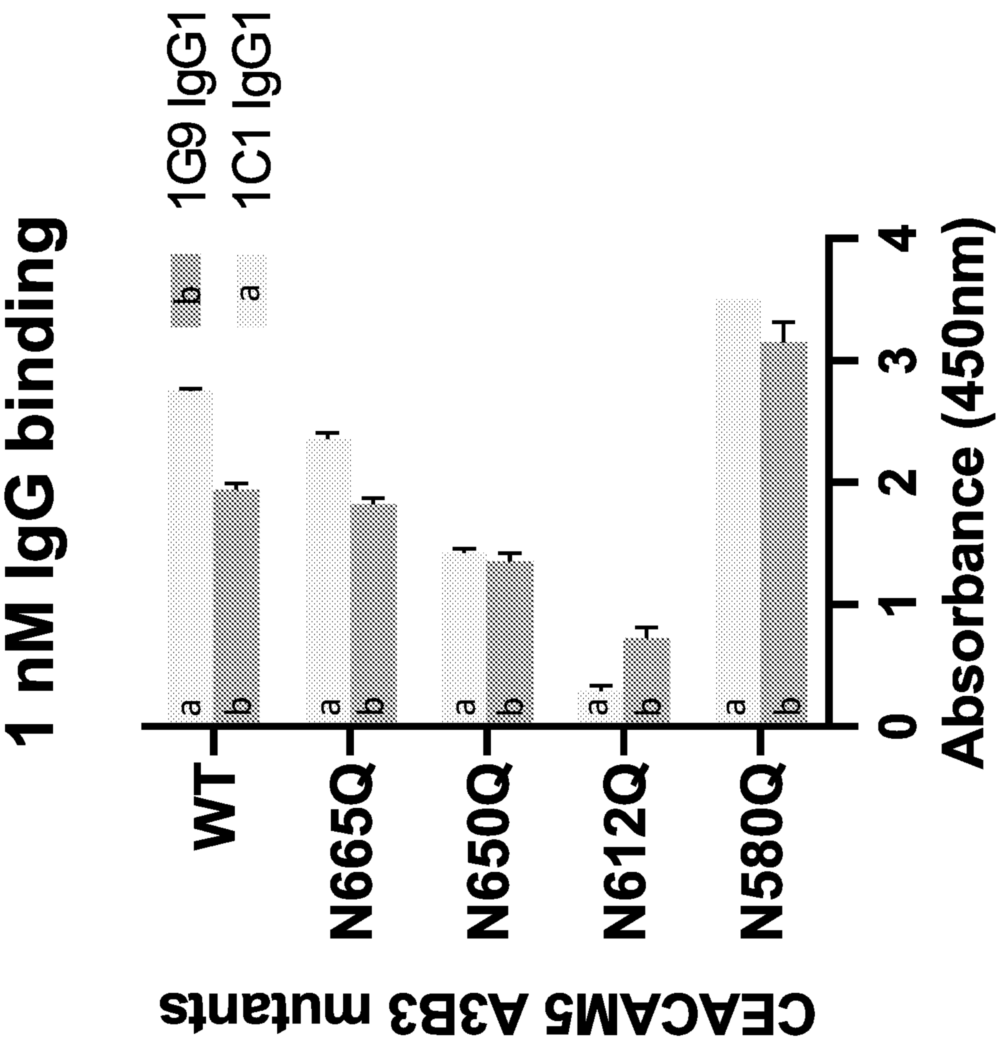
FIG. 31. Binding of 1G9 and 1C1 hIgG1 to mutants of A3B3 domain.
Figure 32:
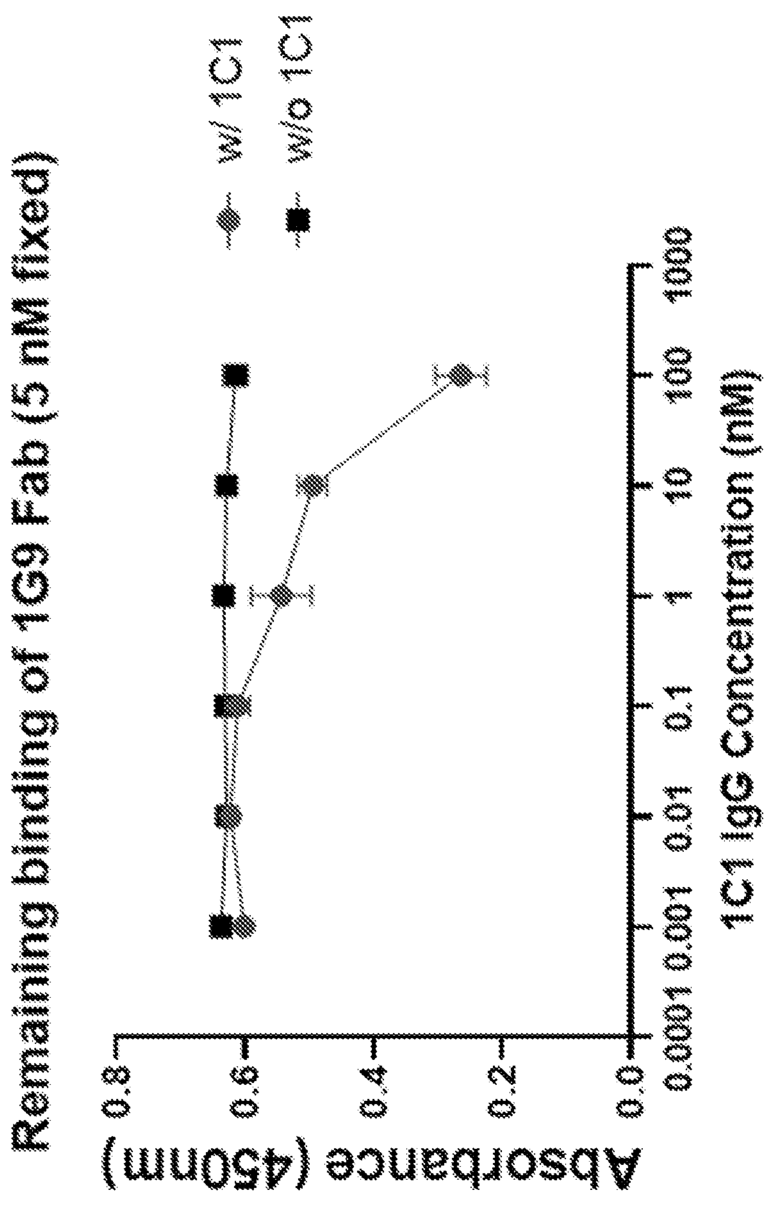
FIG. 32. Competitive ELISA of 1G9 Fab with or without 1C1 IgG1 for binding to CEACAM5.
Figure 34:
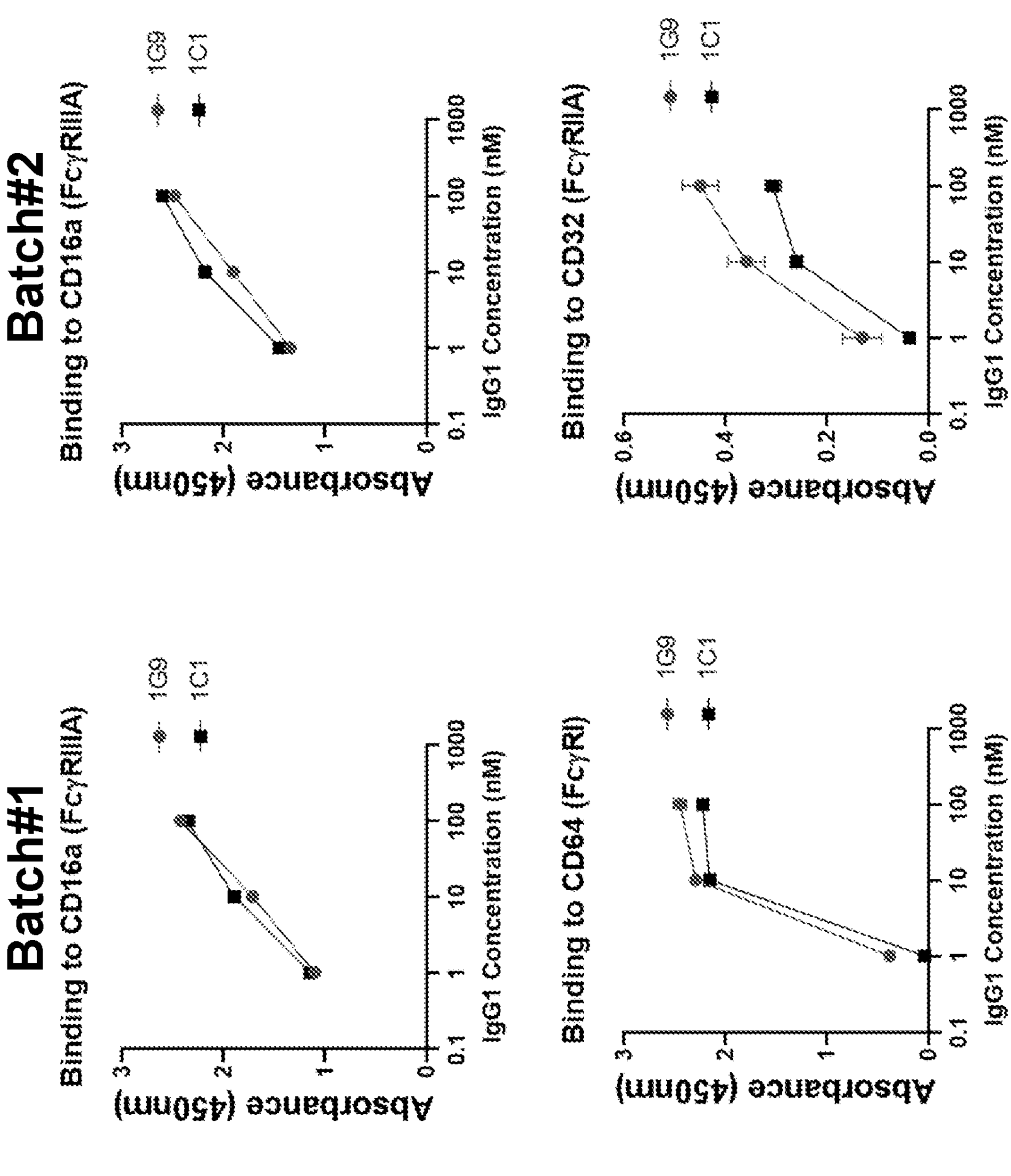
FIG. 34. Binding of 1G9 and 1C1 hIgG1 to Fc gamma receptors (CD16a, CD65, and CD32).
Figure 35:
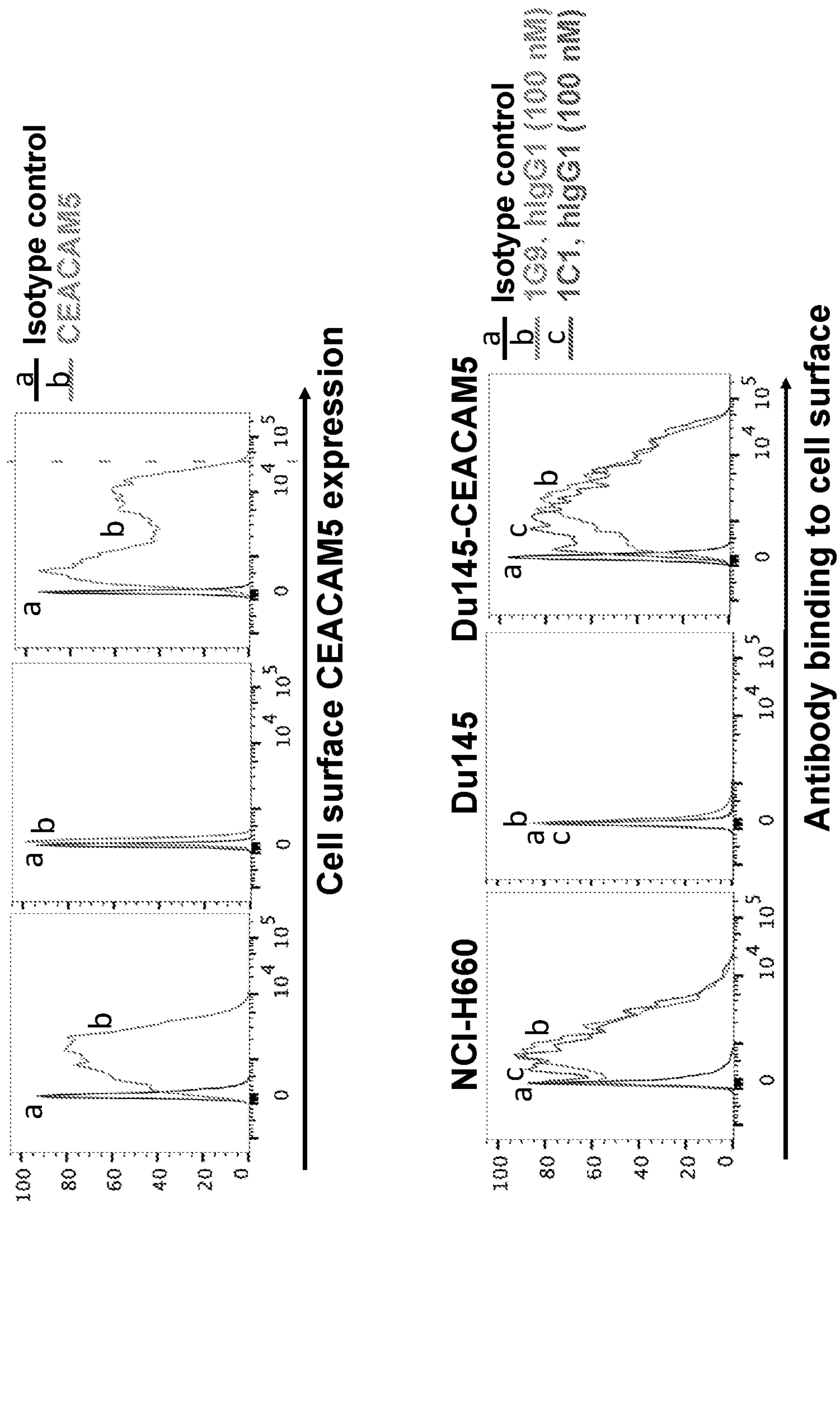
FIG. 35. Binding of 1G9 and 1C1 hIgG1 to CEACAM5-positive NEPC cell line (NCI-H660), stably CEACAM5-expressing PrAd Du145 cell line (Du145-CEACAM5), and CEACAM5-negative PrAd cell line (Du145).
Figure 36:
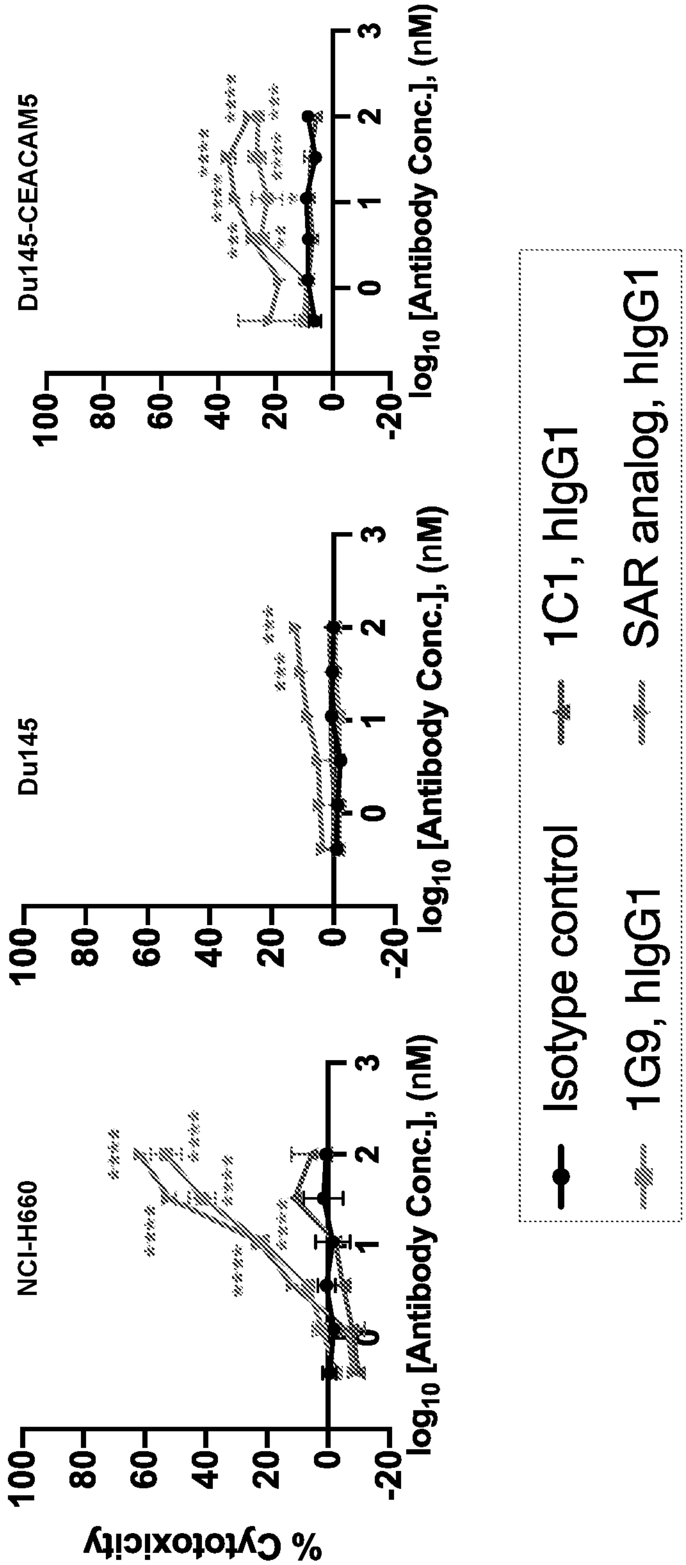
FIG. 36. ADCC activity with 1G9 and 1C1 hIgG1 against CEACAM5-positive cell lines (NCI-H660 and CEACAM5-positive Du145 cells) and CEACAM5-negative cell line (Du145) in the presence ofNK cells (E:T ratio=5:1).
Figure 37:
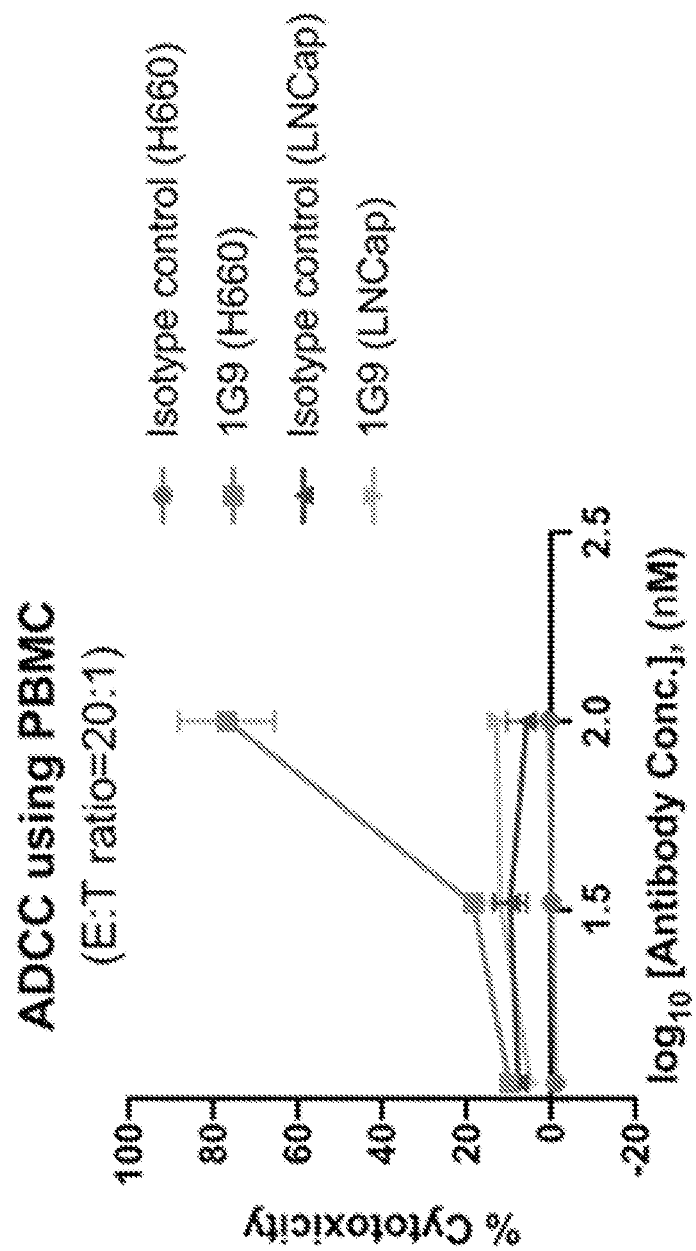
FIG. 37. ADCC activity with 1G9 and 1C1 hIgG1 against CEACAM5-positive cell line (NCI-H660) in the presence of PBMCs.
Figure 38:
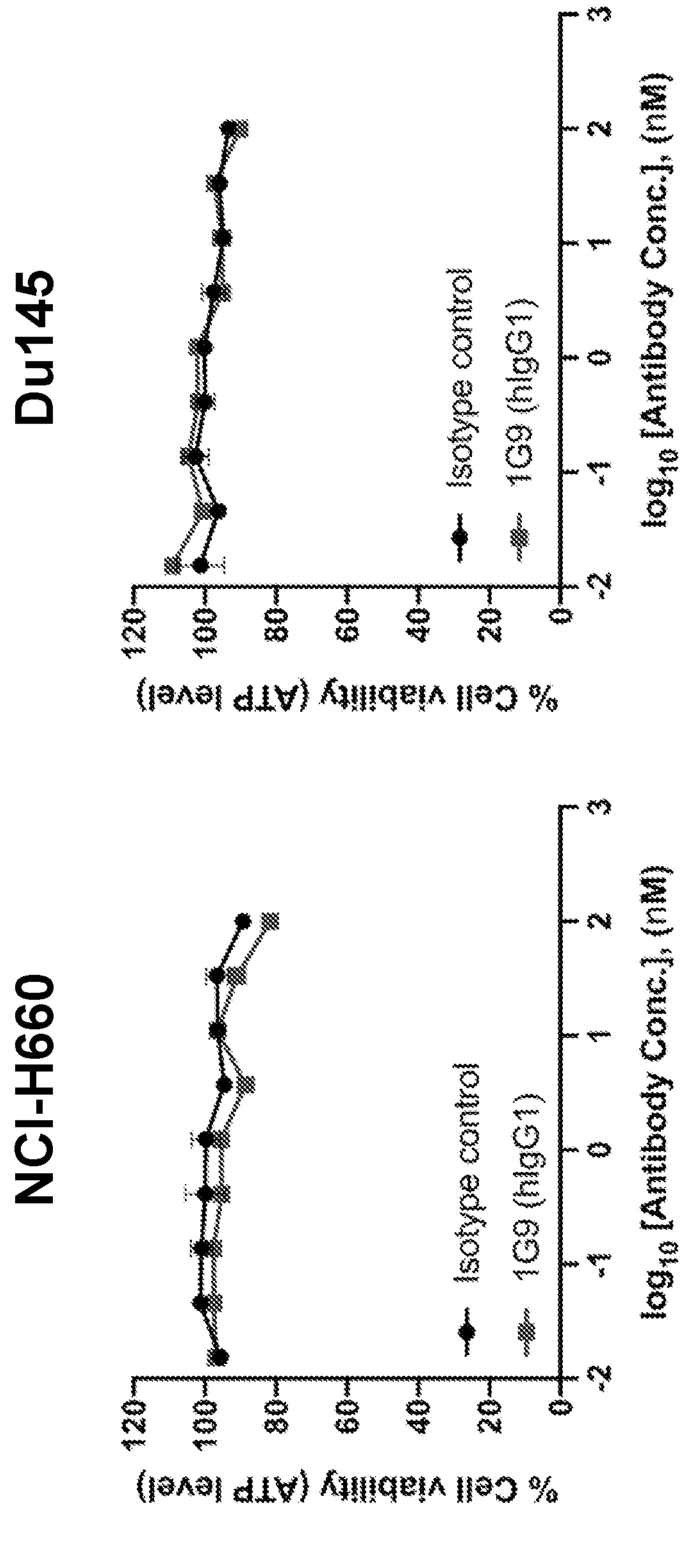
FIG. 38. Cell viability assay after treatment of 1G9 hIgG1 in the absence of immune cells in CEACAM5-positive cell line (NCI-H660) and CEACAM5-negative cell line (Du145) for 72 hours.
Figure 40:
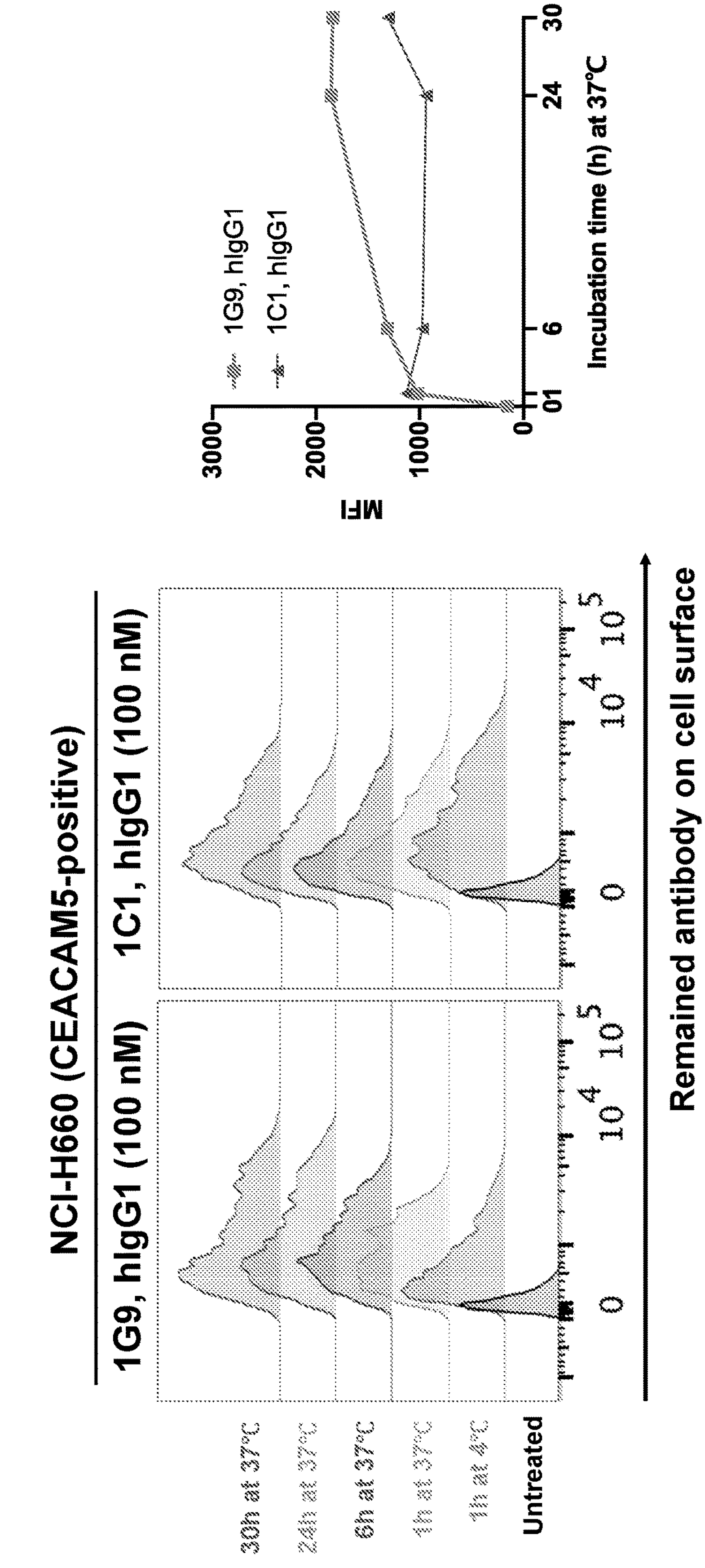
FIG. 40. Fluorescence intensity histogram of the remained antibody levels (1G9 and 1C1 hIgG1) on NCI-H660 cell surface after the indicated incubation times at 37° C. and the quantification of mean fluorescence intensity (MFI) for 1G9 and 1C1 hIgG1.
Figure 41:
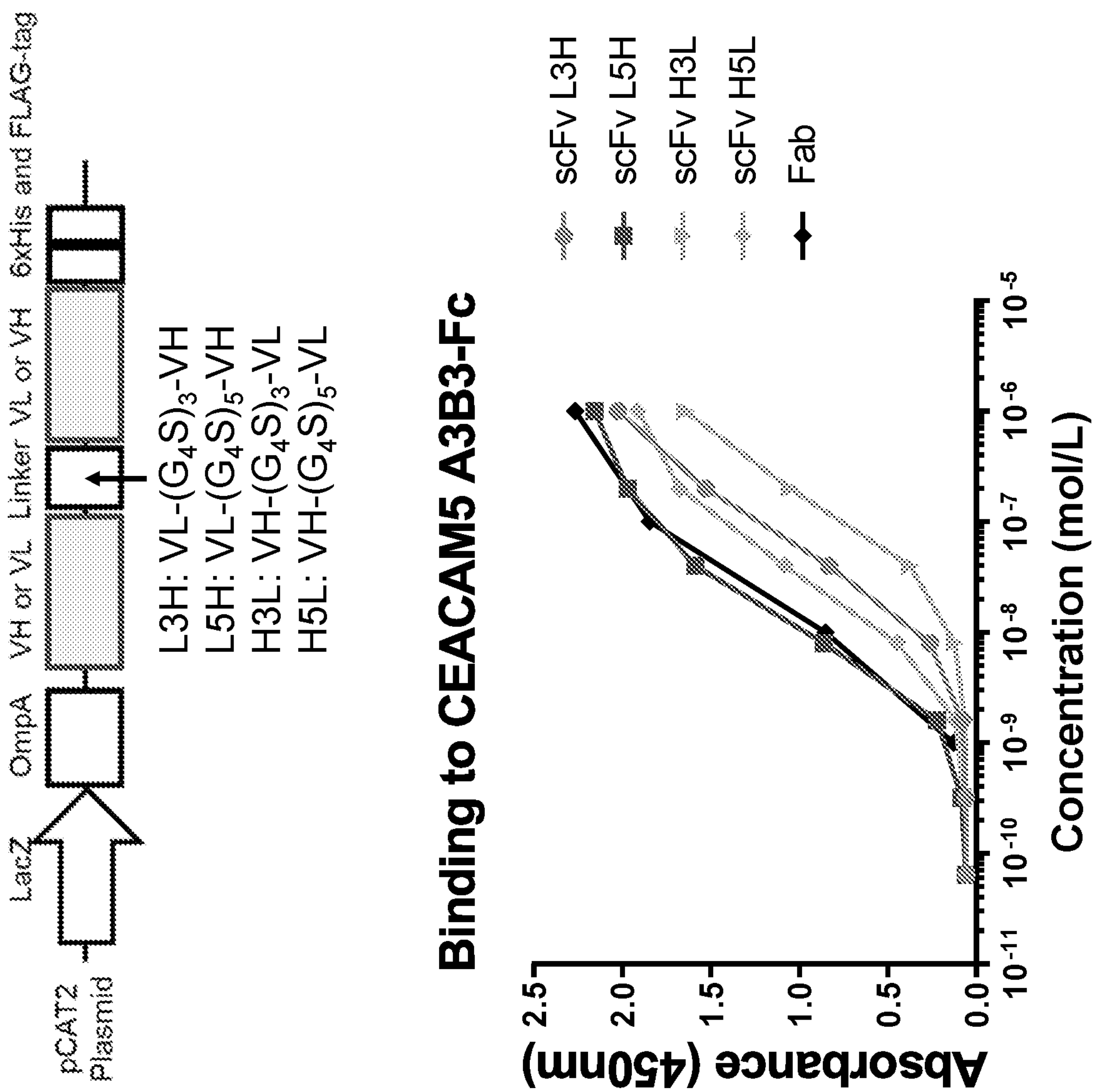
FIG. 41. Design of scFv of 1G9, and the binding of scFv of 1G9 in different VH/VL orientations and in use of linkers to A3B3 domain of CEACAM5. Linker sequences shown include SEQ ID NOs: 78, 101, 78, and 101, respectively, in order of appearance.

During the characterization of 1G9, Clone #2 Fab (also referred to as 1C1 Fab) also was isolated. The 1C1 hIgG1 specifically bound to A3B3 domains of CEACAM5 like 1G9 hIgG1 (FIG. 30) and also showed similar binding to mutants of A3B3 domains, suggesting that N-linked glycans at N580, N612, and N650 were also involved in epitope for 1C1 (FIG. 31). In competitive ELISA, those two antibodies competed for binding to CEACAM5, suggesting that two antibodies bind overlapping epitope in A3B3 domains (FIG. 32). The binding of 1G9 and 1C1 hIgG1 to CEACAM5-positive NCI-H660 and CEACAM5-negative Du145 cells was assessed then. Both 1G9 and 1C1 hIgG1 showed specific binding to NCI-H660 cells. Notably, Du145-CEACAM5 cells, engineered to express CEACAM5, displayed binding of 1G9 and 1C1 hIgG1 on the cell surface distinct from CEACAM5-negative Du145 cells (FIG. 35). Next, the ADCC activity of 1G9 and 1C1 hIgG1 were tested against CEACAM5-positive target cells using an LDH release cytotoxicity assay. Primary NK cells enriched from human peripheral blood mononuclear cells (PBMCs) as effector cells and NCI-H660 or Du145 cells as target cells were used. 1G9 hIgG1 caused a dose-dependent ADCC activity against CEACAM5-positive NCI-H660 cells and CEACAM5-positive Du145 cells, but not CEACAM5-negative Du145 cells (FIG. 36) and LNCap (FIG. 37). Interestingly, no ADCC activity was observed in treatment of 1C1 hIgG1, although 1C1 hIgG1 showed a similar binding affinity to A3B3 domains of CEACAM5 and cells as well as Fc gamma receptor (FcγR) (FIG. 34). To examine why 1C1 hIgG1 showed a different ADCC activity from 1G9, electro microscopic (EM) images were examined to elucidate minor differences such as binding orientation or binding site, but 1C1 hIgG1 bound to A3B3 domains similar to 1G9 hIgG1 and both antibodies dominantly bound to B3 domain of CEACAM5 in EM image. Second, cell killing activity of 1G9 or 1C1 hIgG1 was tested in absence of immune cells but no cytotoxic activity against NCI-H660 cells was found (FIG. 38) by both antibodies. This result indicated that cell killing activity of 1G9 hIgG1 was clearly dependent on recruiting of FcγR-expressing immune cells including NK cells but targeting CEACAM had no effects on cell viability in absence of immune cells. Third, the rate of internalization for 1G9 and 1C1 hIgG1 was evaluated by measuring the remained antibody on the NCI-H660 cell surface after antibody treatment at 37° C. in time-course by flow cytometry (FIG. 40). Both hIgG1s did not undergo internalization up to 30 hours, suggesting that the difference in ADCC activity for both hIgG1s was unlikely to be caused by different internalization kinetics.

1G9 hIgG1 Inhibits Cell Migration and Invasion

Figure 39:
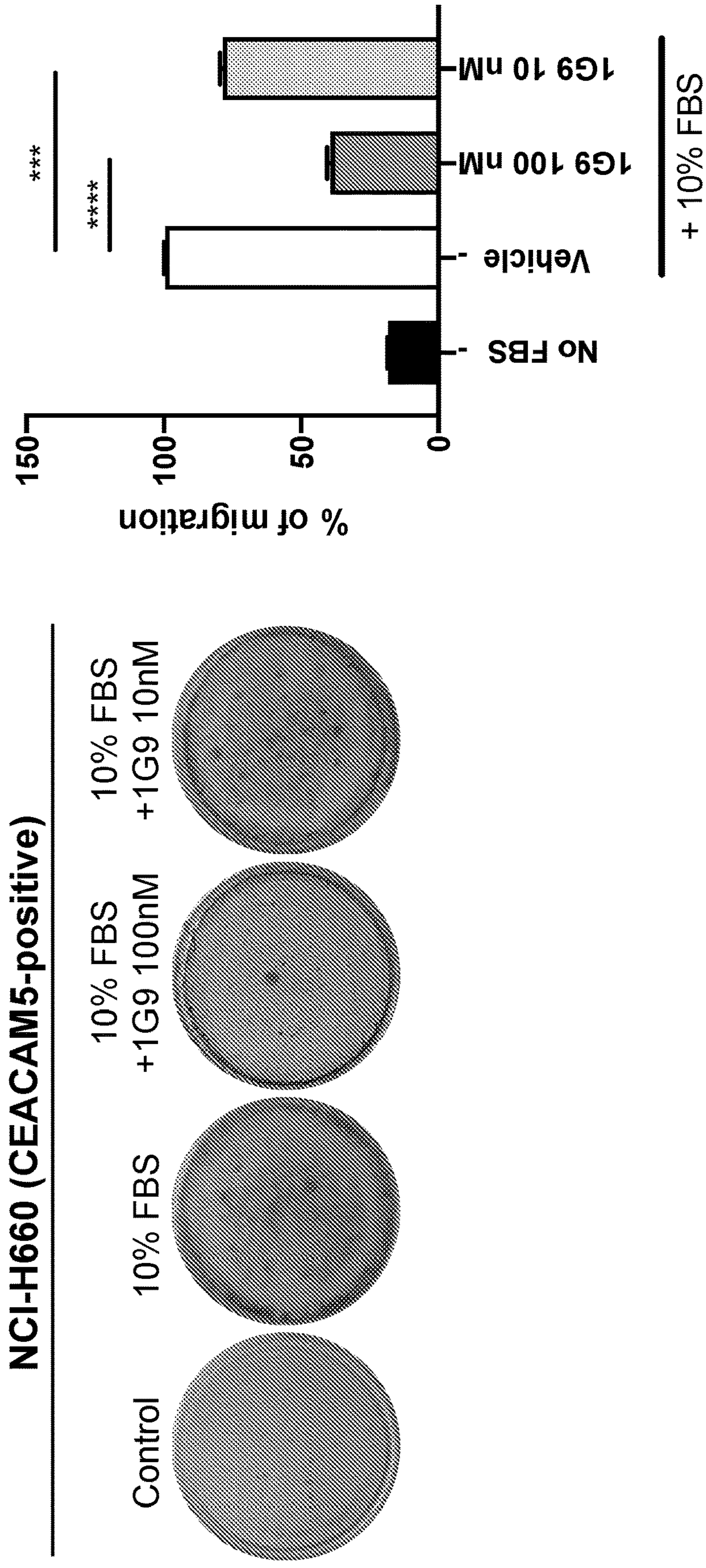
FIG. 39. Transwell migration assay after treatment of 1G9 hIgG1 in CEACAM5-positive cell line (NCI-H660). Representative images and quantification of migrated cells through the transwell are shown.

As CEACAM5 play a role in regulation of cell adhesion and migration as cell adhesion molecule, the role of 1G9 hIgG1 in prostate cancer cell migration was explored using transwell assay. The NCI-H660 and Du145-CEACAM5 cells exhibited impaired migration by treatment of 1G9 hIgG1, in a dose-dependent manner, compared with serum-treated cells while no migration effects of 1G9 hIgG1 were observed in CEACAM5-negative Du145 cells (FIG. 39). Similarly, analog of Sanofi's antibody targeting CEACAM5 (SAR408701) inhibited cell migration. These results suggested that targeting CEACAM5 by 1G9 hIgG1 can impede CEACAM5-mediated cell migration.

Figure 42:
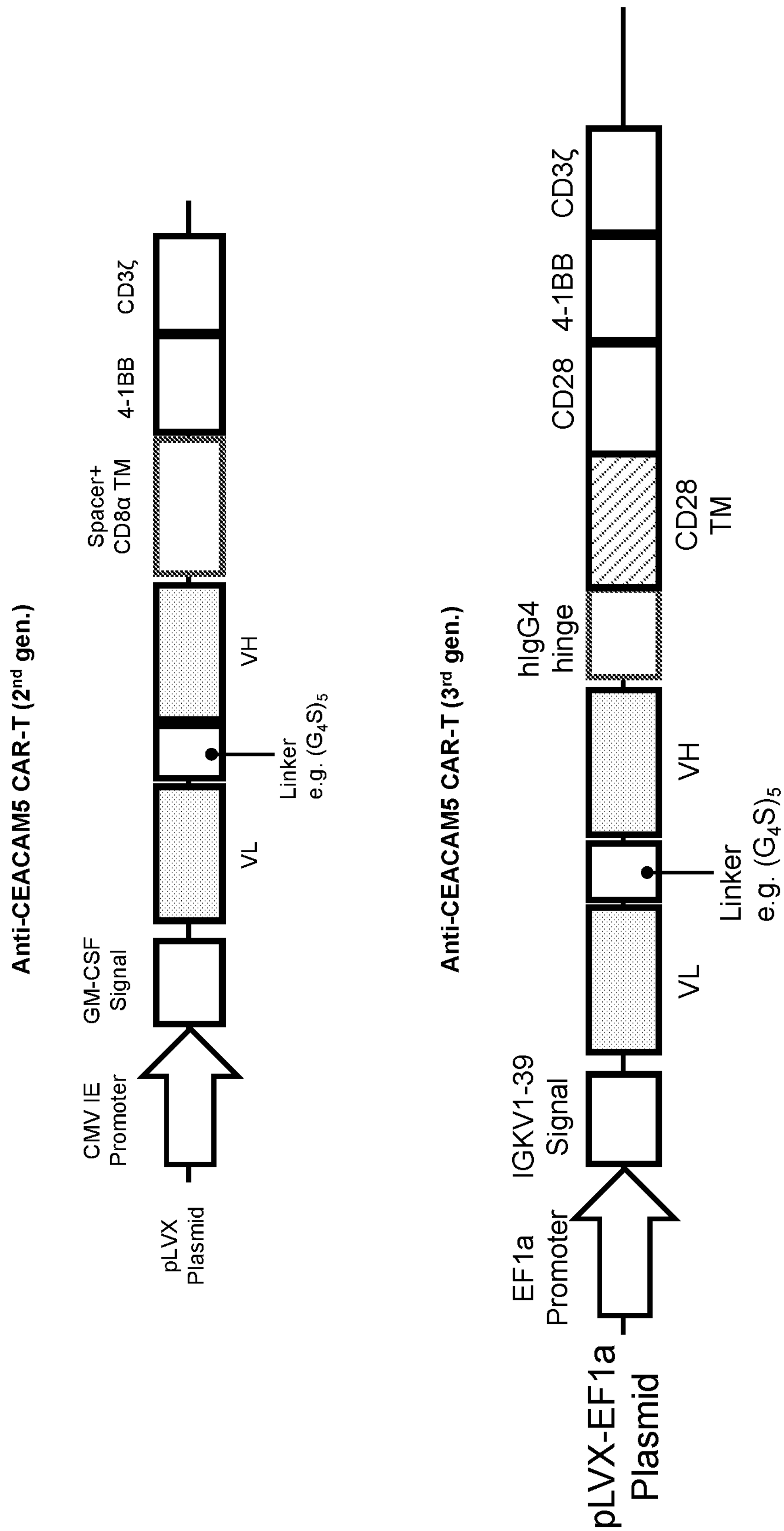
FIG. 42. Genetic components for exemplary CARs (e.g., $2^{nd}$ generation and $3^{rd}$ generation CARs). Linker sequence shown is SEQ ID NO: 101.
Figure 43:
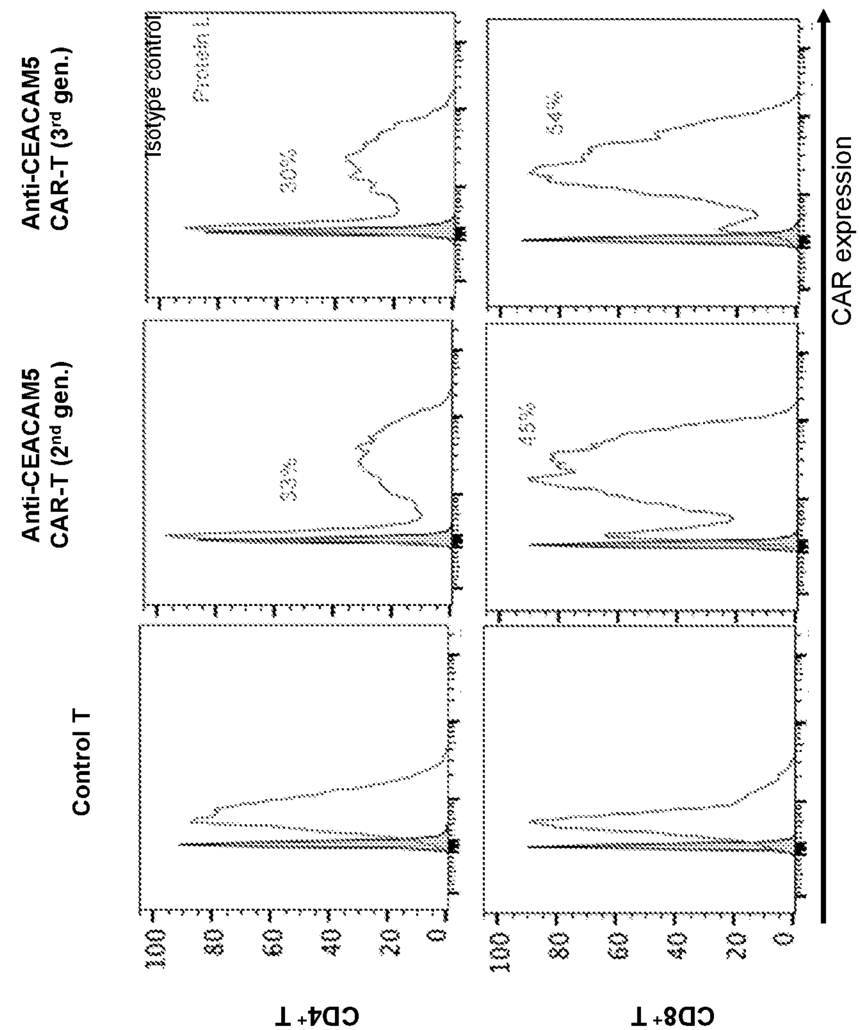
FIG. 43. CAR expression on $CD4^+$ T and $CD8^+$ T population in the control T cells and anti-CEACAM5 CAR-T cells ($2^{nd}$ and $3^{rd}$ generation CAR-T cells).

Anti-CEACAM5 CAR-T Shows Strong Cytotoxicity Against CEACAM5-Positive Prostate Cancer Cells Based on the epitope mapping and limited internalization of hIgG1 1G9, it was concluded that the 1G9 antibody could be used for CAR-T cell therapy. Lentiviral $2^{nd}$ and $3^{rd}$ generation anti-CEACAM5 CAR constructs encoding a single chain variable fragment (scFv) derived from 1G9, a transmembrane domain, and a costimulatory intracellular domain as shown in FIG. 42 were generated. T cells were transduced with the $2^{nd}$ and $3^{rd}$ generation CAR constructs, and CAR expression was confirmed by flow cytometry. The expression level of $3^{rd}$ generation CAR in transduced T cells was 84%, including 30% in $CD4^+$ T cells and 54% in $CD8^+$ T cells, which was similar to the expression level of $2^{nd}$ generation CAR, which totaled at 78% (FIG. 43).

Figure 44:
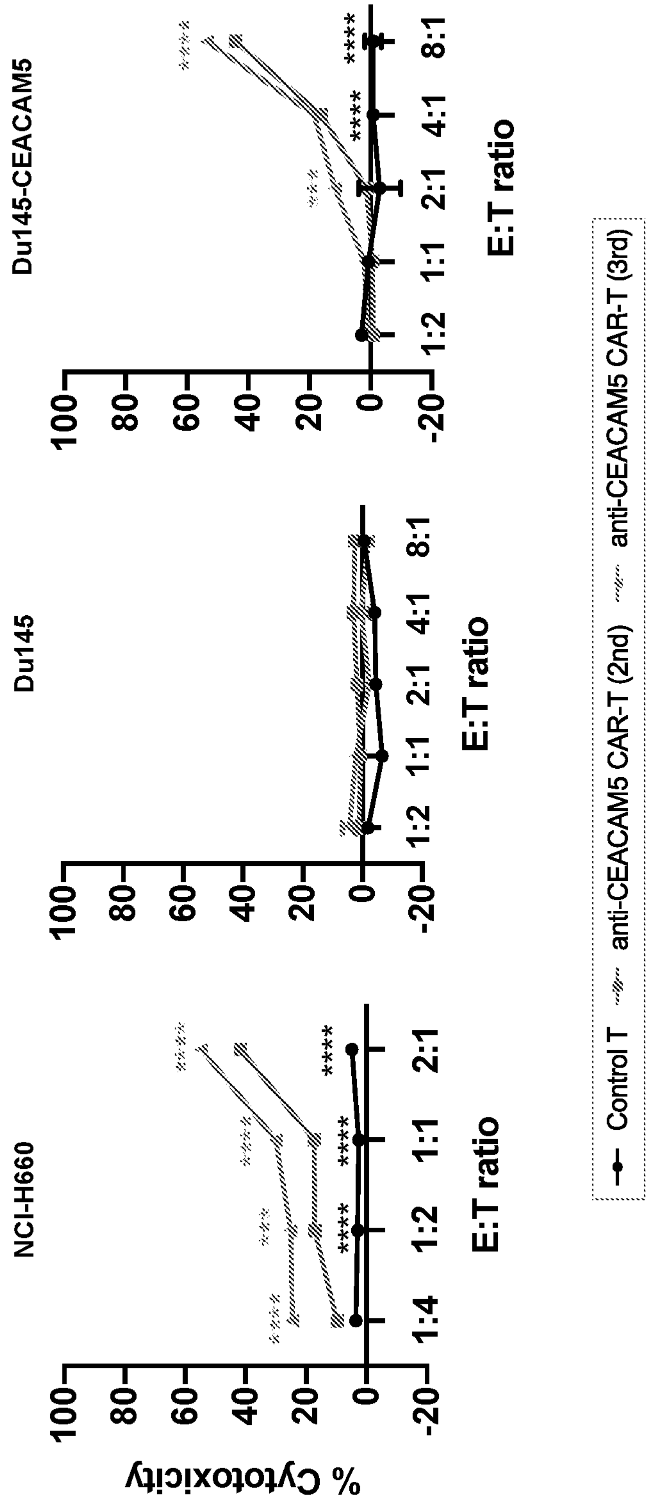
FIG. 44. Cytotoxic activity of anti-CEACAM5 CAR-T against CEACAM5-positive cell line (NCI-H660), stably CEACAM5-expressing Du145 cell line (Du145-CEACAM5), and CEACAM5-negative cell line (Du145).
Figure 46:
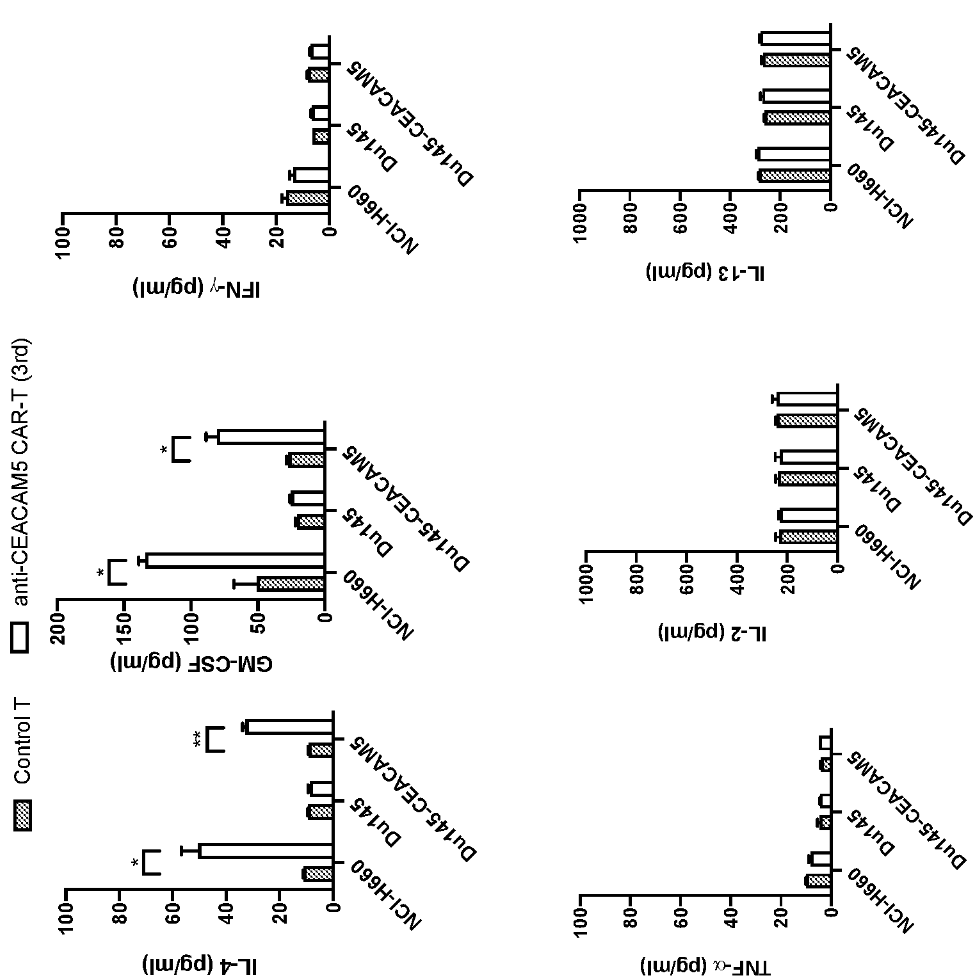
FIG. 46. Cytokine secretion measured in cell supernatants from the indicated cell cultures.
Figure 47:
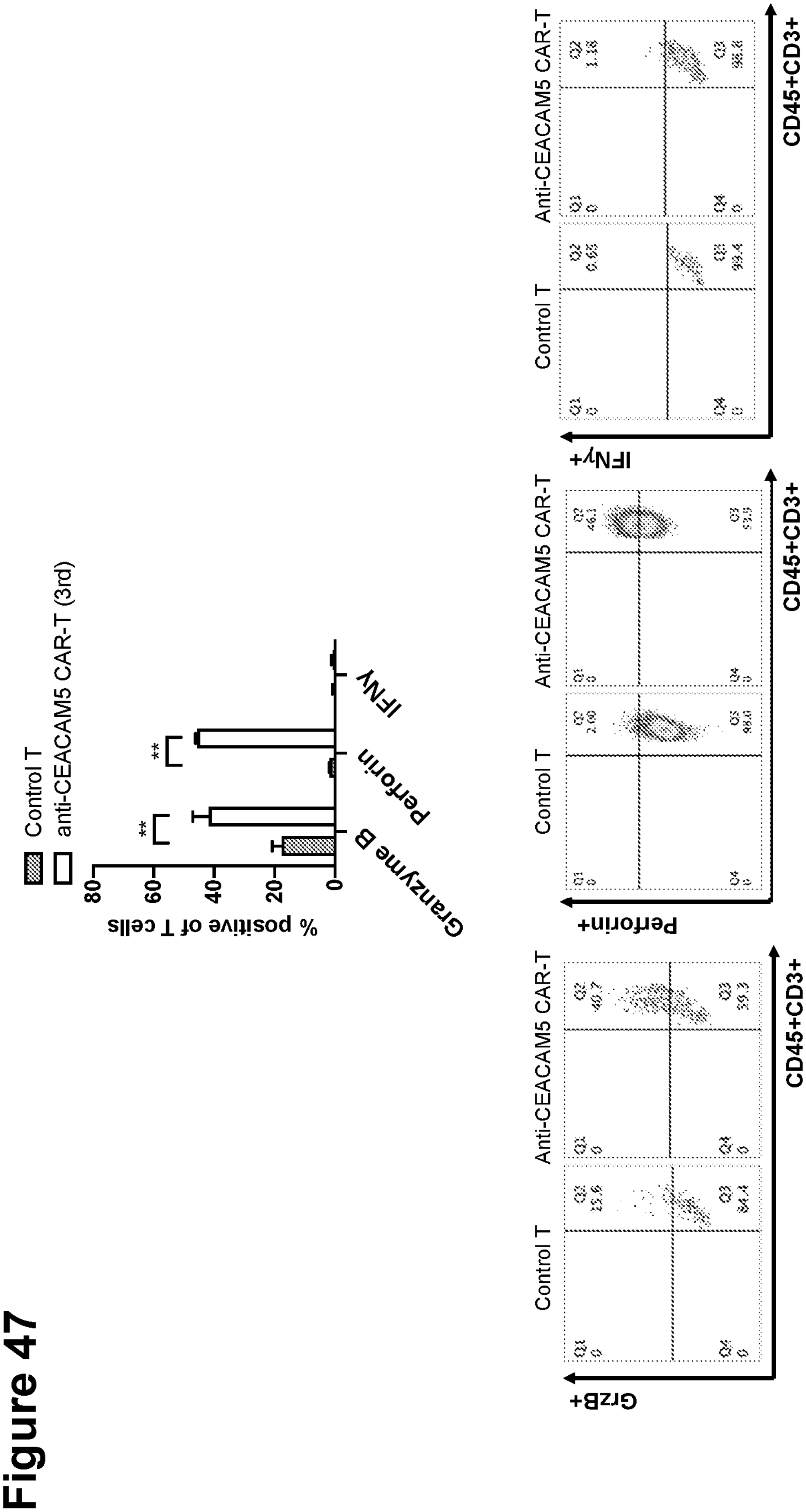
FIG. 47. Granzyme B, Perforin and IFNγ-positive T cells population (%) in the supernatant at 48 hours (E:T ratio: 2:1) after co-culture of $3^{rd}$ generation anti-CEACAM5 CAR-T with NCI-H660 cells analyzed by intracellular staining.

To determine the cytotoxicity of anti-CEACAM5 CAR-T cells for target cells in vitro, anti-CEACAM5 CAR-T cells were co-cultured with CEACAM5-positive NCI-H660 and Du145-CEACAM5, at the E:T ratios of 1:4, 1:2, 1:1, 2:1, 4:1 and 8:1 for 24 hours. The cytotoxicity (%) of $2^{nd}$ and $3^{rd}$ generation CAR-T cells against NCI-H660 cells was higher than that of the control T cell group at every E:T ratio. The $3^{rd}$ generation CAR-T cells exhibited more potent cytotoxicity compared to the $2^{nd}$ generation CAR-T cells (FIG. 44). Cytotoxicity of the $3^{rd}$ generation CAR-T cell group against Du145-CEACAM5 cells was observed at E:T ratios of 8:1, 4:1, and 2:1, but not against Du145 cells (FIG. 44). To further investigate the cytotoxic mechanism of anti-CEACAM5 CAR-T cells, the production of IFN-gamma (IFNγ), TNFα, IL-2, IL-4, IL-13, and GM-CSF from the supernatant of CAR-T after co-culture with target cells for 48 hours was analyzed. Secretion of IL-4 and GM-CSF was significantly enhanced by treatment of $3^{rd}$ generation anti-CEACAM5 CAR-T cells in CEACAM5-expressing NCI-H 660 and Du145-CEACAM5 cells, but not CEACAM5-negative Du145 cells (FIG. 46). Additionally, analysis of the supernatant at 48 hours for granzyme B (GrzB), perforin, and IFNγ intracellular staining revealed enhanced GrzB and perforin release from 3rd generation anti-CEACAM5 CAR-T cells in CEACAM5-positive NCI-H660 cell cultures (FIG. 47). The 3rd generation anti-CEACAM5 CAR-T cells resulted in remarkable cytotoxicity in CEACAM5-positive NEPC cells via IL-4, GM-CSF cytokine secretion and GrzB/perforin release, likely due to the membrane proximity of 1G9 binding to the A3B3 domain, in combination with a well-designed CAR spacer.

Example 3—In Vivo Pre-Clinical Efficacy Assessment for hIgG1 and CAR-T In Vivo Study For evaluation of hIgG1 1G9, Du145 and Du145-CEACAM5 cells ($1\times10^7$ cell/mice) in 200 μL of a 1:1 mixture of PBS/Matrigel (BD Biosciences, 354234) were injected subcutaneously (s.c.) into the right flank of Balb/c scid mice (6-8 weeks old, male, The Jackson Laboratory). When the tumor volume reached approximately 200 $mm^3$, mice were randomized, and hIgG1 1G9 (20 mg/kg or 5 mg/kg) or vehicle (buffer control) were intraperitoneally administered twice per week. For validation of CAR-T, NOD-scid $IL2Rg^{null}$ mice (NSG mice, 6-8 weeks old, male, The Jackson Laboratory) were engrafted s.c. (right flank) with Du145 and Du145-CEACAM5 ($1\times10^7$ cells/mice) in 200 μL of a 1:1 mixture of PBS/Matrigel. When the tumors were 150 $mm^3$, mice were treated with control T cells or CAR-T cells ($5\times10^6$ cells/mice) every 4 days, two times, via tail vein. Tumor dimensions were measured with caliper, and tumor volume was calculated by the formula $V=\frac{1}{2}\times length\times(width)^2$. Animals were euthanized when the tumor volume reached >1.0 $cm^3$.

Results

Figure 48:
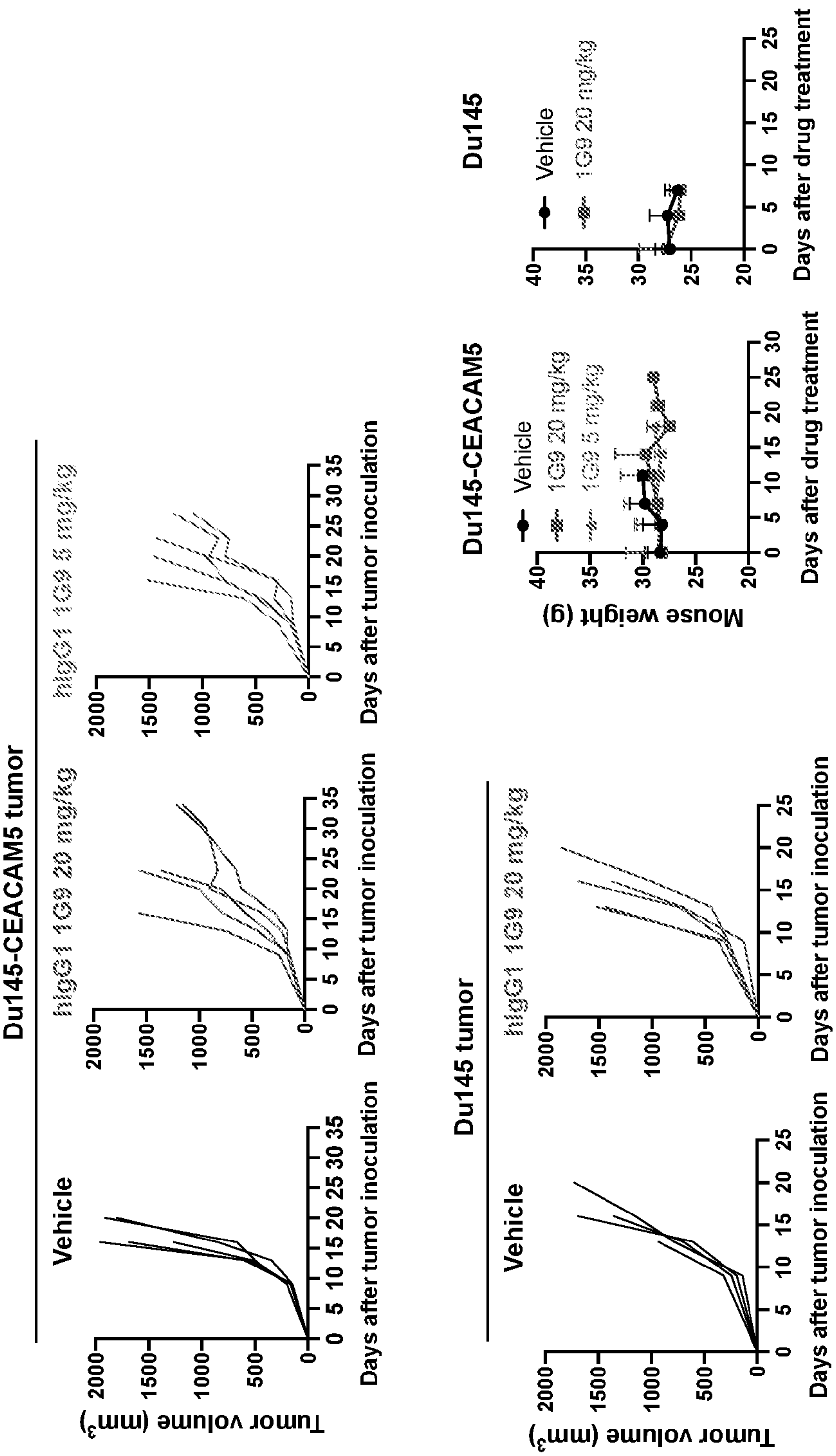
FIG. 48. Tumor growth curves and body weight of individual mice for the indicated hIgG1 treatment groups in Du145-CEACAM5 and Du145 tumors.

Anti-CEACAM5 hIgG1 IG9 and CAR-T Cells Inhibited Growth of CEACAM5-Positive Prostate Cancer Xenografts To evaluate the cytotoxic potential of hIgG1 1G9 in vivo, mouse xenograft models of Du145 and Du145-CEACAM5 were used. Mice bearing approximately 200 $mm^3$ tumors were treated with hIgG1 1G9 at 20 or 5 mg/kg. hIgG1 1G9 significantly slowed the growth of Du145-CEACAM5 tumor (FIG. 48) and improved mouse survival compared to those of vehicle-treated mice. For CEACAM5-negative Du145 tumors, no significant difference was observed in tumor growth and mouse survival between vehicle and hIgG1 1G9. The body weight of mice, monitored as an indicator of drugs toxicity, was similar in the treatment and vehicle groups.

Figure 49:
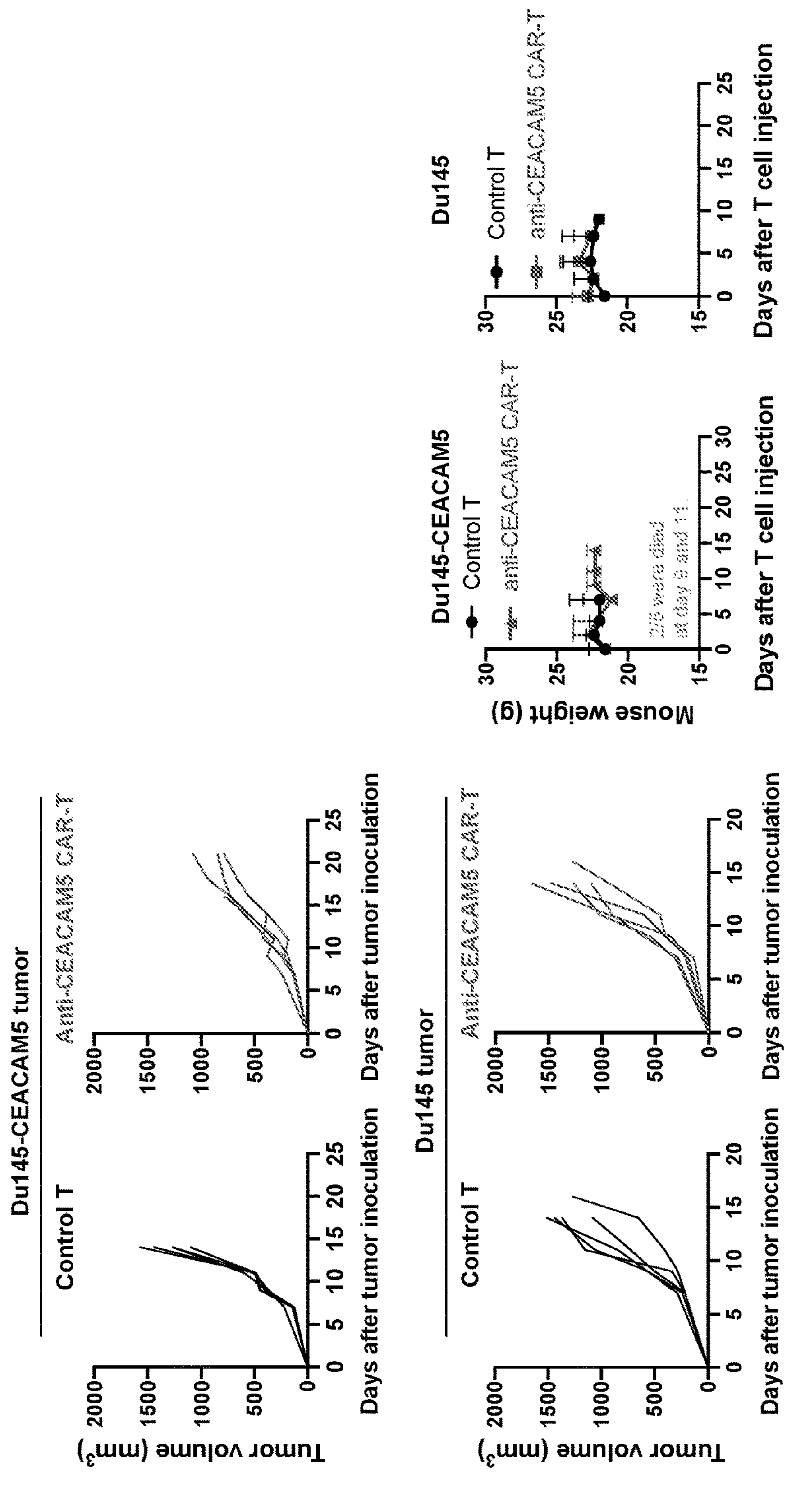
FIG. 49. Tumor growth curves and body weight of individual mice for the indicated CAR-T treatment groups in Du145-CEACAM5 and Du145 tumors.
Figure 50:
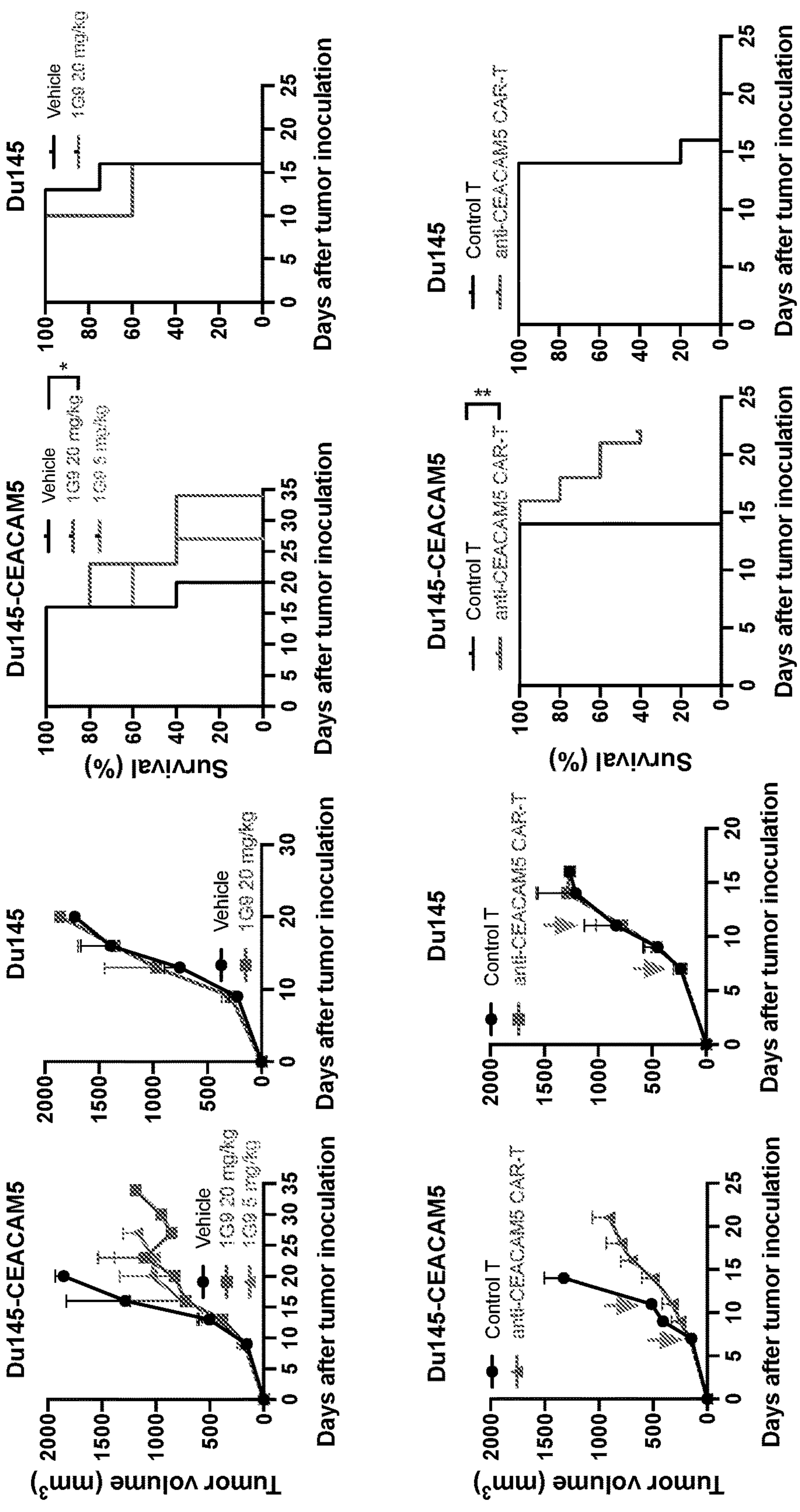
FIG. 50. Overall tumor growth inhibition and survival rate after treatment using 1G9 hIgG1 or CAR-T cells.

The cytotoxicity of anti-CEACAM5 CAR-T cells also was investigated in mice using xenograft models. NSG mice were s.c. implanted with Du145 and Du145-CEACAM5 cells, and control T cells or anti-CEACAM5 CAR-T cells were intravenously injected into mice via tail vein two times. Anti-CEACAM5 CAR-T cell-treated mice suppressed tumor growth and had longer survival compared to control T cell-treated mice in Du145-CEACAM5 tumor, but not Du145 tumor (FIG. 49). During CAR-T cell treatment, 2 of 5 mice showed 10% body weight loss for Du145-CEACAM5 tumors, but not Du145 tumors, and they died at day 9 and 11 after CAR-T injection. This result suggests that the anti-CEACAM5 CAR-T cells exhibited target-mediated systemic toxicity in association with potent anti-tumor effects in some mice. Taken together, these results demonstrate that anti-CEACAM5 hIgG1 1G9 and CAR-T cells exhibit in vivo anti-tumor efficacy depending on CEACAM5 expression, consistent with in vitro results (FIG. 50).

Example 4—Designing BiKE's from Binders Having the Ability to Bind to a Human CD66e Polypeptide The heavy and light variable domains of the Fab's of Clones #1 and #2 along with an anti-NKG2A are used to create vectors designed to express BiKEs (BiKE #1 and BiKE #2) having the ability to bind to CD66e polypeptides and NKG2A polypeptides.

Preparation of Anti-CEA×NKG2A BiKE

A synthesized gene for digested gene for anti-CEA×NKG2A BiKE is digested by NotI and NheI restriction enzymes and then is ligated into pCAT2 vector by T4 DNA ligase. Re-circularized plasmid DNA is transformed into HB2151 *E. coli* competent cells, and then transformants are selected in ampicillin containing LB plate (100 μg/mL final concentration) for overnight in incubator at 37° C. Next day, a colony is inoculated in liquid LB+ampicillin media and is cultured in 37° C. shaking incubator until mid-log growth phase. At $OD_{600}$ of between 0.4~0.6, 0.1 mM of isopropyl 3-D-1-thiogalactopyranoside (IPTG) is added to the culture, and it is continued to grow on shaking incubator at 30° C. and 200 rpm. Next day, induced *E. coli* cells are harvested by centrifugation at 6,000 g for 10 minutes. The cell pellet is resuspended in 1/10 volume of periplasm extraction buffer containing polymyxin B (0.5 mg/mL in PBS pH 7.4) and is then incubated on ice for an hour. The supernatant is collected by centrifugation at 12,000 g for 20 minutes. Filtered supernatant is loaded into a disposable column, which is pre-packed with Ni-NTA resin. After loading, the resin is washed with 5-bed volume of 30 mM imidazole in PBS pH 7.4, then Bound BiKE molecule is eluted by adding 300 mM imidazole in PBS pH 7.4. The remaining imidazole is removed through PD-10 desalting column, pre-packed with PBS pH 7.4.

Example 5—Other Embodiments

Embodiment 1. An antibody comprising:

(i) a heavy chain variable domain or region comprising the amino acid sequences set forth in SEQ ID NO:1 (or SEQ ID NO:1 with one, two, or three amino acid additions, deletions, or substitutions), SEQ ID NO:2 (or SEQ ID NO:2 with one, two, or three amino acid additions, deletions, or substitutions), and SEQ ID NO:3 (or SEQ ID NO:3 with one, two, or three amino acid additions, deletions, or substitutions), and a light chain variable domain or region comprising the amino acid sequences set forth in SEQ ID NO:9 (or SEQ ID NO:9 with one, two, or three amino acid additions, deletions, or substitutions), SEQ ID NO:10 (or SEQ ID NO:10 with one, two, or three amino acid additions, deletions, or substitutions), and SEQ ID NO:11 (or SEQ ID NO:11 with one, two, or three amino acid additions, deletions, or substitutions); or (ii) a heavy chain variable domain or region comprising the amino acid sequences set forth in SEQ ID NO:17 (or SEQ ID NO:17 with one, two, or three amino acid additions, deletions, or substitutions), SEQ ID NO:18 (or SEQ ID NO:18 with one, two, or three amino acid additions, deletions, or substitutions), and SEQ ID NO:19 (or SEQ ID NO:19 with one, two, or three amino acid additions, deletions, or substitutions), and a light chain variable domain or region comprising the amino acid sequences set forth in SEQ ID NO:25 (or SEQ ID NO:25 with one, two, or three amino acid additions, deletions, or substitutions), SEQ ID NO:26

(or SEQ ID NO:26 with one, two, or three amino acid additions, deletions, or substitutions), and SEQ ID NO:27 (or SEQ ID NO:27 with one, two, or three amino acid additions, deletions, or substitutions).

Embodiment 2. The antibody of embodiment 1, wherein said antibody comprises the ability to bind to SEQ ID NO:150 or SEQ ID NO:151.

Embodiment 3. The antibody of any one of embodiments 1-2, wherein said antibody comprises said heavy chain variable domain or region of said (i).

Embodiment 4. The antibody of embodiment 3, wherein said heavy chain variable domain or region comprises an amino acid sequence having at least 90 percent identity to the amino acid sequence set forth in SEQ ID NO:8.

Embodiment 5. The antibody of any one of embodiments 1-2, wherein said antibody comprises said light chain variable domain or region of said (i).

Embodiment 6. The antibody of embodiment 5, wherein said light chain variable domain or region comprises an amino acid sequence having at least 90 percent identity to the amino acid sequence set forth in SEQ ID NO:16.

Embodiment 7. The antibody of any one of embodiments 1-2, wherein said antibody comprises said heavy chain variable domain or region of said (ii).

Embodiment 8. The antibody of embodiment 7, wherein said heavy chain variable domain or region comprises an amino acid sequence having at least 90 percent identity to the amino acid sequence set forth in SEQ ID NO:24.

Embodiment 9. The antibody of any one of embodiments 1-2, wherein said antibody comprises said light chain variable domain or region of said (ii).

Embodiment 10. The antibody of embodiment 9, wherein said light chain variable domain or region comprises an amino acid sequence having at least 90 percent identity to the amino acid sequence set forth in SEQ ID NO:32.

Embodiment 11. An antigen binding fragment comprising:

(i) a heavy chain variable domain or region comprising the amino acid sequences set forth in SEQ ID NO:1 (or SEQ ID NO:1 with one, two, or three amino acid additions, deletions, or substitutions), SEQ ID NO:2 (or SEQ ID NO:2 with one, two, or three amino acid additions, deletions, or substitutions), and SEQ ID NO:3 (or SEQ ID NO:3 with one, two, or three amino acid additions, deletions, or substitutions), and a light chain variable domain or region comprising the amino acid sequences set forth in SEQ ID NO:9 (or SEQ ID NO:9 with one, two, or three amino acid additions, deletions, or substitutions), SEQ ID NO:10 (or SEQ ID NO:10 with one, two, or three amino acid additions, deletions, or substitutions), and SEQ ID NO:11 (or SEQ ID NO:11 with one, two, or three amino acid additions, deletions, or substitutions); or (ii) a heavy chain variable domain or region comprising the amino acid sequences set forth in SEQ ID NO:17 (or SEQ ID NO:17 with one, two, or three amino acid additions, deletions, or substitutions), SEQ ID NO:18 (or SEQ ID NO:18 with one, two, or three amino acid additions, deletions, or substitutions), and SEQ ID NO:19 (or SEQ ID NO:19 with one, two, or three amino acid additions, deletions, or substitutions), and a light chain variable domain or region comprising the amino acid sequences set forth in SEQ ID NO:25 (or SEQ ID NO:25 with one, two, or three amino acid additions, deletions, or substitutions), SEQ ID NO:26 (or SEQ ID NO:26 with one, two, or three amino acid additions, deletions, or substitutions), and SEQ ID NO:27 (or SEQ ID NO:27 with one, two, or three amino acid additions, deletions, or substitutions).

Embodiment 12. The antigen binding fragment of embodiment 11, wherein said antigen binding fragment comprises the ability to bind to SEQ ID NO:150 or SEQ ID NO:151.

Embodiment 13. The antigen binding fragment of any one of embodiments 11-12, wherein said antigen binding fragment comprises said heavy chain variable domain or region of said (i).

Embodiment 14. The antigen binding fragment of embodiment 13, wherein said heavy chain variable domain or region comprises an amino acid sequence having at least 90 percent identity to the amino acid sequence set forth in SEQ ID NO:8.

Embodiment 15. The antigen binding fragment of any one of embodiments 11-12, wherein said antigen binding fragment comprises said light chain variable domain or region of said (i).

Embodiment 16. The antigen binding fragment of embodiment 15, wherein said light chain variable domain or region comprises an amino acid sequence having at least 90 percent identity to the amino acid sequence set forth in SEQ ID NO:16.

Embodiment 17. The antigen binding fragment of any one of embodiments 11-12, wherein said antigen binding fragment comprises said heavy chain variable domain or region of said (ii).

Embodiment 18. The antigen binding fragment of embodiment 17, wherein said heavy chain variable domain or region comprises an amino acid sequence having at least 90 percent identity to the amino acid sequence set forth in SEQ ID NO:24.

Embodiment 19. The antigen binding fragment of any one of embodiments 11-12, wherein said antigen binding fragment comprises said light chain variable domain or region of said (ii).

Embodiment 20. The antigen binding fragment of embodiment 19, wherein said light chain variable domain or region comprises an amino acid sequence having at least 90 percent identity to the amino acid sequence set forth in SEQ ID NO:32.

Embodiment 21. The antibody of any one of embodiments 1-10, wherein said antibody is a monoclonal antibody.

Embodiment 22. The antibody of any one of embodiments 1-10 and 21, wherein said antibody is an scFv antibody.

Embodiment 23. The antigen binding fragment of any one of embodiments 11-20, wherein said antigen binding fragment is monoclonal.

Embodiment 24. The antigen binding fragment of any one of embodiments 11-20 and 23, wherein said antigen binding fragment is an Fab.

Embodiment 25. A chimeric antigen receptor comprising an antigen binding domain, a hinge, a transmembrane domain, and one or more signaling domains, wherein said antigen binding domain comprises an antibody or an antigen-binding fragment of any one of embodiments 1-24.

Embodiment 26. The chimeric antigen receptor of embodiment 25, wherein said antigen binding domain comprises a scFv having the ability to bind to a CD66e polypeptide.

Embodiment 27. The chimeric antigen receptor of any one of embodiments 25-26, wherein said hinge comprises a hinge set forth in FIG. 13.

Embodiment 28. The chimeric antigen receptor of any one of embodiments 25-27, wherein said transmembrane domain comprises a transmembrane domain set forth in FIG. 14.

Embodiment 29. The chimeric antigen receptor of any one of embodiments 25-28, wherein said chimeric antigen receptor comprises one or more signaling domains set forth in FIG. 15.

Embodiment 30. A cell comprising a chimeric antigen receptor of any one of embodiments 25-29.

Embodiment 31. The cell of embodiment 30, wherein said cell is a T cell, a stem cell, or an NK cell.

Embodiment 32. A cell engager comprising a first antigen binding domain, a linker, and a second antigen binding domain, wherein said first antigen binding domain comprises an antibody or an antigen-binding fragment of any one of embodiments 1-24.

Embodiment 33. The cell engager of embodiment 32, wherein said first antigen binding domain comprises a scFv having the ability to bind to a CD66e polypeptide.

Embodiment 34. The cell engager of embodiment 32, wherein said first antigen binding domain is an IgG having the ability to bind to a CD66e polypeptide.

Embodiment 35. The cell engager of any one of embodiments 32-34, wherein said linker comprises a linker set forth in FIG. 10 or FIG. 13.

Embodiment 36. The cell engager of any one of embodiments 32-35, wherein said second antigen binding domain binds to a polypeptide expressed on the surface of T cells.

Embodiment 37. The cell engager of embodiment 36, wherein said polypeptide expressed on the surface of T cells is a CD3 polypeptide.

Embodiment 38. The cell engager of embodiment 36, wherein said second antigen binding domain is an antigen binding domain set forth in FIG. 18.

Embodiment 39. The cell engager of any one of embodiments 32-35, wherein said second antigen binding domain binds to a polypeptide expressed on the surface of NK cells.

Embodiment 40. The cell engager of embodiment 39, wherein said polypeptide expressed on the surface of NK cells is a CD16a, NKG2A, NKG2D, NKp30, NKp44, or NKp46 polypeptide.

Embodiment 41. The cell engager of embodiment 39, wherein said second antigen binding domain is an antigen binding domain set forth in FIG. 19.

Embodiment 42. The cell engager of any one of embodiments 32-41, wherein said cell engager comprises a third antigen binding domain.

Embodiment 43. The cell engager of embodiment 42, wherein said third antigen binding domain binds to a polypeptide expressed on the surface of NK cells.

Embodiment 44. The cell engager of embodiment 43, wherein said polypeptide expressed on the surface of NK cells is a CD16a, NKG2A, NKG2D, NKp30, NKp44, or NKp46 polypeptide.

Embodiment 45. The cell engager of embodiment 43, wherein said third antigen binding domain is an antigen binding domain set forth in FIG. 19.

Embodiment 46. A nucleic acid comprising a nucleic acid sequence encoding at least part of an antibody or an antigen-binding fragment of any one of embodiments 1-24.

Embodiment 47. The nucleic acid of embodiment 46, wherein said nucleic acid sequence encodes said heavy chain variable domain or region of any one of said (i)-(ii) of embodiment 1.

Embodiment 48. The nucleic acid of any one of embodiments 46-47, wherein said nucleic acid sequence encodes said light chain variable domain or region of any one of said (i)-(ii) of embodiment 1.

Embodiment 49. The nucleic acid of any one of embodiments 46-48, wherein said nucleic acid is a viral vector.

Embodiment 50. The nucleic acid of any one of embodiments 46-48, wherein said nucleic acid is a phagemid.

Embodiment 51. A nucleic acid comprising a nucleic acid sequence encoding a chimeric antigen receptor of any one of embodiments 25-29 or a cell engager of any one of embodiments 32-45.

Embodiment 52. The nucleic acid of embodiment 51, wherein said nucleic acid is a viral vector.

Embodiment 53. The nucleic acid of embodiment 51, wherein said nucleic acid is a phagemid.

Embodiment 54. A host cell comprising a nucleic acid of any one of embodiments 46-52.

Embodiment 55. A host cell that expresses a chimeric antigen receptor of any one of embodiments 25-29 or a cell engager of any one of embodiments 32-45.

Embodiment 56. The host cell of any one of embodiments 54-55, wherein said host cell is a T cell, stem cell, or NK cell.

Embodiment 57. An antibody-drug conjugate (ADC) comprising an antigen binding domain covalently linked to a drug, wherein said antigen binding domain comprises an antibody or an antigen binding fragment of any one of embodiments 1-24.

Embodiment 58. The ADC of embodiment 57, wherein said antigen binding domain comprises a scFv having the ability to bind to a CD66e polypeptide.

Embodiment 59. The ADC of embodiment 57, wherein said antigen binding domain is an IgG having the ability to bind to a CD66e polypeptide.

Embodiment 60. The ADC of any one of embodiments 57-59, wherein said drug is selected from the group consisting of auristatins, mertansine, or pyrrolobenzodiazepine (PBD) dimers.

Embodiment 61. A composition comprising an antibody or an antigen binding fragment of any one of embodiments 1-24.

Embodiment 62. The composition of embodiment 61, wherein said composition comprises said antibody of any one of embodiments 1-10, 21, and 22.

Embodiment 63. The composition of embodiment 61, wherein said composition comprises said antigen binding fragment of any one of embodiments 11-20, 23, and 24.

Embodiment 64. A composition comprising a cell engager of any one of embodiments 32-45.

Embodiment 65. A composition comprising a cell of any one of embodiments 30, 31, and 53-56.

Embodiment 66. A composition comprising an ADC of any one of embodiments 57-60.

Embodiment 67. The composition of any one of embodiments 61-66, wherein said composition comprises a checkpoint inhibitor.

Embodiment 68. The composition of embodiment 67, wherein said checkpoint inhibitor is selected from the group consisting of cemiplimab, nivolumab, pembrolizumab, JTX-4014, spartalizumab, camrelizumab, sintilimab, tislelizumab, toripalimab, dostarlimab, INCMGA00012, AMP-224, AMP-514, avelumab, durvalumab, atezolizumab, KN035, CK-301, AUNP12, CA-170, BMS-986189, and ipilimumab.

Embodiment 69. A method of treating a mammal having cancer, wherein said method comprises administering, to said mammal, a composition of any one of embodiments 61-68.

Embodiment 70. The method of embodiment 69, wherein said mammal is a human.

Embodiment 71. The method of any one of embodiments 69-70, wherein said cancer is a $CD66e^+$ cancer.

Embodiment 72. The method of embodiment 71, wherein said CD66e$^+$ cancer is selected from the group consisting of CD66e$^+$ lung cancer, CD66e$^+$ prostate cancer, CD66e$^+$ esophageal cancer, CD66e$^+$ stomach cancer, CD66e$^+$ colorectal cancer, CD66e$^+$ liver cancer, CD66e$^+$ vaginal cancer, or CD66e$^+$ cervical cancer.

Embodiment 73. The method of any one of embodiments 69-72, wherein the number of cancer cells within said mammal is reduced following said administering step.

Embodiment 74. A method of treating a mammal having cancer, wherein said method comprises:

(a) administering, to said mammal, said composition of any one of embodiments 98-104, and
(b) administering, to said mammal, a composition comprising a checkpoint inhibitor.

Embodiment 75. The method of embodiment 74, wherein said mammal is a human.

Embodiment 76. The method of any one of embodiments 74-75, wherein said cancer is a CD66e$^+$ cancer.

Embodiment 77. The method of embodiment 76, wherein said CD66e$^+$ cancer is selected from the group consisting of CD66e$^+$ lung cancer, CD66e$^+$ prostate cancer, CD66e$^+$ esophageal cancer, CD66e$^+$ stomach cancer, CD66e$^+$ colorectal cancer, CD66e$^+$ liver cancer, CD66e$^+$ vaginal cancer, or CD66e$^+$ cervical cancer.

Embodiment 78. The method of any one of embodiments 74-77, wherein said checkpoint inhibitor is selected from the group consisting of cemiplimab, nivolumab, pembrolizumab, JTX-4014, spartalizumab, camrelizumab, sintilimab, tislelizumab, toripalimab, dostarlimab, INCMGA00012, AMP-224, AMP-514, avelumab, durvalumab, atezolizumab, KN035, CK-301, AUNP12, CA-170, BMS-986189, and ipilimumab.

Embodiment 79. The method of any one of embodiments 74-78, wherein the number of cancer cells within said mammal is reduced following said administering steps (a) and (b).

Embodiment 80. A method for binding a binding molecule to a CD66e polypeptide, wherein said method comprises contacting said CD66e polypeptide with an antibody or an antigen binding fragment of any one of embodiments 1-24.

Embodiment 81. The method of embodiment 80, wherein said contacting is performed in vitro.

Embodiment 82. The method of embodiment 80, wherein said contacting is performed in vivo.

Embodiment 83. The method of embodiment 82, wherein said contacting is performed within a mammal by administering said antibody or said antigen binding fragment to said mammal.

Embodiment 84. The method of embodiment 84, wherein said mammal is a human.

Embodiment 85. A method for binding a binding molecule to a CD66e polypeptide, wherein said method comprises contacting said CD66e polypeptide with a chimeric antigen receptor of any one of embodiments 25-29, a cell engager of any one of embodiments 32-45, or an ADC of any one of embodiments 57-60.

Embodiment 86. The method of embodiment 85, wherein said contacting is performed in vitro.

Embodiment 87. The method of embodiment 85, wherein said contacting is performed in vivo.

Embodiment 88. The method of embodiment 87, wherein said contacting is performed within a mammal by administering said chimeric antigen receptor, said cell engager, or said ADC to said mammal.

Embodiment 89. The method of embodiment 88, wherein said mammal is a human.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An antibody or antigen binding fragment thereof comprising:
   (i) a heavy chain variable domain (VH) and alight chain variable domain (VL), wherein said VH comprises a VH-CDR1 sequence of SEQ ID NO:1, a VH-CDR2 sequence of SEQ ID NO: 2, and a VH-CDR3 sequence of SEQ ID NO: 3, and said VL comprises a VL-CDR1 sequence of SEQ ID NO: 9, a VL-CDR2 sequence of SEQ ID NO: 10, and a VL-CDR3 sequence of SEQ ID NO: 11; or
   (ii) a heavy chain variable domain (VH) and alight chain variable domain (VL), wherein said VH comprises a VH-CDR1 sequence of SEQ ID NO: 17, a VH-CDR2 sequence of SEQ ID NO: 18, and a VH-CDR3 sequence of SEQ ID NO: 19, and said VL comprises a VL-CDR1 sequence of SEQ ID NO: 25, a VL-CDR2 sequence of SEQ ID NO: 26, and a VL-CDR3 sequence of SEQ ID NO: 27;
   wherein said antibody or antigen binding fragment thereof binds CD66e.

2. The antibody or antigen binding fragment thereof of claim 1, wherein said antibody or antigen binding domain thereof comprises the ability to bind to SEQ ID NO:150 or SEQ ID NO:151.

3. A chimeric antigen receptor comprising an antigen binding domain, a hinge, a transmembrane domain, and one or more signaling domains, wherein said antigen binding domain comprises the antibody or antigen binding fragment thereof of claim 1.

4. The chimeric antigen receptor of claim 3, wherein said antigen binding domain is an scFv.

5. A cell comprising the chimeric antigen receptor of claim 3.

6. The cell of claim 5, wherein said cell is a T cell, a stem cell, or an NK cell.

7. A cell engager comprising a first antigen binding domain, a linker, and a second antigen binding domain, wherein said first antigen binding domain comprises the antibody or antigen binding fragment thereof of claim 1.

8. The cell engager of claim 7, wherein said first antigen binding domain is an scFv.

9. The cell engager of claim 7, wherein said first antigen binding domain is an IgG.

10. The cell engager of claim 7, wherein said second antigen binding domain binds to a polypeptide expressed on the surface of T cells.

11. The cell engager of claim 10, wherein said polypeptide expressed on the surface of T cells is a CD3 polypeptide.

12. The cell engager of claim 7, wherein said second antigen binding domain binds to a polypeptide expressed on the surface of NK cells.

13. The cell engager of claim 12, wherein said polypeptide expressed on the surface of NK cells is a CD16a, NKG2A, NKG2D, NKp30, NKp44, or NKp46 polypeptide.

14. An antibody-drug conjugate (ADC) comprising an antigen binding domain covalently linked to a drug, wherein said antigen binding domain comprises the antibody or antigen binding fragment thereof of claim 1.

15. A method of treating a mammal having cancer, wherein said method comprises administering, to said mammal, a composition comprising (a) an antibody comprising (i) or (ii), (b) an antigen binding fragment comprising said (i) or said (ii), (c) a cell expressing a chimeric antigen receptor comprising an antigen binding domain comprising said (i) or said (ii), a hinge, a transmembrane domain, and one or more signaling domains, (d) a cell engager comprising a first antigen binding domain comprising said (i) or said (ii), a linker, and a second antigen binding domain, or (e) an ADC comprising a drug covalently linked to an antigen binding domain comprising said (i) or said (ii), wherein said
   (i) is a heavy chain variable domain (VH) and a light chain variable domain (VL), wherein said VH comprises a VH-CDR1 sequence of SEQ ID NO: 1, a VH-CDR2 sequence of SEQ ID NO: 2, and a VH-CDR3 sequence of SEQ ID NO: 3, and said VL comprises a VL-CDR1 sequence of SEQ ID NO: 9, a VL-CDR2 sequence of SEQ ID NO: 10, and a VL-CDR3 sequence of SEQ ID NO: 11, and wherein said
   (ii) is a heavy chain variable domain (VH) and a light chain variable domain (VL), wherein said VH comprises a VH-CDR1 sequence of SEQ ID NO: 17, a VH-CDR2 sequence of SEQ ID NO: 18, and a VH-CDR3 sequence of SEQ ID NO: 19, and said VL comprises a VL-CDR1 sequence of SEQ ID NO: 25, a VL-CDR2 sequence of SEQ ID NO: 26, and a VL-CDR3 sequence of SEQ ID NO: 27;
   wherein said antibody, antigen binding fragment, cell, cell engager, or ADC binds CD66e.

16. A method for binding a binding molecule to a CD66e polypeptide, wherein said method comprises contacting said CD66e polypeptide with the antibody or antigen binding fragment thereof of claim 1.

17. A method for binding a binding molecule to a CD66e polypeptide, wherein said method comprises contacting said CD66e polypeptide with (a) a chimeric antigen receptor comprising an antigen binding domain comprising (i) or (ii), a hinge, a transmembrane domain, and one or more signaling domains, (b) a cell engager comprising a first antigen binding domain comprising said (i) or said (ii), a linker, and a second antigen binding domain, or (c) an ADC comprising a drug covalently linked to an antigen binding domain comprising said (i) or said (ii), wherein said
   (i) is a heavy chain variable domain (VH) and a light chain variable domain (VL), wherein said VH comprises a VH-CDR1 sequence of SEQ ID NO: 1, a VH-CDR2 sequence of SEQ ID NO: 2, and a VH-CDR3 sequence of SEQ ID NO: 3, and said VL comprises a VL-CDR1 sequence of SEQ ID NO: 9, a VL-CDR2 sequence of SEQ ID NO: 10, and a VL-CDR3 sequence of SEQ ID NO: 11, and wherein said
   (ii) is a heavy chain variable domain (VH) and a light chain variable domain (VL), wherein said VH comprises a VH-CDR1 sequence of SEQ ID NO: 17, a VH-CDR2 sequence of SEQ ID NO: 18, and a VH-CDR3 sequence of SEQ ID NO: 19, and said VL comprises a VL-CDR1 sequence of SEQ ID NO: 25, a VL-CDR2 sequence of SEQ ID NO: 26, and a VL-CDR3 sequence of SEQ ID NO: 27;

wherein said chimeric antigen receptor, cell engager, or ADC binds CD66e.

* * * * *

SEQUENCE LISTING

```
<160> NUMBER OF SEQ ID NOS: 256

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Tyr Tyr Met Ser
1               5


<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Ile Ser Ser Ser Gly Ser Thr Ile Tyr Tyr Ala Asp Ser Val Lys
1               5                   10                  15
```

-continued

```
Gly


<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Gly Arg Tyr Ser Tyr Gly Leu Arg Ser Tyr Tyr Tyr Tyr Gly Met
1               5                   10                  15

Asp Val


<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30


<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Ile Arg Gln Ala Pro Gly Lys Gly Leu Glu Trp Val Ser
1               5                   10


<210> SEQ ID NO 6
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30


<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Gly Gln Gly Thr Thr Val Thr Val Ser Ser
```

1 5 10

<210> SEQ ID NO 8
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Ile Gly Arg Tyr Ser Tyr Gly Leu Arg Ser Tyr Tyr Tyr Tyr
100 105 110

Gly Met Asp Val Trp Gly Gln Gly Thr Thr Val Thr Val Ser Ser
115 120 125

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Arg Ala Ser Gln Ser Ile Ser Ser Tyr Leu Asn
1 5 10

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Ala Ala Ser Ser Leu Gln Ser
1 5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Met Gln Ala Leu Gln Thr Pro Val Thr
1 5

```
<210> SEQ ID NO 12
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys
            20


<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Trp Tyr Gln Gln Lys Pro Gly Lys Ala Pro Lys Leu Leu Ile Tyr
1               5                   10                  15


<210> SEQ ID NO 14
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Gly Val Tyr Tyr Cys
            20                  25                  30


<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Gly Gln Gly Thr Arg Leu Glu Ile Lys Arg
1               5                   10


<210> SEQ ID NO 16
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30
```

```
Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Val Tyr Tyr Cys Met Gln Ala Leu Gln Thr Pro Val
                85                  90                  95

Thr Phe Gly Gln Gly Thr Arg Leu Glu Ile Lys Arg
            100                 105


<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Tyr Tyr Met Ser
1               5


<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Tyr Ile Ser Ser Ser Gly Ser Thr Ile Tyr Tyr Ala Asp Ser Val Lys
1               5                   10                  15

Gly


<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Val Ala Arg Gln Tyr Arg Lys Ser Tyr Tyr Tyr Tyr Gly Met Asp Val
1               5                   10                  15


<210> SEQ ID NO 20
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30


<210> SEQ ID NO 21
<211> LENGTH: 14
```

<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Trp Ile Arg Gln Ala Pro Gly Lys Gly Leu Glu Trp Val Ser
1 5 10

<210> SEQ ID NO 22
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

Arg Phe Thr Ile Ser Arg Asp Asn Ala Lys Asn Ser Leu Tyr Leu Gln
1 5 10 15

Met Asn Ser Leu Arg Ala Glu Asp Thr Ala Met Tyr Tyr Cys Ala Arg
20 25 30

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Trp Gly Gln Gly Thr Thr Val Thr Val Ser Ser
1 5 10

<210> SEQ ID NO 24
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Met Tyr Tyr Cys
85 90 95

Ala Arg Val Ala Arg Gln Tyr Arg Lys Ser Tyr Tyr Tyr Tyr Gly Met
100 105 110

Asp Val Trp Gly Gln Gly Thr Thr Val Thr Val Ser Ser
115 120 125

<210> SEQ ID NO 25

<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Arg Ala Ser Gln Ser Ile Ser Ser Tyr Leu Asn
1               5                   10
```

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Ala Ala Ser Ser Leu Gln Ser
1               5
```

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Met Gln Ala Leu Gln Thr Pro Leu Thr
1               5
```

<210> SEQ ID NO 28
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Trp Tyr Gln Gln Lys Pro Gly Lys Ala Pro Lys Leu Leu Ile Tyr
1               5                   10                  15
```

<210> SEQ ID NO 30
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 30

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Gly Val Tyr Tyr Cys
            20                  25                  30


<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Phe Gly Gly Gly Thr Lys Leu Glu Ile Lys Arg
1               5                   10


<210> SEQ ID NO 32
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Gly Val Tyr Tyr Cys Met Gln Ala Leu Gln Thr Pro Leu
                85                  90                  95

Thr Phe Gly Gly Gly Thr Lys Leu Glu Ile Lys Arg
            100                 105


<210> SEQ ID NO 33
<211> LENGTH: 98
<212> TYPE: PRT
<213> ORGANISM: Homo sapiens

<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

-continued

```
                85                  90                  95

Lys Val


<210> SEQ ID NO 34
<211> LENGTH: 106
<212> TYPE: PRT
<213> ORGANISM: Homo sapiens

<400> SEQUENCE: 34

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105


<210> SEQ ID NO 35
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

caagttcaat tagtggagag cggcggcgga ttggttaaac cgggggggcag tctgcgttta     60

agctgcgcag cttccgggtt tactttttcg gattactata tgagctggat tcgtcaggct    120

cccggtaaag ggttggaatg ggttagctac atctcaagtt ccggctctac aatctactat    180

gcagattccg tgaaagggcg cttcaccatc tctcgtgaca atgcaaagaa cagtttatac    240

ttacaaatga actcgctgcg tgcggaagat acggctgtgt attactgtgc acggattggg    300

cggtacagct atggtctccg gtcctactac tactacggta tggacgtctg gggccaaggg    360

accacggtca ccgtctcctc a                                              381


<210> SEQ ID NO 36
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

gatattcaaa tgacccagtc tccttcttcc ttgagcgcgt ctgtgggaga ccgtgtaact     60

atcacgtgtc gtgcatccca aagcatttcg agttacttga actggtatca acaaaagcct    120

ggtaaagcgc ccaaactgtt gatctatgct gccagtagtc ttcaatctgg tgtgccctcg    180

cgcttctcag gttcggggtc aggaacggac tttaccctga ccattagctc tctgcaaccg    240

gaggattttg ggtttatta ctgcatgcaa gctctacaaa ctccggtcac cttcggccaa     300
```

gggacacgac tggagattaa acgt 324

<210> SEQ ID NO 37
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37
caagttcaat tagtggagag cggcggcgga ttggttaaac cggggggcag tctgcgttta 60
agctgcgcag cttccgggtt tactttttcg gattactata tgagctggat tcgtcaggct 120
cccggtaaag ggttggaatg ggttagctac atctcaagtt ccggctctac aatctactat 180
gcagattccg tgaaagggcg cttcaccatc tctcgtgaca atgcaaagaa cagtttatac 240
ttacaaatga actcgctgcg tgcggaagat acggccatgt attactgtgc gagagtggca 300
cggcaatatc ggaaaagcta ctactactac ggtatggacg tctggggcca agggaccacg 360
gtcaccgtct cctca 375

<210> SEQ ID NO 38
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38
gatattcaaa tgacccagtc tccttcttcc ttgagcgcgt ctgtgggaga ccgtgtaact 60
atcacgtgtc gtgcatccca aagcatttcg agttacttga actggtatca acaaaagcct 120
ggtaaagcgc ccaaactgtt gatctatgct gccagtagtc ttcaatctgg tgtgccctcg 180
cgcttctcag gttcggggtc aggaacggac tttaccctga ccattagctc tctgcaaccg 240
gaggatgttg ggtttatta ctgcatgcaa gctctacaaa ctccgctcac tttcggcgga 300
gggaccaagc tggagatcaa acgt 324

<210> SEQ ID NO 39
<211> LENGTH: 15
<212> TYPE: PRT
<213> ORGANISM: Homo sapiens

<400> SEQUENCE: 39

Glu Pro Lys Ser Cys Asp Lys Thr His Thr Cys Pro Pro Cys Pro
1 5 10 15

<210> SEQ ID NO 40
<211> LENGTH: 45
<212> TYPE: DNA
<213> ORGANISM: Homo sapiens

<400> SEQUENCE: 40
gagcccaaat cttgtgacaa aactcacaca tgcccaccgt gccca 45

<210> SEQ ID NO 41
<211> LENGTH: 217
<212> TYPE: PRT
<213> ORGANISM: Homo sapiens

<400> SEQUENCE: 41

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 42
<211> LENGTH: 651
<212> TYPE: DNA
<213> ORGANISM: Homo sapiens

<400> SEQUENCE: 42

```
gcacctgaac tcctgggggg accgtcagtc ttcctcttcc ccccaaaacc caaggacacc     60

ctcatgatct cccggacccc tgaggtcaca tgcgtggtgg tggacgtgag ccacgaagac    120

cctgaggtca agttcaactg gtacgtggac ggcgtggagg tgcataatgc caagacaaag    180

ccgcgggagg agcagtacaa cagcacgtac cgtgtggtca gcgtcctcac cgtcctgcac    240

caggactggc tgaatggcaa ggagtacaag tgcaaggtct ccaacaaagc cctcccagcc    300

cccatcgaga aaaccatctc caaagccaaa gggcagcccc gagaaccaca ggtgtacacc    360

ctgcccccat cccgggatga gctgaccaag aaccaggtca gcctgacctg cctggtcaaa    420

ggcttctatc ccagcgacat cgccgtggag tgggagagca atgggcagcc ggagaacaac    480

tacaagacca cgcctcccgt gctggactcc gacggctcct tcttcctcta cagcaagctc    540

accgtggaca agagcaggtg gcagcagggg aacgtcttct catgctccgt gatgcatgag    600

gctctgcaca accactacac gcagaagagc ctctccctgt ctccgggtaa a             651
```

<210> SEQ ID NO 43
<211> LENGTH: 87
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: NON_CONS
<222> LOCATION: (30)..(31)
<223> OTHER INFORMATION: Residues at these positions can be separated by a CDR1 sequence of Variable Heavy Region of unknown length
<220> FEATURE:
<221> NAME/KEY: NON_CONS
<222> LOCATION: (44)..(45)
<223> OTHER INFORMATION: Residues at these positions can be separated by a CDR2 sequence of Variable Heavy Region of unknown length
<220> FEATURE:
<221> NAME/KEY: NON_CONS
<222> LOCATION: (76)..(77)
<223> OTHER INFORMATION: Residues at these positions can be separated by a CDR3 sequence of Variable Heavy Region of unknown length

<400> SEQUENCE: 43

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Trp Ile
            20                  25                  30

Arg Gln Ala Pro Gly Lys Gly Leu Glu Trp Val Ser Arg Phe Thr Ile
        35                  40                  45

Ser Arg Asp Asn Ala Lys Asn Ser Leu Tyr Leu Gln Met Asn Ser Leu
    50                  55                  60

Arg Ala Glu Asp Thr Ala Val Tyr Tyr Cys Ala Arg Trp Gly Gln Gly
65                  70                  75                  80

Thr Thr Val Thr Val Ser Ser
                85
```

<210> SEQ ID NO 44
<211> LENGTH: 81
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: NON_CONS
<222> LOCATION: (23)..(24)
<223> OTHER INFORMATION: Residues at these positions can be separated by a CDR1 sequence of Variable Light Region of unknown length
<220> FEATURE:
<221> NAME/KEY: NON_CONS
<222> LOCATION: (38)..(39)
<223> OTHER INFORMATION: Residues at these positions can be separated by a CDR2 sequence of Variable Light Region of unknown length
<220> FEATURE:
<221> NAME/KEY: NON_CONS
<222> LOCATION: (70)..(71)
<223> OTHER INFORMATION: Residues at these positions can be separated by a CDR3 sequence of Variable Light Region of unknown length

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Ala
            20                  25                  30

Pro Lys Leu Leu Ile Tyr Gly Val Pro Ser Arg Phe Ser Gly Ser Gly
        35                  40                  45

Ser Gly Thr Asp Phe Thr Leu Thr Ile Ser Ser Leu Gln Pro Glu Asp
    50                  55                  60

Phe Gly Val Tyr Tyr Cys Phe Gly Gln Gly Thr Arg Leu Glu Ile Lys
65                  70                  75                  80

Arg
```

<210> SEQ ID NO 45
<211> LENGTH: 260
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 45

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Val Tyr Tyr Cys Met Gln Ala Leu Gln Thr Pro Val
                85                  90                  95

Thr Phe Gly Gln Gly Thr Arg Leu Glu Ile Lys Arg Gly Gly Gly Gly
            100                 105                 110

Ser Gly Gly Gly Gly Ser Gly Gly Gly Gly Ser Gly Gly Gly Gly Ser
        115                 120                 125

Gly Gly Gly Gly Ser Gln Val Gln Leu Val Glu Ser Gly Gly Gly Leu
    130                 135                 140

Val Lys Pro Gly Gly Ser Leu Arg Leu Ser Cys Ala Ala Ser Gly Phe
145                 150                 155                 160

Thr Phe Ser Asp Tyr Tyr Met Ser Trp Ile Arg Gln Ala Pro Gly Lys
                165                 170                 175

Gly Leu Glu Trp Val Ser Tyr Ile Ser Ser Ser Gly Ser Thr Ile Tyr
            180                 185                 190

Tyr Ala Asp Ser Val Lys Gly Arg Phe Thr Ile Ser Arg Asp Asn Ala
        195                 200                 205

Lys Asn Ser Leu Tyr Leu Gln Met Asn Ser Leu Arg Ala Glu Asp Thr
    210                 215                 220

Ala Val Tyr Tyr Cys Ala Arg Ile Gly Arg Tyr Ser Tyr Gly Leu Arg
225                 230                 235                 240

Ser Tyr Tyr Tyr Tyr Gly Met Asp Val Trp Gly Gln Gly Thr Thr Val
                245                 250                 255

Thr Val Ser Ser
            260
```

<210> SEQ ID NO 46
<211> LENGTH: 780
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 46

```
gatattcaaa tgacccagtc tccttcttcc ttgagcgcgt ctgtgggaga ccgtgtaact     60

atcacgtgtc gtgcatccca aagcatttcg agttacttga actggtatca acaaaagcct    120

ggtaaagcgc ccaaactgtt gatctatgct gccagtagtc ttcaatctgg tgtgccctcg    180
```

```
cgcttctcag gttcggggtc aggaacggac tttaccctga ccattagctc tctgcaaccg    240

gaggattttg gggtttatta ctgcatgcaa gctctacaaa ctccggtcac cttcggccaa    300

gggacacgac tggagattaa acgtggaggc ggtgggagcg ggggcggagg tagtggcggt    360

ggagggagcg gtggcggggg aagtggaggg ggtggcagcc aagttcaatt agtggagagc    420

ggcggcggat tggttaaacc ggggggcagt ctgcgtttaa gctgcgcagc ttccgggttt    480

actttttcgg attactatat gagctggatt cgtcaggctc ccggtaaagg gttggaatgg    540

gttagctaca tctcaagttc cggctctaca atctactatg cagattccgt gaaagggcgc    600

ttcaccatct ctcgtgacaa tgcaaagaac agtttatact tacaaatgaa ctcgctgcgt    660

gcggaagata cggctgtgta ttactgtgca cggattgggc ggtacagcta tggtctccgg    720

tcctactact actacggtat ggacgtctgg ggccaaggga ccacggtcac cgtctcctca    780
```

<210> SEQ ID NO 47
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Val Tyr Tyr Cys Met Gln Ala Leu Gln Thr Pro Val
                85                  90                  95

Thr Phe Gly Gln Gly Thr Arg Leu Glu Ile Lys Arg Gly Gly Gly Gly
            100                 105                 110

Ser Gly Gly Gly Gly Ser Gly Gly Gly Gly Ser Gln Val Gln Leu Val
        115                 120                 125

Glu Ser Gly Gly Gly Leu Val Lys Pro Gly Gly Ser Leu Arg Leu Ser
    130                 135                 140

Cys Ala Ala Ser Gly Phe Thr Phe Ser Asp Tyr Tyr Met Ser Trp Ile
145                 150                 155                 160

Arg Gln Ala Pro Gly Lys Gly Leu Glu Trp Val Ser Tyr Ile Ser Ser
                165                 170                 175

Ser Gly Ser Thr Ile Tyr Tyr Ala Asp Ser Val Lys Gly Arg Phe Thr
            180                 185                 190

Ile Ser Arg Asp Asn Ala Lys Asn Ser Leu Tyr Leu Gln Met Asn Ser
        195                 200                 205

Leu Arg Ala Glu Asp Thr Ala Val Tyr Tyr Cys Ala Arg Ile Gly Arg
    210                 215                 220

Tyr Ser Tyr Gly Leu Arg Ser Tyr Tyr Tyr Tyr Gly Met Asp Val Trp
225                 230                 235                 240

Gly Gln Gly Thr Thr Val Thr Val Ser Ser
                245                 250
```

<210> SEQ ID NO 48
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
gatattcaaa tgacccagtc tccttcttcc ttgagcgcgt ctgtgggaga ccgtgtaact     60

atcacgtgtc gtgcatccca aagcatttcg agttacttga actggtatca acaaaagcct    120

ggtaaagcgc ccaaactgtt gatctatgct gccagtagtc ttcaatctgg tgtgccctcg    180

cgcttctcag gttcggggtc aggaacggac tttaccctga ccattagctc tctgcaaccg    240

gaggattttg ggtttatta ctgcatgcaa gctctacaaa ctccggtcac cttcggccaa    300

gggacacgac tggagattaa acgtggcggt ggagggagcg gtggcggggg aagtggaggg    360

ggtggcagcc aagttcaatt agtggagagc ggcggcggat tggttaaacc ggggggcagt    420

ctgcgtttaa gctgcgcagc ttccgggttt actttttcgg attactatat gagctggatt    480

cgtcaggctc ccggtaaagg gttggaatgg gttagctaca tctcaagttc cggctctaca    540

atctactatg cagattccgt gaaagggcgc ttcaccatct ctcgtgacaa tgcaaagaac    600

agtttatact tacaaatgaa ctcgctgcgt gcggaagata cggctgtgta ttactgtgca    660

cggattgggc ggtacagcta tggtctccgg tcctactact actacggtat ggacgtctgg    720

ggccaaggga ccacggtcac cgtctcctca                                     750
```

<210> SEQ ID NO 49
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ile Gly Arg Tyr Ser Tyr Gly Leu Arg Ser Tyr Tyr Tyr Tyr
            100                 105                 110

Gly Met Asp Val Trp Gly Gln Gly Thr Thr Val Thr Val Ser Ser Gly
        115                 120                 125

Gly Gly Gly Ser Gly Gly Gly Gly Ser Gly Gly Gly Gly Ser Gly Gly
    130                 135                 140

Gly Gly Ser Gly Gly Gly Gly Ser Asp Ile Gln Met Thr Gln Ser Pro
145                 150                 155                 160
```

-continued

```
Ser Ser Leu Ser Ala Ser Val Gly Asp Arg Val Thr Ile Thr Cys Arg
                165                 170                 175

Ala Ser Gln Ser Ile Ser Ser Tyr Leu Asn Trp Tyr Gln Gln Lys Pro
            180                 185                 190

Gly Lys Ala Pro Lys Leu Leu Ile Tyr Ala Ala Ser Ser Leu Gln Ser
        195                 200                 205

Gly Val Pro Ser Arg Phe Ser Gly Ser Gly Ser Gly Thr Asp Phe Thr
    210                 215                 220

Leu Thr Ile Ser Ser Leu Gln Pro Glu Asp Phe Gly Val Tyr Tyr Cys
225                 230                 235                 240

Met Gln Ala Leu Gln Thr Pro Val Thr Phe Gly Gln Gly Thr Arg Leu
                245                 250                 255

Glu Ile Lys Arg
            260
```

<210> SEQ ID NO 50
<211> LENGTH: 780
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 50

```
caagttcaat tagtggagag cggcggcgga ttggttaaac cggggggcag tctgcgttta     60

agctgcgcag cttccgggtt tactttttcg gattactata tgagctggat tcgtcaggct    120

cccggtaaag ggttggaatg ggttagctac atctcaagtt ccggctctac aatctactat    180

gcagattccg tgaaagggcg cttcaccatc tctcgtgaca atgcaaagaa cagtttatac    240

ttacaaatga actcgctgcg tgcggaagat acggctgtgt attactgtgc acggattggg    300

cggtacagct atggtctccg gtcctactac tactacggta tggacgtctg ggccaagggg    360

accacggtca ccgtctcctc aggaggcggt gggagcgggg gcggaggtag tggcggtgga    420

gggagcggtg gcgggggaag tggagggggt ggcagcgata ttcaaatgac ccagtctcct    480

tcttccttga gcgcgtctgt gggagaccgt gtaactatca cgtgtcgtgc atcccaaagc    540

atttcgagtt acttgaactg gtatcaacaa aagcctggta aagcgcccaa actgttgatc    600

tatgctgcca gtagtcttca atctggtgtg ccctcgcgct tctcaggttc ggggtcagga    660

acggacttta ccctgaccat tagctctctg caaccggagg attttggggt ttattactgc    720

atgcaagctc tacaaactcc ggtcaccttc ggccaaggga cacgactgga gattaaacgt    780
```

<210> SEQ ID NO 51
<211> LENGTH: 250
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
```

-continued

```
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ile Gly Arg Tyr Ser Tyr Gly Leu Arg Ser Tyr Tyr Tyr Tyr
            100                 105                 110

Gly Met Asp Val Trp Gly Gln Gly Thr Thr Val Thr Val Ser Ser Gly
        115                 120                 125

Gly Gly Gly Ser Gly Gly Gly Gly Ser Gly Gly Gly Gly Ser Asp Ile
    130                 135                 140

Gln Met Thr Gln Ser Pro Ser Ser Leu Ser Ala Ser Val Gly Asp Arg
145                 150                 155                 160

Val Thr Ile Thr Cys Arg Ala Ser Gln Ser Ile Ser Ser Tyr Leu Asn
                165                 170                 175

Trp Tyr Gln Gln Lys Pro Gly Lys Ala Pro Lys Leu Leu Ile Tyr Ala
            180                 185                 190

Ala Ser Ser Leu Gln Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Gly Val Tyr Tyr Cys Met Gln Ala Leu Gln Thr Pro Val Thr Phe
225                 230                 235                 240

Gly Gln Gly Thr Arg Leu Glu Ile Lys Arg
                245                 250


<210> SEQ ID NO 52
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

caagttcaat tagtggagag cggcggcgga ttggttaaac cggggggcag tctgcgttta     60

agctgcgcag cttccgggtt tactttttcg gattactata tgagctggat tcgtcaggct    120

cccggtaaag ggttggaatg ggttagctac atctcaagtt ccggctctac aatctactat    180

gcagattccg tgaaagggcg cttcaccatc tctcgtgaca atgcaaagaa cagtttatac    240

ttacaaatga actcgctgcg tgcggaagat acggctgtgt attactgtgc acggattggg    300

cggtacagct atggtctccg gtcctactac tactacggta tggacgtctg gggccaaggg    360

accacggtca ccgtctcctc aggcggtgga gggagcggtg gcgggggaag tggagggggt    420

ggcagcgata ttcaaatgac ccagtctcct tcttccttga gcgcgtctgt gggagaccgt    480

gtaactatca cgtgtcgtgc atcccaaagc atttcgagtt acttgaactg gtatcaacaa    540

aagcctggta aagcgcccaa actgttgatc tatgctgcca gtagtcttca atctggtgtg    600

ccctcgcgct tctcaggttc ggggtcagga acggacttta ccctgaccat tagctctctg    660

caaccggagg attttggggt ttattactgc atgcaagctc tacaaactcc ggtcaccttc    720

ggccaaggga cacgactgga gattaaacgt                                     750


<210> SEQ ID NO 53
<211> LENGTH: 87
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: NON_CONS
<222> LOCATION: (30)..(31)
<223> OTHER INFORMATION: Residues at these positions can be separated by
      a CDR1 sequence of Variable Heavy Region of unknown length
<220> FEATURE:
<221> NAME/KEY: NON_CONS
<222> LOCATION: (44)..(45)
<223> OTHER INFORMATION: Residues at these positions can be separated by
      a CDR2 sequence of Variable Heavy Region of unknown length
<220> FEATURE:
<221> NAME/KEY: NON_CONS
<222> LOCATION: (76)..(77)
<223> OTHER INFORMATION: Residues at these positions can be separated by
      a CDR3 sequence of Variable Heavy Region of unknown length

<400> SEQUENCE: 53

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Trp Ile
            20                  25                  30

Arg Gln Ala Pro Gly Lys Gly Leu Glu Trp Val Ser Arg Phe Thr Ile
        35                  40                  45

Ser Arg Asp Asn Ala Lys Asn Ser Leu Tyr Leu Gln Met Asn Ser Leu
    50                  55                  60

Arg Ala Glu Asp Thr Ala Met Tyr Tyr Cys Ala Arg Trp Gly Gln Gly
65                  70                  75                  80

Thr Thr Val Thr Val Ser Ser
                85


<210> SEQ ID NO 54
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: NON_CONS
<222> LOCATION: (23)..(24)
<223> OTHER INFORMATION: Residues at these positions can be separated by
      a CDR1 sequence of Variable Light Region of unknown length
<220> FEATURE:
<221> NAME/KEY: NON_CONS
<222> LOCATION: (38)..(39)
<223> OTHER INFORMATION: Residues at these positions can be separated by
      a CDR2 sequence of Variable Light Region of unknown length
<220> FEATURE:
<221> NAME/KEY: NON_CONS
<222> LOCATION: (70)..(71)
<223> OTHER INFORMATION: Residues at these positions can be separated by
      a CDR3 sequence of Variable Light Region of unknown length

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Ala
            20                  25                  30

Pro Lys Leu Leu Ile Tyr Gly Val Pro Ser Arg Phe Ser Gly Ser Gly
        35                  40                  45

Ser Gly Thr Asp Phe Thr Leu Thr Ile Ser Ser Leu Gln Pro Glu Asp
    50                  55                  60

Val Gly Val Tyr Tyr Cys Phe Gly Gly Gly Thr Lys Leu Glu Ile Lys
```

65 70 75 80

Arg

<210> SEQ ID NO 55
<211> LENGTH: 248
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 55

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Gly Val Tyr Tyr Cys Met Gln Ala Leu Gln Thr Pro Val
85 90 95

Thr Phe Gly Gln Gly Thr Arg Leu Glu Ile Lys Arg Gly Gly Gly Gly
100 105 110

Ser Gly Gly Gly Gly Ser Gly Gly Gly Gly Ser Gln Val Gln Leu Val
115 120 125

Glu Ser Gly Gly Gly Leu Val Lys Pro Gly Gly Ser Leu Arg Leu Ser
130 135 140

Cys Ala Ala Ser Gly Phe Thr Phe Ser Asp Tyr Tyr Met Ser Trp Ile
145 150 155 160

Arg Gln Ala Pro Gly Lys Gly Leu Glu Trp Val Ser Tyr Ile Ser Ser
165 170 175

Ser Gly Ser Thr Ile Tyr Tyr Ala Asp Ser Val Lys Gly Arg Phe Thr
180 185 190

Ile Ser Arg Asp Asn Ala Lys Asn Ser Leu Tyr Leu Gln Met Asn Ser
195 200 205

Leu Arg Ala Glu Asp Thr Ala Met Tyr Tyr Cys Ala Arg Val Ala Arg
210 215 220

Gln Tyr Arg Lys Ser Tyr Tyr Tyr Tyr Gly Met Asp Val Trp Gly Gln
225 230 235 240

Gly Thr Thr Val Thr Val Ser Ser
245

<210> SEQ ID NO 56
<211> LENGTH: 248
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 56

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Met Tyr Tyr Cys
85 90 95

Ala Arg Val Ala Arg Gln Tyr Arg Lys Ser Tyr Tyr Tyr Tyr Gly Met
100 105 110

Asp Val Trp Gly Gln Gly Thr Thr Val Thr Val Ser Ser Gly Gly Gly
115 120 125

Gly Ser Gly Gly Gly Gly Ser Gly Gly Gly Gly Ser Asp Ile Gln Met
130 135 140

Thr Gln Ser Pro Ser Ser Leu Ser Ala Ser Val Gly Asp Arg Val Thr
145 150 155 160

Ile Thr Cys Arg Ala Ser Gln Ser Ile Ser Ser Tyr Leu Asn Trp Tyr
165 170 175

Gln Gln Lys Pro Gly Lys Ala Pro Lys Leu Leu Ile Tyr Ala Ala Ser
180 185 190

Ser Leu Gln Ser Gly Val Pro Ser Arg Phe Ser Gly Ser Gly Ser Gly
195 200 205

Thr Asp Phe Thr Leu Thr Ile Ser Ser Leu Gln Pro Glu Asp Phe Gly
210 215 220

Val Tyr Tyr Cys Met Gln Ala Leu Gln Thr Pro Val Thr Phe Gly Gln
225 230 235 240

Gly Thr Arg Leu Glu Ile Lys Arg
245

<210> SEQ ID NO 57
<211> LENGTH: 91
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: NON_CONS
<222> LOCATION: (25)..(26)
<223> OTHER INFORMATION: Residues at these positions can be separated by a CDR1 sequence of Variable Heavy Region of unknown length
<220> FEATURE:
<221> NAME/KEY: NON_CONS
<222> LOCATION: (42)..(43)
<223> OTHER INFORMATION: Residues at these positions can be separated by a CDR2 sequence of Variable Heavy Region of unknown length
<220> FEATURE:
<221> NAME/KEY: NON_CONS
<222> LOCATION: (80)..(81)
<223> OTHER INFORMATION: Residues at these positions can be separated by a CDR3 sequence of Variable Heavy Region of unknown length

<400> SEQUENCE: 57

Glu Val Gln Leu Val Gln Ser Gly Gly Gly Leu Val Gln Pro Gly Gly
1 5 10 15

Ser Leu Arg Leu Ser Cys Ser Ala Ser Met His Trp Val Arg Gln Ala
20 25 30

Pro Gly Lys Gly Leu Glu Tyr Val Ser Ala Tyr Tyr Ala Asp Ser Val
35 40 45

Lys Gly Arg Phe Thr Ile Ser Arg Asp Asn Ser Lys Asn Thr Leu Tyr

```
    50                  55                  60

Leu Gln Met Asn Ser Leu Arg Ala Glu Asp Thr Ala Val Tyr Tyr Cys
65                  70                  75                  80

Trp Gly Gln Gly Thr Met Val Thr Val Ser Ser
                85                  90


<210> SEQ ID NO 58
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Glu Val Gln Leu Val Gln Ser Gly Gly Gly Leu Val Gln Pro Gly Gly
1               5                   10                  15

Ser Leu Arg Leu Ser Cys Ser Ala Ser
            20                  25


<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Met His Trp Val Arg Gln Ala Pro Gly Lys Gly Leu Glu Tyr Val Ser
1               5                   10                  15

Ala


<210> SEQ ID NO 60
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35


<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Trp Gly Gln Gly Thr Met Val Thr Val Ser Ser
1               5                   10


<210> SEQ ID NO 62
<211> LENGTH: 90
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: NON_CONS
<222> LOCATION: (26)..(27)
<223> OTHER INFORMATION: Residues at these positions can be separated by
      a CDR1 sequence of Variable Light Region of unknown length
<220> FEATURE:
<221> NAME/KEY: NON_CONS
<222> LOCATION: (43)..(44)
<223> OTHER INFORMATION: Residues at these positions can be separated by
      a CDR2 sequence of Variable Light Region of unknown length
<220> FEATURE:
<221> NAME/KEY: NON_CONS
<222> LOCATION: (79)..(80)
<223> OTHER INFORMATION: Residues at these positions can be separated by
      a CDR3 sequence of Variable Light Region of unknown length

<400> SEQUENCE: 62

Glu Ala Thr Leu Thr Gln Ser Pro Ser Ser Leu Ser Ala Ser Val Gly
1               5                   10                  15

Asp Arg Val Thr Ile Thr Cys Arg Ala Ser Leu Asn Trp Tyr Gln Gln
            20                  25                  30

Lys Pro Gly Arg Ala Pro Lys Leu Leu Ile Tyr Ser Leu Gln Ser Gly
        35                  40                  45

Val Pro Ser Arg Phe Ser Gly Ser Gly Ser Gly Thr Asp Phe Thr Leu
    50                  55                  60

Thr Ile Ser Ser Leu Gln Pro Glu Asp Phe Ala Thr Tyr Tyr Cys Phe
65                  70                  75                  80

Gly Gln Gly Thr Arg Leu Glu Ile Lys Arg
                85                  90


<210> SEQ ID NO 63
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Glu Ala Thr Leu Thr Gln Ser Pro Ser Ser Leu Ser Ala Ser Val Gly
1               5                   10                  15

Asp Arg Val Thr Ile Thr Cys Arg Ala Ser
            20                  25


<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Asn Trp Tyr Gln Gln Lys Pro Gly Arg Ala Pro Lys Leu Leu Ile
1               5                   10                  15

Tyr


<210> SEQ ID NO 65
<211> LENGTH: 36
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 65

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 66
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: NON_CONS
<222> LOCATION: (25)..(26)
<223> OTHER INFORMATION: Residues at these positions can be separated by
      a CDR1 sequence of Variable Heavy Region of unknown length
<220> FEATURE:
<221> NAME/KEY: NON_CONS
<222> LOCATION: (42)..(43)
<223> OTHER INFORMATION: Residues at these positions can be separated by
      a CDR2 sequence of Variable Heavy Region of unknown length
<220> FEATURE:
<221> NAME/KEY: NON_CONS
<222> LOCATION: (80)..(81)
<223> OTHER INFORMATION: Residues at these positions can be separated by
      a CDR3 sequence of Variable Heavy Region of unknown length

<400> SEQUENCE: 66

Glu Val Gln Leu Val Gln Ser Gly Gly Gly Leu Val Gln Pro Gly Gly
1               5                   10                  15

Ser Leu Arg Leu Ser Cys Ala Ala Ser Met Thr Trp Val Arg Gln Ala
            20                  25                  30

Pro Gly Lys Gly Leu Glu Trp Val Ser Thr Tyr Tyr Ala Asp Ser Val
        35                  40                  45

Lys Gly Arg Phe Thr Ile Ser Arg Asp Asn Asp Lys Asn Thr Leu Tyr
    50                  55                  60

Leu Gln Met Asn Ser Leu Arg Ala Asp Asp Thr Ala Val Tyr Tyr Cys
65                  70                  75                  80

Trp Gly Gln Gly Thr Leu Val Thr Val Ser Ser
                85                  90

<210> SEQ ID NO 67
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Glu Val Gln Leu Val Gln Ser Gly Gly Gly Leu Val Gln Pro Gly Gly
1               5                   10                  15

Ser Leu Arg Leu Ser Cys Ala Ala Ser
            20                  25

<210> SEQ ID NO 68
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 68

Met Thr Trp Val Arg Gln Ala Pro Gly Lys Gly Leu Glu Trp Val Ser
1               5                   10                  15

Thr


<210> SEQ ID NO 69
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Tyr Tyr Ala Asp Ser Val Lys Gly Arg Phe Thr Ile Ser Arg Asp Asn
1               5                   10                  15

Asp Lys Asn Thr Leu Tyr Leu Gln Met Asn Ser Leu Arg Ala Asp Asp
            20                  25                  30

Thr Ala Val Tyr Tyr Cys
        35


<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Trp Gly Gln Gly Thr Leu Val Thr Val Ser Ser
1               5                   10


<210> SEQ ID NO 71
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: NON_CONS
<222> LOCATION: (25)..(26)
<223> OTHER INFORMATION: Residues at these positions can be separated by
      a CDR1 sequence of Variable Light Region of unknown length
<220> FEATURE:
<221> NAME/KEY: NON_CONS
<222> LOCATION: (42)..(43)
<223> OTHER INFORMATION: Residues at these positions can be separated by
      a CDR2 sequence of Variable Light Region of unknown length
<220> FEATURE:
<221> NAME/KEY: NON_CONS
<222> LOCATION: (78)..(79)
<223> OTHER INFORMATION: Residues at these positions can be separated by
      a CDR3 sequence of Variable Light Region of unknown length

<400> SEQUENCE: 71

Gln Ser Val Val Thr Gln Pro Pro Ser Ala Ser Gly Ser Pro Gly Gln
1               5                   10                  15

Ser Val Thr Ile Ser Cys Thr Gly Thr Val Ser Trp Tyr Gln Gln His
            20                  25                  30

Pro Gly Lys Ala Pro Lys Leu Leu Ile Tyr Glu Arg Pro Ser Gly Val
```

```
        35                  40                  45

Pro Asp Arg Phe Ser Gly Ser Lys Ser Asp Asn Lys Ala Ser Leu Thr
    50                  55                  60

Ile Ile Gly Leu Gln Thr Glu Asp Glu Ala Asp Tyr Tyr Cys Phe Gly
65                  70                  75                  80

Thr Gly Thr Lys Leu Thr Val Leu Arg
                85


<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Ser Val Val Thr Gln Pro Pro Ser Ala Ser Gly Ser Pro Gly Gln
1               5                   10                  15

Ser Val Thr Ile Ser Cys Thr Gly Thr
            20                  25


<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Val Ser Trp Tyr Gln Gln His Pro Gly Lys Ala Pro Lys Leu Leu Ile
1               5                   10                  15

Tyr


<210> SEQ ID NO 74
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Arg Pro Ser Gly Val Pro Asp Arg Phe Ser Gly Ser Lys Ser Asp
1               5                   10                  15

Asn Lys Ala Ser Leu Thr Ile Ile Gly Leu Gln Thr Glu Asp Glu Ala
            20                  25                  30

Asp Tyr Tyr Cys
        35


<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Phe Gly Thr Gly Thr Lys Leu Thr Val Leu Arg
1               5                   10
```

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Gly Gly Gly Gly Ser Gly Gly Ser Gly Ser Gly Gly Gly Gly Ser
1 5 10 15

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Gly Gly Gly Gly Ser Gly Gly Ser Gly Ser Ser Gly Gly Gly Ser
1 5 10 15

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 78

Gly Gly Gly Gly Ser Gly Gly Gly Gly Ser Gly Gly Gly Gly Ser
1 5 10 15

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 79

Gly Gly Gly Gly Ser Gly Ser Gly Ala Ser Ser Gly Gly Gly Ser
1 5 10 15

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 80

Gly Gly Gly Gly Ser Gly Ser Gly Ala Ser Gly Gly Gly Gly Ser
1 5 10 15

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 81

```
Ser Gly Gly Gly Ser Gly Gly Gly Gly Ser Gly Gly Gly Gly Ser
1               5                   10                  15


<210> SEQ ID NO 82
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Ser Thr Ser Gly Ser Gly Lys Pro Gly Ser Gly Glu Gly Ser Thr
1               5                   10                  15

Lys Gly


<210> SEQ ID NO 83
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Pro Asn Gly Ala Ser Gln Ser Ser Ser Ala Ser His Thr Gly Ser Ala
1               5                   10                  15

Pro Gly Ser


<210> SEQ ID NO 84
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Pro Asn Gly Ala Ser Asn Ser Gly Ser Ala Pro Asp Thr Ser Ser Ala
1               5                   10                  15

Pro Gly Ser


<210> SEQ ID NO 85
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Pro Asn Gly Ala Ser His Ser Gly Ser Ala Pro Asn Thr Ser Ser Ala
1               5                   10                  15

Pro Gly Ser


<210> SEQ ID NO 86
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86
```

```
Pro Asn Gly Ala Ser Glu Ser Gly Ser Ala Ser Lys Thr Ser Ser Ala
1               5                   10                  15

Ser Gly Ser


<210> SEQ ID NO 87
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Pro Asn Gly Ala Ser Asn Ser Gly Ser Ala Pro Lys Thr Gly Ser Ala
1               5                   10                  15

Ser Gly Ser


<210> SEQ ID NO 88
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Pro Asn Gly Ala Ser Lys Ser Gly Ser Ala Ser Gln Thr Ser Ser Ala
1               5                   10                  15

Pro Gly Ser


<210> SEQ ID NO 89
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Pro Asn Gly Ala Ser His Ser Ser Ser Ala Ser Gln Thr Gly Ser Ala
1               5                   10                  15

Pro Gly Ser


<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Pro Asn Gly Ala Ser Lys Arg Ser Ala Pro Gly Ser
1               5                   10


<210> SEQ ID NO 91
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Pro Asn Gly Ala Ser His Ser Gly Ser Ala Pro His Thr Ser Ser Ala
```

-continued 1 5 10 15

Ser Gly Ser

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

Arg Gly Arg Gly Arg Gly Arg Gly Arg Ser Arg Gly Gly Gly Ser
1 5 10 15

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 93

Ser His Gly Gly Ser His Gly Gly Gly Ser Gly Gly Gly Gly Ser
1 5 10 15

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

Gly Gln Ala Gly Arg
1 5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 95

Gly Gly Gly Ser Gly Gly Gly Gly
1 5

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 96

Ser Gly Gly Gly Gly
1 5

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 97

Gly Gly Gly Gly Ser
1 5

<210> SEQ ID NO 98
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 98

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser
20 25 30

<210> SEQ ID NO 99
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 99

Gly Gly Gly Gly Gly Ser Gly Gly Gly Gly Ser Gly Gly Gly Gly Ser
1 5 10 15

<210> SEQ ID NO 100
<211> LENGTH: 26
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 100

Gly Gly Gly Gly Gly Ser Gly Gly Gly Gly Ser Gly Gly Gly Gly Ser
1 5 10 15

Gly Gly Gly Gly Ser Gly Gly Gly Gly Ser
20 25

<210> SEQ ID NO 101
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 101

Gly Gly Gly Gly Ser Gly Gly Gly Gly Ser Gly Gly Gly Gly Ser Gly
1 5 10 15

Gly Gly Gly Ser Gly Gly Gly Gly Ser
20 25

<210> SEQ ID NO 102
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 102

Ala Ala Ala
1

<210> SEQ ID NO 103
<211> LENGTH: 22
<212> TYPE: PRT
<213> ORGANISM: Homo sapiens

<400> SEQUENCE: 103

Met Asp Met Arg Val Pro Ala Gln Leu Leu Gly Leu Leu Leu Leu Trp
1 5 10 15

Leu Arg Gly Ala Arg Cys
20

<210> SEQ ID NO 104
<211> LENGTH: 66
<212> TYPE: DNA
<213> ORGANISM: Homo sapiens

<400> SEQUENCE: 104
atggatatga gggtccccgc acaattgctc ggtctccttc tgctttggct ccggggcgcg 60
cggtgc 66

<210> SEQ ID NO 105
<211> LENGTH: 15
<212> TYPE: PRT
<213> ORGANISM: Homo sapiens

<400> SEQUENCE: 105

Glu Pro Lys Ser Cys Asp Lys Thr His Thr Cys Pro Pro Cys Pro
1 5 10 15

<210> SEQ ID NO 106
<211> LENGTH: 15
<212> TYPE: PRT
<213> ORGANISM: Homo sapiens

<400> SEQUENCE: 106

Asp Lys Thr His Thr Cys Pro Pro Cys Pro Ala Pro Pro Val Ala
1 5 10 15

<210> SEQ ID NO 107
<211> LENGTH: 12
<212> TYPE: PRT
<213> ORGANISM: Homo sapiens

<400> SEQUENCE: 107

Glu Ser Lys Tyr Gly Pro Pro Cys Pro Pro Cys Pro
1 5 10

<210> SEQ ID NO 108
<211> LENGTH: 12
<212> TYPE: PRT
<213> ORGANISM: Homo sapiens

<400> SEQUENCE: 108

Glu Ser Lys Tyr Gly Pro Pro Cys Pro Ser Cys Pro
1 5 10

<210> SEQ ID NO 109
<211> LENGTH: 49
<212> TYPE: PRT
<213> ORGANISM: Homo sapiens

<400> SEQUENCE: 109

```
Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
        35                  40                  45

Tyr
```

<210> SEQ ID NO 110
<211> LENGTH: 39
<212> TYPE: PRT
<213> ORGANISM: Homo sapiens

<400> SEQUENCE: 110

```
Ile Glu Val Met Tyr Pro Pro Pro Tyr Leu Asp Asn Glu Arg Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35
```

<210> SEQ ID NO 111
<211> LENGTH: 47
<212> TYPE: PRT
<213> ORGANISM: Homo sapiens

<400> SEQUENCE: 111

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45
```

<210> SEQ ID NO 112
<211> LENGTH: 45
<212> TYPE: PRT
<213> ORGANISM: Homo sapiens

<400> SEQUENCE: 112

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 113
<211> LENGTH: 21
<212> TYPE: PRT
<213> ORGANISM: Homo sapiens

<400> SEQUENCE: 113

```
Leu Cys Tyr Leu Leu Asp Gly Ile Leu Phe Ile Tyr Gly Val Ile Leu
```

-continued

```
1               5                   10                  15

Thr Ala Leu Phe Leu
            20


<210> SEQ ID NO 114
<211> LENGTH: 22
<212> TYPE: PRT
<213> ORGANISM: Homo sapiens

<400> SEQUENCE: 114

Met Ala Leu Ile Val Leu Gly Gly Val Ala Gly Leu Leu Leu Phe Ile
1               5                   10                  15

Gly Leu Gly Ile Phe Phe
            20


<210> SEQ ID NO 115
<211> LENGTH: 21
<212> TYPE: PRT
<213> ORGANISM: Homo sapiens

<400> SEQUENCE: 115

Ile Tyr Ile Trp Ala Pro Leu Ala Gly Thr Cys Gly Val Leu Leu Leu
1               5                   10                  15

Ser Leu Val Ile Thr
            20


<210> SEQ ID NO 116
<211> LENGTH: 24
<212> TYPE: PRT
<213> ORGANISM: Homo sapiens

<400> SEQUENCE: 116

Ile Tyr Ile Trp Ala Pro Leu Ala Gly Thr Cys Gly Val Leu Leu Leu
1               5                   10                  15

Ser Leu Val Ile Thr Leu Tyr Cys
            20


<210> SEQ ID NO 117
<211> LENGTH: 22
<212> TYPE: PRT
<213> ORGANISM: Homo sapiens

<400> SEQUENCE: 117

Ile Trp Ala Pro Leu Ala Gly Thr Cys Gly Val Leu Leu Leu Ser Leu
1               5                   10                  15

Val Ile Thr Leu Tyr Cys
            20


<210> SEQ ID NO 118
<211> LENGTH: 19
<212> TYPE: PRT
<213> ORGANISM: Homo sapiens

<400> SEQUENCE: 118

Ile Trp Ala Pro Leu Ala Gly Thr Cys Gly Val Leu Leu Leu Ser Leu
1               5                   10                  15

Val Ile Thr


<210> SEQ ID NO 119
<211> LENGTH: 27
<212> TYPE: PRT
<213> ORGANISM: Homo sapiens
```

<400> SEQUENCE: 119

```
Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 120
<211> LENGTH: 21
<212> TYPE: PRT
<213> ORGANISM: Homo sapiens

<400> SEQUENCE: 120

```
Phe Trp Leu Pro Ile Gly Cys Ala Ala Phe Val Val Val Cys Ile Leu
1               5                   10                  15

Gly Cys Ile Leu Ile
            20
```

<210> SEQ ID NO 121
<211> LENGTH: 113
<212> TYPE: PRT
<213> ORGANISM: Homo sapiens

<400> SEQUENCE: 121

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg
```

<210> SEQ ID NO 122
<211> LENGTH: 42
<212> TYPE: PRT
<213> ORGANISM: Homo sapiens

<400> SEQUENCE: 122

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 123
<211> LENGTH: 37
<212> TYPE: PRT
<213> ORGANISM: Homo sapiens

<400> SEQUENCE: 123

-continued

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu
        35


<210> SEQ ID NO 124
<211> LENGTH: 41
<212> TYPE: PRT
<213> ORGANISM: Homo sapiens

<400> SEQUENCE: 124

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 125
<211> LENGTH: 42
<212> TYPE: PRT
<213> ORGANISM: Homo sapiens

<400> SEQUENCE: 125

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
        35                  40


<210> SEQ ID NO 126
<211> LENGTH: 38
<212> TYPE: PRT
<213> ORGANISM: Homo sapiens

<400> SEQUENCE: 126

Cys Trp Leu Thr Lys Lys Lys Tyr Ser Ser Ser Val His Asp Pro Asn
1               5                   10                  15

Gly Glu Tyr Met Phe Met Arg Ala Val Asn Thr Ala Lys Lys Ser Arg
            20                  25                  30

Leu Thr Asp Val Thr Leu
        35


<210> SEQ ID NO 127
<211> LENGTH: 24
<212> TYPE: PRT
<213> ORGANISM: Homo sapiens

<400> SEQUENCE: 127

Leu Cys Ala Arg Pro Arg Arg Ser Pro Ala Gln Glu Asp Gly Lys Val
1               5                   10                  15

Tyr Ile Asn Met Pro Gly Arg Gly
            20


<210> SEQ ID NO 128
<211> LENGTH: 52
<212> TYPE: PRT
<213> ORGANISM: Homo sapiens
```

<400> SEQUENCE: 128

Tyr Phe Leu Gly Arg Leu Val Pro Arg Gly Arg Gly Ala Ala Glu Ala
1               5                   10                  15

Ala Thr Arg Lys Gln Arg Ile Thr Glu Thr Glu Ser Pro Tyr Gln Glu
            20                  25                  30

Leu Gln Gly Gln Arg Ser Asp Val Tyr Ser Asp Leu Asn Thr Gln Arg
        35                  40                  45

Pro Tyr Tyr Lys
    50

<210> SEQ ID NO 129
<211> LENGTH: 48
<212> TYPE: PRT
<213> ORGANISM: Homo sapiens

<400> SEQUENCE: 129

Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45

<210> SEQ ID NO 130
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Ser Ser Tyr Leu Asn Trp Tyr Gln Gln Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Gly Val Tyr Tyr Cys Met Gln
            100                 105                 110

Ala Leu Gln Thr Pro Val Thr Phe Gly Gln Gly Thr Arg Leu Glu Ile
        115                 120                 125

Lys Gly Gly Gly Gly Gly Ser Gly Gly Gly Gly Ser Gly Gly Gly Gly
    130                 135                 140

Ser Gly Gly Gly Gly Ser Gly Gly Gly Gly Ser Gln Val Gln Leu Val
145                 150                 155                 160

Glu Ser Gly Gly Gly Leu Val Lys Pro Gly Gly Ser Leu Arg Leu Ser
                165                 170                 175

Cys Ala Ala Ser Gly Phe Thr Phe Ser Asp Tyr Tyr Met Ser Trp Ile
            180                 185                 190

-continued

```
Arg Gln Ala Pro Gly Lys Gly Leu Glu Trp Val Ser Tyr Ile Ser Ser
        195                 200                 205

Ser Gly Ser Thr Ile Tyr Tyr Ala Asp Ser Val Lys Gly Arg Phe Thr
    210                 215                 220

Ile Ser Arg Asp Asn Ala Lys Asn Ser Leu Tyr Leu Gln Met Asn Ser
225                 230                 235                 240

Leu Arg Ala Glu Asp Thr Ala Val Tyr Tyr Cys Ala Arg Ile Gly Arg
                245                 250                 255

Tyr Ser Tyr Gly Leu Arg Ser Tyr Tyr Tyr Tyr Gly Met Asp Val Trp
            260                 265                 270

Gly Gln Gly Thr Thr Val Thr Val Ser Ser Ala Ala Ala Glu Ser Lys
        275                 280                 285

Tyr Gly Pro Pro Cys Pro Ser Cys Pro Phe Trp Val Leu Val Val Val
    290                 295                 300

Gly Gly Val Leu Ala Cys Tyr Ser Leu Leu Val Thr Val Ala Phe Ile
305                 310                 315                 320

Ile Phe Trp Val Arg Ser Lys Arg Ser Arg Leu Leu His Ser Asp Tyr
                325                 330                 335

Met Asn Met Thr Pro Arg Arg Pro Gly Pro Thr Arg Lys His Tyr Gln
            340                 345                 350

Pro Tyr Ala Pro Pro Arg Asp Phe Ala Ala Tyr Arg Ser Lys Arg Gly
        355                 360                 365

Arg Lys Lys Leu Leu Tyr Ile Phe Lys Gln Pro Phe Met Arg Pro Val
    370                 375                 380

Gln Thr Thr Gln Glu Glu Asp Gly Cys Ser Cys Arg Phe Pro Glu Glu
385                 390                 395                 400

Glu Glu Gly Gly Gly Gly Ser Arg Val Lys Phe Ser Arg Ser Ala Asp
                405                 410                 415

Ala Pro Ala Tyr Gln Gln Gly Gln Asn Gln Leu Tyr Asn Glu Leu Asn
            420                 425                 430

Leu Gly Arg Arg Glu Glu Tyr Asp Val Leu Asp Lys Arg Arg Gly Arg
        435                 440                 445

Asp Pro Glu Met Gly Gly Lys Pro Gln Arg Arg Lys Asn Pro Gln Glu
    450                 455                 460

Gly Leu Tyr Asn Glu Leu Gln Lys Asp Lys Met Ala Glu Ala Tyr Ser
465                 470                 475                 480

Glu Ile Gly Met Lys Gly Glu Arg Arg Arg Gly Lys Gly His Asp Gly
                485                 490                 495

Leu Tyr Gln Gly Leu Ser Thr Ala Thr Lys Asp Thr Tyr Asp Ala Leu
            500                 505                 510

His Met Gln Ala Leu Pro Pro Arg
        515                 520
```

<210> SEQ ID NO 131
<211> LENGTH: 1560
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131

```
atggatatga gggtccccgc acaattgctc ggtctccttc tgctttggct ccggggcgcg     60

cggtgcgata ttcagatgac ccagagcccg tcctcacttt cagctagcgt cggtgaccgg    120

gtgaccatta catgcagggc aagtcaaagt atcagctcat atttgaattg gtaccagcag    180
```

-continued

```
aaaccaggta aagcccccaa gctccttatt tacgcagctt catcactgca atccggagta    240
ccgtctagat tctctggcag tggcagcggg accgacttta cgttgactat ttcttccctt    300
caacctgagg actttggtgt ttactactgc atgcaagcgc tccagactcc tgttacattt    360
ggccagggca cccggcttga aattaagggc gggggcggtg gaagtggggg aggaggatca    420
gggggtggtg ggtctggagg gggaggtagt ggcggtggag gaagtcaagt gcaattggta    480
gagagcggcg gcggactagt aaaacctggg ggaagcctgc ggctgtcctg cgcagcaagc    540
ggattcactt tcagtgatta ttacatgagc tggattcgcc aggcgcctgg taaaggtttg    600
gagtgggtgt cctacatcag ttcatccggg tccacaatct actatgcgga tagtgtgaaa    660
ggtcggttca caataagtag ggataatgca aagaactcac tgtatctcca gatgaatagt    720
cttagagccg aagataccgc tgtctattat tgtgcgcgaa tcggtcgata ttcatacggg    780
ttgagaagct attactatta tggcatggac gtttggggcc agggtactac agtcactgta    840
tctagtgcgg ccgcggagtc taaatacggt cctccatgtc ccagctgtcc cttttgggtt    900
ctcgtcgtag tcggaggagt attggcctgc tattctcttc tcgtaactgt cgcttttata    960
attttctggg tacgaagtaa gcgaagtagg ttgcttcata gtgattacat gaatatgaca   1020
ccacgacggc ccggccccac tcggaagcac taccaaccgt atgctccccc tcgagacttt   1080
gccgcgtatc gatctaaacg gggccgaaaa aagttgctgt acatctttaa acaaccattt   1140
atgagaccag ttcaaacgac ccaggaagaa gatggatgct catgccgctt cccagaagag   1200
gaagaagggg ggggtggttc acgggttaaa ttctcaaggt ctgctgatgc cccccgcctat   1260
caacagggac agaatcagtt gtacaacgag ctcaatcttg gaaggcgcga agagtatgat   1320
gtgttggata aaagaagagg tcgcgaccct gaaatggggg gcaagcctca gagacgcaaa   1380
aaccctcagg agggactcta taatgagttg cagaaggata agatggccga agcatactca   1440
gagataggta tgaaagggga gcgacgaaga gggaagggac atgatgggct gtaccaaggg   1500
ctcagtactg cgacgaagga cacatatgac gcactccata tgcaggcttt gccacctcgc   1560
```

<210> SEQ ID NO 132
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

```
Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110
```

```
Thr Pro Val Thr Val Ser Ser
        115


<210> SEQ ID NO 133
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg
            100                 105


<210> SEQ ID NO 134
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Met
        35                  40                  45

Gly Leu Ile Asn Pro Tyr Lys Gly Val Ser Thr Tyr Asn Gln Lys Phe
    50                  55                  60

Lys Asp Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Thr Leu Thr Val Phe Ser
        115                 120


<210> SEQ ID NO 135
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 135

Met Asp Ile Gln Met Thr Gln Thr Thr Ser Ser Leu Ser Ala Ser Leu
1 5 10 15

Gly Asp Arg Val Thr Ile Ser Cys Arg Ala Ser Gln Asp Ile Arg Asn
20 25 30

Tyr Leu Asn Trp Tyr Gln Gln Lys Pro Asp Gly Thr Val Lys Leu Leu
35 40 45

Ile Tyr Tyr Thr Ser Arg Leu His Ser Gly Val Pro Ser Lys Phe Ser
50 55 60

Gly Ser Gly Ser Gly Thr Asp Tyr Ser Leu Thr Ile Ser Asn Leu Glu
65 70 75 80

Gln Glu Asp Ile Ala Thr Tyr Phe Cys Gln Gln Gly Asn Thr Leu Pro
85 90 95

Trp Thr Phe Ala Gly Gly Thr Lys Leu Glu Ile Lys
100 105

<210> SEQ ID NO 136
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 136

Glu Val Gln Leu Val Glu Ser Gly Gly Gly Val Val Arg Pro Gly Gly
1 5 10 15

Ser Leu Arg Leu Ser Cys Ala Ala Ser Gly Phe Thr Phe Asp Asp Tyr
20 25 30

Gly Met Ser Trp Val Arg Gln Ala Pro Gly Lys Gly Leu Glu Trp Val
35 40 45

Ser Gly Ile Asn Trp Asn Gly Gly Ser Thr Gly Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Gly Arg Ser Leu Leu Phe Asp Tyr Trp Gly Gln Gly Thr Leu
100 105 110

Val Thr Val Ser Arg
115

<210> SEQ ID NO 137
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 137

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Lys Asn Asn Arg Pro Ser Gly Ile Pro Asp Arg Phe Ser Gly Ser

```
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Gly
            100                 105


<210> SEQ ID NO 138
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Glu Ile Ser Ser Gly Gly Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Gly Asp Tyr Pro Arg Phe Phe Asp Val Trp Gly Gln Gly
            100                 105                 110

Thr Thr Val Thr Val Ser Ser
        115


<210> SEQ ID NO 139
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Ser Tyr
            20                  25                  30

Ile Tyr Trp Tyr Gln Gln Lys Pro Gly Gln Ala Pro Arg Leu Leu Ile
        35                  40                  45

Tyr Leu Thr Ser Asn Leu Ala Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Trp Ser Gly Asn Pro Tyr
                85                  90                  95

Thr Phe Gly Gln Gly Thr Lys Leu Glu Ile Lys
            100                 105
```

<210> SEQ ID NO 140
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Leu Gly Asp Gly Thr Tyr Phe Asp Tyr Trp Gly
            100                 105                 110

Gln Gly Thr Thr Val Thr Val Ser Ser
        115                 120
```

<210> SEQ ID NO 141
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

```
Gln Ser Ala Leu Thr Gln Pro Ala Ser Val Ser Gly Ser Pro Gly Gln
1               5                   10                  15

Ser Ile Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Phe Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110
```

<210> SEQ ID NO 142
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

```
Gln Val Gln Leu Val Gln Ser Gly Ala Glu Val Lys Lys Pro Gly Ala
1               5                   10                  15
```

```
Ser Val Lys Val Ser Cys Lys Ala Ser Gly His Thr Phe Thr Ser Tyr
            20                  25                  30

Phe Met His Trp Val Arg Gln Ala Pro Gly Gln Gly Leu Glu Trp Met
        35                  40                  45

Gly Ile Ile Asn Pro Ser Asp Asp Tyr Ala Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Ala Ile Phe Asp Tyr Trp Gly Gln Gly Thr Leu Val Thr Val
            100                 105                 110

Ser Ser


<210> SEQ ID NO 143
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Gln Val Gln Leu Val Gln Ser Gly Ala Glu Val Lys Lys Pro Gly Ala
1               5                   10                  15

Ser Val Lys Val Ser Cys Lys Ala Ser Gly His Thr Phe Thr Ser Tyr
            20                  25                  30

Phe Met His Trp Val Arg Gln Ala Pro Gly Gln Gly Leu Glu Trp Met
        35                  40                  45

Gly Ile Ile Asn Pro Ser Asp Asp Tyr Ala Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Ala Ile Phe Asp Tyr Trp Gly Gln Gly Thr Pro Val Thr Val
            100                 105                 110

Ser Ser


<210> SEQ ID NO 144
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

-continued

```
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105


<210> SEQ ID NO 145
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Ile Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Phe His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

His Asp Lys Ala Thr Ile Ile Ala Asp Ile Ser Ser Asn Thr Ala Tyr
65                  70                  75                  80

Leu Gln Phe Ser Ser Leu Thr Ser Glu Asp Thr Ala Val Tyr Tyr Cys
                85                  90                  95

Ala Ala Asn Arg Tyr Gly Tyr Trp Gly Gln Gly Thr Thr Leu Thr Val
            100                 105                 110

Ser Ser


<210> SEQ ID NO 146
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Asp Ile Val Met Thr Gln Ala Ala Pro Ser Ile Pro Val Thr Pro Gly
1               5                   10                  15

Glu Ser Val Ser Ile Ser Cys Arg Ser Ser Lys Ser Leu Leu Tyr Ile
            20                  25                  30

Asn Gly Asn Thr His Leu Phe Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110


<210> SEQ ID NO 147
<211> LENGTH: 120
<212> TYPE: PRT
<213> ORGANISM: Artificial Sequence
```

<220> FEATURE:
<223> OTHER INFORMATION: Description of Artificial Sequence: Synthetic
polypeptide

<400> SEQUENCE: 147

```
Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Asn Trp Gly Lys Gln Arg Ser Gly Gln Gly Leu Glu Trp Ile
        35                  40                  45

Gly Glu Ile Tyr Pro Gly Ser Gly Thr Asn Tyr Tyr Asn Glu Lys Phe
    50                  55                  60

Lys Ala Lys Ala Thr Leu Thr Ala Asp Lys Ser Ser Asn Ile Ala Tyr
65                  70                  75                  80

Met Gln Leu Ser Ser Leu Thr Ser Glu Asp Ser Ala Val Tyr Phe Cys
                85                  90                  95

Ala Arg Arg Gly Arg Tyr Gly Leu Tyr Ala Met Asp Tyr Trp Gly Gln
            100                 105                 110

Gly Thr Ser Val Thr Val Ser Ser
        115                 120
```

<210> SEQ ID NO 148
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 148

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Asn Asn Leu Glu Gln
65                  70                  75                  80

Glu Asp Ile Ala Thr Tyr Phe Cys Gln Gln Gly Asn Thr Arg Pro Trp
                85                  90                  95

Thr Phe Gly Gly Gly Thr Lys Leu Glu Ile Lys
            100                 105
```

<210> SEQ ID NO 149
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 149

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30
```

```
Gly Met Ser Trp Val Arg Gln Ala Pro Gly Lys Gly Leu Glu Trp Ile
        35                  40                  45

Gly Ser Ile Tyr Tyr Ser Gly Ser Thr Asn Tyr Asn Pro Ser Leu Lys
    50                  55                  60

Ser Leu Val Thr Ile Ser Arg Asp Asn Ser Lys Asn Thr Leu Tyr Leu
65                  70                  75                  80

Gln Met Asn Ser Leu Arg Ala Glu Asp Thr Ala Thr Tyr Tyr Cys Ala
                85                  90                  95

Arg Glu Ser Ile Asp Tyr Trp Gly Gln Gly Thr Leu Val Thr Val Ser
            100                 105                 110

Ser


<210> SEQ ID NO 150
<211> LENGTH: 702
<212> TYPE: PRT
<213> ORGANISM: Homo sapiens

<400> SEQUENCE: 150

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285
```

-continued

```
Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Lys Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
    530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
    610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr Ser Pro Gly Leu Ser Ala Gly Ala Thr
        675                 680                 685

Val Gly Ile Met Ile Gly Val Leu Val Gly Val Ala Leu Ile
    690                 695                 700
```

<210> SEQ ID NO 151
<211> LENGTH: 182
<212> TYPE: PRT
<213> ORGANISM: Homo sapiens

<400> SEQUENCE: 151

```
Pro Lys Pro Ser Ile Ser Ser Asn Asn Ser Lys Pro Val Glu Asp Lys
1               5                   10                  15

Asp Ala Val Ala Phe Thr Cys Glu Pro Glu Ala Gln Asn Thr Thr Tyr
            20                  25                  30

Leu Trp Trp Val Asn Gly Gln Ser Leu Pro Val Ser Pro Arg Leu Gln
        35                  40                  45

Leu Ser Asn Gly Asn Arg Thr Leu Thr Leu Phe Asn Val Thr Arg Asn
    50                  55                  60

Asp Ala Arg Ala Tyr Val Cys Gly Ile Gln Asn Ser Val Ser Ala Asn
65                  70                  75                  80

Arg Ser Asp Pro Val Thr Leu Asp Val Leu Tyr Gly Pro Asp Thr Pro
                85                  90                  95

Ile Ile Ser Pro Pro Asp Ser Ser Tyr Leu Ser Gly Ala Asn Leu Asn
            100                 105                 110

Leu Ser Cys His Ser Ala Ser Asn Pro Ser Pro Gln Tyr Ser Trp Arg
        115                 120                 125

Ile Asn Gly Ile Pro Gln Gln His Thr Gln Val Leu Phe Ile Ala Lys
    130                 135                 140

Ile Thr Pro Asn Asn Asn Gly Thr Tyr Ala Cys Phe Val Ser Asn Leu
145                 150                 155                 160

Ala Thr Gly Arg Asn Asn Ser Ile Val Lys Ser Ile Thr Val Ser Ala
                165                 170                 175

Ser Gly Thr Ser Pro Gly
            180
```

<210> SEQ ID NO 152
<211> LENGTH: 8
<212> TYPE: PRT
<213> ORGANISM: Homo sapiens

<400> SEQUENCE: 152

```
Glu Pro Lys Ser Cys Asp Lys Thr
1               5
```

<210> SEQ ID NO 153
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

```
Gly Gly Gly Gly Ser Gly Gly Gly Gly Ser Gly Gly Gly Gly Ser Gln
1               5                   10                  15

Val Gln Leu Val Gln Ser Gly Gly Gly Val Val Gln Pro Gly Arg Ser
            20                  25                  30

Leu Arg Leu Ser Cys Lys Ala Ser Gly Tyr Thr Phe Thr Arg Tyr Thr
        35                  40                  45

Met His Trp Val Arg Gln Ala Pro Gly Lys Gly Leu Glu Trp Ile Gly
    50                  55                  60

Tyr Ile Asn Pro Ser Arg Gly Tyr Thr Asn Tyr Asn Gln Lys Val Lys
65                  70                  75                  80
```

```
Asp Arg Phe Thr Ile Ser Arg Asp Asn Ser Lys Asn Thr Ala Phe Leu
                85                  90                  95

Gln Met Asp Ser Leu Arg Pro Glu Asp Thr Gly Val Tyr Phe Cys Ala
            100                 105                 110

Arg Tyr Tyr Asp Asp His Tyr Cys Leu Asp Tyr Trp Gly Gln Gly Thr
        115                 120                 125

Pro Val Thr Val Ser Ser Gly Gly Gly Gly Ser Gly Gly Gly Gly Ser
    130                 135                 140

Gly Gly Gly Gly Ser Gly Gly Gly Gly Ser Gly Gly Gly Gly Ser Gly
145                 150                 155                 160

Gly Gly Gly Ser Asp Ile Gln Met Thr Gln Ser Pro Ser Ser Leu Ser
                165                 170                 175

Ala Ser Val Gly Asp Arg Val Thr Ile Thr Cys Ser Ala Ser Ser Ser
            180                 185                 190

Val Ser Tyr Met Asn Trp Tyr Gln Gln Thr Pro Gly Lys Ala Pro Lys
        195                 200                 205

Arg Trp Ile Tyr Asp Thr Ser Lys Leu Ala Ser Gly Val Pro Ser Arg
    210                 215                 220

Phe Ser Gly Ser Gly Ser Gly Thr Asp Tyr Thr Phe Thr Ile Ser Ser
225                 230                 235                 240

Leu Gln Pro Glu Asp Ile Ala Thr Tyr Tyr Cys Gln Gln Trp Ser Ser
                245                 250                 255

Asn Pro Phe Thr Phe Gly Gln Gly Thr Lys Leu Gln Ile Thr Arg
            260                 265                 270
```

<210> SEQ ID NO 154
<211> LENGTH: 813
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 154

```
ggaggtggcg ggtctggtgg aggcggaagc ggtggtggcg gatcccaggt ccaactggtg     60

caaagtggag gcggcgtagt acagcccggt cggtccctgc ggctcagctg taaagcaagt    120

gggtacactt tcaccagata tacaatgcac tgggttagac aggcccccgg caagggtctt    180

gaatggatag gatatatcaa cccatcccgc ggatatacaa actacaatca gaaggtgaag    240

gaccggttca cgattagtag agacaactcc aaaaacactg cgttccttca aatggactca    300

ttgcgacccg aggacactgg agtgtatttc tgtgccaggt attatgacga ccattattgc    360

ctggactact gggggcaagg cacaccggtt acggtatctt ccggaggtgg cgggtctggt    420

ggaggcggaa gcggtggtgg cggatccggg ggaggaggct ctggcggagg cggatcaggg    480

ggtggaggtt ccgacattca aatgacacaa tcccctagtt ctttgtctgc gtccgtgggg    540

gatcgggtaa caatcacttg ctctgcatca agcagtgttt cttatatgaa ctggtatcag    600

cagacacccg gtaaggcccc aaaacgatgg atttatgaca cgagtaaact cgcatccggg    660

gtgccttcac gcttctccgg ttctggttcc ggcacggatt acactttcac catcagtagc    720

ctgcaacctg aggacattgc aacttattac tgtcaacaat ggagcagtaa tccattcacg    780

ttcggccaag ggacaaaact gcagattact agg                                 813
```

<210> SEQ ID NO 155
<211> LENGTH: 22

```
<212> TYPE: PRT
<213> ORGANISM: Homo sapiens

<400> SEQUENCE: 155

Met Asp Met Arg Val Leu Ala Gln Leu Leu Gly Leu Leu Leu Leu Cys
1               5                   10                  15

Phe Pro Gly Ala Arg Cys
            20


<210> SEQ ID NO 156
<211> LENGTH: 20
<212> TYPE: PRT
<213> ORGANISM: Homo sapiens

<400> SEQUENCE: 156

Met Glu Ala Pro Ala Gln Leu Leu Phe Leu Leu Leu Leu Trp Leu Pro
1               5                   10                  15

Asp Thr Thr Gly
            20


<210> SEQ ID NO 157
<211> LENGTH: 20
<212> TYPE: PRT
<213> ORGANISM: Homo sapiens

<400> SEQUENCE: 157

Met Val Leu Gln Thr Gln Val Phe Ile Ser Leu Leu Leu Trp Ile Ser
1               5                   10                  15

Gly Ala Tyr Gly
            20


<210> SEQ ID NO 158
<211> LENGTH: 19
<212> TYPE: PRT
<213> ORGANISM: Homo sapiens

<400> SEQUENCE: 158

Met Leu Pro Ser Gln Leu Ile Gly Phe Leu Leu Leu Trp Val Pro Ala
1               5                   10                  15

Ser Arg Gly


<210> SEQ ID NO 159
<211> LENGTH: 22
<212> TYPE: PRT
<213> ORGANISM: Homo sapiens

<400> SEQUENCE: 159

Met Asp Met Arg Val Pro Ala Gln Leu Leu Gly Leu Leu Leu Leu Trp
1               5                   10                  15

Leu Ser Gly Ala Arg Cys
            20


<210> SEQ ID NO 160
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Gln Val Gln Leu Val Gln Ser Gly Ala Glu Val Lys Lys Pro Gly Ala
1               5                   10                  15
```

-continued

```
Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Arg Ile Asp Pro Tyr Asp Ser Glu Thr His Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser Ser
        115                 120                 125
```

<210> SEQ ID NO 161
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 161

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Arg
                85                  90                  95

Thr Phe Gly Gly Gly Thr Lys Val Glu Ile Lys
            100                 105
```

<210> SEQ ID NO 162
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 162

```
Gly Gly Gly Gly Ser Gly Gly Gly Gly Ser Gly Gly Gly Gly Ser
1               5                   10                  15
```

<210> SEQ ID NO 163
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 163

```
ggaggtggcg ggtctggtgg aggcggaagc ggtggtggcg gatcc                  45


<210> SEQ ID NO 164
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Val Tyr Tyr Cys Met Gln Ala Leu Gln Thr Pro Val
                85                  90                  95

Thr Phe Gly Gln Gly Thr Arg Leu Glu Ile Lys Gly Gly Gly Gly Ser
            100                 105                 110

Gly Gly Gly Gly Ser Gly Gly Gly Gly Ser Gln Val Gln Leu Val Glu
        115                 120                 125

Ser Gly Gly Gly Leu Val Lys Pro Gly Gly Ser Leu Arg Leu Ser Cys
    130                 135                 140

Ala Ala Ser Gly Phe Thr Phe Ser Asp Tyr Tyr Met Ser Trp Ile Arg
145                 150                 155                 160

Gln Ala Pro Gly Lys Gly Leu Glu Trp Val Ser Tyr Ile Ser Ser Ser
                165                 170                 175

Gly Ser Thr Ile Tyr Tyr Ala Asp Ser Val Lys Gly Arg Phe Thr Ile
            180                 185                 190

Ser Arg Asp Asn Ala Lys Asn Ser Leu Tyr Leu Gln Met Asn Ser Leu
        195                 200                 205

Arg Ala Glu Asp Thr Ala Val Tyr Tyr Cys Ala Arg Ile Gly Arg Tyr
    210                 215                 220

Ser Tyr Gly Leu Arg Ser Tyr Tyr Tyr Tyr Gly Met Asp Val Trp Gly
225                 230                 235                 240

Gln Gly Thr Thr Val Thr Val Ser Ser Gly Gly Gly Gly Ser Gln Val
                245                 250                 255

Gln Leu Val Gln Ser Gly Ala Glu Val Lys Lys Pro Gly Ala Ser Val
            260                 265                 270

Lys Val Ser Cys Lys Ala Ser Gly Tyr Thr Phe Thr Ser Tyr Trp Met
        275                 280                 285

Asn Trp Val Arg Gln Ala Pro Gly Gln Gly Leu Glu Trp Met Gly Arg
    290                 295                 300

Ile Asp Pro Tyr Asp Ser Glu Thr His Tyr Ala Gln Lys Leu Gln Gly
305                 310                 315                 320

Arg Val Thr Met Thr Thr Asp Thr Ser Thr Ser Thr Ala Tyr Met Glu
                325                 330                 335

Leu Arg Ser Leu Arg Ser Asp Asp Thr Ala Val Tyr Tyr Cys Ala Arg
            340                 345                 350
```

```
Gly Gly Tyr Asp Phe Asp Val Gly Thr Leu Tyr Trp Phe Phe Asp Val
        355                 360                 365

Trp Gly Gln Gly Thr Thr Val Thr Val Ser Ser Val Glu Gly Gly Ser
    370                 375                 380

Gly Gly Ser Gly Gly Ser Gly Gly Ser Gly Gly Val Asp Asp Ile Gln
385                 390                 395                 400

Met Thr Gln Ser Pro Ser Ser Leu Ser Ala Ser Val Gly Asp Arg Val
                405                 410                 415

Thr Ile Thr Cys Arg Ala Ser Glu Asn Ile Tyr Ser Tyr Leu Ala Trp
            420                 425                 430

Tyr Gln Gln Lys Pro Gly Lys Ala Pro Lys Leu Leu Ile Tyr Asn Ala
        435                 440                 445

Lys Thr Leu Ala Glu Gly Val Pro Ser Arg Phe Ser Gly Ser Gly Ser
    450                 455                 460

Gly Thr Asp Phe Thr Leu Thr Ile Ser Ser Leu Gln Pro Glu Asp Phe
465                 470                 475                 480

Ala Thr Tyr Tyr Cys Gln His His Tyr Gly Thr Pro Arg Thr Phe Gly
                485                 490                 495

Gly Gly Thr Lys Val Glu Ile Lys His His His His His His
            500                 505                 510
```

<210> SEQ ID NO 165
<211> LENGTH: 1530
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 165

```
gacatccaaa tgacgcagag cccgagctca ctttcagcct ctgtgggaga ccgcgtcacg     60

atcacttgcc gcgcaagtca gtccattagc tcatatctta attggtacca acagaaaccc    120

ggtaaagcac cgaaactgtt aatctatgct gccagctccc ttcagagcgg agtcccttcc    180

cgttttagtg ggtccggaag tggtacagac ttcacactga ctatcagttc cttacaacct    240

gaagacttcg gtgtctatta ttgtatgcaa gcgctgcaaa ccccggtgac tttcggccaa    300

ggaacacgtt tggaaatcaa gggcggcgga ggctcgggag gcgggggcag tggtggtgga    360

ggctctcaag tgcagcttgt agaaagtggg gggggtctgg tgaagccggg ggggtcactt    420

cgcctgtcct gtgcagcttc aggatttaca ttttcggatt attatatgag ctggattcgc    480

caagctccag gcaagggact ggagtgggtc tcgtacatct catcaagcgg gagcactatc    540

tattatgcag actcggtcaa aggacgtttc accatttctc gcgataatgc caagaacagc    600

ctttacttac aaatgaattc acttcgcgcc gaagacacag cagtatatta ttgtgctcgc    660

atcggtcgtt atagttacgg gttgcgctct tactattatt acgggatgga cgtatggggt    720

cagggcacta cggtcaccgt cagctcgggg ggtggtggga gccaggttca gctggtgcaa    780

tccggagctg aagtcaaaaa gcctggggca agtgttaagg tttcttgtaa ggccagtggt    840

tatacattta cgtcatattg gatgaactgg gtgcgtcaag cgccaggaca gggtcttgag    900

tggatgggcc gtattgatcc ttatgattct gagacacatt acgcacagaa attacaaggt    960

cgtgtaacga tgacgacaga cacatccacc tcgaccgcct atatggaatt gcgtagctta   1020

cgttccgacg atactgcggt gtattattgc gcgcgtggag gttacgattt cgacgttggc   1080

actttgtatt ggttcttcga cgtttgggga caaggaacga cggtaacagt gtcctccgtg   1140
```

-continued

```
gagggaggat caggggggtag tggcggctct ggcgggagcg ggggggtgga tgacatccag   1200

atgactcagt ctcccagtag tttaagtgct tcggtgggag atcgcgtgac cattacctgc   1260

cgcgcctcgg agaatatcta ctcatatttg gcctggtatc aacaaaaacc ggggaaagcc   1320

cccaaattac tgatttataa cgctaaaaca ctggccgaag gagtgccgtc acgcttttca   1380

gggagcggct ccggaactga cttcacatta acaattagtt ctctgcaacc ggaagacttc   1440

gccacttact attgtcagca tcattacggt actccacgta ccttcggggg gggtactaag   1500

gtggagatta agcatcacca ccaccaccat                                    1530
```

<210> SEQ ID NO 166
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 166

```
Ser Tyr Tyr Met Ser
1               5
```

<210> SEQ ID NO 167
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 167

```
Asp Tyr Ala Met Ser
1               5
```

<210> SEQ ID NO 168
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 168

```
Asp Tyr Tyr Thr Ser
1               5
```

<210> SEQ ID NO 169
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 169

```
Asp Tyr Tyr Met His
1               5
```

<210> SEQ ID NO 170
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 170

Asn Tyr Tyr Met Ser
1 5

<210> SEQ ID NO 171
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 171

Asp Asn Tyr Met Ser
1 5

<210> SEQ ID NO 172
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 172

Asp Tyr Gly Met Ser
1 5

<210> SEQ ID NO 173
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 173

Asp Tyr Tyr Met Asn
1 5

<210> SEQ ID NO 174
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 174

Gly Tyr Tyr Met Ser
1 5

<210> SEQ ID NO 175
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 175

Asp Ala Tyr Met Ser
1 5

<210> SEQ ID NO 176
<211> LENGTH: 17
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 176

Val Ile Ser Ser Ser Gly Ser Thr Ile Tyr Tyr Ala Asp Ser Val Lys
1               5                   10                  15

Gly

<210> SEQ ID NO 177
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Tyr Val Ser Ser Gly Ser Thr Ile Tyr Tyr Ala Asp Ser Val Lys Gly
1               5                   10                  15

<210> SEQ ID NO 178
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Tyr Ile Gly Ser Ser Gly Ser Thr Ile Tyr Tyr Ala Asp Ser Val Lys
1               5                   10                  15

Gly

<210> SEQ ID NO 179
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Tyr Ile Ser Tyr Ser Gly Ser Thr Ile Tyr Tyr Ala Asp Ser Val Lys
1               5                   10                  15

Gly

<210> SEQ ID NO 180
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Tyr Ile Ser Ser Asp Gly Ser Thr Ile Tyr Tyr Ala Asp Ser Val Lys
1               5                   10                  15

Gly

<210> SEQ ID NO 181
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 181

Tyr Ile Ser Ser Ser Ser Ser Thr Ile Tyr Tyr Ala Asp Ser Val Lys
1 5 10 15

Gly

<210> SEQ ID NO 182
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 182

Tyr Ile Ser Ser Ser Gly Gly Thr Ile Tyr Tyr Ala Asp Ser Val Lys
1 5 10 15

Gly

<210> SEQ ID NO 183
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 183

Tyr Ile Ser Ser Ser Gly Ser Ser Ile Tyr Tyr Ala Asp Ser Val Lys
1 5 10 15

Gly

<210> SEQ ID NO 184
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 184

Tyr Ile Ser Ser Ser Gly Ser Thr Thr Tyr Tyr Ala Asp Ser Val Lys
1 5 10 15

Gly

<210> SEQ ID NO 185
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 185

Tyr Ile Ser Ser Ser Gly Ser Thr Ile His Tyr Ala Asp Ser Val Lys
1 5 10 15

Gly

<210> SEQ ID NO 186
<211> LENGTH: 18
<212> TYPE: PRT

-continued

<213> ORGANISM: Artificial Sequence
<220> FEATURE:
<223> OTHER INFORMATION: Description of Artificial Sequence: Synthetic peptide

<400> SEQUENCE: 186

Leu Gly Arg Tyr Ser Tyr Gly Leu Arg Ser Tyr Tyr Tyr Tyr Gly Met
1 5 10 15

Asp Val

<210> SEQ ID NO 187
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 187

Ile Ser Arg Tyr Ser Tyr Gly Leu Arg Ser Tyr Tyr Tyr Tyr Gly Met
1 5 10 15

Asp Val

<210> SEQ ID NO 188
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 188

Ile Gly Lys Tyr Ser Tyr Gly Leu Arg Ser Tyr Tyr Tyr Tyr Gly Met
1 5 10 15

Asp Val

<210> SEQ ID NO 189
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 189

Ile Gly Arg Phe Ser Tyr Gly Leu Arg Ser Tyr Tyr Tyr Tyr Gly Met
1 5 10 15

Asp Val

<210> SEQ ID NO 190
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 190

Ile Gly Arg Tyr Thr Tyr Gly Leu Arg Ser Tyr Tyr Tyr Tyr Gly Met
1 5 10 15

Asp Val

<210> SEQ ID NO 191
<211> LENGTH: 18

<212> TYPE: PRT
<213> ORGANISM: Artificial Sequence
<220> FEATURE:
<223> OTHER INFORMATION: Description of Artificial Sequence: Synthetic peptide

<400> SEQUENCE: 191

Ile Gly Arg Tyr Ser Phe Gly Leu Arg Ser Tyr Tyr Tyr Tyr Gly Met
1 5 10 15

Asp Val

<210> SEQ ID NO 192
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 192

Ile Gly Arg Tyr Ser Tyr Ser Leu Arg Ser Tyr Tyr Tyr Tyr Gly Met
1 5 10 15

Asp Val

<210> SEQ ID NO 193
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 193

Ile Gly Arg Tyr Ser Tyr Gly Ile Arg Ser Tyr Tyr Tyr Tyr Gly Met
1 5 10 15

Asp Val

<210> SEQ ID NO 194
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 194

Ile Gly Arg Tyr Ser Tyr Gly Leu Lys Ser Tyr Tyr Tyr Tyr Gly Met
1 5 10 15

Asp Val

<210> SEQ ID NO 195
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 195

Ile Gly Arg Tyr Ser Tyr Gly Leu Arg Thr Tyr Tyr Tyr Tyr Gly Met
1 5 10 15

Asp Val

<210> SEQ ID NO 196

<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gln Ala Ser Gln Ser Ile Ser Ser Tyr Leu Asn
1               5                   10

<210> SEQ ID NO 197
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Arg Met Ser Gln Ser Ile Ser Ser Tyr Leu Asn
1               5                   10

<210> SEQ ID NO 198
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Arg Ala Arg Gln Ser Ile Ser Ser Tyr Leu Asn
1               5                   10

<210> SEQ ID NO 199
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Arg Ala Ser Glu Ser Ile Ser Ser Tyr Leu Asn
1               5                   10

<210> SEQ ID NO 200
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Arg Ala Ser Gln Gly Ile Ser Ser Tyr Leu Asn
1               5                   10

<210> SEQ ID NO 201
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Arg Ala Ser Gln Ser Ile Arg Ser Tyr Leu Asn
1 5 10

<210> SEQ ID NO 202
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 202

Arg Ala Ser Gln Ser Ile Ser Asn Tyr Leu Asn
1 5 10

<210> SEQ ID NO 203
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 203

Arg Ala Ser Gln Ser Ile Ser Ser Trp Leu Asn
1 5 10

<210> SEQ ID NO 204
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 204

Arg Ala Ser Gln Ser Ile Ser Ser Tyr Leu Ala
1 5 10

<210> SEQ ID NO 205
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 205

Trp Ala Ser Gln Ser Ile Ser Ser Tyr Leu Asn
1 5 10

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 206

Asp Ala Ser Ser Leu Gln Ser
1 5

<210> SEQ ID NO 207
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 207

Ala Ala Lys Ser Leu Gln Ser
1               5

<210> SEQ ID NO 208
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ala Ala Ser Thr Leu Gln Ser
1               5

<210> SEQ ID NO 209
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ala Ala Ser Ser Leu Glu Ser
1               5

<210> SEQ ID NO 210
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ala Ala Ser Ser Leu Gln Thr
1               5

<210> SEQ ID NO 211
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ser Ala Ser Ser Leu Gln Ser
1               5

<210> SEQ ID NO 212
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ala Ala Pro Ser Leu Gln Ser
1               5

<210> SEQ ID NO 213
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 213

Ala Ala Ser Asn Leu Gln Ser
1 5

<210> SEQ ID NO 214
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 214

Ala Ala Ser Ser Leu His Ser
1 5

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 215

Ala Ala Ser Ser Leu Gln Pro
1 5

<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 216

Gln Gln Ala Leu Gln Thr Pro Val Thr
1 5

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 217

Met Arg Ala Leu Gln Thr Pro Val Thr
1 5

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 218

Met Gln Tyr Leu Gln Thr Pro Val Thr
1 5

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 219

Met Gln Ala Asn Gln Thr Pro Val Thr
1 5

<210> SEQ ID NO 220
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 220

Met Gln Ala Leu Ser Thr Pro Val Thr
1 5

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 221

Met Gln Ala Leu Gln Tyr Pro Val Thr
1 5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 222

Met Gln Ala Leu Gln Thr Pro Ala Thr
1 5

<210> SEQ ID NO 223
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 223

Met Gln Ala Leu Gln Thr Pro Ile Thr
1 5

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 224

Met Gln Ala Leu Gln Thr Pro Leu Thr
1 5

<210> SEQ ID NO 225
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 225

Lys Gln Ala Leu Gln Thr Pro Val Thr
1 5

<210> SEQ ID NO 226
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 226

Ile Ala Arg Gln Tyr Arg Lys Ser Tyr Tyr Tyr Tyr Gly Met Asp Val
1 5 10 15

<210> SEQ ID NO 227
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 227

Val Val Arg Gln Tyr Arg Lys Ser Tyr Tyr Tyr Tyr Gly Met Asp Val
1 5 10 15

<210> SEQ ID NO 228
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 228

Val Ala Lys Gln Tyr Arg Lys Ser Tyr Tyr Tyr Tyr Gly Met Asp Val
1 5 10 15

<210> SEQ ID NO 229
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 229

Val Ala Arg Asn Tyr Arg Lys Ser Tyr Tyr Tyr Tyr Gly Met Asp Val
1 5 10 15

<210> SEQ ID NO 230
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 230

Val Ala Arg Gln Phe Arg Lys Ser Tyr Tyr Tyr Tyr Gly Met Asp Val
1 5 10 15

<210> SEQ ID NO 231
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 231

Val Ala Arg Gln Tyr Lys Lys Ser Tyr Tyr Tyr Tyr Gly Met Asp Val
1 5 10 15

<210> SEQ ID NO 232
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 232

Val Ala Arg Gln Tyr Arg Arg Ser Tyr Tyr Tyr Tyr Gly Met Asp Val
1 5 10 15

<210> SEQ ID NO 233
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 233

Val Ala Arg Gln Tyr Arg Lys Thr Tyr Tyr Tyr Tyr Gly Met Asp Val
1 5 10 15

<210> SEQ ID NO 234
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 234

Val Ala Arg Gln Tyr Arg Lys Ser Phe Tyr Tyr Tyr Gly Met Asp Val
1 5 10 15

<210> SEQ ID NO 235
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 235

Val Ala Arg Gln Tyr Arg Lys Ser Tyr Phe Tyr Tyr Gly Met Asp Val
1 5 10 15

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 236

Gln Gln Ala Leu Gln Thr Pro Leu Thr
1 5

<210> SEQ ID NO 237
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 237

Met Arg Ala Leu Gln Thr Pro Leu Thr
1 5

<210> SEQ ID NO 238
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 238

Met Gln Tyr Leu Gln Thr Pro Leu Thr
1 5

<210> SEQ ID NO 239
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 239

Met Gln Ala Asn Gln Thr Pro Leu Thr
1 5

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 240

Met Gln Ala Leu Ser Thr Pro Leu Thr
1 5

<210> SEQ ID NO 241
<211> LENGTH: 9
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 241

Met Gln Ala Leu Gln Tyr Pro Leu Thr
1               5

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Met Gln Ala Leu Gln Thr Ser Leu Thr
1               5

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Met Gln Ala Leu Gln Thr Pro Ile Thr
1               5

<210> SEQ ID NO 244
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Lys Gln Ala Leu Gln Thr Pro Leu Thr
1               5

<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Met Lys Ala Leu Gln Thr Pro Leu Thr
1               5

<210> SEQ ID NO 246
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 246

His His His His His His
1               5

<210> SEQ ID NO 247
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 247

Leu Gly Arg Tyr Ser Tyr Gly Leu Arg Ser Tyr Tyr Tyr Tyr Gly Met
1 5 10 15

Asp Val

<210> SEQ ID NO 248
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 248

Ile Ser Arg Tyr Ser Tyr Gly Leu Arg Ser Tyr Tyr Tyr Tyr Gly Met
1 5 10 15

Asp Val

<210> SEQ ID NO 249
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 249

Ile Gly Lys Tyr Ser Tyr Gly Leu Arg Ser Tyr Tyr Tyr Tyr Gly Met
1 5 10 15

Asp Val

<210> SEQ ID NO 250
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 250

Ile Gly Arg Phe Ser Tyr Gly Leu Arg Ser Tyr Tyr Tyr Tyr Gly Met
1 5 10 15

Asp Val

<210> SEQ ID NO 251
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 251

Ile Gly Arg Tyr Thr Tyr Gly Leu Arg Ser Tyr Tyr Tyr Tyr Gly Met
1 5 10 15

Asp Val

<210> SEQ ID NO 252
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 252

Ile Gly Arg Tyr Ser Phe Gly Leu Arg Ser Tyr Tyr Tyr Tyr Gly Met
1 5 10 15

Asp Val

<210> SEQ ID NO 253
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 253

Ile Gly Arg Tyr Ser Tyr Ser Leu Arg Ser Tyr Tyr Tyr Tyr Gly Met
1 5 10 15

Asp Val

<210> SEQ ID NO 254
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 254

Ile Gly Arg Tyr Ser Tyr Gly Ile Arg Ser Tyr Tyr Tyr Tyr Gly Met
1 5 10 15

Asp Val

<210> SEQ ID NO 255
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 255

Ile Gly Arg Tyr Ser Tyr Gly Leu Lys Ser Tyr Tyr Tyr Tyr Gly Met
1 5 10 15

Asp Val

<210> SEQ ID NO 256
<211> LENGTH: 18
<212> TYPE: PRT
<213> ORGANISM: Artificial Sequence
<220> FEATURE:
<223> OTHER INFORMATION: Description of Artificial Sequence: Synthetic
peptide -continued

<400> SEQUENCE: 256

```
Ile Gly Arg Tyr Ser Tyr Gly Leu Arg Thr Tyr Tyr Tyr Tyr Gly Met
1               5                   10                  15

Asp Val
```